(12) United States Patent
Poehmerer et al.

(10) Patent No.: US 10,407,676 B2
(45) Date of Patent: Sep. 10, 2019

(54) HIGH EFFICIENCY, SMALL VOLUME NUCLEIC ACID SYNTHESIS

(71) Applicants: LIFE TECHNOLOGIES CORPORATION, Carlsbad, CA (US); THERMO FISHER SCIENTIFIC GENEART GMBH, Regensburg (DE); LIFE TECHNOLOGIES AS, Oslo (NO)

(72) Inventors: Thomas Poehmerer, Regensburg (DE); Phillip Kuhn, Regensburg (DE); Frank Notka, Regenstauf (DE); Andreas Zeidler, Sulzbach an der Donau (DE); Korbinian Heil, Munich (DE); Axel Trefzer, Tegernheim (DE); Geir Fonnum, Fjellhamar (NO); Federico Katzen, San Marcos, CA (US); Kristian Andersson, Lillestrøm (NO)

(73) Assignees: LIFE TECHNOLOGIES CORPORATION, Carlsbad, CA (US); THERMO FISHER SCIENTIFIC GENEART GMBH, Regensburg (DE); LIFE TECHNOLOGIES AS, Oslo (NO)

( * ) Notice: Subject to any disclaimer, the term of this patent is extended or adjusted under 35 U.S.C. 154(b) by 705 days.

(21) Appl. No.: 14/964,060

(22) Filed: Dec. 9, 2015

(65) Prior Publication Data

US 2016/0186166 A1 Jun. 30, 2016

Related U.S. Application Data

(60) Provisional application No. 62/145,359, filed on Apr. 9, 2015, provisional application No. 62/089,590, filed on Dec. 9, 2014.

(51) Int. Cl.
*C12N 15/10* (2006.01)
*C25B 3/10* (2006.01)
(Continued)

(52) U.S. Cl.
CPC ...... *C12N 15/101* (2013.01); *B01L 3/502761* (2013.01); *B03C 5/026* (2013.01);
(Continued)

(58) Field of Classification Search
CPC ... C12N 15/101; B03C 5/026; B03C 2201/26; B01L 3/502761; B01L 2200/0642;
(Continued)

(56) References Cited

U.S. PATENT DOCUMENTS 4,652,639 A 3/1987 Stabinsky
5,512,439 A 4/1996 Hornes et al.
(Continued)

FOREIGN PATENT DOCUMENTS

CN 101397587 4/2009
CN 201901669 7/2011
(Continued)

OTHER PUBLICATIONS

Kurakazu et al., Selctive retrieval of microparticles in microchambers using electrolytically generated bubbles for cell array applications, (2011), Sensor and Actuators B 159, pp. 229-233.*
(Continued)

*Primary Examiner* — Arun S Phasge
(74) *Attorney, Agent, or Firm* — Life Technologies Corporation; Stephen G. Whiteside

(57) ABSTRACT

The disclosure generally relates to compositions and methods for the production of nucleic acid molecules. In some aspects, the invention allows for the microscale generation of nucleic acid molecules, optionally followed by assembly of these nucleic acid molecules into larger molecules. In
(Continued)

some aspects, the invention allows for efficient production of nucleic acid molecules (e.g., large nucleic acid molecules such as genomes).

9 Claims, 58 Drawing Sheets

Specification includes a Sequence Listing.

(51) Int. Cl.
    *C25B 11/04* (2006.01)
    *C25B 15/02* (2006.01)
    *C25B 9/18* (2006.01)
    *B01L 3/00* (2006.01)
    *B03C 5/02* (2006.01)

(52) U.S. Cl.
    CPC .......... *C25B 3/10* (2013.01); *C25B 9/18* (2013.01); *C25B 11/04* (2013.01); *C25B 15/02* (2013.01); *B01J 2219/005* (2013.01); *B01J 2219/00468* (2013.01); *B01J 2219/00653* (2013.01); *B01J 2219/00695* (2013.01); *B01J 2219/00722* (2013.01); *B01L 3/502715* (2013.01); *B01L 2200/0642* (2013.01); *B01L 2200/0647* (2013.01); *B01L 2300/0819* (2013.01); *B01L 2300/0893* (2013.01); *B01L 2400/046* (2013.01); *B01L 2400/0487* (2013.01); *B03C 2201/26* (2013.01)

(58) Field of Classification Search
    CPC ....... B01L 2400/0487; B01L 2400/046; B01L 2300/0893; B01L 2300/0819; B01L 3/502715; B01L 2200/0647; C25B 9/18; C25B 15/02; C25B 11/04; C25B 3/10; B01J 2219/00722; B01J 2219/00695; B01J 2219/00653; B01J 2219/005; B01J 2219/00468
    See application file for complete search history.

(56) References Cited

U.S. PATENT DOCUMENTS

| | | | |
|---|---|---|---|
| 5,514,789 A | 5/1996 | Kempe | |
| 5,538,848 A | 7/1996 | Livak et al. | |
| 5,580,759 A | 12/1996 | Yang et al. | |
| 5,624,827 A | 4/1997 | Rosenblum et al. | |
| 5,738,829 A | 4/1998 | Kempe | |
| 5,786,464 A | 7/1998 | Seed | |
| 5,807,522 A | 9/1998 | Brown et al. | |
| 5,837,858 A | 11/1998 | Brennan | |
| 5,851,808 A | 12/1998 | Elledge et al. | |
| 5,869,644 A | 2/1999 | Shortle et al. | |
| 5,888,732 A | 3/1999 | Hartley et al. | |
| 6,083,726 A | 7/2000 | Mills, Jr. et al. | |
| 6,093,302 A | 7/2000 | Montgomery et al. | |
| 6,110,668 A | 8/2000 | Stizhov et al. | |
| 6,143,527 A | 11/2000 | Pachuk et al. | |
| 6,143,557 A | 11/2000 | Hartley et al. | |
| 6,335,438 B1 | 1/2002 | Fonnum | |
| 6,355,412 B1 | 3/2002 | Stewart et al. | |
| 6,391,576 B1 | 5/2002 | Tsuchida et al. | |
| 6,444,111 B1 | 9/2002 | Montgomery | |
| 6,472,184 B1 | 10/2002 | Hegemann | |
| 6,495,318 B2 | 12/2002 | Harney | |
| 6,509,156 B1 | 1/2003 | Stewart | |
| 6,521,427 B1 | 2/2003 | Evans | |
| 6,887,431 B1 | 5/2005 | Vann et al. | |
| 6,964,861 B1 | 11/2005 | Gerard et al. | |
| 7,202,264 B2 | 4/2007 | Ravikumar et al. | |
| 7,211,148 B2 | 5/2007 | Bryning et al. | |
| 7,323,321 B2 | 1/2008 | Rayapati et al. | |
| 7,347,975 B2 | 3/2008 | Vann et al. | |
| 7,384,606 B2 | 6/2008 | Vann et al. | |
| 7,670,823 B1 | 3/2010 | Hartley et al. | |
| 7,670,832 B2 | 3/2010 | Wittwer et al. | |
| 7,704,690 B2 | 4/2010 | Young | |
| 7,820,412 B2 | 10/2010 | Belshaw et al. | |
| 7,833,759 B2 | 11/2010 | Padgett et al. | |
| 7,838,210 B2 | 11/2010 | Ludwig et al. | |
| 8,173,368 B2 | 5/2012 | Staehler et al. | |
| 2002/0143166 A1 | 10/2002 | Pires et al. | |
| 2003/0152984 A1 | 8/2003 | Aygun et al. | |
| 2004/0219516 A1 | 11/2004 | Bennett et al. | |
| 2004/0229229 A1 | 11/2004 | Cheo et al. | |
| 2004/0265863 A1 | 12/2004 | Chesnut et al. | |
| 2006/0115850 A1 | 6/2006 | Schatz | |
| 2006/0127920 A1 | 6/2006 | Church et al. | |
| 2006/0128006 A1 | 6/2006 | Gerhardt et al. | |
| 2007/0059752 A1 | 3/2007 | Cook | |
| 2007/0141557 A1 | 6/2007 | Raab | |
| 2007/0231805 A1 | 10/2007 | Baynes et al. | |
| 2007/0292954 A1 | 12/2007 | Elledge | |
| 2008/0113361 A1 | 5/2008 | Vann | |
| 2008/0145913 A1 | 6/2008 | Padgett | |
| 2008/0187969 A1 | 8/2008 | Castle et al. | |
| 2008/0281466 A1 | 11/2008 | Vann et al. | |
| 2009/0032401 A1 | 2/2009 | Ronaghi et al. | |
| 2009/0275086 A1 | 11/2009 | Gibson et al. | |
| 2009/0324546 A1 | 12/2009 | Notka et al. | |
| 2010/0062495 A1 | 3/2010 | Liu et al. | |
| 2010/0137143 A1 | 6/2010 | Rothberg et al. | |
| 2010/0184020 A1 | 7/2010 | Beer | |
| 2010/0216648 A1 | 8/2010 | Staehler et al. | |
| 2010/0291633 A1 | 11/2010 | Selmer et al. | |
| 2011/0109031 A1 | 5/2011 | Stauber | |
| 2011/0114490 A1 | 5/2011 | Pamula et al. | |
| 2011/0119778 A1 | 5/2011 | Liss | |
| 2011/0124049 A1 | 5/2011 | Li et al. | |
| 2011/0165630 A1 | 7/2011 | Maresca et al. | |
| 2012/0053087 A1 | 3/2012 | Gibson et al. | |
| 2012/0220497 A1 | 8/2012 | Jacobson et al. | |
| 2012/0270748 A1 | 10/2012 | Chee et al. | |
| 2013/0109596 A1 | 5/2013 | Peterson et al. | |

FOREIGN PATENT DOCUMENTS

| | | |
|---|---|---|
| JP | 2006291359 | 10/2006 |
| WO | WO-93/22480 | 11/1993 |
| WO | WO-1998/001221 | 1/1998 |
| WO | WO-2000/061647 | 10/2000 |
| WO | WO-2003/020415 | 3/2003 |
| WO | WO-2006/105037 | 10/2006 |
| WO | WO-2007/087377 | 8/2007 |
| WO | WO-2009/140671 | 11/2009 |
| WO | WO-2010/006166 | 1/2010 |
| WO | WO-2010/040531 | 4/2010 |
| WO | WO-2010/138182 | 12/2010 |
| WO | WO-2010/147078 | 12/2010 |
| WO | WO-2011/071943 | 6/2011 |
| WO | WO-2011/102802 | 8/2011 |
| WO | WO-2011/109031 | 9/2011 |
| WO | WO-2013/049227 | 4/2013 |
| WO | WO-2014/065758 | 5/2014 |
| WO | WO-2014/153188 | 9/2014 |
| WO | WO-2016/079269 | 5/2016 |

OTHER PUBLICATIONS

Cook, Brian, "Introduction to fuel cells and hydrogen technology", *Engineering Science and Education Journal*, Dec. 2002, 205-216.

Luder, , "Acids and Bases: Their Relationship to Oxidizing and Reducing Agents", *Journal of Chemical Education*, Jan. 1942, 24-26.

Tsvetanova, et al., "Genetic Assembly Tools for Synthetic Biology", *Methods in Enzymology*, vol. 498, 2011, 327-348.

Avenier, et al., "Combining Medium Effects and Cofactor Catalysis: Metal-Coordinated Synzymes Accelerate Phosphate Transfer by 108", *Chemistry: A European Journal*, vol. 15, No. 45, Nov. 16, 2009, 12371-12380.

(56) References Cited

OTHER PUBLICATIONS

Azevedo, et al., "An ordered collection of Bacillus subtilis DNA segments cloned in yeast artificial chromosomes", *Proceedings of the National Academy of Sciences*, vol. 90, No. 13, Jul. 1, 1993, 6047-6051.
Belfort, et al., "Homing endonucleases: keeping the house in order", *Nucleic Acids Research*, vol. 25, No. 17, Sep. 1, 1997, 3379-3388.
Berry, et al., "New Methods to Transport Fluids in Micro-Sized Devices", *Lincoln Laboratory Journal*, vol. 17, No. 2, 2008, 74-80.
Burk, , "Sustainable production of industrial chemicals from sugars.", *International Sugar Journal*, vol. 112,, 2010, 30-35.
Cardullo, et al., "Detection of Nucleic Acid Hybridization by Non Radiative Fluorescence Resonance Energy Transfer", *Proceedings of the National Academy of Sciences*, vol. 85, 1988, 8790-8794.
Dexter, , "A Theory of Sensitized Luminescence in Solids", *The Journal of Chemical Physics*, vol. 21, 1953, 836-850.
Egeland, et al., "Electrochemically directed synthesis of oligonucleotides for DNA microarray fabrication", *Nucleic Acids Research*, vol. 33, No. 14, 2005, e125 (1-7).
Egeland, Ryan D. , "An Electrochemical System for DNA Microarray Fabrication", *Thesis presented to the University of Oxford in fulfilment of the thesis requirement for the degree of Doctor of Philosophy in Biochemistry*, Lincoln College, University of Oxford, England, 2003, 1-301.
Fuhrmann, et al., "Removal of mismatched bases from synthetic genes by enzymatic mismatch cleavage", *Nucleic Acids Research*, vol. 33, No. 6, 2005, e58 (1-8).
Gibson, et al., "Complete Chemical Synthesis, Assembly, and Cloning of a Mycoplasma genitalium Genome", *Science*, vol. 319, No. 5867, Feb. 29, 2008, 1215-1220.
Gibson, , "Enzymatic Assembly of Overlapping DNA Fragments", *Methods in Enzymology*, vol. 498, Jan. 1, 2011, 349-361.
Gyuris, et al., "High-efficiency transformation of *Saccharomyces cerevisiae* cells by bacterial minicell protoplast fusion.", *Molecular and Cellular Biology*, vol. 6, No. 9, Sep. 1986, 3295-3297.
Heuer, et al., "Cloning of prokaryotic genomes in yeast artificial chromosomes: Application to the population genetics fo Pseudomonas aeruginosa", *Electrophoresis*, vol. 19, No. 4, Apr. 1998, 486-494.
Hochstrasser, et al., "Distance distribution in a dye linked oligonucleotide determined by time-resolved fluorescence energy transfer", *Biophysical Chemistry*, vol. 45, No. 2, Dec. 1992, 133-141.
Huang, et al., "A simple, high sensitivity mutation screeing using Ampligase mediated T7 endonuclease I and Surveyor nuclease with microfluidic capillary electrophoresis", *Electrophoresis*, vol. 33, No. 5, Mar. 21, 2012, 788-796.
Invitrogen/Life Technologies, , "Geneart® High-Order Genetic Assembly Systems", Catalog Nos. A13285, A13286, 2013, 1-45.
Invitrogen/Life Technologies, et al., "Geneart® Seamless Cloning and Assembly Kit", Catalog No. A13288, 2014, 1-28.
Jordan, et al., "Asymmetric phosphorylation through catalytic P(III) phosphoramidite transfer: Enantioselective synthesis of d-myo-inositol-6-phosphate", *Proceedings of the National Academy of Sciences*, vol. 107, 48, Nov. 30, 2010, 20620-20624.
Kornberg, , "Eukaryotic transcriptional control.", *Trends Cin ell Biology*, vol. 9, No. 12, Dec. 1999, M46-M49.
Kozak, , "Initiation of translation in prokaryotes and eukaryotes.", *Gene*, vol. 234, No. 2, Jul. 9, 1999, 187-208.
Kuspa, et al., "Physical mapping of the Myxococcus xanthus genome by random cloning in yeast artificial chromosomes", *Proceedings of the National Academy of Science*, vol. 86, No. 22, Nov. 1, 2012, 8917-8921.
Landy, , "Dynamic, structural and regulatory aspects of lambda site-specific recombination.", *Annual Reviews of Biochemistry*, vol. 58, 1989, 913-949.
Lartique, et al., "Genome transplantation in bacteria: changing one species to another.", *Science*, vol. 317, No. 5838, Epub. Jun. 28, 2007, Aug. 3, 2007, 632-638.

Lashkari, et al., "An automated multiplex oligonucleotide synthesizer: Development of high-throughput, low-cost DNA synthesis", *Proceedings of the National Academy of Sciences*, vol. 92, No. 17, Aug. 15, 1995, 7912-7915.
Liang, et al., "Recombination-Based DNA Assembly and Mutagenesis Methods for Metabolic Engineering", *Methods in Molecular Biology*, vol. 834, Jan. 1, 2012, 93-109.
Life Technologies Corporation, "Ion AmpliSeq™ Cancer Panel", *Application Note*, Products Catalog No. 4472395, Jan. 10, 2012, 1-4.
Livak, et al., "Oligonucleotides with Fluorescent Dyes at Opposite Ends Provide a Quenched Probe System Useful for Detecting PCR Product and Nucleic Acid Hybridization" *PCR Methods and Applications*, vol. 4, No. 6, Jun. 1995, 357-362.
Matzas, et al., "High-fidelity gene synthesis by retrieval of sequence-verified DNA identified using high-throughput pyrosequencing", *Nature Biotechnology*, vol. 28, 2010, 1291-1294.
Maurer, et al., "Electrochemically Generated Acid and Its Containment to 100 Micron Reaction Areas for the Production of DNA Microarrays", *PLos One*, Issue 1, Dec. 2006, e34 (1-7).
Mhlanga, et al., "Using Molecular Beacons to Detect Single-Nucleotide Polymorphisms with Real-Time PCR", *Methods*, vol. 25, No. 4, Dec. 2001, 463-471.
Nakazawa, et al., "Efficient selection of hybrids by protoplast fusion using drug resistance markers and reporter genes in *Saccharomyces cerevisiae*.", *Journal of Bioscience and Bioengineering*, vol. 98, No. 5, 2004, 353-358.
Ninomiya, et al., "Highly Efficient Gene Replacement in Neurospora Strains Deficient for Nonhomologous End-Joining", *Proceedings of the National Academy of Sciences*, vol. 101, No. 33, Aug. 17, 2004, 12248-12253.
Notka, et al., "Reprogramming a GFP reporter gene subjects it to complex lentiviral gene regulation", *Methods in Molecular Biology*, vol. 813, 2012, 85-106.
Pachuk, et al., "Chain reaction cloning: a one-step method for directional ligation of multiple DNA fragments", *Gene*, vol. 243, Nos. 1-2, Feb. 8, 2000, 19-25.
PCT/US2015/064700, , "International Search Report mailed", dated Mar. 16, 2016, 6 Pages.
Peng, L. et al., "Integrated DNA purification, PCR, samle cleanup, and capillary electrophoresis microchip for forensic human identification", *Lab Chip*, vol. 11, Jan. 2011, 1041-1048.
Quan, et al., "Circular polymerase extension cloning for high-throughput cloning of complex and combinatorial DNA libraries", *Nature Protocols*, vol. 6, Feb. 3, 2011, 242-251.
Quan, et al., "Circular polymerase extension cloning of complex gene libraries and pathways.", *PLoS One*, vol. 4, No. 7, Jul. 2009, e6441 (6 pages).
Ramakrishna, S. et al., "Heterogeneous immunoassays using magnetic beads on a digital microfluidic platform", *Lab Chip*, vol. 8, Oct. 14, 2008, 2188-2196.
Saha, , "Quantitation of HIV-1 by real-time PCR with a unique fluorogenic probe", *Journal of Virological Methods*, vol. 93, Nos. 1-2, 33-42, Apr. 2001.
Sauer, , "Site-specific recombination: developments and applications", *Current Opinion in Biotechnology*, vol. 5, No. 5, Oct. 1994, 521-527.
Selvin, , "Fluorescence Resonance Energy Transfer", *Methods in Enzymology*, vol. 246, 1995, 300-334.
Seokheun, C. et al., "Microfluidic-based biosensors toward point-of-care detection of nucleic acids and proteins", *Microfluid Nanofluid*, vol. 10, Jun. 2, 2010, 231-247.
Smith, et al., "Generating a synthetic genome by whole genome assembly: ΦX174 bacteriophage from synthetic oligonucleotides", *Proceedings of the National Academy of Sciences*, vol. 100, No. 26, Dec. 23, 2003, 15440-15445.
Steinberg, , "Long-Range Nonradiative Transfer of Electronic Excitation Energy in Proteins and Polypeptides", *Annual Review of Biochemistry*, vol. 40, Jul. 1971, 83-114.
Stinchcomb, et al., "Eukaryotic DNA segments capable of autonomous replication in yeast", *Proceedings of the National Academy of Sciences*, vol. 77, No. 8, Aug. 1, 1980, 4559-4563.

(56) References Cited

OTHER PUBLICATIONS

Stryer, , "Fluorescence Energy Transfer as a Spectroscopic Ruler", *Annual Review of Biochemistry*, vol. 47, Jul. 1978, 819-846.
Ventana Medical Systems, Inc., , "LCS (predilute)", www.ventana_.com/product/208?type=218, Catalog No. 650-010, Apr. 15, 2014, 1.
Wang, et al., "Design and Synthesis of New Fluorogenic HIV Protease Substrates Based on Resonance Energy Transfer", *Tetrahedron Letters*, vol. 31, No. 45, 1990, 6493-6496.
Wang, et al., "Rapid Sizing of Short Tandem Repeat Alleles Using Capillary Array Electrophoresis and Energy-Transfer Fluorescent Primers", *Analytical Chemistry*, vol. 67, No. 7, Apr. 1, 1995, 1197-1203.
Yang, et al., "Construction of recombinant DNA by exonuclease recession.", *Nucleic Acids Research*, vol. 21, No. 8, Apr. 25, 1993, 1889-1893.
Zhou, et al., "Microfluidic PicoArray synthesis of oligonucleotides and simultaneous assembling of multiple DNA sequences", *Nucleic Acids Research*, vol. 32, No. 18, Oct. 2004, 5409-5417.
Chiu, Sheng-Hung et al., "An air-bubble-actuated micropump for on-chip blood transportation", *Lab on a Chip, The Royal Society of Chemistry*, vol. 9, No. 11, Jun. 7, 2009, 1481-1644.
Tan, Wei-Heong et al., "A trap-and-release integrated microfluidic system for dynamic microarray applications", *PNAS*, vol. 104, No. 4, Jan. 23, 2007, 1146-1151.

\* cited by examiner

| Codon | 85 | 86 | 87 | 88 | 89 | 90 | 91 | 92 | 93 | 94 | 95 | |
|---|---|---|---|---|---|---|---|---|---|---|---|---|
| WT | TTC | CTT | CCT | GCT | ACT | GGT | GGC | GTT | TTC | CGU | AAT | (SEQ ID NO:17) |
|   | Phe | Leu | Pro | Ala | Thr | Gly | Gly | Val | Phe | Arg | Asn | (SEQ ID NO:18) |
| Variant 1 |   |   |   | GGT | ACC |   |   |   |   |   |   | |
|   |   |   |   | Gly | Thr |   |   |   |   |   |   | |
| Variant 2 |   |   |   | GGT |   |   |   |   |   |   |   | |
|   |   |   |   | Gly |   |   |   |   |   |   |   | |
| Variant 3 |   |   |   | CCT |   | ACC | ACT |   |   |   |   | |
|   |   |   |   | Pro |   | Thr | Thr |   |   |   |   | |

Columns 88–91 labeled: Domain Linker

FIG. 12A

Domain Linker

| Codon | 85 | 86 | 87 | 88 | 89 | 90 | 91 | 92 | 93 | 94 | 95 | |
|---|---|---|---|---|---|---|---|---|---|---|---|---|
| WT | TTC Phe | CTT Leu | CCT Pro | GCT Ala | ACT Thr | GGT Gly | GGC Gly | GTT Val | TTC Phe | CGU Arg | AAT Asn | (SEQ ID NO:17) |
|  |  |  |  |  |  |  |  |  |  |  | Asn | (SEQ ID NO:18) |
| V1 | TTC Phe | CTC Leu | CCC Pro | GCC Ala | ACC Thr | GGC Gly | GGC Gly | GTC Val | TTC Phe | AGA Arg | AAT Asn | (SEQ ID NO:19) |
|  |  |  |  |  |  |  |  |  |  |  | Asn | (SEQ ID NO:18) |
| V2 | TTC Phe | CTA Leu | CCA Pro | GCC Ala | ACT Thr | GGA Gly | GGC Gly | GTC Val | TTC Phe | AGG Arg | AAT Asn | (SEQ ID NO:20) |
|  |  |  |  |  |  |  |  |  |  |  | Asn | (SEQ ID NO:18) |
| V3 | TTC Phe | CTT Leu | CCG Pro | GCA Ala | ACA Thr | GGT Gly | GGG Gly | GTG Val | TTC Phe | CGC Arg | AAT Asn | (SEQ ID NO:21) |
|  |  |  |  |  |  |  |  |  |  |  | Asn | (SEQ ID NO:18) |
| V4 | TTC Phe | CTT Leu | CCC Pro | GCG Ala | ACC Thr | GGT Gly | GGG Gly | GTA Val | TTC Phe | CGU Arg | AAC Asn | (SEQ ID NO:22) |
|  |  |  |  |  |  |  |  |  |  |  | Asn | (SEQ ID NO:18) |

FIG. 12B

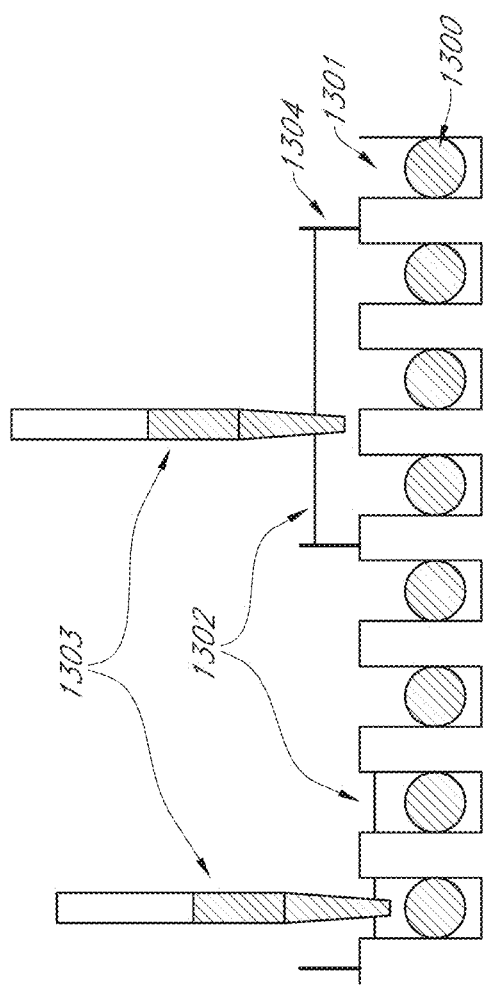

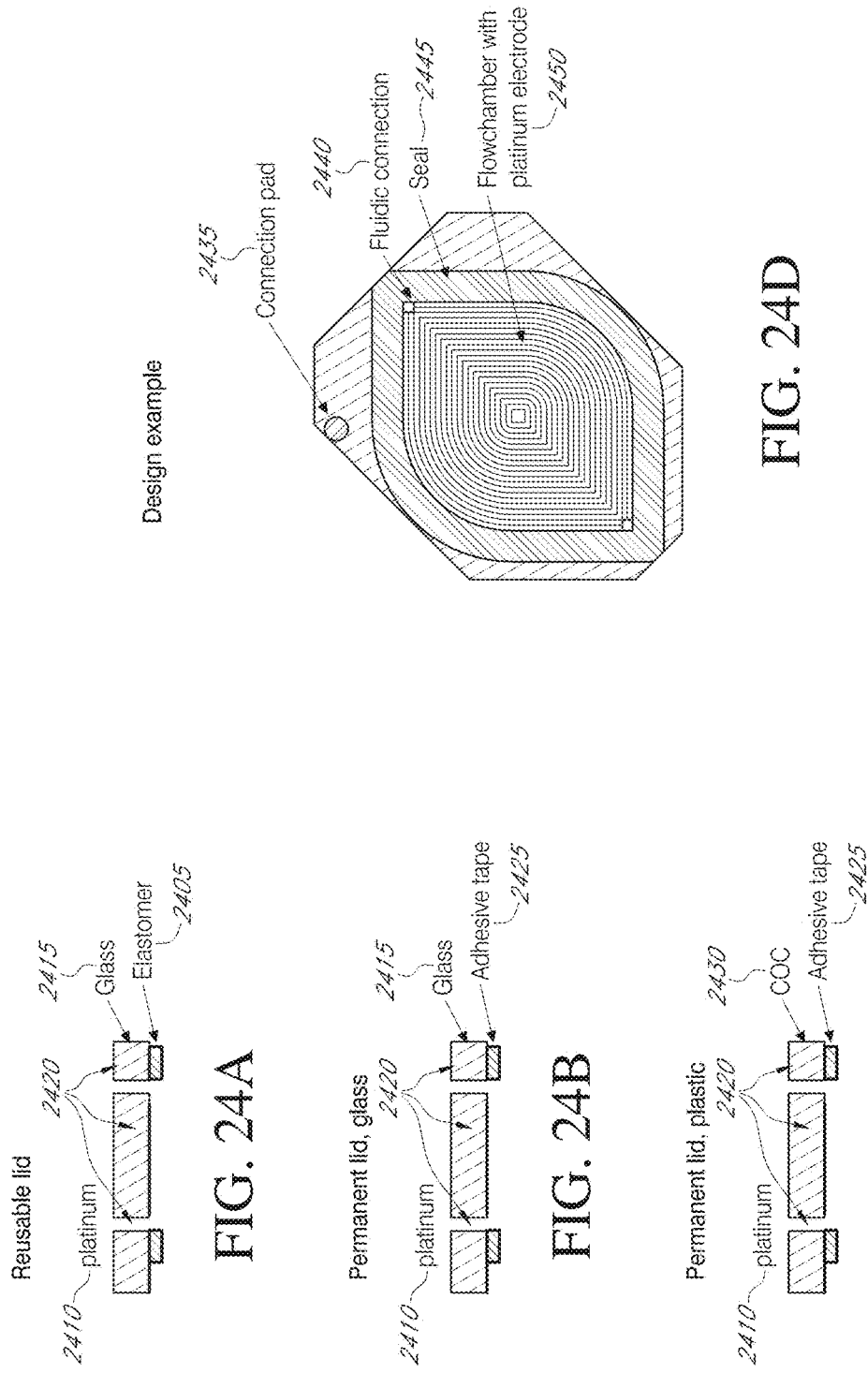

| | Size of chip (square) [mm] | Active area [%] | well diameter [μm] | distance between wells [μm]; 75% of diameter | Number of wells | well depth [μm] 125% of well diameter | well volume [μl] | diameter of bead in acetonitrile [μm]; 87.5% of well diameter |
|---|---|---|---|---|---|---|---|---|
| exemplary configuration | 18 | 73 | 40 | 30 | 35,237 | 50 | 6.28E-05 | 35 |
| variation of chip size | 5 | 73 | 40 | 30 | 2,719 | 50 | 6.28E-05 | 35 |
| | 10 | 73 | 40 | 30 | 10,876 | 50 | 6.28E-05 | 35 |
| | 20 | 73 | 40 | 30 | 43,502 | 50 | 6.28E-05 | 35 |
| | 30 | 73 | 40 | 30 | 97,880 | 50 | 6.28E-05 | 35 |
| variation of active area | 18 | 40 | 40 | 30 | 10,580 | 50 | 6.28E-05 | 35 |
| | 18 | 60 | 40 | 30 | 23,804 | 50 | 6.28E-05 | 35 |
| | 18 | 80 | 40 | 30 | 42,318 | 50 | 6.28E-05 | 35 |
| | 18 | 95 | 40 | 30 | 59,676 | 50 | 6.28E-05 | 35 |
| variation of well diameter and distance | 18 | 73 | 5 | 3.75 | 2,255,146 | 6.25 | 1.23E-07 | 4.38 |
| | 18 | 73 | 10 | 7.5 | 563,786 | 12.5 | 9.81E-07 | 8.75 |
| | 18 | 73 | 20 | 15 | 140,947 | 25 | 7.85E-06 | 17.5 |
| | 18 | 73 | 30 | 22.5 | 62,643 | 37.5 | 2.65E-05 | 26.25 |
| | 18 | 73 | 50 | 30 | 26,978 | 62.5 | 1.23E-04 | 43.75 |
| | 18 | 73 | 60 | 30 | 21,316 | 75 | 2.12E-04 | 52.5 |
| | 18 | 73 | 70 | 30 | 17,266 | 87.5 | 3.37E-04 | 61.25 |
| | 18 | 73 | 80 | 30 | 14,269 | 100 | 5.02E-04 | 70 |
| | 18 | 73 | 90 | 30 | 11,990 | 112.5 | 7.15E-04 | 78.75 |
| | 18 | 73 | 100 | 30 | 10,217 | 125 | 9.81E-04 | 87.5 |

FIG. 35

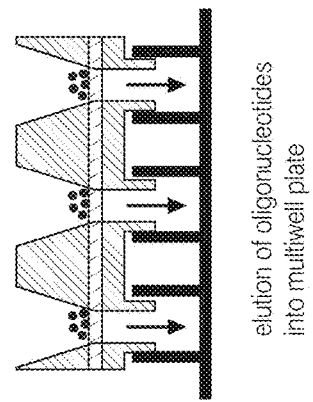
FIG. 45C
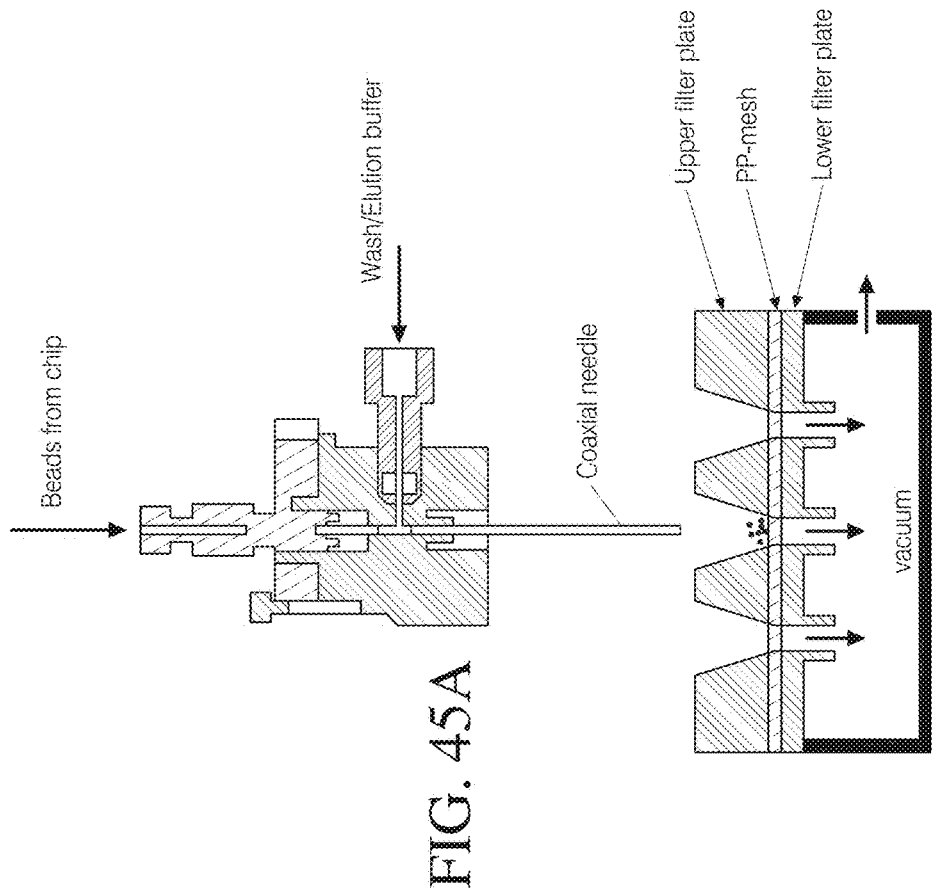
FIG. 45A
FIG. 45B

SEQUENCE LISTING

<160> NUMBER OF SEQ ID NOS: 24

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
atcgcatgcg                                                              10

<210> SEQ ID NO 2
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
atgaccatga ttacgccaag cttggccgtc gttttacaac g                           41

<210> SEQ ID NO 3
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gggaaaaccc tggcgttacc caacttaatc gccttgcagc a                           41

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gccagctggc gtaatagcga agaggcccgc accgatcg                               38

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gttgcgcagc ctgaatggcg aatggcgcct gatgcg                                 36

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ttctccttac gcatctgtgc ggtatttcac accgca                                 36

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cgccagggtt ttcccagtca cgacgttgta aaacgacggc                              40

<210> SEQ ID NO 8
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ttacgccagc tggcgaaagg gggatgtgct gcaaggcgat t                            41

<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tcaggctgcg caactgttgg aagggcgat cggtgcggg                                39

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
acagatgcgt aaggagaaaa taccgcatca ggcgcc                                  36

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
attgtactga gagtgcacca tatgcggtgt gaaataccg                               39

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atgaccatga ttacgccaag cttgg                                              25

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
attgtactga gagtgcacca tatgc                                          25

<210> SEQ ID NO 14
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
acccgtaaag cgagtttagt tttgaaaaac aaatgacata atgacatcat ccc ctgattg   60 tgttttaca                                                            69

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aattctaccc gtaaagcgag tttagttttg aaaaac                              36

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
aatgacatca tccctgatt gtgttttaca agtaga                               36

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: CDS
<222> LOCATION: (1)..(33)

<400> SEQUENCE: 17 ttc ctt cct gct act ggt ggc gtt ttc cgu aat                          33
Phe Leu Pro Ala Thr Gly Gly Val Phe Arg Asn
1               5                   10

<210> SEQ ID NO 18
<211> LENGTH: 11
<212> TYPE: PRT

```
<213> ORGANISM: Artificial Sequence
<220> FEATURE:
<223> OTHER INFORMATION: Description of Artificial Sequence: Synthetic
      oligonucleotide

<400> SEQUENCE: 18

Phe Leu Pro Ala Thr Gly Gly Val Phe Arg Asn
1               5                   10

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(33)

<400> SEQUENCE: 19 ttc ctc ccc gcc acc ggc ggc gtc ttc aga aat                      33
Phe Leu Pro Ala Thr Gly Gly Val Phe Arg Asn
1               5                   10

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(33)

<400> SEQUENCE: 20 ttc cta cca gcc act gga ggc gtc ttc agg aat                      33
Phe Leu Pro Ala Thr Gly Gly Val Phe Arg Asn
1               5                   10

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(33)

<400> SEQUENCE: 21 ttc ctt ccg gca aca ggt ggg gtg ttc cgc aat                      33
Phe Leu Pro Ala Thr Gly Gly Val Phe Arg Asn
1               5                   10

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: CDS
<222> LOCATION: (1)..(33)
```

```
<400> SEQUENCE: 22 ttc ctt ccc gcg acc ggt ggg gta ttc cgu aac                      33
Phe Leu Pro Ala Thr Gly Gly Val Phe Arg Asn
1               5                   10

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
acgtagccgg aatttgctag                                            20

<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ctgagagtcc aaagacagtt ttgaacaagt cgctgacttg                      40
```

HIGH EFFICIENCY, SMALL VOLUME NUCLEIC ACID SYNTHESIS

CROSS-REFERENCES TO RELATED APPLICATIONS

This application claims the benefit of U.S. Provisional Application Nos. 62/089,590, filed Dec. 9, 2014, and 62/145,359, filed Apr. 9, 2015, whose disclosure is incorporated by reference in its entirety.

SEQUENCE LISTING

The instant application contains a Sequence Listing which has been submitted electronically in ASCII format and is hereby incorporated by reference in its entirety. Said ASCII copy, created on Feb. 3, 2016, is named LT00964PCT_SL.txt and is 7,820 bytes in size.

FIELD OF THE INVENTION

The disclosure generally relates to compositions and methods for the production of nucleic acid molecules. In some aspects, the invention allows for the microscale generation of nucleic acid molecules, optionally followed by assembly of these nucleic acid molecules into larger molecules, as disclosed in U.S. application Ser. No. 13/627,819, which reference is hereby incorporated by reference. In some aspects, the invention allows for efficient production of nucleic acid molecules (e.g., large nucleic acid molecules such as genomes).

BACKGROUND

Production of nucleic acid molecules can be fairly simple or complex depending on factors such as the type of nucleic acid molecules to be produced. For example, historically, short single stranded nucleic acid molecules such as primers have been typically generated by chemical synthesis (see, e.g., U.S. Pat. No. 5,837,858, the disclosure of which is incorporated herein by reference). Further, longer nucleic acid molecules have typically been generated by polymerase chain reaction (PCR). One disadvantage of PCR is that generally template nucleic acid is required.

Many nucleic acid synthesis methods have limited capabilities for the generation of large de novo nucleic acid molecules. One aspect of the current disclosure is to address this limitation.

Furthermore, nucleic acid molecules that are used for gene synthesis are usually produced using expensive automated machines with limited throughput. For this reason, alternative approaches are being investigated, such as the use of microarrays as a source for nucleic acid molecules for gene synthesis. Microarrays can have hundreds of thousands of different nucleic acid molecules on a small surface and can be fabricated at very low cost.

However, approaches to nucleic acid molecule synthesis that are based on microarrays may suffer from drawbacks such as low amounts of nucleic acid molecules produced per spot. This may not be problematic for the use of hybridization assays, the application for which two-dimensional microarrays were initially developed. However, when two-dimensional microarrays are used for gene synthesis (i.e., nucleic acid molecules are fabricated on a planar surface) they may lack at least two important features. First, the quantity of nucleic acid molecules may not be large enough to assemble a fragment, such as a fragment that can be used for gene assembly. In certain instances only attomoles may be obtained. For this reason, the nucleic acid molecules generated typically need to be copied by PCR to reach quantities that are useful for fragment assembly. Moreover, the quantity of nucleic acid molecules may be further reduced by synthesis reagents, such as acids, that can act to degrade the nucleic acid molecules after synthesis.

Second, it is difficult to release synthesized nucleic acid molecules from microarrays individually, or in pools needed for the assembly of one fragment. Rather, the nucleic acid molecules are typically released together, often resulting in complex pools of thousands of different nucleic acid molecules that may not be amenable for gene synthesis without post-processing. Complicated processes like dial-out PCR or sequencing for identification and amplification of the desired nucleic acid molecules are thus often needed to make use of these pools.

SUMMARY OF THE INVENTION

The invention relates, in part, to compositions and methods for the synthesis of nucleic acid molecules. The invention further relates to compositions and methods for the retrieval of synthesized nucleic acid molecules, as well as compositions and methods for the assembly of nucleic acid molecules to form molecules such as plasmids, chromosomes and genomes.

In some aspects, the invention relates to multiwell plates for non-template directed synthesis of nucleic acid molecules. In some embodiments, the plate comprises a bead (e.g., a magnetic bead) located in each of a plurality of wells of the plate and an electrochemically generated acid (EGA) being present in one or more of the plurality of wells. Instead of or in addition to having EGA in one or more wells, wells of the plate may contain other reagents set out elsewhere associated with the synthesis of nucleic acid molecules. In certain embodiments disclosed herein, a photogenerated acid (PGA) may be present in one or more of the plurality of wells instead of or in addition to an EGA. The EGA or PGA is used to remove the protecting group (e.g., DMT) before the next amidite is added to the nucleic acid molecule attached to the solid support. In some embodiments, at least one proton carrier, such as 2-chloro-6-methylpyridine or diphenylamine, may be present in the solution with the EGA or PGA. The at least one proton carrier may act to reduce the effect of DNA degradation by accepting protons from the EGA or PGA, thereby adjusting the acidity of the solution.

In one aspect, the PGA is used in methods of generating assembled nucleic acids, the methods comprising a) synthesizing a plurality of nucleic acid molecules, wherein each nucleic acid molecule is prepared in a well of a plate or a microchip, wherein the well is operably connected to a light source for the production of a PGA and optionally contains a proton carrier, such as 2-chloro-6-methylpyridine or diphenylamine; b) combining some or all of the nucleic acid molecules generated in (a) to produce a pool; c) joining some or all of the nucleic acid molecules present in the pool formed in (b) to form a plurality of larger nucleic acid molecules; d) eliminating nucleic acid molecules which contain sequence errors from the plurality of larger nucleic acid molecules formed in (c) to produce an error corrected nucleic acid molecule pool; and e) assembling the nucleic acid molecules in the error corrected nucleic acid molecule pool to form the assembled nucleic acid molecule. Bead sizes used in the practice of the invention may vary widely but include beads with diameters between 0.01 μm and 100 μm, 0.005 μm and 100 μm, 0.005 μm and 10 μm, 0.01 μm and 100 µm, 0.01 µm and 1,000 µm, between 1.0 µm and 2.0 µm, between 1.0 µm and 100 µm, between 2.0 µm and 100 µm, between 3.0 µm and 100 µm, between 0.5 µm and 50 µm, between 0.5 µm and 20 µm, between 1.0 µm and 10 µm, between 1.0 µm and 20 µm, between 1.0 µm and 30 µm, between 10 µm and 40 µm, between 10 µm and 60 µm, between 10 µm and 80 µm, or between 0.5 µm and 10 µm. In certain embodiments, the beads may have a diameter between 30 µm and 40 µm, such as a diameter of 31 µm or 32 µm or 33 µm or 34 µm or 35 µm. As one skilled in the art would recognize, when solid particles fall below a particular size, they begin to acquire attributes of fluids (e.g., form the equivalent of colloidal suspensions). Thus, in some instances (e.g., with the use of beads below about 100 nm in diameter), it may be desirable to treat the bead as a fluid. This may mean removal of a bead from a surface, a well or from a magnetic tip, for example, by agitation, washing, or with the use of a surfactant.

In specific embodiments of the invention, the bead size may be chosen depending on the size of the well to allow only one single bead to occupy a well. In other embodiments, more than one bead (or nucleic acid synthesis substrates of other shapes) may be in some or all of the wells. In some instances, the number of beads per well may be one, between two and twenty, between two and thirty, between two and ten, between four and twenty, between four and ten, between four and fifty, etc.

In certain embodiments, each well of the multiwell plate for synthesizing nucleic acids is configured to accommodate a monodisperse bead having a diameter of about 35-40 µm, or about 35 µm or about 29 to 33 µm. In certain embodiments, the monodisperse bead is composed of a synthetic polymer, such as polystyrene.

The number of wells may also vary widely and is limited by factors such as the amount of nucleic acid to be produced, time constraints, economic factors, and technical factors such as manufacturability and mechanic factors related to use (e.g., the lower size limit of (magnetic) bead extractors). Thus, depending on various factors, the desired synthetic scale may vary and the number of wells can be adjusted to accommodate the desired synthetic scale. In any event, the number of wells may be in number, for example, between 10 and 10,000,000, between 10 and 5,000,000, between 10 and 2,000,000, between 10 and 1,000,000, between 10 and 800,000, between 10 and 650,000, between 10 and 500,000, between 500 and 500,000, between 500 and 200,000, between 10 and 50,000, between 1,000 and 500,000, between 10,000 and 500,000, between 20,000 and 500,000, between 1,000 and 50,000, between 10 and 50,000, between 10 and 25,000, between 10 and 10,000, between 10 and 5,000, between 10 and 2,500, between 100 and 50,000, between 100 and 25,000, between 100 and 10,000, between 100 and 5,000, between 100 and 2,500, between 350 and 50,000, between 350 and 25,000, between 350 and 10,000, between 350 and 5,000, between 350 and 2,500, between 1000 and 50,000, between 1000 and 25,000, between 1000 and 10,000, between 1000 and 5,000, between 1000 and 2,500, between 1,500 and 50,000, between 1,500 and 25,000, between 1,500 and 10,000, between 1,500 and 5,000, between 1500 and 2,500, between 20,000 and 50,000, between 20,000 and 40,000, or about 35,000. In certain embodiments, the number of wells may be, for example, 35,440. In certain other exemplary embodiments, the number of wells may be, for example, about 196,000, such as 196,160, or, for example, about 9,000, such as 9020. Further, multiwell surfaces have been prepared with wells numbering in the range of 10 million. Thus, under some instances, the number of wells may be less than 5 million, 10 million, 20 million, etc.

The total volume of each well is another item which may vary and may be, for example, between $1.0\times10^{-9}$ µl and 50 µl, between $1.0\times10^{-9}$ µl and 10 µl, between $1.0\times10^{-9}$ µl and 1.0 µl, between $1.0\times10^{-9}$ µl and 0.1 µl, between $1.0\times10^{-9}$ µl and $1.0\times10^{-2}$ µl, between $1.0\times10^{-9}$ µl and $1.0\times10^{-3}$ µl, between $1.0\times10^{-9}$ µl and $1.0\times10^{-4}$ µl, between $1.0\times10^{-9}$ µl and 50 µl, between $1.0\times10^{-5}$ µl and $1.0\times10^{-6}$ µl, between $1.0\times10^{-9}$ µl and $1.0\times10^{-7}$ µl, between $2.5\times10^{-9}$ µl and $1.0\times10^{-2}$ µl, between $2.5\times10^{-9}$ µl and $1.0\times10^{-3}$ µl, between $2.5\times10^{-9}$ µl and $1.0\times10^{-4}$ µl, between $2.5\times10^{-9}$ µl and $1.0\times10^{-5}$ µl, between $2.5\times10^{-9}$ µl and $1.0\times10^{-6}$ µl, between $1.0\times10^{-8}$ µl and $1.0\times10^{-6}$ µl, between $1.0\times10^{-8}$ µl and $1.0\times10^{-5}$ µl, between $1.0\times10^{-7}$ µl and $1.0\times10^{-5}$ µl, between $1.0\times10^{-7}$ µl and $1.0\times10^{-4}$ µl, between $1.0\times10^{-7}$ µl and $1.0\times10^{-3}$ µl, between $1.0\times10^{-7}$ µl and $1.0\times10^{-2}$ µl, between 0.1 µl and 50 µl, between 0.01 µl and 50 µl, between 0.01 µl and 25 µl, between 0.01 µl and 15 µl, between 0.01 µl and 10 µl, between 0.001 µl and 50 µl, between 0.001 µl and 5 µl, between 0.001 µl and 1 µl, between 0.001 µl and 0.01 µl, between 0.001 µl and 1 µl, between 1 µl and 50 µl, between 1 µl and 25 µl, between 1 µl and 10 µl, between 10 µl and 50 µl, between 10 µl and 25 µl, or between 15 µl and 25 µl. In certain exemplary embodiments, the total volume of each well may be between $1\times10^{-6}$ µl and $1\times10^{-4}$ µl, between $1\times10^{-5}$ µl and $1\times10^{-4}$ µl, such as about $6.3\times10^{-5}$ µl.

In many instances, multiwell plates of the invention or multiwell plates suitable for use with the invention will be operably connected to either one electrode or a set (e.g., one or several pairs) of electrodes. As discussed elsewhere herein, these electrodes can be used to generate a microenvironment associated with catalysis of one or more chemical reactions (e.g., EGA for nucleotide deprotection or EGB for cleavage of a nucleic acid molecule from solid support). Further, these electrodes, when arranged at or near a bottom portion of an individual well, can be used to generate a mechanism for bead removal for the wells, e.g., electrolysis, as discussed further below.

In certain instances, the multiwell plate disclosed herein may be operably connected to at least one light source, such as a fiber optic device. As disclosed herein, the at least one light source can be used to selectively generate a photo-generated acid (PGA) in one or more wells of the multiwell plate. The PGA is used in turn to selectively deprotect the terminal nucleotide attached to a bead or other suitable solid support in the one or more wells of the multiwell plate.

In some embodiments, multiwell plates of the invention or multiwell plates suitable for use with the invention will be connected to microfluidic channels for the introduction and removal of reagents. This allows for efficient and automated controlling of reagents.

In some embodiments, the invention provides for methods of retrieving nucleic acids linked to solid supports by a base-cleavable linker comprising:

a) generating an electrochemically generated base;

b) cleaving the nucleic acid from the solid support with the electrochemically generated base in an aqueous or organic solution;

c) contacting the cleaved nucleic acid with a material for retaining the nucleic acid; and d) eluting the nucleic acid with an agent for removing a protecting group from the nucleic acid, optionally wherein the eluting may occur in a small volume to concentrate and/or enrich the nucleic acids. For example, elution may occur in a volume of about 1 to about 10 µl, such as e.g.

about 5 µl. Alternatively, step d) may comprise eluting the nucleic acid in a solvent without removing the protecting groups and may be followed by an additional step e) comprising removing protecting groups from the nucleic acid.

The invention further provides methods for retrieving nucleic acid molecules from multiwell plates for non-directed synthesis of nucleic acid molecules, the method comprising:

a) synthesizing a first copy of a plurality of nucleic acid molecules, wherein each nucleic acid molecule is prepared in a well of a first multiwell plate in an average amount of from about 50 femtomoles to about 15,000 femtomoles;

b) synthesizing a second copy of the same plurality of nucleic acid molecules, wherein each nucleic acid molecule is prepared in a well of a second multiwell plate in an average amount of from about 50 femtomoles to about 15,000 femtomoles;

c) deprotecting and cleaving the first copy of the plurality of nucleic acid molecules from the first multiwell plate;

d) deprotecting the second copy of the plurality of nucleic acid molecules from the second multiwell plate;

e) contacting the first copy of the plurality of nucleic acid molecules with the second copy of the plurality of nucleic acid molecules under hybridizing conditions to generate hybridized nucleic acid molecules;

f) denaturing the hybridized nucleic acid molecules by adding a denaturing solution to the second multiwell plate; and g) retrieving the denatured nucleic acid molecules from the second multiwell plate.

In some embodiments, the invention provides for methods of cleaving nucleic acids linked to solid supports by photocleavable linkers comprising generating lightwaves from a light source and cleaving the nucleic acid from the solid support with the lightwaves. In other exemplary embodiments, the invention provides for methods of cleaving nucleic acids linked to solid supports by reductive cleavable linkers comprising generating an electrochemically reduced compound and cleaving the nucleic acid from the solid support with the electrochemically reduced compound. After the nucleic acids have been cleaved from the solid support, they may be retrieved by the methods disclosed herein. As is also disclosed herein, in certain embodiments, the nucleic acids together with the solid supports may first be retrieved before cleavage.

The invention also provides methods for the generation of assembled nucleic acid molecules formed from smaller chemically synthesized nucleic acid molecules. In some embodiments, such methods may comprise one or more of the following steps:

(a) synthesizing a plurality of nucleic acid molecules, wherein each nucleic acid molecule is prepared in a microquantity in the well of a plate;

(b) combining the nucleic acid molecules generated in (a), or a portion thereof, to produce a pool;

(c) joining some or all of the nucleic acid molecules present in the pool formed in (b) to form a plurality of larger nucleic acid molecules;

(d) eliminating nucleic acid molecules which contain sequence errors from the plurality of larger nucleic acid molecules formed in (c) to produce an error corrected nucleic acid molecule pool; and (e) assembling the nucleic acid molecules in the error corrected nucleic acid molecule pool to form the assembled nucleic acid molecule.

In some embodiments, the joining of nucleic acid molecules present in the pool will be mediated by polymerase chain reaction (PCR).

In some embodiments step (b) may further comprise combining nucleic acid molecules generated in (a) with nucleic acid molecules obtained by other means to form a pool, wherein said other means include PCR, restriction enzyme digest, exonuclease treatment, or template-independent synthesis using a nucleotidyl transferase enzyme. In some instances, the assembled nucleic acid molecule generated in (c) and/or (e) may be assembled and introduced into a vector (e.g., a cloning vector, a destination vector, etc.).

The number of nucleic acid molecules assembled by methods of the invention can vary and, when appropriate, will correlate with the number of pooled nucleic acid molecules. In any event, nucleic acid molecules assembled in methods of the invention may be composed of at least five other (e.g., smaller) nucleic acid molecules (e.g., from about five to about five thousand, from about five to about twenty thousand, from about five to about one hundred thousand, from about fifty to about five thousand, from about fifty to about twenty thousand, from about fifty to about one hundred thousand, from about one hundred to about five thousand, from about one hundred to about one hundred thousand, from about five hundred to about five thousand, from about five hundred to about one hundred thousand, etc. nucleic acid molecules).

Nucleic acid molecules assembled by methods of the invention may vary greatly and include molecules of at least 20 kilobases (e.g., between from about 0.5 kilobase and to about 10 megabases, between from about 0.5 kilobase and to about 5 megabases, between from about 0.5 kilobase and to about 1 megabase, between from about 0.5 kilobase and to about 500 kilobases, between from about 0.5 kilobase and to about 100 kilobases, between from about 0.5 kilobase and to about 10 megabases, between from about 0.5 kilobase and to about 1 kilobase, between from about 1 kilobase and to about 10 megabases, between from about 10 kilobases and to about 5 megabases, between from about 1 kilobase and to about 5 megabases, between from about 1 kilobase and to about 2 megabases, between from about 1 kilobase and to about 1 megabase, between from about 1 kilobase and to about 500 kilobases, between from about 10 kilobases and to about 1 megabases, between from about 10 kilobase and to about 500 kilobases, between from about 10 kilobase and to about 100 kilobases, etc.).

Nucleic acid molecule assembled by methods of the invention may be, for example, single stranded, partly single stranded or double stranded, closed, circular (e.g., a plasmid); nicked, circular; or linear (e.g., a plasmid, a chromosome, etc.). Further, methods of the invention may be performed such that two or more (e.g., two, three, four, five, six, ten, twenty, etc.) assembled nucleic acid molecules are simultaneously formed in the same reaction mixture.

The invention further provides methods for producing product nucleic acid molecules. In some instances such the methods comprise:

(a) designing a product nucleic acid molecule of between 10 kilobases and 500 kilobases in size (e.g., between 500 bases and 500 kilobases, between 500 bases and 100 kilobases, between 500 bases and 1 kilobase, between 500 bases and 800 bases between 2 kilobases and 100 kilobases, between 2 kilobases and 50 kilobases, between 2 kilobases and 5 kilobases, between 10 kilobases and 500 kilobases, between 10 kilobases and 300 kilobases, between 10 kilobases and 200 kilobases, between 10 kilobases and 100 kilobases, between 10 kilobases and 50 kilobases, etc.), wherein the product nucleic acid molecule is defined by nucleotide sequence;

(b) synthesizing a plurality of individual nucleic acid molecules which differ in nucleotide sequence, wherein each individual nucleic acid molecule is synthesized to prepare a quantity of between 1,000 and $1.0 \times 10^9$ copies and wherein the individual nucleic acid molecules are capable of hybridizing with one or more of the other individual nucleic acid molecules;

(c) combining the individual nucleic acid molecules synthesized in (b) under conditions which allow for hybridization of the individual nucleic acid molecules under conditions which allow for the formation of at least one larger nucleic acid molecule; and (d) combining the at least one larger nucleic acid molecule formed in (c) with one or more additional nucleic acid molecules to form the product nucleic acid molecule, wherein the product nucleic acid molecule contains less than one sequence error per kilobase.

In many instances, an error correction process is employed during generation of product nucleic acid molecules. One place in the above work flow where an error correction process may be performed is after step (b). Error correction processes are described elsewhere herein and will often include the use of one or more mis-match repair endonucleases.

The number of individual nucleic acid molecules synthesized as part of the preparation of product nucleic acid molecules may vary greatly but include between 1,000 and $1.0 \times 10^{13}$ copies, between 1,000 and $1.0 \times 10^{12}$ copies, between 1,000 and $1.0 \times 10^{11}$ copies, between 1,000 and $1.0 \times 10^{10}$ copies, between 1,000 and $1.0 \times 10^9$ copies, between $2.0 \times 10^9$ and $1.0 \times 10^{13}$ copies, between $5.0 \times 10^9$ and $1.0 \times 10^{13}$ copies, between $7.0 \times 10^9$ and $1.0 \times 10^{13}$ copies, between $2.0 \times 10^9$ and $8.0 \times 10^{12}$ copies, between $2.0 \times 10^9$ and $5.0 \times 10^{12}$ copies, between $5.0 \times 10^6$ and $1.0 \times 10^{11}$ copies, between $1.0 \times 10^7$ and $1.0 \times 10^{11}$ copies, between $1.0 \times 10^9$ and $1.0 \times 10^{11}$ copies, etc.

In many instances, polymerase chain reactions may be used to amplify the at least one larger nucleic acid molecule formed in step (c) in the above product nucleic acid molecule preparation processes.

Plate formats for the synthesis of nucleic acid molecules are described elsewhere herein and they may be used in the above product nucleic acid molecule preparation processes. Further, when individual nucleic acid molecules are synthesized on beads, wherein each bead may be contained in a well. Further, beads used in this aspect of the invention, as well as other aspects of the invention may be, for example of sizes such as between 1 μm and 100 μm in diameter, between 5 μm and 50 μm in diameter, between 3 μm and 100 μm in diameter, between 5 μm and 100 μm in diameter, between 20 μm and 100 μm in diameter, between 5 μm and 60 μm in diameter, between 10 μm and 100 μm in diameter, etc. In some embodiments beads may be of a size of about 30 μm in diameter (e.g., between 28 and 32 μm). In some embodiments, beads may range from about 30 μm to about 40 μm in diameter such as about 35 μm in diameter.

The invention also includes methods for producing nucleic acid molecule in small amounts and with high sequence fidelity. In some aspects, the invention includes a method for generating a nucleic acid molecule, the method comprising synthesizing the nucleic acid molecule in a total amount of between $1 \times 10^{11}$ and $1 \times 10^{13}$ molecules, wherein the number of sequence errors is between 1 in 100 to 1 in 2,500 (e.g., from about 1 in 200 to about 1 in 2,500, from about 1 in 500 to about 1 in 2,500, from about 1 in 1,000 to about 1 in 2,500, from about 1 in 1,500 to about 1 in 2,500, from about 1 in 1,000 to about 1 in 2,000, etc.). As discussed elsewhere herein, error correction can be used to lower the number of sequence errors.

The invention thus includes methods for the generation of collections of nucleic acid molecules, including methods comprising:

(a) synthesizing a plurality of nucleic acid molecules, wherein each nucleic acid molecule is prepared in a microquantity;

(b) combining the nucleic acid molecules generated in (a) to produce a pool;

(c) joining some or all of the nucleic acid molecules present in the pool formed in (b) to form a plurality of larger nucleic acid molecules; and (d) assembling the plurality of larger nucleic acid molecules to form the collection of nucleic acid molecules, wherein the collection of nucleic acid molecules from bioinformatic information selected from the group consisting of:

(1) a copy DNA (cDNA) library containing only DNA corresponding to messenger RNA (mRNA) molecules;

(2) a partial cDNA library containing DNA molecules corresponding to less than the full complement of mRNA molecules found in the cell type that the bioinformatic information was derived from; and (3) a collection of nucleic acid molecules in which some or all of the nucleic acid molecules are codon altered variants of nucleic acid molecules found in the cell type that the bioinformatic information was derived from.

The invention also provides method for the generation of self-replicating nucleic acid molecules formed from smaller chemically synthesized nucleic acid molecules. In some embodiments, such method may comprise one or more of the following steps:

(a) synthesizing a plurality of nucleic acid molecules, wherein each nucleic acid molecule is prepared in a microquantity;

(b) combining the nucleic acid molecules generated in (a) to produce a pool;

(c) joining some or all of the nucleic acid molecules present in the pool formed in (b) to form a plurality of larger nucleic acid molecules; and (d) assembling the plurality of larger nucleic acid molecules to form the self-replicating nucleic acid molecule.

The invention also includes methods for synthesizing and assembling nucleic acid molecules which encode more than one expression product, the methods comprising:

(a) synthesizing a plurality of nucleic acid molecules, wherein each nucleic acid molecule is prepared in a microquantity;

(b) combining the nucleic acid molecules generated in (a) to produce a pool (c) joining some or all of the nucleic acid molecules present in the pool formed in (a) to form a plurality of larger nucleic acid molecules; and (d) assembling the plurality of larger nucleic acid molecules to form the nucleic acid molecules which encode more than one expression product.

In various aspects of the invention, the more than one expression products may be proteins involved in the same biological pathway. In more specific aspects, the more than one expression products may be proteins involved in the same biological pathway are enzymes that catalyze a series of chemical reactions in the biological pathway. Further, such chemical reactions in the same biological pathway may be sequential reactions in the sense that one chemical reaction follows another either directly (directly sequential) or after one or more intervening reaction has occurred.

As one skilled in the art would understand, many aspects of the invention are well suited for automation. Automated systems are often driven by software which may perform repetitive tasks, especially when integrated with hardware designed for micromanipulation of components and reagent flows. Thus, according to various embodiments described herein, methods of assembling and synthesizing nucleic acids may be implemented on a computing system. Further, according to various embodiments described herein, processor-executable instructions for assembling and synthesizing nucleic acids are disclosed. Thus, in some aspects the invention includes non-transitory computer-readable storage media encoded with instructions, executable by a processor, for generating assembled nucleic acid molecules, the instructions comprising instructions for:

(a) synthesizing a plurality of nucleic acid molecules, wherein each nucleic acid molecule is prepared in a micro-quantity in the well of a plate or a microchip;

(b) combining the nucleic acid molecules generated in (a) to produce a pool;

(c) joining some or all of the nucleic acid molecules present in the pool formed in (b) to form a plurality of larger nucleic acid molecules;

(d) eliminating nucleic acid molecules which contain sequence errors from the plurality of larger nucleic acid molecules formed in (c) to produce an error corrected nucleic acid molecule pool; and (e) assembling the nucleic acid molecules in the error corrected nucleic acid molecule pool to form the assembled nucleic acid molecule.

The invention also includes systems for generating assembled nucleic acid molecules, the system comprising:
a processor; and
a memory encoded with processor-executable instructions for:

(a) synthesizing a plurality of nucleic acid molecules, wherein each nucleic acid molecule is prepared in a micro-quantity in the well of a plate or a microchip;

(b) combining the nucleic acid molecules generated in (a) to produce a pool;

(c) joining some or all of the nucleic acid molecules present in the pool formed in (b) to form a plurality of larger nucleic acid molecules;

(d) eliminating nucleic acid molecules which contain sequence errors from the plurality of larger nucleic acid molecules formed in (c) to produce an error corrected nucleic acid molecule pool; and (e) assembling the nucleic acid molecules in the error corrected nucleic acid molecule pool to form the assembled nucleic acid molecule.

In other aspects, methods for removing beads from fluid-filled wells of a microchip for synthesizing nucleic acid molecules, wherein one or more nucleic acid molecules are attached to the bead, are disclosed. These methods can comprise providing a voltage between a first electrode that is arranged at a bottom of the fluid-filled well and a second electrode, wherein the voltage is sufficient to cause fluid in the fluid-filled well to undergo electrolysis producing one or more bubbles in the fluid to rise to a top of the fluid-filled well along with the bead or lift the bead to the top of the fluid-filled well. In other embodiments, beads can be removed from the synthetic microchip using other techniques, including, but not limited to micro-manipulation such as micropipetting, optical forces, such as optical tweezers; generation of gas bubbles; acoustic force, gravity-fed techniques, magnetic techniques (e.g., magnetic beads), dielectrophoresis, valving, or using a weir structure on the microchip.

The first electrode can be composed of platinum and in certain embodiments, the voltage is about 0.1V to about 10,000V, about 1V to about 1000V, about 2V to about 100V, or about 5V to about 15V. The second electrode can be arranged above the first electrode. A third (reference) electrode can be used in certain embodiments, as discussed further below.

The oligonucleotide synthesis microchip can comprise a lid operable to be formed on a top surface of the microchip and operable to provide a fluid flow path into and out of the well. In some examples, the second electrode can be formed in the lid.

In certain embodiments, each well of the microchip used for nucleic acid synthesis can have a depth of about 45 to 60 μm, including about 50 μm, about 55 μm, or about 60 μm. The skilled person will understand that the well sizes may depend on the dimension and/or density (i.e., the number of wells) of a microchip as described elsewhere herein. In some examples, each well of the microchip is individually addressable by a controller. In some examples, the microchip is a complementation metal-oxide-semiconductor ("CMOS") chip.

The bead can be composed of: a synthetic polymer, a modified naturally occurring polymer, glass, controlled pore glass, magnetic controlled pore glass, magnetic beads, ceramics, or one or more metals. In certain embodiments, the bead is composed of a synthetic polymer such as polystyrene. In certain embodiments, at least 50% of the oligonucleotide synthesized on the bead is between 2-200 or 50-100 base pairs in length. In certain embodiments, the bead is monodisperse as described herein, having, for example, a bead diameter that is smaller than the diameter of each well by about 5% to about 20%, about 8% to 15%, about 10 to about 30% or about 12.5%. In certain embodiments, the diameter of the monodisperse bead varies less than 10%. In certain embodiments, the diameter of the monodisperse bead is between 30-40 μm. In certain embodiments, the diameter of the monodisperse bead is about 35 μm or about 32 μm, the diameter of each well is about 40 μl or about 42 μm or between about 40 to about 45 μm, and the depth of each well is about 50 μm or about 55 μm or between about 45 μm to about 55 μm. In certain instances, the diameter of a bead used in aspects of the invention will depend on the size of the well, whereas the size of a well may be defined by the dimension and/or density of a microchip. For example, a microchip of a given size may have a higher number of smaller wells or a lower number of larger wells. Thus, a microchip of higher well density with smaller wells will require beads of smaller sizes than a microchip of lower density with larger wells, as illustrated, e.g., in the table in FIG. 35.

In certain embodiments, the monodisperse bead has a pore volume of 0.1 to 2.5 ml/g of polymer. In certain embodiments, the monodisperse bead has a surface area of 100-500 $m^2/g$ or 350-400 $m^2/g$ (e.g., 380 $m^2/g$). In certain embodiments, the monodisperse bead is coated with a reactive group, such as an amino group. In certain embodiments, the amount of amine group in the coating ranges from 0.1% to 5% (weight % nitrogen per gram of beads). In certain embodiments, the monodisperse bead has a linker loading capacity of the oligonucleotide synthesis substrate within a range of 10 to 500 μmol/g, 30 to 100 μmol/g, or 40 to 80

μmol/g. In certain embodiments, the monodisperse bead carries a universal linker such as, e.g., a UnyLinker™.

After displacing beads from the microchip, the methods can further comprise collecting and concentrating the beads that have been displaced from the microchip using a microfluidic or bead-collection device. The bead-collection device can transfer the collected beads to a suitable container, such as the well of a first multiwell collection plate. In some examples, the bead collection device can be in fluid communication with the fluid flow path and comprise a first channel to allow for the bead to move a first direction and a second channel to allow for fluid to move in a second direction different than the first direction, for example in an opposite direction or an orthogonal direction. The bead collection device can comprise an acoustic module that is controllable by a controller to facilitate movement of the bead in the first channel, the fluid in the second channel, or both.

In certain embodiments, the first multiwell collection plate can comprise a plurality of well structures and a fluid-permeable structure formed on a top surface of or within the plurality of well structures. The fluid-permeable structure can be a material that is semipermeable to fluids, but not to the beads and can include, but is not limited to, a mesh, a filter, a porous material, or a membrane, e.g., ion-track etched membrane. For example, the material that is semipermeable to fluids may be a thin foil, (such as, e.g., a polypropylene foil) with holes or pores that are small enough to retain beads of sizes described elsewhere herein. Such holes or pores may be generated, e.g., by laser micro milling (e.g., Oxford Lasers can drill 10 μm holes into 100 μm polypropylene foils) or by other methods known in the art. In certain embodiments, the first multiwell collection plate can comprise a plurality of well structures and further comprise a second multiwell collection plate, wherein the second multiwell collection plate comprises a plurality of well structures and a fluid-permeable structure formed on a bottom surface of the plurality of well structures, wherein the second multiwell collection plate is placed on top of the first multiwell collection plate such that the plurality of well structures in the second multiwell collection plate are aligned with the plurality of well structures in the first multiwell collection plate.

In certain embodiments, the bead collection device can comprise a needle structure that is operable to 1) place the bead from the nucleic acid molecule synthesis microchip into a well of the first multiwell collection plate by puncturing the fluid-permeable structure, and/or 2) remove fluid from the well in which the bead was placed. The needle structure can comprise a first lumen that is operable to place the bead from the nucleic acid molecule synthesis microchip into a well of the multiwell collection plate by puncturing the fluid-permeable structure and a second lumen that is operable to remove fluid from the well in which the bead was placed.

In other embodiments, rather than using a needle to puncture the fluid-permeable structure, pressure is applied to the top of a selected well in the multiwell collection plate, the pressure being sufficient to rupture the fluid-permeable structure and deposit one or more beads into the selected well of the multiwell collection plate.

In other embodiments the bead collection device comprises a needle structure that is operable to place the bead from the nucleic acid molecule synthesis microchip into a well of the first multiwell collection plate, and/or 2) deliver fluid to the well of the first multiwell collection plate in which the bead was placed. The needle structure can comprise a first lumen that is operable to place the bead from the nucleic acid molecule synthesis microchip into a well of the multiwell collection plate and a second lumen that is operable to deliver fluid to the well in which the bead was placed.

In other embodiments, the oligonucleotides synthesized on the microchip can be pooled, concentrated, cleaved and deprotected on a fluid-permeable structure arranged on a top surface of or within a multiwell collection plate. The cleaved oligonucleotides can then be eluted into the well of a multiwell collection plate without having to puncture or otherwise rupture the fluid-permeable structure.

The methods of collecting the beads from the microchip can comprise moving the bead collection device in one or more degrees of freedom to deliver the beads into the plurality of wells of the first multiwell collection plate. The microchip can be programmed to extract the bead from a specific well of interest from the microchip and deliver the bead via the bead collection device to an addressable well in the plurality of wells in the first multiwell collection plate.

When beads are flushed out of the synthesis chip, they disperse into a larger volume, as additional fluid is used to transport the beads out of the microchip. The bead-collection device is able to pool beads containing the same oligonucleotides and/or beads containing other oligonucleotides required for the assembly of larger nucleic acid fragments and concentrate them from a first larger volume into a second smaller volume in and into a suitable collection container, such as a multiwell collection plate. Thus methods of pooling and concentrating beads, as disclosed herein, comprise transferring in a first volume of fluid one or more beads from a plurality of well structures formed on the microchip to a second volume of fluid in a well of a first multiwell collection plate, wherein a nucleic acid that has been synthesized on the microchip is attached to the one or more beads, wherein the one or more beads are transferred using a bead collection device (e.g., a microfluidic device or a device comprising a needle structure), wherein the bead collection device is in fluid connection with the microchip and the first multiwell collection plate, wherein the first multiwell collection plate comprises a plurality of wells, and wherein the second volume of fluid in the well of the first multiwell collection plate is less than the first volume of fluid, thereby concentrating the nucleic acid molecule synthesized on the microchip. In certain instances the concentrating comprises reducing the first volume of fluid by a factor of about 5 to about 50, about 10 to about 100, about 10 to about 1,000, about 100 to about 10,000. In certain embodiments, the total volume of each well of the first multiwell collection plate can be between 1 and about 200 μl, between 50 and about 200 μl, between 1 and 50 μl, between 1 and 25 μl, between 3 and 12 μl or about 10 μl.

According to the present disclosure, systems for synthesis of nucleic acid molecules are disclosed. These systems can comprise one or more microchips comprising a plurality of well structures formed thereon, each well of the plurality of well structures sized to accommodate a bead for synthesis of the nucleic acid molecule, wherein each well has formed therein a first electrode at a bottom of the well that is individually controllable by a controller; and a lid member arranged on top of the microchip and comprising a fluidic channel formed therein to provide fluid path for the bead, wherein the lid member comprises a second electrode, wherein the controller is operable to provide a voltage between the first electrode and the second electrode that is sufficient to cause fluid in the well to undergo electrolysis producing one or more bubbles in the fluid to rise to a top of the well along with the bead.

These systems can further comprise a bead-collection device operable to collect and concentrate the beads that are removed from the synthesis chip. These systems can further comprise a first multiwell collection plate operable to receive one or more beads that were collected using the bead-collection device.

The bead collection device can be in fluid communication with the fluid path for the bead and comprises a first channel to allow for the bead to move a first direction toward a first multiwell collection device and a second channel to allow for fluid to move in a second direction different than the first direction, for example in opposite directions, orthogonal, or any suitable direction. The bead collection devices can comprise an acoustic module that is controllable by a controller to facilitate movement of the bead in the first channel, the fluid in the second channel, or both.

In these systems, the first electrode can be composed of platinum and in certain embodiments, the voltage is about 0.1V to about 10,000V, about 1V to about 1000V, about 2V to about 100V, or about 5 to about 15 volts. The second electrode can be arranged above the first electrode. A third (reference) electrode can be used in certain embodiments, as discussed further below.

The bead collection devices can be caused to move, by a controller, in one or more degrees of freedom to deliver the beads that are collected in the bead collection device into the plurality of wells of the first multiwell collection plate. The microchip or other computer system can be programmed to extract the bead from a specific well of interest on the microchip and deliver the bead via the bead collection device to an addressable well in the plurality of wells in the first multiwell collection plate.

According to the present disclosure, non-transitory computer-readable storage media encoded with instructions, executable by a processor, for removing one or more beads from a fluid-filled well of a microchip for synthesizing nucleic acid molecules, where nucleic acid molecules are attached to the bead, are disclosed. Also disclosed are systems comprising a processor and a memory encoded with processor-executable instructions for removing one or more beads from a fluid-filled well of a microchip for synthesizing nucleic acid molecules, where the nucleic acid molecules are attached to the bead. Instructions for the computer-readable storage media or the systems can comprise instructions for providing a voltage between a first electrode that is arranged at a bottom of the fluid-filled well and a second electrode, wherein the voltage is sufficient to cause fluid in the fluid-filled well to undergo electrolysis producing one or more bubbles in the fluid to rise to a top of the fluid-filled well along with the bead.

According to the present disclosure, methods for selectively removing one or more beads from a microchip for synthesizing nucleic acid molecules having a plurality of fluid-filled wells, wherein each of the plurality of wells comprises an electrode formed at the bottom of the well and each bead of the one or more beads occupies a single well on the microchip are disclosed. These methods can comprise: identifying one or more wells that contain one or more beads to be removed; providing a voltage between a first electrode in the one or more wells that have been identified and a second electrode, wherein the voltage is sufficient to cause fluid in the one or more wells to undergo electrolysis producing one or more bubbles to rise to a top of the one or more wells along with the one or more beads contained within the one or more wells; collecting the one or more beads that have risen to the top of the fluid-filled well with a bead-collection device; and transferring the one or more beads that were collected to one or more wells of a first multiwell collection plate or other suitable collection container where the beads can be concentrated and further processed (e.g., cleavage and deprotection) before assembly into longer nucleic acid fragments.

BRIEF DESCRIPTION OF THE FIGURES

FIGS. 12A and 12B shows a series of variant nucleic acid molecules that may be prepared by methods of the invention and their encoded amino acid sequences. FIG. 12A shows variant nucleic acid molecules that encode different amino acid sequences. FIG. 12B shows variant nucleic acid molecules that use different codons but encode the same amino acid sequence.

FIG. 13 shows two different fluid removal options for microwell plate embodiments of synthesis platforms.

FIG. 14A is a top view and FIG. 14B is a side view. Shown in the figure are fluidic channels 1401, two electrodes associated with each channel/row of wells 1402 and a series of wells containing nucleic acid synthesis substrates (e.g., individual beads) located in wells 1400. In some embodiments, the wells will be spaced 300 μm apart and will be cylindrical in shape with a diameter of 40 μm and a depth of 35 μm.

FIG. 21 also shows a bead collection method involving the use of a needle structure to puncture a fluid-permeable structure (e.g., micromesh) for placing one or more beads from the synthesis chip into a well of a multiwell collection plate or for removing fluid from one or more wells of a multiwell collection plate.

FIGS. 24A, 24B, 24C, and 24D show example side-views and top-view of the fluidic lid for the microchip according to the invention.

FIG. 35 shows variations of numbers of wells and various physical parameters.

FIG. 41A is an rpHPLC chromatogram of ten different oligonucleotides sequenced simultaneously on a microfluidic chip. FIG. 41B shows the order and arrangement of the oligonucleotides for assembly of the lacZ gene.

FIGS. 45A, 45B and 45C show a coaxial needle assembly and a filter plate comprising a fluid-permeable micromesh for use in a bead collection device.

DETAILED DESCRIPTION OF THE INVENTION

Definitions

Figure 1:
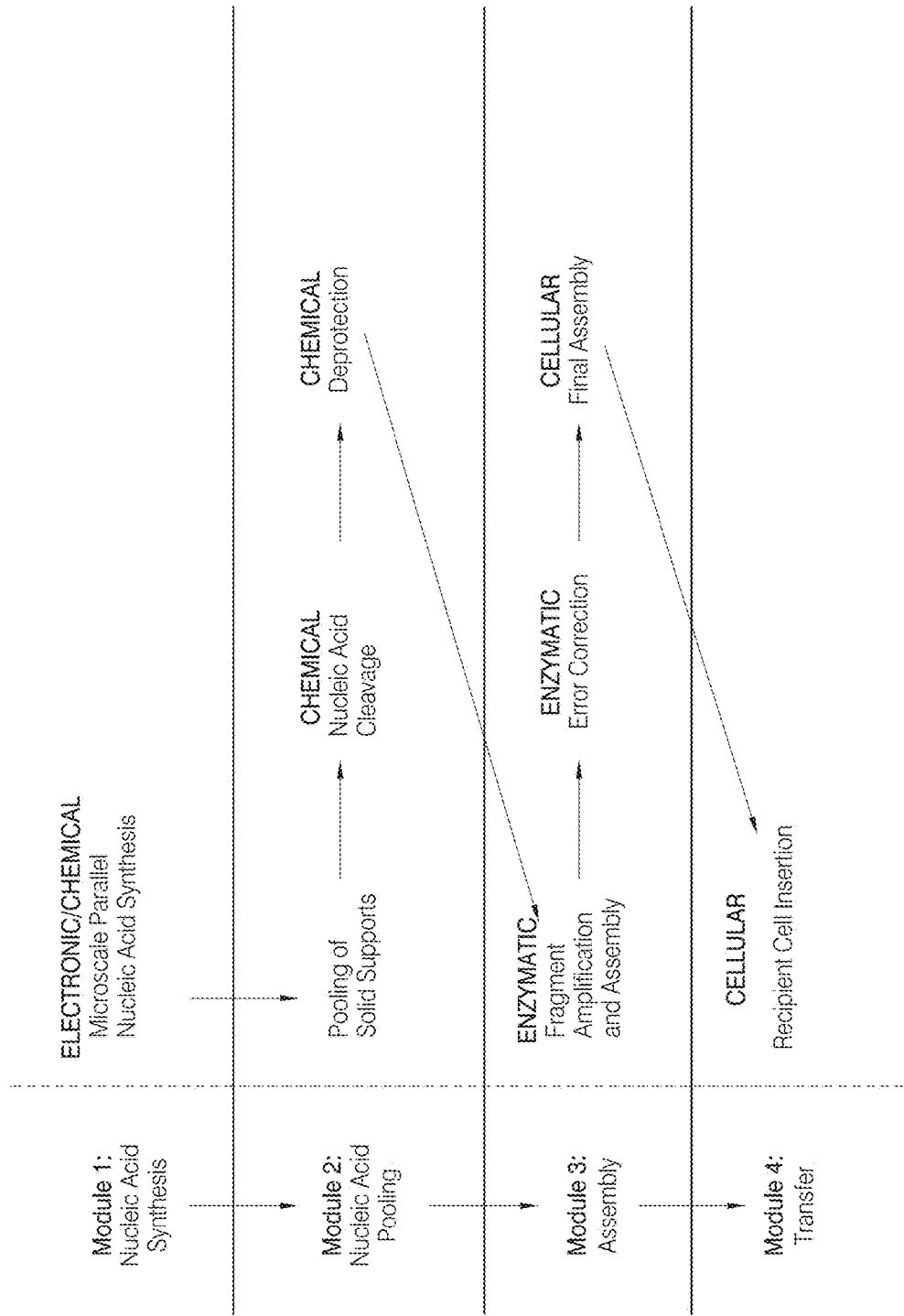
FIG. 1 is a general description of aspects of work flows of the invention. The work flow is broken into four sections, referred to as "modules" for ease of description. The work flow on the right side of the figure shows some specific step included in some aspects of methods of the invention.

Microchip, chip, synthesis chip, synthesis microchip, array, microarray: As used herein, the terms microchip, chip, synthesis chip, synthesis microchip, array, microarray or similar variations thereof will refer to an electronic computer chip on which oligonucleotide synthesis can occur.

Multiwell plate, microplate, microwell plate, plate: As used herein, the term multiwell plate, microplate, microwell plate, plate or similar variations thereof will refer to a two-dimensional array of multiple wells located on a substantially flat surface. Multiwell plates can comprise any number of wells of any width or depth. In certain instances, a multiwell plate may be configured as a microchip. For example, when a material with well-like structures is overlaid onto a microchip.

Solid Support: As used herein, the term solid support refers to a porous or non-porous material on which polymers such as nucleic acid molecules can be synthesized and/or immobilized. As used herein "porous" means that the material contains pores which may be of non-uniform or uniform diameters (for example in the nm range). Porous materials include paper, synthetic filters etc. In such porous materials, the reaction may take place within the pores. The solid support can have any one of a number of shapes, such as pin, strip, plate, disk, rod, fiber, bends, cylindrical structure, planar surface, concave or convex surface or a capillary or column. The solid support can be a particle, including bead, microparticles, nanoparticles and the like. The solid support can be a non-bead type particle (e.g., a filament) of similar size. The support can have variable widths and sizes. For example, sizes of a bead (e.g., a magnetic bead) which may be used in the practice of the invention are described elsewhere herein. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers such as filter paper, chromatographic paper or the like. The support can be immobilized at an addressable position of a carrier. The support can be loose (such as, e.g., a resin material or a bead in a well) or can be reversibly immobilized or linked to the carrier (e.g. by cleavable chemical bonds or magnetic forces etc.).

In some embodiments, solid support may be fragmentable. Solid supports may be synthetic or modified naturally occurring polymers, such as nitrocellulose, carbon, cellulose acetate, polyvinyl chloride, polyacrylamide, cross linked dextran, agarose, polyacrylate, polyethylene, polypropylene, poly (4-methylbutene), polystyrene, polymethacrylate, poly (ethylene terephthalate), nylon, poly(vinyl butyrate), polyvinylidene difluoride (PVDF) membrane, glass, controlled pore glass, magnetic controlled pore glass, magnetic or non-magnetic beads, ceramics, metals, and the like; either used by themselves or in conjunction with other materials.

In some embodiments, the support can be in a chip, array, microarray or microwell plate format. In many instances, a support generated by methods of the invention will be one where individual nucleic acid molecules are synthesized on separate or discrete areas to generate features (i.e., locations containing individual nucleic acid molecules) on the support.

In some embodiments, the size of the defined feature is chosen to allow formation of a microvolume droplet or reaction volume on the feature, each droplet or reaction volume being kept separate from each other. As described herein, features are typically, but need not be, separated by interfeature spaces to ensure that droplets or reaction volumes or between two adjacent features do not merge. Interfeatures will typically not carry any nucleic acid molecules on their surface and will correspond to inert space. In some embodiments, features and interfeatures may differ in their hydrophilicity or hydrophobicity properties. In some embodiments, features and interfeatures may comprise a modifier. In one embodiment of the invention the feature is a well or microwell or a notch.

Nucleic acid molecules may be covalently or non-covalently attached to the surface or deposited or synthesized or assembled on the surface.

In one embodiment of the invention, Module 1 can involve the use of more than one solid support. In some embodiments, two or more solid supports may be arranged on a plate. Any arrangement of the solid supports could be employed such as rows or columns or a combination thereof. For example, rows can be aligned and/or the columns can be aligned. In other embodiments, rows and/or columns are equally spaced and staggered. Spacing between rows and/or between columns can be variable. The number of the solid supports comprised in, for example, a plate may be variable. In some embodiments, a plate may contain up to 1,536 (or more) solid supports.

Nucleic Acid Molecule: As used herein the term "nucleic acid molecule" refers to a covalently linked sequence of nucleotides or bases (e.g., ribonucleotides for RNA and deoxyribonucleotides for DNA but also include DNA/RNA hybrids where the DNA is in separate strands or in the same strands) in which the 3' position of the pentose of one nucleotide is joined by a phosphodiester linkage to the 5' position of the pentose of the next nucleotide. Nucleic acid molecule may be single- or double-stranded or partially double-stranded. Nucleic acid molecule may appear in linear or circularized form in a supercoiled or relaxed formation with blunt or sticky ends and may contain "nicks". Nucleic acid molecule may be composed of completely complementary single strands or of partially complementary single strands forming at least one mismatch of bases. Nucleic acid molecule may further comprise two self-complementary sequences that may form a double-stranded stem region, optionally separated at one end by a loop sequence. The two regions of nucleic acid molecule which comprise the double-stranded stem region are substantially complementary to each other, resulting in self-hybridization. However, the stem can include one or more mismatches, insertions or deletions.

Nucleic acid molecules may comprise chemically, enzymatically, or metabolically modified forms of nucleic acid molecules or combinations thereof. Chemically synthesized nucleic acid molecules may refer to nucleic acids typically less than or equal to 150 nucleotides long (e.g., between 5 and 150, between 10 and 100, between 15 and 50 nucleotides in length) whereas enzymatically synthesized nucleic acid molecules may encompass smaller as well as larger nucleic acid molecules as described elsewhere in the application. Enzymatic synthesis of nucleic acid molecules may include stepwise processes using enzymes such as polymerases, ligases, exonucleases, endonucleases or the like or a combination thereof. Thus, the invention provides, in part, compositions and combined methods relating to the enzymatic assembly of chemically synthesized nucleic acid molecules.

Nucleic acid molecule also refers to short nucleic acid molecules, often referred to as, for example, primers or probes. Primers are often referred to as single-stranded starter nucleic acid molecules for enzymatic assembly reactions whereas probes may be typically used to detect at least partially complementary nucleic acid molecules. A nucleic acid molecule has a "5'-terminus" and a "3'-terminus" because nucleic acid molecule phosphodiester linkages occur between the 5' carbon and 3' carbon of the pentose ring of the substituent mononucleotides. The end of a nucleic acid molecule at which a new linkage would be to a 5' carbon is its 5' terminal nucleotide. The end of a nucleic acid molecule at which a new linkage would be to a 3' carbon is its 3' terminal nucleotide. A terminal nucleotide or base, as used herein, is the nucleotide at the end position of the 3'- or 5'-terminus. A nucleic acid molecule sequence, even if internal to a larger nucleic acid molecule (e.g., a sequence region within a nucleic acid molecule), also can be said to have 5'- and 3'-ends.

Transition: As used herein, the term "transition", when used in reference to the nucleotide sequence of a nucleic acid molecule refers to a point mutation that changes a purine nucleotide to another purine (A↔G) or a pyrimidine nucleotide to another pyrimidine (C↔T).

Transversion: As used herein, the term "transversion", when used in reference to the nucleotide sequence of a nucleic acid molecule refers to a point mutation involving the substitution of a (two ring) purine for a (one ring) pyrimidine or a (one ring) pyrimidine for a (two ring) purine.

Indel: As used herein, the term "indel", refers to the insertion or deletion of one or more bases in a nucleic acid molecule.

Overview:

The invention relates, in part, to compositions and methods for the preparation of nucleic acid molecules. While the invention has numerous aspects and variations associated with it, some of these aspects and variations are set out in FIG. 1 in outline form.

One advantage of the invention is that for many applications, small amounts of synthesized nucleic acid are suitable for achieving an intended purpose (e.g., preparation of microarrays, construction of a plasmid which contains a selectable marker, etc.). In some instances, small amounts of nucleic acid are suitable for working with due to factors such as enzymatic (e.g., PCR) and intracellular amplification.

The left side of FIG. 1 shows four general "modules" representing different portions of some embodiments of the invention. Thus, in some aspects, the invention involves one or more of the following: (1) nucleic acid molecule synthesis, (2) pooling of nucleic acid molecules, (3) assembly of a plurality of nucleic acid molecules, and/or (4) transfer of assembled nucleic acids (e.g., transfer to a cell).

In relation to more specific embodiments of the invention, the right side of FIG. 1 shows some additional details related to the modules shown on the left side of the figure. Above a number of the text blocks are bolded terms such as "ENZYMATIC" and "CELLULAR". These terms indicate exemplary general means by which the process referred to can be performed. As one skilled in the art would understand, some processes can be performed, for example, either chemically, enzymatically, or in a cell.

Module 1, as shown in FIG. 1 refers to a single process termed "Microscale Parallel Nucleic Acid Molecule Synthesis". As set out elsewhere herein, this process will typically involve several steps which will vary with how the process is performed. In many embodiments, the general function of Module 1 will be the generation of a plurality of nucleic acid molecules. These nucleic acid molecules may be designed as a group to be joined to form one or more larger nucleic acid molecule or when contacted with additional nucleic acid molecules (e.g., "stitching" nucleic acid molecules).

Module 2, as shown in FIG. 1 refers to processes termed "Pooling of Solid Supports", "Nucleic Acid Molecule Cleavage", and "Deprotection". The general function of Module 2 will be the preparation of nucleic acid molecules for participation in one or more process referred to in Module 3. This will often mean combining nucleic acid molecules which differ in sequence and the removal of any chemical groups which are either not necessary or not desirable for the performance of one or more processes referred to in Module 3.

Using Module 2 as an example, as one skilled in the art would recognize, FIG. 1 shows general embodiments of the invention. More specifically, Module 2 refers to the pooling of solid supports. These supports will typically contain nucleic acid molecules. In some embodiments, nucleic acid molecules may be obtained in a form free of solid supports, then pooled.

Module 3, as shown in FIG. 1 refers to the processes termed "Fragment Amplification and Assembly", "Error Correction", and "Final Assembly". The general function of Module 3 processes is the generation of assembled nucleic acid molecules with high sequence fidelity, with comparison to the sequence of nucleic acid molecules which were sought to be produced.

Module 4, as shown in FIG. 1 refers to the processes of termed "Recipient Cell Insertion". As one skilled in the art would understand, introduction of nucleic acid molecules generated by methods of the invention into cells is only one application. In most instances, a nucleic acid molecule assembled according to methods of the invention will be designed for a specific application. Applications vary widely and include biofuel production, bioremediation, and chemical precursor production.

In some embodiments, monodispersed particles obtained by methods as described in U.S. Pat. No. 6,335,438, the disclosure of which is incorporated herein by reference, may be used in the practice of the invention. For example, in certain embodiments disclosed herein and as disclosed in U.S. Pat. No. 6,335,438, use may be made of support matrices comprising a polyvinyl backbone and having amino groups that are optionally acylated. The support matrices may be obtained by polymerizing at least one monovinyl monomer with at least one di-, tri-, or polyvinyl monomer. At least one of the monomers is a vinyl aromatic monomer, and the polymerization reaction may occur in the presence of at least one amino vinyl aromatic monomer, such as aminostyrene. For example, in certain embodiments disclosed herein, the solid support may be aminostyrene beads made from the polymerization of at least one monovinyl monomer and at least one di-, tri-, or polyvinyl monomer in the presence of amino vinyl aromatic monomers. In alternative embodiments, an amino vinyl aliphatic monomer may be used instead of a vinyl aromatic monomer to modify or adapt the reactivity and/or amine content of a bead as disclosed elsewhere herein. For example instead of aminostyrene, vinylbenzyl-chloride may be used.

In certain other embodiments disclosed herein, solid support beads may be prepared by the methods recited in Lewandowski, K. et al., "Preparation of Macroporous, Monodisperse, Functionalized Styrene-divinylbenzene Copolymer Beads: Effect of the Nature of the Monomers and Total Porogen Volume on the Porous Properties," J. App. Polymer Science, 67: 597-607 (1998), incorporated herein by reference. For example, in certain embodiments, monodisperse beads may be used that have been prepared from the polymerization of mixtures of styrene and substituted styrene monomers, such as 4-methylstyrene, 4-aminostyrene, 3-aminostyrene, 4-acetoxystyrene, and 4-tert-butoxycarbonyl oxystyrene, with divinylbenzene. The monodisperse beads may be prepared in the presence of various porogens.

Module 1

In the invention, the nucleic acid molecules may be attached to solid supports, such as particles or beads (e.g., controlled pore glass beads or polystyrene beads). In one embodiment, magnetic or non-magnetic microbeads are used as solid supports. In many instances, porous μm-size microbeads with large surface to volume ratios may be used in the current invention. The uniform nature of such monodispersed particles generally provides for uniform reaction rates particularly suited to synthesis in automated chemical synthesizers (e.g., nucleic acid molecule synthesizers). These beads may be obtained with various chemical activation groups suitable for use for different applications.

In some aspects, the invention relates to a multiwell plate for non-template directed synthesis of nucleic acid molecules (e.g., chemical synthesis). In a preferred embodiment, the multiwell plate comprises a plurality of wells, wherein each well is configured to accommodate one or more monodisperse beads. In some instances, each well of the multiwell plate may be configured to accommodate one monodisperse bead.

A well according to the invention may be defined by its depth. A minimal depth of a well should at least slightly exceed the diameter of a bead to guarantee that the bead can be covered (e.g., homogenously covered) with reagents/EGA. The depth of a well may be, for example, 110%, 120%, 130%, 140%, 150%, 160%, 170%, 180%, 190% or less than 200% of the bead diameter. However, the maximum depth of a well will typically be configured such that only a defined number of beads (e.g., only a single bead) can be placed in the well. For example, the depth of a well will typically not exceed about 150% of the bead diameter to ensure that a second bead cannot be placed in a well already occupied by a first bead.

In certain instances a bead may be of a size or diameter to tightly fit into a well. For example, a bead with a diameter of about 35 to 40 μm may be placed in a well that has an inner diameter of 40 μm and a depth of 55 μm. This would result in the bead fitting into the well with narrow tolerance. As explained elsewhere herein, due to certain aspects of structural heterogeneity of beads that may be used in the practice of the invention, fairly tight bead/well tolerances fall within the scope of the invention. For example, beads may be smaller than wells by 20% or less (e.g., from about 1% to about 10%, from about 2% to about 10%, from about 4% to about 10%, from about 5% to about 10%, from about 2% to about 8%, from about 5% to about 10%, from about 4% to about 8%, from about 1% to about 15%, from about 5% to about 15%, from about 8% to about 15%, from about 5% to about 20%, from about 10% to about 20%, from about 15% to about 20%, etc.) in terms of bead diameter compared to well diameter. For purposes of illustration, if a bead with a diameter of about 35 μm is placed in a well with a diameter of about 40 μm, then the bead is smaller than the well by 12.5%.

In instances where a well is configured to accommodate a single bead, the diameter of the bead may be approximately 80-90% of the inner diameter of a well to ensure that the bead surface will be homogenously brought in contact with and/or covered by reagents and/or EGA and the entire bead surface area will be used equally efficient for synthesis of nucleic acid molecules. By using a bead with a diameter of less than 100% of the inner well diameter it can also be ensured that heat developed in the well can freely pass off the well/can escape from the well. For example, the distance between the bead surface and the inner wall of a well may be about 2 to 10% of the bead diameter, such as, for example, about 5% of the bead diameter. In many instances the bead will be spherical and the well will have a round or cylindrical shape. However, other forms and shapes are also possible. In certain instances the well may, e.g., have a rectangular, square, octagonal or filamentous shape. For example, in a setting where a bead is sized to essentially exactly fit into a square-shaped well, heat could escape from the "corners" of the well. Well size and shape is preferably chosen to allow efficient fluid exchange when switching reagents.

In a preferred aspect of the invention, the bead is a monodisperse/monosized porous bead. In some embodiments the bead may be a magnetic bead or a non-magnetic bead. The use of monodisperse beads in wells of defined size as described above helps in ensuring that all beads are (1) equally and homogenously contacted by reagents/EGA in the well and (2) provides equal loading capacity and (3) equal amounts of reactive synthesis positions per well, therefore assisting in the preparation of equal starting conditions for parallel reactions.

The term monodisperse is used herein to characterize a population of particles or beads with low heterogeneity and a homogenous size distribution. The size distribution of a bead may be defined by the percentage CV (coefficient of variation). The CV for a plurality of beads may for example be within a range of 50 to 100%. Monodisperse beads used in aspects of the invention are characterized by a low CV which may be within a range of 1 to 10%, 1 to 20%, 1 to 30%, 1 to 30%, 3 to 20%, 5 to 15%, 2 to 10%, 10 to 25%, less than 10%, preferably less than 5% or less than 3%. For example, a monodisperse bead population may have more than 90%, preferably more than 95% of the beads with sizes within their mean diameter of ±5%. Monodisperse beads for use in embodiments of the invention may be obtained according to a process as described, for example, in Patent Publication No. WO 2000/061647.

With many oligonucleotide synthesis systems, synthesis efficiency decreases once nucleic acid molecules reach certain lengths. Further, the lengths at which synthesis efficiency decreases can vary with synthesis parameters. One reason that synthesis efficiency is believed to decrease is due to steric hindrance effects. In particular, oligonucleotides are three dimensional compounds that occupy space. Thus, once the local space surrounding an oligonucleotide chain becomes limited, steric hindrance effects interfere with the addition of new bases to the molecule. The invention includes compositions and methods for providing synthesis parameters to lessen decreases in oligonucleotide related length synthesis efficiency.

A number of parameters may be adjusted to lessen decreases in oligonucleotide related length synthesis efficiency. Further, different parameters may be adjusted in relation to each other. The relation of well size to bead size as described above in combination with bead-specific parameters (bead surface area, pore volume, amine content, linker loading capacity, etc.) may be adjusted. To increase yields of correctly synthesized longer oligonucleotides, a bead with (1) a larger pore volume to surface ratio and (2) lower linker loading may be advantageous. These parameters present a situation where increased yield of longer oligonucleotides of the desired sequence in terms of percentage of "correct" oligonucleotides produced is partially the result of synthesizing fewer oligonucleotides per unit area of bead. In particular, the lessening of steric hindrance effects typically requires that oligonucleotides being synthesized be provided sufficient space to prevent them from "bumping" into each other during the synthesis process. This requires a lower loading capacity on the bead than is technically feasible. The net result is that fewer oligonucleotides are produced per unit area of bead surface as compared to that which is technically possible. Depending on the desired length, quality and yield, adjustment of these parameters can be used to achieve an optimal result as further described below. Thus, in some aspects, the invention includes compositions and methods employing beads having a lower linker loading capacity than that which is technically feasible. Data related to linker loading capacity and efficiency of oligonucleotide synthesis is set out elsewhere herein.

As used herein, the term "long oligonucleotides" refers to oligonucleotides of a length where most standard commercially used and available oligonucleotide synthesis platforms begin to exhibit increased synthesis error rates. In many instances, these errors result from increases in the percentage of oligonucleotide molecules exhibit "missing" bases. In other words, the rate at which bases are not added to oligonucleotide molecules being synthesized increases significantly. For example, in some instances the addition of each base, also referred to as "coupling", is approximately 99% efficient. In such instances, when an oligonucleotide of a certain length n is to be synthesized, only $0.99^{n-1}$ of the oligonucleotides will be correct based on the accumulation of inefficient coupling events. Also, other factors such as side reactions or the concentration or ratio of reactive compounds may contribute to less efficient coupling thereby adding to the overall error rate with increasing length of the oligonucleotide. For purposes of illustration, assume that an oligonucleotide is synthesized where there is a 1.5% error rate of failure to add a base for each base addition, for each oligonucleotide being synthesized. Further, this "failure to add" error rate remains constant from base 2 to base 35, then increases to 2% at base 36, 3% for base 37 and 5% for base 38 and 8% for base 39. In such an instance, oligonucleotides over 35 bases in length would be considered to be "long oligonucleotides". In most instances, long oligonucleotides are oligonucleotides of more than 35, more than 40, more than 45, more than 50, more than 55, more than 60, more than 80, more than 100, more than 120, more than 150, up to about 200 etc., bases in length.

Errors such as deletions, insertions or mutations may occur for various reasons. In some instances, errors may result from inefficient or incomplete deblocking events (e.g., incomplete removal of the 5'-DMT protecting groups). If deblocking is not achieved quantitatively, added bases cannot be coupled to all oligonucleotides synthesized on a bead. The protecting group of one or more oligonucleotides that has not been removed in a given synthesis cycle may, however, be removed in subsequent synthesis cycles followed by coupling of further bases. In this case, one or more oligonucleotides may carry one or more deletions. Whereas certain conditions during synthesis may result in oligonucleotides having deletions, other conditions may lead to the incorporation of one or more wrong bases resulting in insertions or mutations. In the latter case, an oligonucleotide may have the intended length but be of incorrect total sequence. The error rate of a specific oligonucleotide (e.g., a population of oligonucleotides intended to have the same sequence) may be determined by various means. The error rate may be determined based on a subset of oligonucleotides comprising the desired length (e.g., HPLC purified) and may not take into account any smaller fragments or truncated oligonucleotides generated as byproducts. One way of determining the error rate (the total amount of insertions, deletions and mutations) of oligonucleotides of a certain length is by direct sequencing. Another way to determine the error rate or the "quality" of oligonucleotides may be based on the efficiency of assembling one or more sets of oligonucleotides into larger nucleic acid molecules of correct sequence. Whether determined by direct or indirect means, a population of oligonucleotides of rather low quality may exhibit an error rate of 2 to 3% such as, for example, 2.5% which would represent about one error in 40 bases. Oligonucleotides of higher quality may exhibit an error rate of less than 1%, less than 0.5%, less than 0.25% or less than 0.1% (1 error in 1000 bases). Therefore, one aspect of the invention is to provide means and methods to synthesize long oligonucleotides of high quality (i.e., with low error rate).

As indicated above, a portion of oligonucleotides synthesized on a support may be truncated (i.e., have a length less than the desired length). A truncated oligonucleotide may, for example, be generated where a 5'-DMT protecting group has been removed but no base coupling has occurred resulting in an unreacted 5'-hydroxyl group which may be subject to additional coupling in a subsequent synthesis step. To avoid accumulation of deletions with each successive cycle a "capping step" is used to block any unreacted 5'-hydroxyl groups. This will, however, result in shorter oligonucleotides as no further bases can be added to capped oligonucleotides in subsequent reactions. Such truncations accumulate with increasing length of oligonucleotides being synthesized. It is therefore desired to generate a large portion or high yield of oligonucleotides having the desired full-length. The yield may be defined as the percentage of oligonucleotides generated per well/bead having the desired length or the amount of full-length oligonucleotides generated per well/bead. For example, a 35 μm bead with a linker loading capacity of 300 femtomole may carry 30 to 50% of full-length oligonucleotides resulting in an amount of 90 to 150 femtomole of oligonucleotide having the desired length. One aspect of the invention is therefore to provide means and methods to synthesize long oligonucleotides at high yield, such as, for example, between 30% and 50%, between 40% and 60%, between 50% and 70% or more than 50% of the total amount of oligonucleotides synthesized in a well/on a bead. Alternatively, the amount of full-length oligonucleotides synthesized in a well/on a bead may be between 90 to 150 femtomole, between 100 and 200 femtomole, between 150 and 300 femtomole, more than 300 femtomole, etc.

It may be desirable to quantify the amounts of nucleic acid molecules (e.g., oligonucleotides) at various points during the synthesis and/or assembly. In some instances, oligonucleotides may be detected on the surfaces of supports (e.g., beads). This detection may be relatively non-quantitative or quantitative. Non-quantitative detection may be of interest, for example, when it is desirable to detect synthesis failure on a bead (e.g., a bead present in a well). In such instances, beads would typically be scored for a minimum amount of nucleic acid present. Quantitative detection may be of interest, for example, when it is desirable to have an estimate of the number of nucleic acid molecules present.

Most quantification methods do not provide for "exact" quantification of a nucleic acid being measured. Variations often occur due to variables such as nucleotide sequence, etc. By quantification it is meant that the measured value is within 85% of the actual amount of nucleic acid present.

In many instances, it will be desirable to be able to detect and/or quantify nucleic acid molecules in a "non-destructive" manner. By this is meant that the detection/quantification method and/or reagent does not damage the DNA molecules being identified and does not interfere with "downstream" uses of detected/quantified nucleic acid molecules. Fluorophores are one type of molecule that may be used in detection/quantification methods. In many instances, fluorophores, as well as other detectable labels, may bind to nucleic acid molecules non-covalently.

Fluorophores, as well as other detectable labels, that may be used in the practice of the invention may bind preferentially to DNA over RNA, preferentially to RNA over DNA, and/or preferentially to single-stranded (ss) nucleic acids over double-stranded (ds) nucleic acids. Thus, fluorophores that may be used in the practice of the invention may bind preferentially to ssDNA over dsRNA.

One desirable feature of fluorophores, as well as other detectable labels, that may be used in the practice of the invention is that they not exhibit substantial labeling activity when associated with solid supports (e.g., beads) and/or chemical groups (e.g., linkers) used for nucleic acid synthesis. In other words, labels will typically be chosen such that solid supports used for nucleic acid synthesis generate little or no signal prior to nucleic acid synthesis.

One example of a fluorophore that may be used to detect and/or quantify nucleic acid molecules is QUANT-iT OLI-GREEN® ss DNA Reagent (Thermo Fisher Scientific Inc.). This reagent binds non-covalently to nucleic acid molecules and may be used for quantification, wherein the quantity and/or length of a given nucleic acid molecule can be determined as a function of fluorescence intensity. Further, this fluorophore preferentially binds to single-stranded DNA and exhibits increased fluorescence when bound to nucleic acid. Also, QUANT-IT OLIGREEN® ss DNA Reagent is non-destructive and thus detected and/or quantified nucleic acid molecules may be used in later processes (e.g., error correction reactions, nucleic acid assembly reactions, etc.).

Additional fluorophores that may be used in the practice of the invention include ones that comprise a cyanine dye, a phenanthridinium dye, a bisbenzimide dye, a bisbenzimidazole dye, an acridine dye, or a chromomycinone dye. In some instances, the fluorophore is QUANT-iT OLIGREEN®, PICOGREEN®, SYBR GREEN®, SYBR GREEN II®, SYBR GOLD®, SYBR SAFE® DNA gel stain, or CYQUANT GR® dye, all of which are available from Thermo Fisher Scientific, Inc. Other fluorophores that may be used include EVAGREEN® (Biotium, Inc.), DAPI (4',6-diamidino-2-phenylindole), ethidium bromide, propidium iodide, dihydroethidium, hexidium iodide, QUANTIFLUOR® ssDNA dye (Promega Corp.), or QUANTIFLUOR® dsDNA dye (Promega Corp.).

The invention thus includes methods comprising the generation of beads comprising bound (e.g., covalently bound) nucleic acid molecules and the detection and/or quantification of the bound nucleic acid molecules.

Related methods include those for determining whether failure of nucleic acid synthesis has occurred in one or more wells of a multiwell plate. Synthesis failure may occur for any number of reasons. One such reason, when EGA based deprotection is used, is that electric current is not supplied to one or more wells at the necessary times. The invention thus includes methods for assessing the functionality of an electronic synthesis chip of a type such as that shown in FIG. 24D. The invention thus also includes methods in which a chip is used for nucleic acid synthesis and, after the addition of a number of synthesis cycles for base addition (e.g., from about 6 to about 15 cycles), beads in the wells of the chip are contacted with a dye (e.g., a fluorophore) to determine whether nucleic acid synthesis has occurred in each well. Further, wells where synthesis has not occurred, if any, may be identified. The number of wells in which synthesis does not occur and their location in the chip may be identified. The operator (or computer with preset parameters) may then choose to take actions such as directing synthesis only in functioning wells or rejecting the chip due to the number of non-functional wells.

The invention also provides methods for determining the length of nucleic acid molecules associated with solid support. This is based upon the principle that detectable labels (e.g., QUANT-IT OLIGREEN®)) may be selected such that they labeled nucleic acid molecules in a manner where detectable labeling activity is proportional to the length of nucleic acid molecules being detected.

In a preferred embodiment of the invention, monodisperse beads are used and they are porous beads and characterized by a specific pore volume, wherein, for example, 1 ml of pore volume per 1 gram of polymer is equal to 50% porosity. For example, a bead with a pore volume of 2.2 ml/g polymer has a porosity of 70%. Bead porosity depends on the polymer used and may be an important factor in achieving synthesis of nucleic acid molecules of a certain length. In certain instances the pore volume of a bead suitable for aspects of the invention may be within a range of 0.1 to 2.5 ml/g polymer. Exemplary percent porosities for crosslinked polystyrene having a density of 1.1 g/ml are indicated in Table 1 below. However, porosities may also be defined on a volume basis. Bead porosities that may be useful for certain aspects of the invention may be within a range of from about 50% to about 70%, from about 60% to about 80%, from about 65% to about 75%, such as e.g. about 70%.

TABLE 1

| ml pore/g polymer | % porosity |
|---|---|
| 0.1 | 10 |
| 0.25 | 22 |
| 0.5 | 35 |
| 0.75 | 45 |
| 1.0 | 52 |
| 1.25 | 58 |
| 1.5 | 62 |
| 1.75 | 66 |
| 2.0 | 69 |
| 2.25 | 71 |
| 2.5 | 73 |

A monodisperse bead may further comprise a linker as defined elsewhere herein and may be characterized by its linker loading capacity. The linker loading capacity of a bead suitable for aspects of the invention may be within a range of 10 to 500 µmol/g, 50 to 350 µmol/g, 70 to 200 µmol/g, 30 to 100 µmol/g, 10 to 40 µmol/g, 20 to 50 µmol/g, 50 to 70 µmol/g or 40 to 80 µmol/g such as, for example, about 60 µmol/g. The length of a nucleic acid molecule that can be synthesized on a bead in quantitative amounts as described elsewhere herein may depend on the linker loading capacity. The higher the linker loading of a support, the higher the overall yield of synthesized oligonucleotides will be. Historically, higher linker loading capacities have been sought to increase the number of oligonucleotides that could be produced per unit area of support. However, for long oligonucleotides a very high yield may not be desirable as it may compromise the quality of the oligonucleotides as discussed supra. Thus, the adaptation of the linker loading capacity of a bead in view of the length of an oligonucleotide to be synthesized is one aspect addressed by methods and compounds of the invention to generate oligonucleotides of high quality with sufficient yields and desired length. Linker loading capacities that may be optimal to achieve synthesis of nucleic acid molecules of a certain length are indicated in Table 2.

TABLE 2

| Length of oligonucleotide | Linker loading capacity [µmol/g] |
|---|---|
| 4-20 | 250-350 |
| 20-30 | 100-250 |
| 30-40 | 70-100 |
| 40-60 | 50-70 |
| 60-80 | 35-50 |
| 80-200 | 35-15 |

A monodisperse bead may be further defined by its surface area. For example, the surface area of a bead may be within a range of 10 to 1000 m$^2$/g, between 100 and 500 m$^2$/g, between 200 and 400 m$^2$/g such as, for example, around 380 m$^2$/g. The surface area of porous monodisperse beads can, for example, be determined according to a method developed by Brunauer, Emmett and Teller referred to as the BET method which is based on the physical adsorption of a vapor or gas onto the surface of a solid (Brunauer, S., Emmett, P. and Teller, E., J. Amer. Chem. Soc. 60 (1938), p. 309). This method uses dry beads for testing so, for accurate measurement, the pores should be of stable volume when exposed to solvents as compared to when dry. In certain embodiments the surface area may be determined for beads dried at 60° C. for 2 hours from tetrahydrofuran or methanol.

A monodisperse bead may be further functionalized or coated with reactive groups which may affect the linker loading capacity. A bead functionalized for oligonucleotide synthesis may, for example, carry amine groups and may be defined by its amine content. The amine content of a solid support may be expressed by weight % nitrogen per gram of beads and may be within a range of 0.01 and 5%, between 0.1% and 3%, between 0.15% and 0.5%, between 2% and 5%, between 0.5% and 1.5%, between 1.5% and 2%. Methods for elemental analysis to determine the weight % nitrogen and calculate amine content of solid supports (mol. amine per gram of support) are known in the art and may, for example, be calculated according to methods described by Dumas A. (1826): Annales de chimie, 33,342 or as further set forth by the US Environmental Protection Agency in method 440.0: Determination of Carbon and Nitrogen in Sediments and Particulates of Estuarine/Coastal Waters Using Elemental Analysis. In certain instances, the amine content may be about 1.8%, about 1.5%, about 1.2%, about 1.0%, about 0.8%, about 0.5%, about 0.25%, about 3%, about 3.5%, about 4% or about 5%. For example, in instances where aminostyrene is used as a monomer the amine content may be theoretically determined as indicated in Table 3 below.

TABLE 3

Exemplary analysis of amine content for beads containing aminostyrene.

| weight % nitrogen/g | Mol amine/g bead | weight % aminostyrene/g bead |
|---|---|---|
| 0.01 | 7.14E−06 | 0.085 |
| 0.05 | 3.57E−05 | 0.426 |
| 0.1 | 7.14E−05 | 0.851 |
| 0.2 | 0.00014 | 1.702 |
| 0.5 | 0.00036 | 4.256 |
| 0.75 | 0.00054 | 6.384 |
| 1.0 | 0.00071 | 8.511 |
| 1.5 | 0.00107 | 12.767 |
| 1.8 | 0.00129 | 15.321 |
| 2.0 | 0.00143 | 17.023 |
| 2.5 | 0.00179 | 21.279 |
| 3.0 | 0.00214 | 25.534 |
| 3.5 | 0.00250 | 29.790 |
| 4.0 | 0.00287 | 34.046 |
| 5.0 | 0.00357 | 42.557 |

The skilled person will understand that the amine content of a solid support depends on the amine-containing compound or monomer used for polymerization. The amine content of a solid support may thus be adapted by using different amounts of an amine-containing monomer. For example, lower amounts of aminostyrene such as, e.g., less than 10 weight % or less than 5 weight % per gram of the total amount of monomers used in a polymerization mixture may be used to generate beads with a lower amine content. In certain aspects of the invention, it may be desired to decrease the amine content to limit the linker loading capacity to an amount that is optimal to achieve synthesis of oligonucleotides of a certain length. Therefore the invention also relates to monodisperse beads with a low amine content of between 0.15% and 0.5%, between. 0.5% and 1.5%, between 1.5% and 2%, or an amine content of less than 3%, less than 2%, less than 1.5%, less than 1%, less than 0.5% or less than 0.25%. Alternatively, the amine content may be modified based on the selection of a different amine containing monomer or a monomer containing a functionalizable group. For example, monomers such as, vinylbenzyl-chloride may be used in the polymerization of a bead suitable for aspects of the invention. Thus, in one embodiment of the invention the amine content of a monosized bead is determined by the amount of vinylbenzyl-chloride used in polymerization.

To achieve efficient synthesis of long oligonucleotides the relation of well size to bead size, as described, above in combination with bead-specific parameters (bead surface area, pore volume, amine content, linker loading capacity) may be important parameters.

Therefore, the invention also relates to a multiwell plate for non-template directed synthesis of nucleic acid molecules, wherein the multiwell plate comprises a plurality of wells, wherein each well is configured to accommodate a monodisperse bead, wherein the diameter of beads varies by less than 10% and wherein the beads are further characterized by having a linker loading capacity of the oligonucleotide synthesis substrate is within a range of 30 to 100 mol/g.

The invention includes compositions comprising a support for oligonucleotide synthesis, the composition comprising a solid support with a loading capacity suitable for use in the synthesis of a long oligonucleotide with a low error rate.

The invention thus includes methods for the synthesis of a long oligonucleotide with a low error rate, the methods comprising synthesizing the long oligonucleotide, wherein the long oligonucleotide is synthesized on a substrate with a linker loading capacity adjusted to allow for the production of a long oligonucleotide with a low error rate.

The invention further comprises compositions and methods wherein the long oligonucleotide synthesized is over 35 nucleotides in length.

The invention further comprises compositions and methods wherein the long oligonucleotide synthesized is of a length of from 35 nucleotides to 60 nucleotides.

The invention further comprises compositions and methods wherein the long oligonucleotide synthesized is of a length of from 50 nucleotides to 100 nucleotides and the average error rate for the synthesis of the first 35 nucleotides is within one standard deviation of the synthesis error rate of nucleotides 36 through 40.

The invention further comprises compositions and methods wherein the long oligonucleotide is synthesized with an error rate of less than 0.5%.

The invention further comprises compositions and methods wherein the long oligonucleotide is synthesized with an error rate of less than 0.5% for each of bases 3 to 50.

The invention further comprises compositions and methods wherein the amount of oligonucleotide of a certain length (e.g. more than 35, more than 40, more than 45, more than 50, more than 55, more than 60, more than 80, more than 100, more than 120, more than 150, up to about 200 bases in length) synthesized in a well/on a bead is between 30% and 50%, between 40% and 60%, between 50% and 70% or more than 50% of the total amount of oligonucleotides synthesized on a bead.

The invention further includes compositions and methods for the synthesis of an oligonucleotide on a monodisperse bead having a diameter between 25 and 40 µm (such as about 35 µm), wherein the amount of oligonucleotide of a certain length synthesized on the bead is selected from the group consisting of:
 1 femtomole to 1 picomole,
 10 femtomoles to 500 femtomoles, and
 50 femtomoles to 250 femtomoles.

In some aspects the invention involves the use of a support such as a monodisperse bead selected for low linker loading capacity (e.g., 35-50 mol/g), resulting in the production of smaller amounts of oligonucleotides than technically feasible. Advantages of this are that the use of low linker loading capacity allows for the production of longer oligonucleotides with low error rates (i.e. a higher percentage of correct full-length oligonucleotides), especially in the terminal region of the oligonucleotide synthesized late in the synthesis process.

The invention includes compositions and methods for the synthesis of an oligonucleotide on a support, wherein the linker loading capacity of the support is within a range selected from the group consisting of:
 70 µmol/g to 100 µmol/g,
 50 µmol/g to 70 µmol/g,
 35 µmol/g to 50 µmol/g, and
 15 µmol/g to 35 µmol/g.

The invention includes compositions and methods for the synthesis of an oligonucleotide on a support (e.g., a monodisperse bead), wherein the linker loading capacity of the support is adjusted to allow for the production of oligonucleotides between 50 and 200 nucleotides in length with an error rate of less than 0.5% and/or at a yield of between 30% and 50%, between 40% and 60%, between 50% and 70% or more than 50% of the total amount of oligonucleotides synthesized on the support.

The invention further includes compositions and methods, wherein the oligonucleotides are between 35 and 80 nucleotides in length.

The invention further includes compositions and methods, wherein the oligonucleotides are between 50 and 80 nucleotides in length.

The invention further includes compositions and methods, wherein the oligonucleotides are between 50 and 100 nucleotides in length.

The invention further includes compositions and methods, wherein the oligonucleotides are between 50 and 200 nucleotides in length.

The invention further includes a monodisperse porous bead for solid-phase synthesis of oligonucleotides of a length of between 35 and 200 bases, wherein the bead is a polystyrene bead coated with reactive groups such as amine groups or hydroxyl groups, and wherein said bead comprises:
 a diameter of between 10 and 100 µm or between 20 and 40 µm with a coefficient of variation of less than 10% or less than 5%,
 a surface area within a range of between 100 and 500 m$^2$/g or within a range of between 150 and 300 m$^2$/g,
 a porosity within a range of 60% to 80%,
 optionally, an amine content of between about 2% and about 8% or between about 3% and about 5%, or less than 3%,
 a linker loading capacity of between about 15 µmol/g to about 100 µmol/g, or between about 35 µmol/g to about 70 µmol/g,
 optionally, wherein said bead carries a linker, and wherein the linker is a universal linker.

Beads with a low amine content as discussed above will comprise a lower surface reactivity and will be occupied with a limited amount of linker molecules. However, beads loaded with linkers may still comprise reactive amine groups on their surface that may interfere with oligonucleotide synthesis. To remove such reactive groups, linker-carrying beads may be subjected to a capping process prior to oligonucleotide synthesis. For example, reagents such as acid anhydride or isocyanate may be used to inactivate reactive amines on the bead surface. Capping may be performed at room temperature for about 48 hours or alternatively at a higher temperature and reduced incubation times (such as, e.g., at 50° C. for 24 hours).

Magnetic bead technology is described in U.S. Pat. No. 5,512,439, which is incorporated herein by reference.

Synthesis substrates other than those composed of CPG or magnetic materials may also be used with the invention and include those composed of polystyrene (e.g., polystyrene-1% divinylbenzene, macroporous polystyrene, and poly(ethylene glycol)-polystyrene (PEG-PS)), polyamide (e.g., polyamide bonded silica gel), silica gel, and cellulose. Some of these substrates are available in resin form. In many instances, substrates that are resins may be placed in wells, instead of or in conjunction with beads, and may be used for nucleic acid synthesis.

Other nucleic acid ligation methods, and arrays which employ them, are known in the art. For example, methods are known which use an amine or a peroxide (which opens to an ether bridge) activated surface. As noted elsewhere herein, for EGA methods in the art, a hydroxyl group has been described and used to link nucleic acid to a silica bead surface. The invention includes such linking methods and compositions which contain them.

In some instances, it may also be desired to use a semi-solid support that may have a gel-like or viscous consistence or matrix instead of a solid support. The invention contemplates this and in suitable instances here where a solid support is referred to a non-solid support may be used.

Factors which determine the amount of nucleic acid which can be synthesized include surface area and size of particles upon which synthesis occurs. Thus, to some extent, support (e.g., bead) parameters can be adjusted to alter the amount of nucleic acid synthesized. Beads which may be used in the practice of the invention may vary widely in terms of size, including the following size ranges: from about 0.01 µm to about 1,000 µm, from about 0.1 µm to about 1,000 µm, from about 1.0 µm to about 1,000 µm, from about 0.01 µm to about 400 µm, from about 0.01 µm to about 200 µm, from about 0.01 µm to about 100 µm, from about 0.1 µm to about 100 µm, from about 0.1 µm to about 50 µm, from about 1.0 µm to about 600 µm, from about 1.0 µm to about 400 µm, from about 1.0 µm to about 200 µm, from about 1.0 µm to about 100 µm, from about 2.0 µm to about 400 µm, from about 2.0 µm to about 200 µm, from about 5.0 µm to about 500 µm, etc. in average diameter. In certain embodiments, the beads may have a diameter between 30 µm and 40 µm, such as a diameter of 31 µm or 32 µm or 33 µm or 34 µm or 35 µm.

Further, beads may be used which allow for an average amount of nucleic acid to be produced in the following amounts: from about 0.00001 nanomoles to about 0.0001 nanomoles, from about 0.00001 nanomoles to about 0.001 nanomoles, from about 0.00001 nanomoles to about 0.01 nanomoles, from about 0.0001 nanomoles to about 0.001 nanomoles, from about 0.0001 nanomoles to about 0.01 nanomoles, from about 0.0001 nanomoles to about 0.1 nanomoles, from about, from about 0.0001 nanomoles to about 1,000 nanomoles, from about 0.001 nanomole to about 1,000 nanomoles, from about 0.01 nanomoles to about 1,000 nanomoles, from about 10 nanomoles to about 1,000 nanomoles, from about 30 nanomoles to about 1,000 nanomoles, from about 50 nanomoles to about 1,000 nanomoles, from about 200 nanomoles to about 1,000 nanomoles, from about 1.0 nanomole to about 500 nanomoles, from about 1.0 nanomole to about 250 nanomoles, from about 10 nanomoles to about 500 nanomoles, etc. In certain exemplary embodiments, beads may be used which allow for an average amount of nucleic acid to be produced in an amount from about 90 femtomoles to about 150 femtomoles. In certain embodiments, beads may be used that allow for the number of nucleic acid molecules produced per bead to range from about $1 \times 10^9$ to about $1 \times 10^{13}$, such as, for example, $1 \times 10^{11}$ nucleic acid molecules.

TABLE 4

| Number of Nucleic Acid Molecules | Nucleic Acid (Nanomoles) |
| --- | --- |
| $1.26 \times 10^5$ | $2.09 \times 10^{-10}$ |
| $3.14 \times 10^6$ | $5.22 \times 10^{-09}$ |
| $1.26 \times 10^7$ | $2.09 \times 10^{-08}$ |

TABLE 4-continued

| Number of Nucleic Acid Molecules | Nucleic Acid (Nanomoles) |
| --- | --- |
| $1.13 \times 10^8$ | $1.88 \times 10^{-07}$ |
| $3.14 \times 10^8$ | $5.22 \times 10^{-07}$ |
| $1.26 \times 10^9$ | $2.09 \times 10^{-06}$ |
| $3.14 \times 10^{10}$ | $5.22 \times 10^{-05}$ |
| $1.26 \times 10^{11}$ | $2.09 \times 10^{-04}$ |
| $3.14 \times 10^{12}$ | $5.22 \times 10^{-03}$ |
| $1.26 \times 10^{13}$ | $2.09 \times 10^{-02}$ |

In many instances, the yield of nucleic acid molecules chemically synthesized decreases once a certain size has been reached. In many embodiments of the invention, chemically synthesized nucleic acid molecules will be in the range of from about 8 to about 100 nucleotides, from about 8 to about 35 nucleotides, from about 8 to about 40 nucleotides, from about 8 to about 50 nucleotides, from about 8 to about 100 nucleotides, from about 15 to about 100 nucleotides, from about 15 to about 75 nucleotides, from about 15 to about 50 nucleotides, from about 20 to about 60 nucleotides, from about 40 to about 400 nucleotides, from about 40 to about 300 nucleotides, from about 40 to about 200 nucleotides, from about 40 to about 100 nucleotides, from about 40 to about 90 nucleotides, from about 50 to about 400 nucleotides, from about 50 to about 300 nucleotides, from about 50 to about 200 nucleotides, from about 50 to about 100 nucleotides, from about 50 to about 90 nucleotides, from about 50 to about 80 nucleotides, from about 75 to about 400 nucleotides, from about 75 to about 300 nucleotides, or from about 75 to about 200 nucleotides.

As one skilled in the art would recognize, the amount of nucleic acid required to be produced will vary with, for examples, the application and the efficiency of assembly methods used. When a replicable molecule (e.g., via PCR, insertion into a cell, etc.) is generated, theoretically only one assembled nucleic acid molecule need be generated. If the number of nucleic acid molecules generated are reduced to the point where theoretically only one fully assembled nucleic acid molecule is generated, then half the time no fully assembled nucleic acid molecule will generated. Thus, one lower limit for the amount of nucleic acid to be produced using methods of the invention is based upon the number of fully assembled nucleic acid molecules which may be generated. This number will often vary with the number of synthetic nucleic acid molecules that must be combined to form the final construct. Methods of the invention will typically be designed to generate, prior to non-assembly amplification (e.g., first PCR assembly resulting in one or more replicable molecules or other final product nucleic acid molecules), from about 1 to about 500,000, from about 10 to about 500,000, from about 100 to about 500,000, from about 500 to about 500,000, from about 1 to about 1,000, from about 1 to about 500, from about 10 to about 1,000, from about 10 to about 500, from about 100 to about 1,000, from about 100 to about 500, from about 100 to about 5,000, from about 100 to about 50,000, from about 100 to about 250,000, from about 1,000 to about 50,000, etc. assembled nucleic acid molecules. As used in this paragraph, "assembled nucleic acid molecules" refers to the number of desired product nucleic acid molecules produced by direct assembly of oligonucleotides initiated by hybridization of overlapping oligonucleotides, as compared to amplification using, for example, terminal primers. Amplification after direct assembly will then result in copies being made of the assembled nucleic acid molecules. One commercial aspect of this feature of the invention is that the number of oligonucleotides synthesized can be minimized to save on cost.

As one skilled in the art would understand, nucleic acid synthesis substrate area directly reflects the number of nucleic acid molecules which may be synthesized on that substrate. Table 5 below shows bead size, surface area calculations and an estimated number of nucleic acid molecules that may be generated on the specified beads.

TABLE 5

| Bead Diam. (μm) | Surface Area (μm$^2$) | No. of Molecules |
|---|---|---|
| 1 | 3.14 | $1.3 \times 10^6$ |
| 5 | 78.5 | $1.62 \times 10^8$ |
| 10 | 314.16 | $1.7 \times 10^9$ |
| 30 | 2,82,7 | $6 \times 10^{10}$ |
| 50 | 7,853 | $2 \times 10^{11}$ |
| 100 | 31,415 | $1.8 \times 10^{12}$ |

In some embodiments, oligonucleotide synthesis will be performed using 2.8 μm beads in a plate with one bead per well. Further, the wells may be designed as cylindrical holes or chambers that are about 4 and 3 μm deep. When well spacing of 100 μm is used, a 10 mm$^2$ chip can accommodate 10,000 wells.

In other embodiments, oligonucleotide synthesis will be performed using 35 μm beads in a plate with one bead per well. The wells may be designed as cylindrical holes or chambers that are about 50 μm deep and about 40 μm in diameter. In certain embodiments, there may be about 30 μm spacing between wells. In certain embodiments, an 18 mm$^2$ chip can accommodate about 35,440 addressable wells.

In many instances when plates are made by etching, the wells will be of a non-cylindrical shapes and may be pyramid, cone or quadratic shaped. In some instances, the wells may be in the shape of a reverse, truncated cone.

The number of individual nucleic acid molecules generated will also vary with the application. While costs savings can be achieved by reagent usage reductions, it will generally be desirable to generate enough nucleic acid molecules need for, for example, efficient assembly. Further, the number of nucleic acid molecules having a particular nucleotide sequence produced will generally reflect the "carrying capacity" of the synthesis substrate. For example, a 35 micron bead typically can be used to generate about $1 \times 10^{11}$ nucleic acid molecules. For example, in many instances, as bead size, decreases, so will the number of nucleic acid molecules that may be produced on each bead.

Methods of the invention may be used to generate from about 100 to about $1 \times 10^{13}$, from about 1,000 to about $1 \times 10^{13}$, from about 10,000 to about $1 \times 10^{13}$, from about 100 to about $1 \times 10^{12}$, from about 1,000 to about $1 \times 10^{12}$, from about 10,000 to about $1 \times 10^{12}$, from about 100 to about $1 \times 10^{11}$, from about 1,000 to about $1 \times 10^{11}$, from about 10,000 to about $1 \times 10^{11}$, from about $1 \times 10^{11}$ to about $1 \times 10^{13}$, from about 100 to about $1 \times 10^9$, from about 1,000 to about $1 \times 10^9$, from about 10,000 to about $1 \times 10^9$, etc. nucleic acid molecules designed to have the same nucleotide sequence. In certain exemplary embodiments, about $1 \times 10^{11}$ nucleic acid molecules may be generated per bead or well, whereas the total amount of nucleic acid molecules designed to have the same nucleotide sequence generated in a plurality of wells may be from about $1 \times 10^5$ to about $1 \times 10^8$, from about $1 \times 10^7$ to about $1 \times 10^{10}$, from about $1 \times 10^9$ to about $1 \times 10^{12}$, from about $1 \times 10^{11}$ to about $1 \times 10^{13}$, from about $1 \times 10^{12}$ to about $1 \times 10^{15}$, from about $1 \times 10^{11}$ to about $1 \times 10^{16}$, such as about $1 \times 10^{12}$ to about $1 \times 10^{13}$.

The number of nucleic acid molecule synthesis sites (e.g., wells) can vary greatly and will be determined by a number of factors including (1) the limitations of engineering and nucleic acid molecule synthesis hardware and (2) the amount of nucleic acid which is desired (see elsewhere herein for a discussion of this factor). As examples, the number of nucleic acid molecule synthesis sites (e.g., wells) in synthesis platforms used in the practice of the invention may vary in total number between 9 and 300,000, between 9 and 100,000, between 9 and 40,000, between 9 and 1,000, between 9 and 500, between 1,000 and 200,000, between 1,000 and 400,000, between 1,000 and 500,000, between 1,000 and 1,00,000, between 1,000 and 10,000,000, between 20,000 and 1,000,000, between 50,000 and 10,000,000, between 10,000 and 5,000,000, between 1,000 and 100,000, between 2,000 and 100,000, between 5,000 and 100,000, between 10,000 and 100,000, between 20,000 and 100,000, between 30,000 and 100,000, between 1,000 and 80,000, between 1,000 and 70,000, between 1,000 and 50,000, between 1,000 and 40,000, between 1,000 and 30,000, between 1,000 and 20,000, between 1,000 and 10,000, between 1,000 and 8,000, between 1,000 and 5,000, between 5,000 and 50,000, between 10,000 and 50,000, between 5,000 and 35,000, etc. In addition, the number of nucleic acid molecule synthesis sites (e.g., wells) may vary between 1,000 and 5,000, between 1,000 and 10,000, between 1,000 and 20,000, between 1,000 and 40,000, between 2,000 and 5,000, between 2,000 and 10,000, between 4,000 and 15,000, between 100 and 1,000, between 100 and 3,000, between 100 and 5,000, between 250 and 5,000, etc. per mm$^2$. In certain embodiments, the number of wells may be, for example, 35,440. In certain other exemplary embodiments, the number of wells may be, for example, 196,160, or, for example, 9020.

The amount of reagent space per nucleic acid molecule synthesis site (e.g., well) will vary with the size and shape of the well and, in particular, the area of the space capable of accepting reagents. This will vary with factors such as whether the nucleic acid molecule synthesis site is a flat surface (e.g., relying on surface tension to keep reagents localized over the synthesis site or a cavity (e.g., a well). Also, the amount of reagent applied may be determined by the amount of reagent necessary to cover the synthesis site, deliver the necessary amount of reactant(s), and/or dilute, remove, or wash away reagents present at the synthesis site. The amount of reagent applied (when the reagent is a liquid) and the amount of reagent space at the synthesis site may vary greatly including between $0.001 \times 10^{-15}$ l (femtoliter) and 100 μl, between $0.01 \times 10^{-15}$ l (femtoliter) and 100 μl, between $0.1 \times 10^{-15}$ l (femtoliter) and 100 μl, between $1.0 \times 10^{-15}$ l (femtoliter) and 100 μl, between $0.1 \times 10^{-15}$ l (femtoliter) and 1 μl, between $0.1 \times 10^{-15}$ l (femtoliter) and 500 nl, between $0.1 \times 10^{-15}$ l (femtoliter) and 100 nl, between $0.1 \times 10^{-15}$ l (femtoliter) and 1 nl, between $0.1 \times 10^{-15}$ l (femtoliter) and 500 pl (picoliter), between $0.1 \times 10^{-15}$ l (femtoliter) and 100 pl, between $0.1 \times 10^{-15}$ l (femtoliter) and 10 pl, between $0.1 \times 10^{-15}$ l (femtoliter) and 1 pl, between $0.001 \times 10^{-15}$ l (femtoliter) and 1 pl, between $0.001 \times 10^{-15}$ l (femtoliter) and $1.0 \times 10^{-15}$ l (femtoliter), between $0.001 \times 10^{-15}$ l (femtoliter) and $100 \times 10^{-15}$ l (femtoliter), between $1.0 \times 10^{-15}$ l (femtoliter) and $500 \times 10^{-15}$ l (femtoliter), etc.

The number and size of wells used in various aspects of the invention will be determined by the overall configuration of a microchip, whereas the diameter of a bead used for synthesis of a nucleic acid molecule will in turn depend on the well dimensions. In certain aspects, the configuration of a microchip may be adapted by the variation of certain parameters. Exemplary configurations showing possible variations of (i) chip size, (ii) active area, and (iii) well diameter/distance are illustrated in the Table of FIG. 35, wherein the active area comprises the total area of a chip where the wells are contained, including the space between the wells. For example, a 18 mm$^2$ microchip may have an active area of about 73% with 35,237 wells of 40 μm in diameter and 50 μm in depth, and with a distance between wells of about 30 μm (75% of well diameter) and a well volume of 6.28×10$^{-5}$ μl. In instances where the wells are configured to accommodate one bead, the bead may have a diameter (measured in acetonitrile) of about 87.5% of the well diameter, which would be 35 μm in this example.

Distances between wells may be within a range of between 10% to 90% of well diameter, such as e.g. between 20% and 50%, between 30% and 70%, between 50% and 90% or between 60% and 80% such, as, e.g., 75%. Furthermore, the depth of a well may be within a range of about 100% to about 200% of the diameter of the well, such as e.g. between about 100% to about 130%, between about 110% to about 150%, between about 120% to about 170%, between about 150% to about 200%, between about 120% to about 130%, such as, e.g., about 125%. In instances, where a well is configured to accommodate a single bead, the bead diameter may be within a range of between about 55% to about 99% of the well diameter, such as, e.g., between about 60% and about 95%, between about 65% and about 85%, between about 75% and about 90%, such as e.g. about 87%. In other instances the microchip may be configured to accommodate two or more beads of smaller sizes in a single well.

In certain embodiments, a microchip may have a shape as illustrated in FIG. 24D with a leaf-like flow chamber whereas in other embodiments the chip may have a rectangular or orthogonal shape. To arrive at an optimal chip configuration, the impact of the variation of certain parameters needs to be considered. Whereas certain parameters (such as, e.g., the number of wells or active area) may provide means for scale-up, other parameters may impact the performance or suitability of the chip for certain uses. For example, a microchip too small in size may not allow for fluidics applications and may therefore have a minimum size of not less than about 10 mm$^2$ whereas a chip too large in size (i.e., larger than about 20 to 25 mm$^2$) may not be compatible with high-yield manufacturing (e.g., when CMOS technology is used). Likewise, the size and dimension of a well should be such that a sufficient amount of oligonucleotides required for the assembly of larger nucleic acid molecules can be produced. For example, wells with a diameter of less than about 10 μm may be suboptimal to product sufficient amounts of oligonucleotides, whereas wells with a diameter of more than about 90 μm to about 110 μm may cause too long diffusion times for reagents, which may be problematic in certain instances, e.g., where EGA is produced.

To make the solid support material suitable for nucleic acid molecule synthesis, non-nucleosidic linkers or nucleoside succinates may be covalently attached to reactive amino groups. If necessary, however, other surface functions such as carboxyl, hydroxyl, or thiol, for example, could be used to attach a linker carrying a hydroxyl group or alternatively a 3'-attached nucleotide.

In many instances a nucleic acid molecule synthesized on a solid support such as, e.g., a bead, may be physically coupled to the support by a linker. In certain exemplary embodiments, the linker, when present, may be a chemical entity that attaches the 3'-O of the nucleic acid molecule to the solid support (e.g., a functional group on a solid support). In other exemplary embodiments, the linker, when present, may have a structure such that it allows for attachment of other functionalities in addition to the 3'-O. Such linker structures are disclosed, for example, in U.S. Pat. No. 7,202,264, and may be used according to certain embodiments disclosed herein. In most cases, the linker will be stable to all the reagents used during nucleic acid molecule synthesis, but cleavable under specific conditions at the end of the synthesis process. One linker commonly used in nucleic acid molecule synthesis is the succinyl linker. Additionally, universal linkers may be used for nucleic acid molecule synthesis according to embodiments disclosed herein and discussed below. A universal linker is a linker that allows for the synthesis of nucleic acid molecules regardless of the nature of the 3'-terminal base of the first nucleotide that is to be sequenced. Different linkers with different properties are known to those skilled in the art and can be selected by the skilled person depending on the downstream process requirements.

Nucleosidic solid supports (e.g., support prederivatized with base) are widely used in nucleic acid molecule synthesis. One example of such a support is one where the 3'-hydroxy group of the 3'-terminal nucleoside residue is attached to the solid support via a 3'-O-succinyl arm. The use of nucleosidic solid supports requires usage of beads prederivatized with different types of bases (one for each base). However, the fact that a nucleosidic solid support has to be selected in a sequence-specific manner (according to the first base required for each nucleic acid molecule) reduces the throughput of the entire synthesis process due to laborious pre-selection and distribution of beads attached to a specific starter base to individual microwells.

A more convenient method for synthesis starts with a universal support where a non-nucleosidic linker is attached to the solid support material. An advantage of this approach is that the same solid support may be used irrespectively of the sequence of the nucleic acid molecule to be synthesized. One example of a universal support that can be used in the current invention is described in U.S. Pat. No. 7,202,264, the disclosure of which is incorporated herein by reference. However, other universal linkers known by the skilled in the art may be equally appropriate to carry out the invention. For the complete removal of the linker and the 3'-terminal phosphate from the assembled nucleic acid molecule, some of the universal solid supports known in the art require gaseous ammonia, aqueous ammonium hydroxide, alcohols, aqueous methylamine or a mixture thereof. Additionally, some of the universal solid supports known in the art may be photocleavable and thus require UV lightwaves for removal. See, for example, Anderson, E. et al., "Novel photocleavable universal support for oligonucleotide synthesis," Nucleosides, Nucleotides and Nucleic Acids, vol. 22 (5-8): 1403-6 (2003), disclosing a photocleaving linker comprising a nucleophilic amine protected with a photocleavable group.

In some embodiments, supports prederivatized with a base (e.g., dU, dA, dT, dC, dG, etc.) present may be employed. For example, a synthesis chip with multiple (e.g., four) loading regions (e.g., reagent flow zones) may be used so that beads prederivatized with the same base can be loaded in the same region. Also, multiple synthesis runs could be made in which the starting base is different in each run. Thus, for example, the first run may be made with nucleic acid molecules that begin with dA, followed by dC, then dT, then dG. Another possibility would be to synthesize nucleic acid segments, wherein all of the nucleic acid molecules being synthesized begin with the same base. For example, synthesis start points could be chosen that begin with a dG, with initial dGs chosen as start points being positioned so that suitable sequence complementarity regions are generated to allow for assembly of a final product nucleic acid molecule.

A number of methods for synthesizing nucleic acid are known. Many of these methods follow a series of basic steps, such as, for example, the following, with appropriate washing steps using, for example, acetonitrile, ethylacetate or other washing reagents suitable for practicing the invention:

a) the first nucleotide, which has been protected at the 5' position (or, in certain embodiments wherein synthesis proceeds in the 5' to 3' direction, the first nucleotide may be protected at the 3' position), is derivatized to a solid support, such as a polystyrene bead or controlled pore glass, or is obtained prederivatized;

b) the sugar group of the first nucleotide is deprotected (e.g., via detritlyation) (a process often referred to as "Deprotection"), using, for example, an EGA, trichloroacetic acid in methylene chloride or dichloroacetic acid in toluene, which results in a colored product which may be monitored for reaction progress;

c) the second nucleotide, which has the phosphorus, sugar and base groups protected, is added to the growing chain, usually in the presence of a catalyst, such as, for example, tetrazole or 4,5-dicyanoimidazole (a process often referred to as "Coupling");

d) unreacted first nucleotide is capped to avoid accumulation of deletions, using, for example, acetic anhydride and N-methylimidazole (a process often referred to as "Capping");

e) the phosphite triester is oxidized to form the more stable phosphate triester, usually using any suitable compound, for example, iodine reagents (a process often referred to as "Oxidizing");

f) the process is repeated as needed depending on the desired length of the nucleic acid molecule; and g) cleavage from the solid support is done, usually using aqueous or gaseous ammonia at elevated temperatures. The skilled in the art will recognize that in certain embodiments of the invention the order of steps may vary or some of the steps including the washing steps may be repeated as appropriate according to the used protocol.

In the current invention, the state of the art phosphoramidite synthesis chemistry is further improved by modification of specific steps of the above protocol. In one embodiment organocatalysts can be used to improve, for example, the efficiency of the coupling step. Organocatalysts and some uses of such catalysts are set out in Avenier and Hollfelder, *Combining Medium Effects and Cofactor Catalysis: Metal-Coordinated Synzymes Accelerate Phosphate Transfer by $10^8$ Chem. Eur. J.* 15:12371-12380 (2009) and Jordan et al., *Asymmetric phosphorylation through catalytic P(III) phosphoramidite transfer: Enantioselective synthesis of D-myo-inositol-6-phosphate, Proc. Nat. Acad. Sci. USA,* 107: 20620-20624 (2010).

Electrochemically and Photogenerated Acids

In some embodiments, the invention makes use of localized chemical reactions through the production of electrochemically generated acid (EGA). In other embodiments, the invention makes use of localized chemical reactions through the production of photogenerated acid (PGA). As an example, addressable electrical or photogenerated signals may be used for the production of acid at sufficient concentration to allow deprotection of the dimethoxytrityl (DMT) protecting group from surface. (Maurer et al., *"Electrochemically Generated Acid and Its Containment to 100 Micron Reaction Areas for the Production of DNA Microarrays" PLoS,* Issue 1, e34 (December 2006).)

One issue with the production of EGA or PGA as part of a nucleic acid molecule synthesis protocol on a surface (e.g., a microsurface) is "splash over" to adjoining regions. "Splash over", which includes diffusion, can result in reactions occurring in unintended location (e.g., caused by diffusion of EGA or PGA). While such effects may be fairly minor when one reaction occurs, when multiple reactions occur in succession splash over effects multiple reaction cycles may result in numerous misincorporated bases. This issue can be addressed in several ways. One way is to overlay the reaction areas with a buffer (e.g., a buffer containing an organic base) which sufficiently neutralizes the acid if it moves from the local environment. Another way is through physical containment or compartmentalization. For example, if the EGA or PGA is generated in a well and catalyzes a reaction in that well, the well may be of sufficient size to prevent the acid from exiting. Containment within the well is thus a factor of the size of the well and the amount of acid generated. In some reaction formats, some acid will invariably exit the well. This should pose no problems unless a quantity sufficient to catalyze a reaction reaches another well in which that reaction is not supposed to occur. As noted above, the use of an overlaying buffer can be used to minimize such reactions.

Factors other than splash over can also result in failed or incomplete nucleic acid synthesis, including bead loss, incomplete filling of the wells with beads, cross contamination of one or more wells, defective electrodes, or incorrect or contaminated reagents. To account for splash over or these other factors, each separate nucleic acid molecule to be synthesized can be assigned to more than one well. In addition, strategic placement of these replicate nucleic acid molecules throughout the microchip can mitigate the effects of splash over or other factors that can lead to failed or incomplete nucleic acid synthesis.

The array of individually addressable electrodes associated with each well permits replicates of the same nucleic acid molecule to be spread throughout the whole microchip. In this way, the effect on any error during the synthesis step can be mitigated. For example, if an unexpected event (e.g., cross contamination of neighboring wells, defective electrodes) occurs within a specific region of the microchip, but the replicates of the same nucleic acid molecule are spread across the microchip rather than being localized in the same region, fewer replicates will be affected. This risk mitigation strategy can be accomplished by mapping the replicates of the same nucleic acid molecule to different regions of the microchip using custom programming.

The number of wells to which a nucleic acid molecule is assigned for synthesis can vary based on factors, such as, the amount of nucleic acid to be produced, how difficult it is to synthesize the nucleic acid molecule, and how many fragments need to be synthesized. The number of wells to which a nucleic acid molecule is assigned may be, for example, between 1 and 10, between 1 and 20, between 1 and 50, between 1 and 100, between 1 and 1000, between 1 and 10,000, between 1 and 34,000, between 1 and 50,000, between 1 and 100,000, between 1 and 500,000, between 5 and 10, between 10 and 20, between 10 and 50, between 10 and 100, between 100 and 1000, between 1000 and 10,000, between 10,000 and 34,000, between 10,000 and 50,000, between 34,000 and 50,000, between 50,000, and 100,000, and between 100,000 and 500,000.

By way of example, for a microchip having 35,440 wells, if each nucleic acid molecule was assigned to 10 wells, 3,544 nucleic acid molecules could be synthesized in parallel on a single microchip. Increasing the number of wells in a microchip usually results in smaller volume sizes for each well. By way of example, for a microchip having 35,440 wells, the wells typically have a volume of about $6.3 \times 10^{-5}$ μl.

Plates which may be used in the practice of the present invention include modified forms of plates described in U.S. Patent Publication No. 2010/0137143 A1, the disclosure of which is incorporated herein by reference, shows such a representative plate format.

Figure 2A:
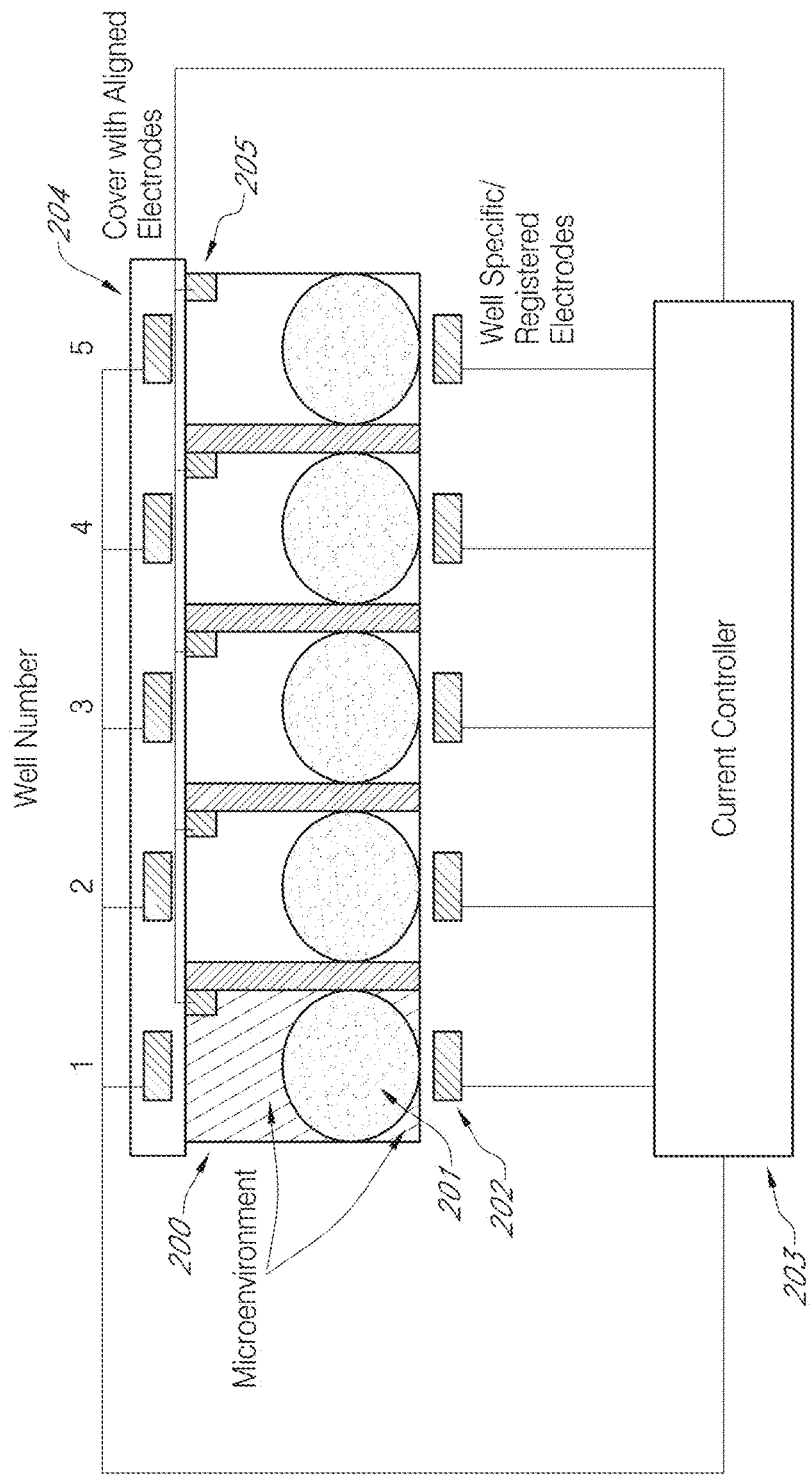
FIGS. 2A and 2B are schematic representations of a row of wells according to an embodiment of the invention. The darker area in well 1 indicates the presence of a reagent (e.g., EGA) not present at a given time in the other wells.
Figure 2B:
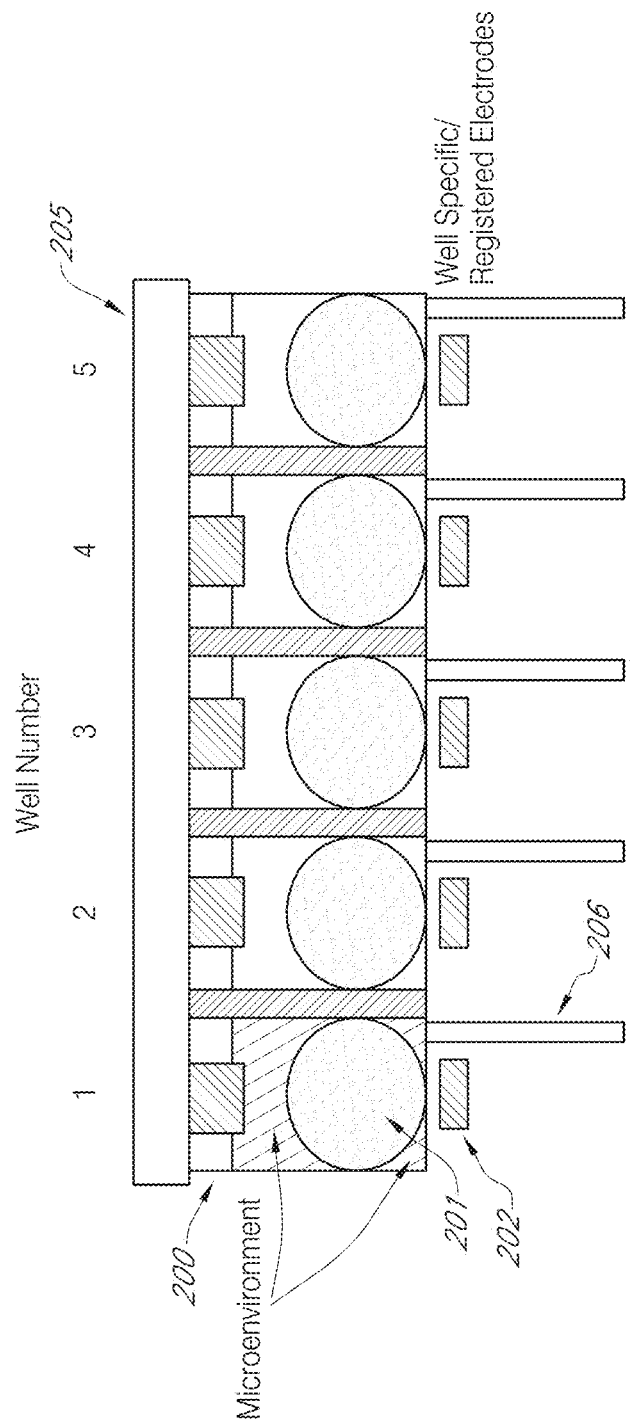

FIGS. 2A and 2B are schematic representations of a row of wells 200 according to an embodiment of the invention. The embodiment of FIGS. 2A and 2B illustrates five wells each containing a magnetic bead 201 at the bottom. Beneath each well is an electrode 202 which can deliver current to the well that it is associated with. Each electrode is communicates with a current controller 203 which regulates current to the electrode. The magnetic bead may contain a linker associated with an initial building block. As an example, the bead may contain first nucleotide (with an A, T, C, G or U base, or a modified base, depending on the first base desired in the nucleic acid molecule to be synthesized). The first base may be added as part of the synthesis process (e.g., with the bead having a protected hydroxyl group) or may be prederivatized prior to insertion into the well. In either event, in most cases, a protective group will be present (e.g., at the 5' position) which must be removed before another base may be covalently connected as part of a nucleic acid molecule chain.

Microfluidic channels (not shown in FIG. 2A) may be included for efficiently addition and removal of reagents from the wells. Thus, the invention includes, in part, a microfluidic plate designed to interface with a microfluidic system for adding and removing fluids from wells of the plate. Microfluidic channels used in similar plates are described in U.S. Patent Publication No. 2010/0137143 A1, the disclosure of which is incorporated herein by reference for background information.

The cover of the plate 204 shown in FIG. 2A contains aligned electrodes which are connected to the current controller. A larger electrode (e.g., an electrode which extends over the tops of all of the wells) may be included in the cover to "close the circuit". Thus, the cover may contain one electrode aligned with each well for which an electrochemical reaction is sought to be, one electrode in operable connection with all wells of the plate, or multiple electrodes some or all of which are in operable connection with two or more wells. In an alternative embodiment, the cover electrode for each well is replaced with one or more electrodes embedded or positioned along one or more sidewall of each well. Thus, it is not critical that electrodes be positioned in the cover. In fact, in many instances, it will be desirable (e.g., ease of manufacturing) to place the electrodes in a place other than the cover.

Reference electrodes (RE) 205 may also be included to provide a stable and pre-defined electric potential. To apply a specific potential on a working electrode (WE), the potential of the WE against the potential of the RE may be measured. Next the potential between counter electrode (CE) and WE may be adjusted until the potential between RE and CE has the correct value.

One method for deprotection may employ the oxidization of hydroquinone to benzoquinone (redox system) on the WE in order to produce protons. To set a specific pH in a well, a constant current may be applied for a specified period of time. In instances of a less active WE, a strong increase of the WE potential will occur. This can lead to unintended reactions (e.g., oxidation of the solvent or damage of WE material at high potential). To avoid this effect, the potential of the WE may be controlled.

Figure 15:
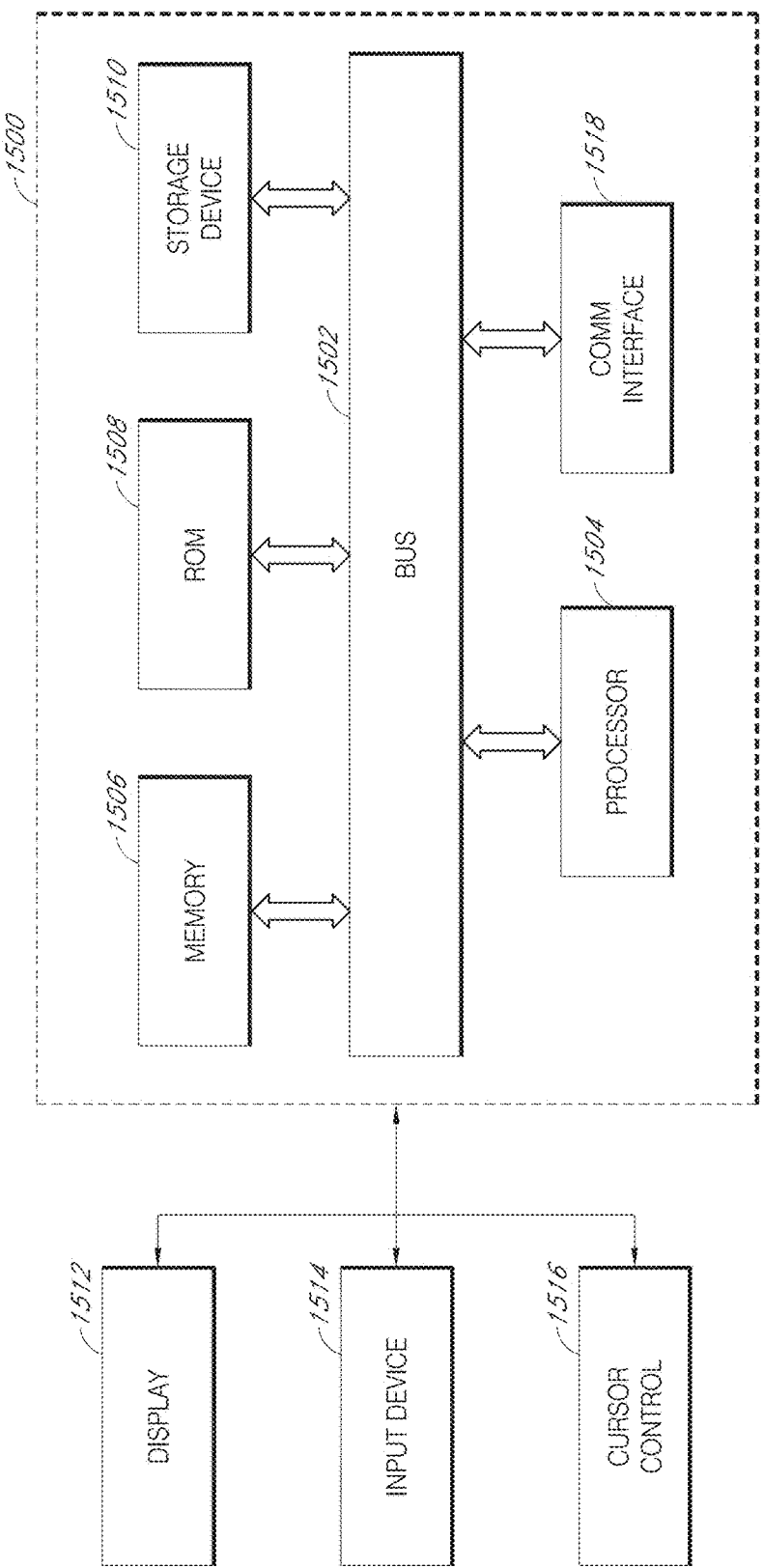
FIG. 15 is a block diagram that illustrates a computing system, upon which embodiments of the present teachings may be implemented.

The current controller (interchangeably, controller) may be a microprocessor or processor, such as shown in FIG. 15, for example. The controller (not shown) may comprise a conventional current control system, including, for example, a microprocessor circuit in communication with a memory circuit. The memory circuit may include instructions for directing the microprocessor circuit to energize one or more of the electrodes (e.g., energize electrodes associated with well 1 or a plurality of wells). Optionally, the memory circuit may include instructions for activating one of a pair of electrodes (e.g., activate the bottom electrode associated with well 1). In still another embodiment, the memory circuit may include instructions for gradually increasing/decreasing bias to the electrodes so as to reduce possibility of a sudden surge at the well.

In another embodiment, the current controller communicates with external processor circuit(s) such as a potentiostat circuit, input/output ("I/O") devices and displays. The circuit or circuit board enables the control of the device and may also be used to communicate with other devices (such as PC, iPad, etc.).

In a variation of the embodiment of FIG. 2A, both electrodes (the anode and the cathode) may be placed at the bottom of the well. This allows for electrical current to be generated near the bottom of the well, thereby generating a localized EGA in the area closely adjacent the bead. Depending on the method by which reagents are added to and/or removed from the wells and other factors, such configuration can be used to limit cross-talk between the wells, interference or unintended EGA contamination.

A related embodiment is shown in FIG. 2B. Here the cover contains aligned electrodes 205 which extends into the reagent portion of the well. Drainage tubes 206 are positioned at the bottom of each well. These drainage tubes serve several functions. One function is removing reagents at the completion of a chemical reaction step (e.g., base addition, washing, deprotection, etc.). Another function is lowering the fluid level for the deprotection step. In other words, fluid may be added to all of the wells, then the fluid level may be lowered through drainage tubes before biasing the wells. Lowering the well's fluid level reduces cross-spillage between wells and increases synthesis fidelity. The lowered fluid level also decreases potential cross-talk and contamination between adjacent wells. The same is true of general fluid removal through the bottle of the well. This is so because cross-well contamination with EGA can result in incorrect base incorporation. Even if EGA generated base mis-incorporation occurs in 0.5% of nucleic acid molecules being synthesized in adjoining wells, the net result could be roughly a doubling of base mis-incorporation. Thus, drawing down the fluid level in the wells and bottom of the well drainage results in increase synthesis fidelity.

One means for removing fluid from wells is from the top of the wells. This can be done by any number of means including the use of pipette tips or the introduction of an absorbent material. In either instance, the goal would be to remove enough fluid from each well to minimize "splash over". In some instance, the only wells that fluid levels will be reduced in will be ones which undergo a reaction (e.g., the generation of EGA, resulting in deprotection). In other words, fluid level reduction can be performed only in wells where one or more reactants are generated.

The construction of the wells can be accomplished by conventional manufacturing methods, including, for example, CMOS and VLSI techniques. The wells can be formed in semiconductor or polymeric substrates. In an exemplary embodiment, the wells are configured in a semiconductor substrate using conventional etching and boring techniques. The insider surface of the wells may be coated with insulating material to reduce cross talk between adjacent wells. In corollary embodiment, well surfaces may be coated to increase conductivity thereby generating EGA more uniformly. Well surfaces may be coated with different layers to reduce cross-talk while increasing electro- or thermal-conductivity inside the well. Thus, the walls may comprise a composite of different material which while reducing cross-talk between the wells, would increase conductivity within each well for rapid EGA generation.

The top surface of the wells (the span between adjacent wells) may also be coated to provide reagent repellent surfaces. By way of example, the top surfaces may be coated with hydrophobic compositions to repel cross-contamination. Methods for reducing well to well cross-contamination are set out in U.S. Pat. No. 6,444,111, the disclosure of which is incorporated herein by reference. This method uses a low concentrated base as proton scavenger which produces a proton gradient with a high concentration at the site of EGA generation and a lower concentration with increasing distance from the reaction center. Ideally, such gradient should allow for efficient removal of the DMT group on the active synthesis position and at the same time prevent protons from reaching a neighboring synthesis position. However, this method suffers from the difficulty of adjusting the scavenger base to a concentration that results in a 100% deprotection at the active synthesis position and 0% deprotection at the adjacent inactive synthesis positions. Whereas a base concentration that is too high would result in an incomplete deprotection reaction at the active synthesis site causing deletions in the growing nucleic acid molecule, a base concentration that is too low would allow protons to escape to neighboring sites causing deprotection and base insertions at those inactive synthesis sites.

Figures 47D, 47E, 47F:
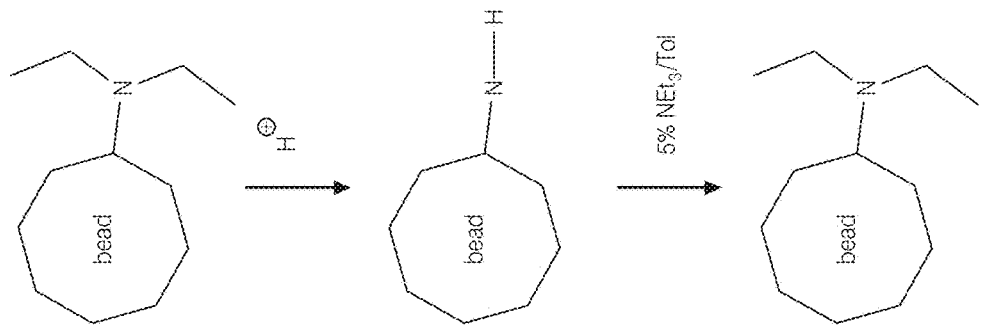
FIGS. 47A, 47B, 47C, 47D, 47E and 47F show the principle of using a solid support proton scavenger to prevent protons from contaminating adjacent reaction sites.
Figures 47A, 47B, 47C:
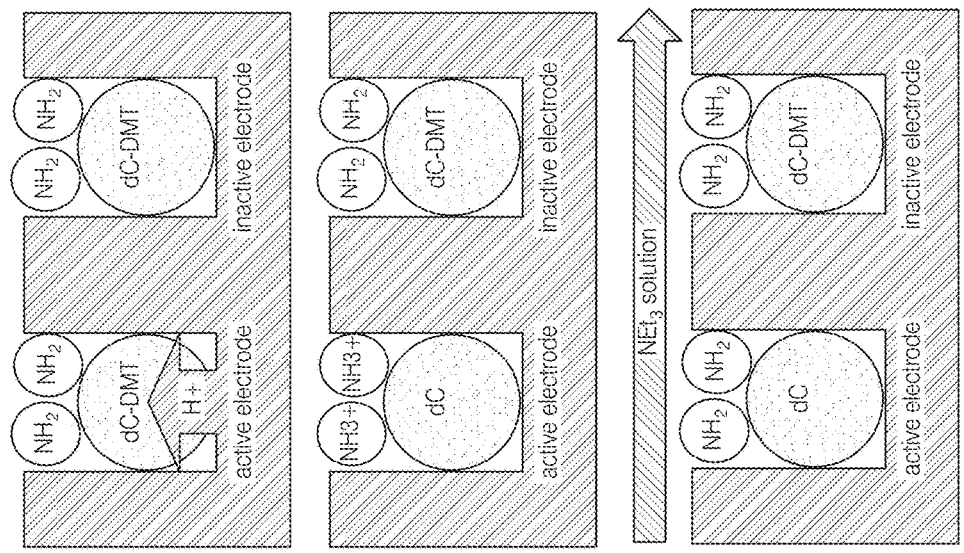

To overcome these limitations, the inventors have developed a method which uses proton scavenger base bound to solid supports. A representative embodiment of using scavenger beads to avoid cross-talk between synthesis sites is illustrated in FIG. 47, Panels A though F. In this example, nucleic acid molecules are synthesized on a ~32 µm porous monodisperse bead ("synthesis support") in a well of a microfluidic chip via EGA generation as described elsewhere herein. Protons (H+) required to remove the temporary DMT protecting group on nucleic acid molecules growing on a synthesis support are generated at the bottom of a first well comprising an active electrode (FIG. 47, Panel A, left part), whereas no protons are produced in an adjacent second well comprising an inactive electrode (FIG. 47 Panel A, right part). Protons generated in the first well diffuse to the top of the well. To prevent protons from leaving the first well, smaller beads ("scavenger beads") coated with basic groups (e.g. alkaline amine groups such as $NH_2$ or $NEt_2$) are placed in the first and second wells to cover the synthesis supports. The basic groups capture protons diffusing from the first well (leading to a conversion of the $NH_2$ group to an $NH_3$ group in this example), such that no protons will reach a second well with an inactive electrode (FIG. 47, Panel B).

In case some of the protons may escape from a first well, they can be captured by scavenger beads present in the second wells before reaching the DMT protecting groups. Finally, a restoring solution is flushed over the wells to remove the protons from the scavenger beads to restore the basic groups on the scavenger beads for the next synthesis cycle. In the example of FIG. 47, Panel C the restoring solution comprises an alkaline molecule (e.g., 5% triethylamine ($NEt_3$) diluted in toluene). Different solutions with base restoring properties are known to those skilled in the art and can be selected by the skilled person depending on the reactivity of the converted scavenger groups.

The proton-mediated conversion and subsequent restoration of base-coated scavenger beads is further illustrated by FIG. 47, Panels D through F.

In some embodiments, the scavenger base does not react with the phosphoramidites used as building blocks for the nucleic acid molecules growing on the synthesis support. This can be achieved by using scavenger groups that are not nucleophilic such as, e.g., triethylamine, lutidine or 1,8-Diazabicycloundec-7-ene or a diethylamine group bound to an aliphatic residue. Alternatively, the scavenger base may be selected to generate an instable product that rapidly decays upon reaction with a phosphoramidite, such as, e.g., a tetrazolium salt. Scavenger beads may be provided with various sizes but the size should be selected to allow placement of multiple scavenger beads into a well in combination with at least one synthesis support. Scavenger bead sizes used in the practice of the invention may vary and depend on the size of a well and/or the size of a synthesis support placed in a well of a given size. Typically, a scavenger bead may have a size that is smaller than the size of a synthesis support used in combination with the scavenger bead. For example, a scavenger bead may have a diameter that is about 10%, 25%, 30%, 50%, 60%, 75% or 80% of the diameter of a synthesis support. In certain embodiments, scavenger beads may include beads with diameters between 0.05 µm and 3 µm, 1 µm and 5 µm, 3 µm and 10 µm, 5 µm and 20 µm, 10 µm and 30 µm.

In some instances, scavenger beads may fill the majority (e.g., greater than 60%) of the void in wells containing synthesis beads. In such cases, scavenger beads would often be small enough to fit into the various void spaces. One such void space is the lower portions of the wells below the synthesis beads. In some instances, scavenger beads may surround synthesis beads. In such instances, synthesis beads will typically not fill the horizontal volume of the wells.

In some instances scavenger beads may be larger than wells containing synthesis beads. In such instances, scavenger beads may be used to "cap" the wells. Such capping scavenger beads may be removed by the flow stream when reagents are exchanged. Further, capping scavenger beads may be used in conjunction with scavenger beads that are smaller than synthesis beads.

In some instances, well depth may be adjusted to allow for the addition of various depths of scavenging beads on top of synthesis beads. In some instances, scavenging beads may be the same size as synthesis beads and the wells may be of a depth that is suitable for holding two beads. In such instances, typically scavenging beads would be located at the top of the wells and synthesis beads would be located at the bottom of the wells.

As further supported by Example 11, the inventors have demonstrated that scavenger beads are capable of efficiently protecting neighboring synthesis sites by avoiding cross-talk of generated protons. Scavenger beads according to the invention can be used in any acidic environment where proton cross-talk between reaction or synthesis sites should be avoided (such as chip or array formats using electrochemically or photogenerated acid as described elsewhere herein). The skilled person would understand that in systems where a base is generated (e.g., an electro-chemically generated base) the scavenging mechanism could be reversed to use scavenger beads carrying acidic groups on the surface. The invention thus includes a method for protecting one or more second synthesis sites in solid phase nucleic acid synthesis from contamination with protons generated at one or more adjacent first synthesis sites, wherein said method comprises (a) providing a solid support carrying basic groups on the surface, (b) placing the solid support at a first synthesis site such that the support is in fluid communication with protons diffusing from that first synthesis site, (c) allowing the basic groups on the solid support to react with the diffusing protons thereby converting the basic groups into the corresponding acid, (d) optionally restoring the basic groups on the solid support by contacting the solid support with a restoring agent.

Furthermore, the invention comprises the use of scavenger beads as specified above for EGA- or PGA-based nucleic acid synthesis platforms.

Finally, the shape of the wells may be configured to reduce cross-contamination while increasing reaction speed. For example, the wells may be configured to have cylindrical, barrel or conical shapes.

In many methods using, for example, the plate configuration of FIGS. 2A-2B, the sugar group of the first nucleotide is deprotected by activating (energizing) a chemical reaction initiated by an electrical signal (or a pulse). As noted elsewhere herein, one method for doing this is through the generation of an electrochemically generated acid (EGA). In other embodiments, the sugar group of the first nucleotide is deprotected by activating (energizing) a chemical reaction initiated by a photogenerated signal. In many cases, it will be desirable to control the amount of chemical reactant made (e.g., EGA or PGA) so as to efficiently catalyze the deprotection reaction while limiting the possibility of reactant from cross-contamination.

Figure 17:
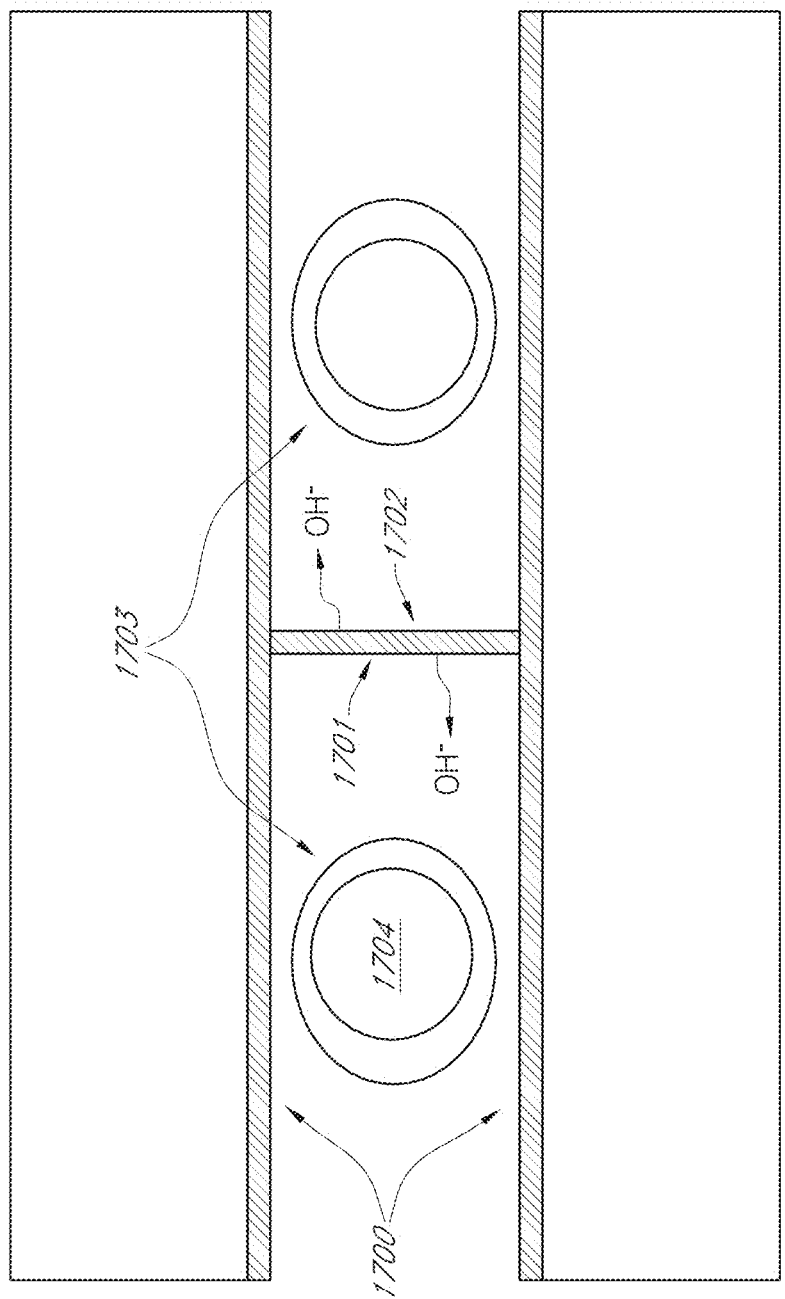
FIG. 17 is a top view schematic of a channel "chip".

FIG. 17 shows a top view of a channel chip design having three electrodes. Counter electrode elements 1700 and 1702 are located at the top of the two side channels and across the bottom of the flow channel 1701. Reference electrodes 1703 surround the two wells with working electrodes 1704 are also present.

In order to limit the flow of protons a series of steps may be taken, including (1) the use of buffers which prevent significant pH shifts in the presence of small amounts of protons, (2) the use of a quinone redox system, and (3) designing the dimensions of wells and channels to maintain substantial distances between them (e.g., using well volume 150 times smaller than according channel volume).

For example, using the schematic shown in FIG. 17 for purposes of illustration, the distances between the working electrode 1704 and counter electrode elements 1700 and 1702 may be about 200 μm. Further, interception of protons by base molecules may be used to decrease the number of protons that reach other wells. Also, reference electrode strips 1703 between wells having the same potential as the counter electrode elements 1700 and 1702 can be used to generate base molecules and further could prevent proton "cross-talk". Methods and components such as these, in addition to other methods set out herein, provide for high fidelity nucleic acid molecule synthesis.

For purposes of illustration, a prederivatized bead (which may be magnetic or non-magnetic) may be placed in wells 1 through 5 of FIGS. 2 and 2B with an "A" bead in wells 1 and 5, a "C' bead in well 2, a "U bead in well 3, and a "G" bead in well 4. All five wells may then be filled with an EGA reagent (e.g., a reagent containing methanol, acetonitrile, hydroquinone, anthraquinone, tetraethylammonium p-toluene sulfonate, and 2,6-lutidine). The next base to be added to chain is G and the only nucleic acid molecule of the molecules to be generated which contains a G at position 2 is in Well 1. Thus, current is applied only to Well 1. This current creates an acidic microenvironment which results in deprotection of the 5' position of the nucleotide only in Well 1. After a fixed (or variable) reaction time, all five wells are washed. A nucleotide, which has the phosphorus, sugar and a base (a T in this instance), is added to all of the wells in the presence of a catalyst (e.g., a tetrazole catalyst). After a predefined reaction time, all five wells are washed and unreacted first nucleotide may be capped to avoid accumulation of deletions, using, for example, acetic anhydride and N-methylimidazole. Again, after a predetermined reaction time, all five wells are washed and phosphite triesters formed by chemical reaction may be oxidized to form the more stable phosphate triester, using, for example, iodine containing reagents. This process is then repeated until the final base of the nucleic acid molecule has been added. Later, the synthesized nucleic acid molecules may be cleaved from the solid support. This may be done, for example, using aqueous or gaseous ammonia with heating. The cleavage method may vary, however, with factors such as the linker used.

The amount of current applied to each well and its duration will vary with parameters such as the amount of reagent to be generated and the size of the well. The applied current may be a pulse of varying shape and/magnitude. The pulse may define a series of varying amplitude pulses (frequency) or a gradual increase/decrease amplitude. The amplitude and duration of the pulse can be adjusted for the optimum generation of reagent. As an example, the current applied to a well may be adjusted for a specified period of time to generate a specified quantity of EGA. The amount of EGA intended for generation will typically be at least enough sufficient to fully catalyze deprotection of the nucleic acid molecules present.

High fidelity nucleic acid synthesis requires that almost complete deprotection of oligonucleotides occurs prior to addition of the next base in the oligonucleotide chain. Incomplete deprotection will typically result in a subset of the oligonucleotides missing a base in the "undeprotected" molecules. Highly acidic environments have been shown to depurinated nucleic acid molecules. This poses a synthesis quality issue because highly acidic conditions will result in near complete deprotection but can also result in depurination of oligonucleotides being deprotected.

Parameters may be adjusted in manner in which near complete deprotection of an oligonucleotide occurs with minimal depurination. Some of the factors that may be adjusted to achieve this goal include the concentration of EGA precursor placed in contact with the synthesis support, the amount of current (direct or alternating) applied to the solution containing the synthesis support, the length of time the current is applied to the solution, the presence of a buffering agent in the solution (including the type, concentration, and pKa of the buffering agent, when present), the number of molecules of oligonucleotide being synthesized, and the length of time that EGA is in contact with the synthesis support. The invention includes compositions and methods where one or more of these parameters, as well as other parameters are altered to adjust the fidelity of nucleic acid synthesis. In many instances, parameters will be adjusted so as to provide for high fidelity nucleic acid synthesis.

Application of current to affect EGA-based DMT deprotection: Current may be applied constantly up to 2 µA and voltage up to 10 V, such as up to 8 V or 7.5 V, is applied to an electrode in the controlled circuit for a time period of up to 30 seconds. Current may also be applied in pulse durations from 1 ms to 2000 ms during a time of 1 ms to 60 seconds. Current may also be applied as in various pulses (e.g., from about two to about 10,000, from about ten to about 10,000, from about fifty to about 10,000, from about 100 to about 10,000, from about 1,000 to about 10,000, from about ten to about 500, etc. pulses) up to 2 µA (e.g., from about 0.02 nA to about 20,000 nA, from about 0.2 nA to about 20,000 nA, from about 0.2 nA to about 5,000 nA, from about 0.2 nA to about 2,000 nA, from about 0.2 nA to about 1,000 nA, from about 0.2 nA to about 5000 nA, from about 2.0 nA to about 20,000 nA, from about 2.0 nA to about 10,000 nA, from about 2.0 nA to about 5,000 nA, from about 2.0 nA to about 2,000 nA, from about 5.0 nA to about 20,000 nA, from about 5.0 nA to about 8,000 nA, from about 10 nA to about 20,000 nA, from about 10 nA to about 8,000 nA, from about 10 nA to about 5,000 nA, from about 20 nA to about 20,000 nA, from about 20 nA to about 8,000 nA, from about 50 nA to about 20,000 nA, from about 50 nA to about 10,000 nA, from about 50 nA to about 5,000 nA, from about 100 nA to about 10,000 nA, from about 500 nA to about 20,000 nA, from about 500 nA to about 10,000 nA, from about 500 nA to about 5,000 nA, from about 1,000 nA to about 20,000 nA, from about 1,000 nA to about 10,000 nA, etc.). In certain embodiments, the current may be applied, either constantly or in pulses, up to about 1 µA, such as up to about 0.5 µA or up to about 0.3 µA. In certain exemplary embodiments, the applied potential between the working electrode and the control electrode is at about 7.5 V.

In some instances, current may be pulsed for anywhere from about 1 second to about 30 seconds, from about 2 second to about 30 seconds, from about 4 second to about 30 seconds, from about 5 second to about 30 seconds, from about 5 second to about 20 seconds, from about 5 second to about 15 seconds, from about 5 second to about 10 seconds, etc. Of course, efficient deprotection and nucleic acid molecule synthesis must be determined as the exact composition and concentration of EGA reagent is influenced by the precise conductive, structural and geometric properties of the electrodes and microwells and the parameters associated with the application (current, voltage and time) of current.

Composition and concentration of EGA components: The exact composition and concentration of EGA reagent is influenced by the precise conductive, structural and geometric properties of the electrodes and microwells and the parameters associated with the application (current, voltage and time) of current to convert the EGA to its acid forms. Generally, the smaller the volume for EGA production to affect deprotection, the smaller the required current strength and/or time of current application. Since the amount of nucleic acid molecule produced in such microscale systems falls below a threshold that can be directly and accurately measured, surrogate assays, such as hybridization or product enrichment following target amplification, for nucleic acid molecule synthesis and coupling efficiency are typically required.

A number of reagents may be used for the production of electronically generated acid. Generally it will be desirable to generate acid locally in order to deprotect terminal nucleotides connected to solid supports (e.g., a bead). A number of reagents are known in the art. These reagents may contain compounds that produce protons when electrons are removed through use of an electrode, a solvent, a buffering agent, and a compound that enhances the conductivity of the reagent mixture. For example, a reagent composed of hydroquinone, quinone, acetonitrile, and tetrabutyl ammonium hexafluorphosphate is set out in PCT Publication WO 2003/020415. Also, a reagent composed of hydroquinone, anthraquinone, acetonitrile, methanol, tetraethyl ammonium p-toluene sulfonate, and 2,6-lutidine is set out in Mauer et al., *PLoS One*, Issue 1:e34 (2006). Further, a similar reagent composed of hydroquinone, benzoquinone, acetonitrile, methanol, tetraethyl ammonium p-toluene sulfonate, and 2,6-lutidine is set out in PCT Publication WO 2006/105037.

These reagents may contain compounds that generate protons when electrons are removed through use of an electrode, a solvent, a buffering agent, and a compound that enhances the conductivity of the reagent mixture. An exemplary reagent composed of hydroquinone, quinone, acetonitrile, and tetrabutyl ammonium hexafluorphosphate is set out in PCT Publication WO 2003/020415. Also, a reagent composed of hydroquinone, anthraquinone, acetonitrile, methanol, tetraethyl ammonium p-toluene sulfonate, and 2,6-lutidine is set out in Mauer et al., *PLoS One*, Issue 1:e34 (2006). Further, a similar reagent composed of hydroquinone, benzoquinone, acetonitrile, methanol, tetraethyl ammonium p-toluene sulfonate, and 2,6-lutidine is set out in PCT Publication WO 2006/105037.

Acetonitrile may be replaced with any suitable solvent capable of dissolving the components to form the deblocking solution for electrochemical deblocking of acid-labile protecting groups, so long as the solvent does not interfere with the chemical synthesis process.

Methanol is present in the deblocking solution to enhance the solubility of hydroquinone, benzoquinone and derivatives of thereof. In brief, the higher the methanol concentration, the more hydroquinone that can be added to the deblock solution. Since hydroquinone is a main proton source when the electric field is applied, the concentration of hydroquinone desirable may be adjusted to generate the desired number of protons under the selected conditions. The methanol may also act as a proton source. Methanol may be replaced with other alcohols as long as methanol function(s) are preserved in the deblocking solution. If solubility of compounds in the solvent is not an issue, then the alcohol may be omitted.

Benzoquinone is believed to react at the cathode to form a hydroquinone derivative. This compound may also be replaced, or even omitted. However, a higher potential is generally required, if no benzoquinone (or similar compound) is present in the mixture. Such higher potentials may (1) harm electrical components and other hardware, (2) induce the formation of undesirable reactants, (3) damage nucleic acid molecules being produced, and (4) cause the formation of gas bubbles.

Tetraethyl ammonium p-toluene sulfonate is a salt that provides conductivity to the deblocking solution to allow electrochemical generation of acidic reagent at active electrodes. This compound may also be replaced with a compound that performs a similar function.

2,6-lutidine is believed to confine the electrochemically generated acidic reagent to the active electrode area by reacting with the acidic reagent as it diffuses away from the space immediately above the active electrode. This compound may also be replaced with a compound that performs a similar function.

TABLE 6

Deblocking Solution Formulations

| Compound | Concentration Referenced Above | Ranges/Specific Concentrations |
|---|---|---|
| Acid Generator - Hydroquinone (or similar compound) | 1M | 0.1M to 2M, 0.75M, 1.3M |
| Base Generator - Benzoquinone (or similar compound) | 10 mM | 0.1 to 100 mM, 5 mM, 16 mM, 30 mM |
| Salt - Tetraethyl ammonium p-toluene sulfonate (or similar compound) | 50 mM | 0.01 to 5M, 75 mM, 95 mM, 120 mM |
| Solvent - Acetonitrile (or similar compound) | 80% | 10% to 99%, 77.5%, 76% |
| Alcohol - Methanol (or similar compound) | 20% | 1% to 90%, 15%, 22.5%, 23% |
| Buffer - 2,6-lutidine (or similar compound) | 5 mM | 0.1 mM to 200 mM, 2.5 mM, 15 mM, 25 mM |

Solvents that may be used for the generation of EGA may be aqueous or non-aqueous. An aqueous, solvent-based, EGA reagent is set out in U.S. Pat. No. 6,093,302 is composed of a sodium phosphate buffer, pH 7.2. Additional aqueous buffers disclosed therein include acetate buffers, borate buffers, carbonate buffers, citrate buffers, HEPES buffers, MOPS buffers, phosphate buffers, TRIS buffers, and KI solutions.

Non-aqueous solvents (e.g., organic solvents) that may be used for the generation of EGA. Representative examples of solvents include methylene chloride, 1,1,1-trichloroethane, 1,1,2-trichloro-1,2-difluoroethane, 1,1,2-trichloroethane, 1,4-dichlorobenzene, 1-butanol, dimethyl sulfoxide, 1-hexene, 1-propanol, 2-(2-butoxyethoxy) ethyl acetate, 2-butoxyethanol acetate, 2-butoxyethyl acetate, 2-ethoxyethanol acetate, 2-ethoxyethanol, triethylene glycol, 2-methoxyethanol acetate, 2-methoxyethanol, 2-methylhexane, 2-nitropropane, acetone alcohol, acetone, acetonitrile, allyl alcohol, benzene, ethylbenzene, ethylene glycol, formamide, furfural, n-methoxynonafluorobutane, n-methylpyrrolidone, n-nonane, n-octane, n-octyl alcohol, n-butyl acetate, n-pentane, n-propyl acetate, n-propyl alcohol, ortho-dichlorobenzene, perchloroethene, propylene glycol diacetate, propylene glycol, t-amyl alcohol, t-butyl alcohol, tetrahydrofuran, toluene, trans-1,2-dichloroethylene, trichloroethene, trichloroethylene, trichloromethane, vinyl choloridediethylene glycol, dimethyl formamide, furfuryl alcohol, heptafluorocyclopentane, heptafluoropropyl methyl ether, heptane, hexachlorocyclohexane, hexane, isoamyl alcohol, isobutyl acetate, isobutyl alcohol, isobutyl isobutyrate, isomethoxynonafluorobutane, isomethoxynonafluorobutane, isophorone, isopropyl acetate, iso-propyl alcohol, methanol, methoxy propyl acetate, methyl amyl ketone, methyl chloride, methyl chloroform, methyl ethyl ketone, methyl glycol acetate methyl isobutyl ketone, nitrobenzene, nitromethane, dipropylene glycol, ethanol, ethyl acetate, ethyl benzene, ethyl ether, ethyl glycol acetate, ethyl glycol, benzyl chloride, biphenyl, diacetone alcohol, dibromomethane, dichlorodiphenyltrichloroethane, dichloroethene, diethyl ether, cycloheptane, cyclohexane, cyclohexanol, cyclohexanone, cyclononane, cyclooctane, cyclopentane, chlorobenzene, chlorobromomethane, methyl propyl ketone, monochlorotoluene, n-amyl alcohol, n-butyl acetate, n-butyl alcohol, n-decane, cyclodecane, and xylene, and combinations thereof.

In some instances, EGA reagents of the invention may contain an alcohol and/or a glycol. Alcohols and glycols that may be used in such reagents include 2-ethoxyethanol acetate, 2-ethoxyethanol, 2-methoxyethanol acetate, 2-methoxyethanol, 1-butanol, 2-butoxyethanol acetate, dimethyl ethanol amine, dipropylene glycol, ethanol, ethyl glycol acetate, ethyl glycol, ethylene glycol, methanol, ethanol, propanol, isobutanol, acetone alcohol, allyl alcohol, cyclohexanol, diacetone alcohol, diethanol amine, diethylene glycol, furfuryl alcohol, isoamyl alcohol, isopropyl alcohol, n-amyl alcohol, n-butyl alcohol, n-octyl alcohol, n-propyl alcohol, propylene glycol diacetate, propylene glycol, t-amyl alcohol, t-butyl alcohol, triethanolamine, and triethylene glycol. In some instances, EGA reagents may contain two or more alcohols or glycols.

In some instances, EGA reagents of the invention may contain one or more salt (e.g., an organic salt). Salts that may be used in such reagents include 1,3-dimethyl-imidazolium bis(pentafluoroethyl)phosphinate, 1,3-dimethyl-imidazolium methyl sulfate, 1,3-dimethyl-imidazolium trifluoromethanesulfonate, 1-butyl-3-methyl-imidazolium 2-(2-methoxyethoxy)ethyl sulfate, 1-butyl-3-methyl-imidazolium bis(trifluoromethyl)imide, 1-butyl-3-methyl-imidazolium cobalt tetracarbonyl, 1-butyl-3-methyl-imidazolium dicyanamide, 1-butyl-3-methyl-imidazolium hexafluorophosphate, 1-butyl-3-methyl-imidazolium methyl sulfate, 1-butyl-3-methyl-imidazolium octylsulfate, 1-butyl-3-methyl-imidazolium tetrafluoroborate, 1-butyl-3-methyl-imidazolium tosylate, 1-benzyl-3-methyl-imidazolium hexafluoroantimonate, 1-benzyl-3-methyl-imidazolium hexafluorophosphate, 1-benzyl-3-methyl-imidazolium methylsulfate, 1-benzyl-3-methyl-imidazolium tetrafluoroborate, 1-benzyl-3-methyl-imidazolium trifluoromethanesulfonate, 1-butyl-1-methyl-pyrrolidinium bis(trifluoromethylsulfonyl)imide, 1-ethyl-2,3-dimethyl-imidazolium trifluoromethanesulfonate, 1-ethyl-3-methyl-imidazolium bis(pentafluoroethyl)phosphinate, 1-ethyl-3-methyl-imidazolium bis(pentafluoroethylsulfonyl)imide, 1-ethyl-3-methyl-imidazolium bis(trifluoromethyl)imide, 1-ethyl-3-methyl-imidazolium bis(trifluoromethylsulfonyl)imide, 1-butyl-1-methyl-pyrrolidinium dicyanamide, tetrabutylammonium hexafluorophosphate, tetraethylammonium p-toluenesulfonate, 1,1-dibutyl-pyrrolidinium bis(trifluoromethylsulfonyl)imide, 1,1-dimethyl-pyrrolidinium tris(pentafluoroethyl)trifluorophosphate, 1,1-dipropyl-pyrrolidinium bis(trifluoromethylsulfonyl)imide, 1,2-dimethyl-3-propylimidazolium bis(trifluoromethylsulfonyl)imide, 1,2-dimethyl-3-propylimidazolium tris(trifluoromethylsulfonyl)methide, 1-butyl-1-methyl-pyrrolidinium hexafluoroantimonate, 1-butyl-1-methyl-pyrrolidinium hexafluorophosphate, 1-butyl-1-methyl-pyrrolidinium methylsulfate, 1-butyl-1-methyl-pyrrolidinium tetracyanoborate, 1-butyl-1-methyl-pyrrolidinium tetrafluoroborate, 1-butyl-1-methyl-pyrrolidinium trifluoromethanesulfonate, 1-butyl-1-methyl-pyrrolidinium tris(pentafluoroethyl)trifluorophosphate, 1-butyl-2,3-dimethyl-imidazolium hexafluoroantimonate, 1-butyl-2,3-dimethyl-imidazolium hexafluorophosphate, 1-butyl-2,3-dimethyl-imidazolium methylsulfate, 1-butyl-2,3-dimethyl-imidazolium tetrafluoroborate, 1-butyl-2,3-dimethyl-imidazolium tosylate, 1-butyl-2,3-dimethyl-imidazolium trifluoromethanesulfonate, 1-butyl-3-ethyl-imidazolium trifluoromethanesulfonate, 1-butyl-3-methyl-imidazolium trifluoroacetate, 1-butyl-3-methyl-imidazolium trifluoromethane sulfonate, 1-butyl-3-methyl-pyridinium bis(trifluoromethylsulfonyl)imide, 1-butyl-4-methyl-pyridinium hexafluorophosphate, 1-butyl-4-methyl-pyridinium tetrafluoroborate, 1-butyl-imidazolium hexafluorophosphate, 1-butyl-imidazolium tetrafluoroborate, 1-butyl-imidazolium tosylate, 1-butyl-imidazolium trifluoromethanesulfonate, 1-ethyl-1-methyl-pyrrolidinium bis(trifluoromethyl)imide, 1-ethyl-1-methyl-pyrrolidinium hexafluoroantimonate, 1-ethyl-1-methyl-pyrrolidinium hexafluorophosphate, 1-ethyl-1-methyl-pyrrolidinium methylsulfate, 1-ethyl-1-methyl-pyrrolidinium tetrafluoroborate, 1-ethyl-1-methyl-pyrrolidinium trifluoromethanesulfonate, 1-ethyl-2,3-dimethyl-imidazolium hexafluoroantimonate, 1-ethyl-3-methyl-imidazolium tosylate, 1-ethyl-3-methyl-imidazolium trifluoroacetate, 1-ethyl-3-methyl-imidazolium trifluoromethanesulfonate, 1-ethyl-3-methyl-imidazolium trifluoromethyltrifluoroborate, 1-hexyl-1-methyl-pyrrolidinium bis(trifluoromethylsulfonyl)imide, 1-hexyl-1-methyl-pyrrolidinium dicyanamide, 1-hexyl-2,3-dimethyl-imidazolium tetrafluoroborate, 1-hexyl-2,3-dimethyl-imidazolium trifluoromethanesulfonate, 1-hexyl-3-methyl-imidazolium bis(trifluoromethylsulfonyl)imide, 1-hexyl-3-methyl-imidazolium bis(trifluoromethylsulfonyl)methane, 1-hexyl-3-methyl-imidazolium dicyanamide, 1-hexyl-3-methyl-imidazolium hexafluoroantimonate, 1-hexyl-3-methyl-imidazolium hexafluorophosphate, 1-hexyl-3-methyl-imidazolium methylsulfate, 1-hexyl-3-methyl-imidazolium tetracyanoborate, 1-ethyl-2,3-dimethyl-imidazolium hexafluorophosphate, 1-ethyl-2,3-dimethyl-imidazolium methylsulfate, 1-ethyl-2,3-dimethyl-imidazolium tetrafluoroborate, 1-ethyl-2,3-dimethyl-imidazolium tosylate, 1-ethyl-3-methyl-imidazolium bis[1,2-benzenediolato(2-)-O,O']-borate, 1-ethyl-3-methyl-imidazolium bis[oxalato(2-)]-borate, 1-ethyl-3-methyl-imidazolium cobalt tetracarbonyl, 1-ethyl-3-methyl-imidazolium dicyanamide, 1-ethyl-3-methyl-imidazolium hexafluoroantimonate, 1-ethyl-3-methyl-imidazolium hexafluorophosphate, 1-ethyl-3-methyl-imidazolium nitrate, 1-ethyl-3-methyl-imidazolium tetrafluoroborate, 1-hexyl-3-methyl-imidazolium tris(heptafluoropropyl)trifluorophosphate, 1-hexyl-3-methyl-imidazolium tris(pentafluoroethyl)trifluorophosphate, 1-hexyl-3-methyl-imidazolium tris(pentafluoroethyl)trifluorophosphate, 1-hexyl-3-methyl-imidazolium tetrafluoroborate, 1-hexyl-3-methyl-imidazolium trifluoromethanesulfonate, 1-methyl-3-(3,3,4,4,5,5,6,6,7,7,8,8-tridecafluorooctyl)-imidazolium-hexafluorophosphate, 1-methyl-3-octyl-imidazolium tetrafluoroborate, 1-methyl-imidazolium hexafluorophosphate, 1-octyl-3-methyl-imidazolium bis(trifluoromethylsulfonyl)imide, 1-octyl-3-methyl-imidazolium bis(trifluoromethylsulfonyl)methane, 1-octyl-3-methyl-imidazolium hexafluoroantimonate, 1-pentyl-3-methyl-imidazolium tris(nonafluorobutyl)trifluorophosphate, 1-pentyl-3-methyl-imidazolium tris(pentafluoroethyl)trifluorophosphate, 1-phenylpropyl-3-methyl-imidazolium hexafluoroantimonate, 1-phenylpropyl-3-methyl-imidazolium trifluoromethanesulfonate, 1-tetradecyl-3-methyl-imidazolium tetrafluoroborate, 3-ethyl-N-butyl-pyridinium hexafluoroantimonate, 3-ethyl-N-butyl-pyridinium hexafluorophosphate, 3-ethyl-N-butyl-pyridinium tetrafluoroborate, 3-ethyl-N-butyl-pyridinium trifluoromethanesulfonate, 1-methyl-imidazolium tetrafluoroborate, 1-methyl-imidazolium tosylate, 1-methyl-imidazolium trifluoromethanesulfonate, 1-octadecyl-3-methyl-imidazolium bis(trifluoromethylsulfonyl)imide, 1-octadecyl-3-methyl-imidazolium hexafluorophosphate, 1-octyl-1-methyl-pyrrolidinium bis(trifluoromethylsulfonyl)imide, 1-octyl-3-methyl-imidazolium hexafluorophosphate, 1-octyl-3-methyl-imidazolium methylsulfate, 1-octyl-3-methyl-imidazolium tetrafluoroborate, 3-methyl-1-propyl-pyridinium bis(trifluoromethylsulfonyl)imide, 3-methyl-N-butyl-pyridinium hexafluoroantimonate, 3-methyl-N-butyl-pyridinium hexafluorophosphate, 3-methyl-N-butyl-pyridinium methylsulfate, 3-methyl-N-butyl-pyridinium tetrafluoroborate, 3-methyl-N-butyl-pyridinium trifluoromethanesulfonate, 4-methyl-N-butyl-pyridinium hexafluorophosphate, 4-methyl-N-butyl-pyridinium tetrafluoroborate, benzyl triphenyl-phosphonium bis(trifluoromethyl)imide, bis(trifluoromethylsulfonyl)imide, bis-tetramethyl ammonium oxalate, butyl dimethyl imidazolium hexafluorophosphate, dimethyl distearyl ammonium bisulfate, dimethyl distearyl ammonium methosulfate, ethyl triphenyl phosphonium acetate, N-butyl-pyridinium trifluoromethanesulfonate, N-hexyl-pyridinium bis(trifluoromethylsulfonyl)imide, guanidinium trifluoromethanesulfonate, guanidinium tris(pentafluoroethyl)Trifluorophosphate, hexamethyl-guanidinium trifluoromethanesulfonate, hexamethyl-guanidinium tris(pentafluoroethyl)trifluorophosphate, N,N,N',N',N''-pentamethyl-N''-isopropyl-guanidinium trifluoromethanesulfonate, N,N,N',N'-tetramethyl-N''-ethyl-guanidinium trifluoromethanesulfonate, N,N,N',N'-tetramethyl-N''-ethyl-guanidinium tris(pentafluoroethyl)trifluorophosphate, N-butyl-pyridinium bis(trifluoromethyl)imide, N-butyl-pyridinium hexafluoroantimonate, N-butyl-pyridinium hexafluorophosphate, N-butyl-pyridinium methylsulfate, N-butyl-pyridinium tetrafluoroborate, N,N,N',N',N''-pentamethyl-N''-isopropyl-guanidinium tris(pentafluoroethyl)trifluorophosphate, N,N,N',N',N''-pentamethyl-N''-propyl-guanidinium trifluoromethanesulfonate, N-hexyl-pyridinium bis(trifluoromethylsulfonyl)methane, O-ethyl-N,N,N',N'-tetramethyl-isouronium trifluoromethanesulfonate, O-ethyl-N,N,N',N'-tetramethyl-isouronium tris(pentafluoroethyl)trifluorophosphate, O-methyl-N,N,N',N'-tetramethyl-isouronium trifluoromethanesulfonate, tetraethyl ammonium tris(pentafluoroethyl)trifluorophosphate, tetramethyl ammonium bis(trifluoromethyl)imide, tetramethyl ammonium bis(trifluoromethylsulfonyl)imide, tetramethyl ammonium bis[oxalato(2-)]-borate, tetramethyl ammonium bis[salicylato(2-)]borate, tetramethyl ammonium hexafluorophosphate, tetramethyl ammonium tetrafluoroborate, tetramethyl ammonium tris(pentafluoroethyl)trifluorophosphate, tributylethyl ammonium ethylsulfate, trihexyl(tetradecyl)-phosphonium bis(2,4,4-trimethylpentyl)phosphinate, trihexyl(tetradecyl)-phosphonium bis(trifluoromethylsulfonyl)imide, trihexyl(tetradecyl)-phosphonium bis(trifluoromethylsulfonyl)methane, N-hexyl-pyridinium hexafluorophosphate, N-hexyl-pyridinium tetrafluoroborate, N-hexyl-pyridinium trifluoromethanesulfonate, N-octyl-pyridinium bis(trifluoromethylsulfonyl)imide, N-octyl-pyridinium tris(trifluoromethylsulfonyl)methane, O-methyl-N,N,N',N'-tetramethyl-isouronium tris(pentafluoroethyl)trifluorophosphate, S-ethyl-N,N,N',N'-tetramethyl isothiouronium trifluoromethanesulfonate, S-ethyl-N,N,N',N'-tetramethylisothiouronium tris(pentafluoroethyl)trifluorophosphate, S-ethyl-N,N,N',N'-tetramethylthiouronium tetrafluoroborate, tetrabutyl ammonium bis(trifluoromethyl)imide, tetrabutyl ammonium bis(trifluoromethylsulfonyl)imide, tetrabutyl ammonium hydrogen sulfate, tetrabutyl ammonium hexafluorophosphate, tetrabutyl ammonium nitrate, tetraethyl ammonium bis(trifluoromethyl)imide, tetraethyl ammonium bis(trifluoromethylsulfonyl)imide, tetrabutyl ammonium perchlorate, tetrabutyl ammonium sulfate, tetrabutyl ammonium tetracyanoborate, tetrabutyl ammonium tetrafluoroborate, tetrabutyl ammonium tris(pentafluoroethyl)trifluorophosphate, tetrabutyl phosphonium acetate, tetrabutyl phosphonium bis(trifluoromethyl)imide, tetrabutyl phosphonium bis[1,2-benzenediolato(2-)-O,O']-borate, tetrabutyl phosphonium bis[oxalato(2-)]-borate, tetrabutyl phosphonium tetracyanoborate, tetrabutyl phosphonium tris(pentafluoroethyl)trifluorophosphate, tetraethyl ammonium bis[1,2-benzenediolato(2-)-O,O']-borate, tetraethyl ammonium bis[2,2'-biphenyldiolato(2-)-O,O']-borate, tetraethyl ammonium bis[malonato(2-)]-borate, tetraethyl ammonium bis[salicylato(2-)]-borate, tetraethyl ammonium hexafluorophosphate, tetraethyl ammonium hydrogen maleate, tetraethyl ammonium tetrafluoroborate, tetraethyl ammonium tosylate, trihexyl(tetradecyl)-phosphonium bis[1,2-benzenediolato(2-)-O,O']-borate, trihexyl(tetradecyl)-phosphonium decanoate, trihexyl(tetradecyl)-phosphonium dicyanamide, trihexyl(tetradecyl)-phosphonium hexafluorophosphate, trihexyl(tetradecyl)-phosphonium tetracyanoborate, trihexyl(tetradecyl)-phosphonium tetrafluoroborate, trihexyl(tetradecyl)-phosphonium, tris(pentafluoroethyl)trifluorophosphate, and tri-iso-butyl(methyl)-phosphonium tosylate, and combinations thereof.

Buffering agents may comprise, for example, an organic base and may be present at concentration of from about 0.0001 mM to about 200 mM. Representative examples of organic bases include N,N-diisopropylethylamine, lutidine (dimethylpyridine isomers),

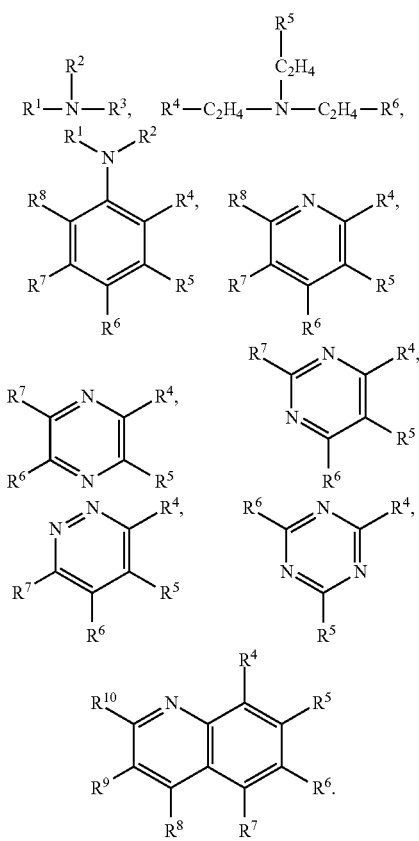

$R_1$, $R_2$, and $R_3$ are independently selected from the group consisting of hydrogen, and substituted and unsubstituted alkyl, alkenyl, alkynyl, cycloalkyl, cycloalkenyl, cycloalkynyl, aryl, heterocyclic ring, and polycyclic group, and halo, amide, carboxy, amino, secondary amino, tertiary amino, hydrazino, azido, alkazoxy, cyano, isocyano, cyanato, thiocyanato, fulminato, selenocyanato, carboxyamido, acylimino, nitroso, aminooxy, hydrazonoyl, oxime, acylhydrazino, amidino, sulfide, thiosulfoxide, sulfone, thiosulfone, thiosulfate, hydroxyl, formyl, hydroperoxy, carbamoyl, trimethyl silyl, nitro, nitroso, oxamoyl, pentazolyl, sulfamoyl, sulfenamoyl, sulfeno, sulfinamoyl, sulfino, sulfo, sulfoamino, hydrothiol, tetrazolyl, thiocarbamoyl, thiocarbazono, thiocarbodiazono, thiocarbonohydrazido, thiocarboxy, thioformyl, thioacyl, thiocyanato, thiosemicarbazido, thiosulfino, thiosulfo, thioureido, triazano, triazeno, triazinyl, trithiosulfo, and phosphoric acid ester.

$R_4$, $R_5$, $R_6$, $R_7$, $R_8$, $R_9$, and $R_{10}$ are independently selected from the group consisting of hydrogen, and substituted and unsubstituted alkyl, alkenyl, alkynyl, cycloalkyl, cycloalkenyl, cycloalkynyl, aryl, heterocyclic ring, and polycyclic group, and halo, amide, alkoxy, acyl, acyloxy, oxycarbonyl, alkoxycarbonyloxy, carboxy, amino, secondary amino, tertiary amino, hydrazino, azido, alkazoxy, cyano, isocyano, cyanato, thiocyanato, fulminato, selenocyanato, carboxyamido, acylimino, nitroso, aminooxy, carboximidoyl, hydrazonoyl, oxime, acylhydrazino, amidino, sulfide, sulfoxide, thiosulfoxide, sulfone, thiosulfone, thiosulfate, hydroxyl, formyl, hydroxyperoxy, hydroperoxy, peroxy acid, carbamoyl, trimethyl silyl, nitro, nitroso, oxamoyl, pentazolyl, sulfamoyl, sulfenamoyl, sulfeno, sulfinamoyl, sulfino, sulfo, sulfoamino, hydrothiol, tetrazolyl, thiocarbamoyl, thiocarbazono, thiocarbodiazono, thiocarbonohydrazido, thiocarboxy, thioformyl, thioacyl, thiocyanato, thiosemicarbazido, thiosulfino, thiosulfo, thioureido, triazano, triazeno, triazinyl, trithiosulfo, and phosphoric acid ester.

Acid generators and base generators, when present, may be any number of compounds, including quinone and non-quinone compounds. In some embodiments, hydroquinone and benzoquinone may be replaced with thiophenol, 1,4-butanedithiol, 1,3-propanedithiol, methylthiophene or another thiol. EGA reagents may contain from about 0.1 mM to about 2.0 M of thiophenol, 1,4-butanedithiol, 1,3-propanedithiol, methylthiophene, or other thiol, or a combination thereof. Other compounds, such as various quinone compounds may also be used. Examples of potentially useful compounds are 2-methylhydroquinone, methylhydroquinone, 2-t-butylhydroquinone, 2,5-di-t-butylhydroquinone, 2,6-di-t-butylhydroquinone, 2,6-dimethylhydroquinone, 2,3,5-trimethylhydroquinone, amylquinone, amyloxyhydroquinone, naphthoquinone, anthraquinone, 4-t-butylcatechol, 4,6-di-t-butylcatechol, 2,3,5,6-tetrachloro-1,4-benzoquinone, methylbenzoquinone, 2,6-dimethylbenzoquinone and various quinhydrones.

EGA reagents, also including hydroquinone and benzoquinone, with tetrabutylammonium hexafluorophosphate or tetraethylammonium paratoluolsulfanate in anhydrous acetonitrile are used to generate electrochemical acid via anodic oxidation to affect deprotection. Other EGA reagents include hydrazine; triphenylmethane derivatives; phenylenediamine; ascorbic acid; derivatives of hydroquinone benzoquinone, and substituted benzoquinones, including, but not limited to tetramethylbenzoquinone, methylhydroquinone, tertbutylhydroquinone, and ditertbutylhydroquinone; cathechols such as 3-methylcathechol and 4-methykcathechol; 1,3-dihydroxynaphthalene; tetracyanoquinodimethane; antrachinone; tetracyanoquinodimethane; iodine; N-halosuccinimides, such as N-chlorosuccinimide; alkyldisulfanes; and aromatic systems with nitrogen such as flavines. EGA reagents at a sufficient concentration to allow deprotection of the protecting group, such as a DMT protecting group, may be prepared and administered to the chip prior to the application of current to affect deprotection. For example, EGA reagents may be provided at a concentration of about 0.1 M to about 1 M, from about 0.5 M to about 5 M, from about 0.5 M to about 2 M, such as about 1 M, wherein the upper limit may depend on the solubility of the used reagents. In determination of the optimal parameters, it will generally be desirable to avoid base damage caused by depurination from over-exposure of DNA to acid.

Likewise, in certain embodiments, localized chemical reactions may occur through the production of photogenerated acid at a sufficient concentration to allow deprotection of the protecting group, such as a DMT protecting group. One aspect of the invention is that the pH of a solution may be changed by photo-generation of acids in a controlled fashion, as disclosed herein.

As used herein, the term photogenerated acid (PGA) refers to an acid that is produced from a PGA precursor reagent (PGAPR) after irradiation or illumination by photons having a certain wavelength. The wavelengths of the photons may be in any appropriate region of the electromagnetic spectrum, including, for example, infrared, visible, ultraviolet, or x-ray wavelengths. In certain embodiments, the wavelength may range from about 390 nm to about 700 nm, such as from about 400 nm to about 600 nm. In certain other embodiments, the wavelength may range from about 200 nm to about 400 nm, such as from about 250 nm to about 350 nm.

The PGAPR may be any chemical compound that produces PGA upon irradiation, for example irradiation with visible and/or ultraviolet light. Non-limiting examples of PGAPRs may include those disclosed in U.S. Pat. No. 6,426,184. For example, PGAPRs that may be used in accordance with various embodiments disclosed herein may include diazonium salts, perhalomethyl triazines, halobisphenyl A, sulfonates, imidylsulfonyl esters, diaryliodonium salts, sulfonium salts, diazosulfonate, and diarylsulfones.

In certain embodiments, the PGAPR may be present in a solution with at least one solvent. The at least one solvent can be any conventional solvent traditionally used in the chemical reaction, such as, for example, $CH_2Cl_2$, $CH_3CN$, toluene, hexane, $CH_3OH$, $H_2O$, and/or an aqueous solution comprising at least one solute, such as NaCl, $MgCl_2$, and phosphate salts. A solution comprising the PGAPR and the at least one solvent may then be irradiated or illuminated by photons having a certain wavelength, resulting in the generation of PGA.

In certain embodiments disclosed herein, the solution comprising the PGAPR and the at least one solvent may further comprise at least one of buffers, neutralizers, photo-sensitizers, stabilizers, and viscosity additives.

As used herein, photo-sensitizers may be defined as chemical compounds having a lower excitation energy than the PGAPR used in the solution. The photo-sensitizer may be excited by irradiation, and the excited photo-sensitizer thereby causes the PGAPR to generate the PGA. Thus, the photo-sensitizer may act to lower the required excitation wavelength for generating PGA. Non-limiting examples of suitable photo-sensitizers that may be used in embodiments disclosed herein include, for example, those disclosed in U.S. Pat. No. 6,426,184, such as anthracene and derivatives thereof, dicyanoanthracene, thioxanthone, chlorothioxanthenes, pyrene, benzophenone, acetophenone, benzoinyl C1-C12 alkyl ethers, benzoyl triphenylphosphine oxide, $Ru^{2+}$ complexes, and their derivatives.

According to certain exemplary embodiments disclosed herein, nucleotide linker molecules may be attached to a solid support, such as a bead, wherein each nucleotide may be protected at the 5'-OH end by an acid-labile protecting group. According to other exemplary embodiments disclosed herein, a universal linker molecule may be attached to the solid support, such as a bead. In certain embodiments, the acid-labile protecting group may be chosen, for example, from dimethoxytrityl (DMT) or methoxytrityl (MMT). In certain embodiments, the nucleotide is attached to a bead, and the bead is located in a well, such as, for example, the well of a multiwell plate.

The wells of the multiwell plate may then be contacted with the PGAPR solution and light, which acts to generate PGA. The PGA then subsequently deprotects the 5'-OH from the acid-labile protecting group. The deprotected 5'-OH groups may then react with a monomer, such as, for example, an additional nucleotide that is also protected at its 5'-OH end with an acid-labile protecting group. The process may then be repeated to grow the nucleic acid chain to the desired length.

Generally, no PGA will be generated in wells that are not exposed to light. Accordingly, a predetermined light pattern may be projected onto the wells of the multiwell plate such that only the beads in designated wells will be exposed to PGA and deprotection. The amount of light applied to each well and its duration will vary with parameters such as the amount of reagent to be generated and the size of the well. The light may define a series of pulses of varying frequency or a gradual increase/decrease in frequency. The frequency and duration of the pulse can be adjusted for the optimum generation of reagent. As an example, the light applied to a well may be adjusted for a specified period of time to generate a specified quantity of PGA. The amount of PGA intended for generation will typically be at least enough sufficient to fully catalyze deprotection of the nucleic acid molecules present.

In embodiments disclosed herein, the multiwell plate may, for example, be a microchip, such as a glass chip with wells comprising a photoresist polymer, such as, for example, SU-8 SUEX (available from by DJ DevCorp). In certain embodiments, the cover of the multiwell plate disclosed herein may be glass, and light may come from an optical semiconductor device, such as a digital micromirror device (DMD). In other exemplary embodiments disclosed herein, the multiwell plate may be a 454 sequencing chip available from Roche. For example, the multiwell plate could be a 454 sequencing chip comprising fiber optic bundles that can be used to direct light through fiber optics to the individual wells or set of wells on the sequencing chip. The microchip may have high density wells, which can capture beads of a size ranging, for example, from about 30 µm to about 40 µm. As one skilled in the art would appreciate, a 454 sequencing chip may be modified as necessary to suit embodiments of the invention disclosed herein.

The wavelength of light necessary for the generation of PGA may be produced by any optical system known in the art. An exemplary optical system may comprise, for example, a light source, at least one filter, at least one condenser lens, a reflector, a DMD, and a projection lens. In certain embodiments, the optical system may be chosen from fiber optic arrays, liquid-crystal displays (LCD), liquid crystal light valves, acousto-optic scanning light modulators (SLMs), Galvanometric laser scanners, and the like. In certain embodiments, use may be made of photomasks, for example photomasks having a computer-controlled spatial optical modulator as disclosed in U.S. Pat. No. 6,426,184.

The use of beads in combination with the deprotection of nucleotides by PGA may have advantages over the use of two-dimensional surfaces in nucleic acid molecule synthesis. For example, up to 1,000 times greater nucleic acid molecule concentration may be available with the use of a porous bead over a two-dimensional surface. Moreover, the use of beads may allow for the ability to separate (and subsequently release and pool together) only the beads belonging to a single desired fragment. The separation can be done by any feasible means, for example, by the methods disclosed herein; by optical forces, such as optical tweezers; generation of gas bubbles, generated for example through laser heating; micropipetting; acoustic force; etc. Further non-limiting exemplary methods for separating beads may be found in U.S. Published Patent Application No. 2010/0216648, incorporated herein by reference.

Electrowetting

In some aspects of the invention, "electrowetting" may be employed. Two aspect of the invention where electrowetting may be particularly useful is for the mixing of reagents for (1) nucleic acid synthesis and pooling (Modules 1 and 2) and (2) assembly (Module 3).

In brief, electrowetting involves modifying the surface tension of liquids on a solid surface using a voltage. Application of an electric field (e.g., alternating or direct), the contact angle between the fluid and surfaces can be modified. For example, by applying a voltage, the wetting properties of a hydrophobic surface can become increasingly hydrophilic and therefore wettable. Electrowetting principle is based on manipulating droplets on a surface comprising an array of electrodes and using voltage to change the interfacial tension. In some embodiments, the array of electrode is not in direct contact with the fluid. In additional embodiments, the array of electrode may be configured such as the support has a hydrophilic side and a hydrophobic side. The droplets subjected to the voltage will move towards the hydrophilic side. In some embodiments, the array or pattern of electrodes may be a high density pattern. When used in conjunction with the phosphoramidite chemistry (as well as other reagents), the array of electrodes should be able to move droplets volumes ranging from 1 pL (and less) to 10 pL. Accordingly, aspects of the invention relate to high voltage complementary semi-conductor microfluidic controller. In some embodiments, the high voltage complementary semi-conductor device (HV-CMOS) has an integrated circuit with high density electrode pattern and high voltage electronics. In some embodiments, the voltage applied is between 15V and 30V. Electrowetting methods are set out in U.S. Patent Publication No. 2012/0220497 A1, the disclosure of which is incorporated herein by reference.

Electrowetting works by using an electric voltage to alter the shape of a liquid drop. In some instances, electrowetting involves a sessile drop positioned on a dielectric-coated electrode. When current is applied, the drop flattens and flows out to the sides, thereby wetting additional surface. When current is removed, the drop returns to its original shape and retracts from the areas covered upon current application. Electrowetting methods are set out in the paper at the following URL: http://www.ll.mit.edu/publications/journal/pdf/vol17_no2/17_2_4Berry.pdf In some embodiments of the invention, nucleic acid synthesis site may have adjacent to is a series of reagents that flow into and recede from the synthesis site when current is applied to the correct reagent location. Thus, the invention includes methods for the synthesis of nucleic acid molecules by the addition and removal of reagents from a synthesis site induced by the addition and removal of current from adjacent reagents. In some instances, the number of reagents adjacent to a nucleic acid synthesis site may be from about 2 to about 10, from about 3 to about 10, from about 4 to about 10, from about 5 to about 10, from about 6 to about 10, etc.

Electrowetting methods may also be used for fragment assembly and error correction (Module 3). Thus, the invention includes methods for mixing reagents using electrowetting for the assembly and error correction of nucleic acid molecules. Reagents that may be contacted with nucleic acid molecules in these aspects of the invention include exonucleases, mist-match repair endonucleases (MMES), ligases, buffers, EDTA solutions, etc.

One problem with electrowetting methods is "splash over" which may occur between mixing areas and also because, in many instances, planar or semi-planar surfaces are used. Thus, unless microfluidic drainage channels, or the like, are employed, there is a possibility of splash over contamination of mixing areas during reagent changes.

Two means for minimizing this mixing is through the use of microfluidic channels and barriers. Barrier may be placed (e.g., physical barriers such as raised areas) to prevent reagents from moving from one mixing area to another. After a desired reaction is finished, the barrier may be removed. Different reactions may be performed sequentially at different and/or overlapping subsets of mixing areas.

As mentioned above, the methods of nucleic acid synthesis may be implemented and controlled in a system according to various embodiments described herein by a processor or computing system, such as the exemplary computing system depicted in FIG. 15. For example, applying current (pulse or continuous wave) to selected wells to generate a specific quantity of EGA to fully catalyze deprotection may be controlled by a computing system executing processor executable instructions according to various embodiments of the present teachings. Likewise, applying a light source to selected wells to generate a specific quantity of PGA may also be controlled by a computer system executing processor executable instructions.

Deblocking may also occur through the use of redox systems. Examples of such system systems include hydroquinone/anthraquinone; pH buffer such as 2,6-lutidine to reduce proton cross talk between active wells and inactive neighboring wells.

Efficient production of nucleic acid molecules may require that nucleic acid synthesis steps be tailored to the molecules being constructed. Consider the example of the construction of nucleic acid molecules designed for construction of viral genome with a CG/AT ratio of 60/40. Nucleic acid molecule building blocks of such a genome will invariable have more Cs and Gs than As and Ts. In such an instance, it may be desirable to have more reactions which add Cs and Gs than As and Ts. As an example, the sequence of base addition may be a repetition of A T C G C A T G C G (SEQ ID NO: 1). Thus, the invention further includes chemical synthesis processes which are tailored for efficient production of specified nucleic acid molecules. In one aspect, this entails adding bases to nucleic acid molecules during chemical synthesis in manner which reflects or closely approximates the prevalence of the bases in those molecules.

The invention includes, for example, methods which result in high fidelity, microscale production of nucleic acid molecules. Thus, the invention includes methods by which nucleic acid molecules are produced with the following parameters: between $1 \times 10^5$ and $5 \times 10^{12}$ copies of a nucleic acid molecule are generated with an average number of base mis-incorporations of between 1 base in 100 and 1 base in 4,000. The invention includes similar methods with the parameters set out in Table 7.

In some instances, all of the copies of a nucleic acid molecule will be produced on a single support (e.g., a single bead). In other instances, copies of a nucleic acid molecule will be produced on more than one single support (e.g., from about two to about 20, from about three to about 20, from about four to about 20, from about five to about 20, from about six to about 20, from about three to about 10, etc.). For purposes of the number of copies of a nucleic acid molecule and the number of base mis-incorporations, these numbers may be expressed as a function of copies of a nucleic acid molecule produced on a single support or as a function of all of the copies of a nucleic acid molecule produced in a synthesis run. For example, if one support is used to produce all of the copies of a nucleic acid molecule, then $1.0 \times 10^{11}$ molecules may be produced with an average error rate of 1 base in 310. As a second example, if two supports are used to produce the copies of the same nucleic acid molecule, then $1.0 \times 10^{11}$ molecules may be produced with an average error rate of 1 base in 300 on one support and $1.0 \times 10^{11}$ molecules may be produced with an average error rate of 1 base in 320 on the second support. In such an instance, $2.0 \times 10^{11}$ molecules may be produced with an average error rate of 1 base in 310.

TABLE 7

| Nucleic Acid Molecule Copies | No. of Base Mis-Incorporations (Avg.) |
|---|---|
| $1 \times 10^6$ and $1.5 \times 10^9$ | 1 in 150 to 1 in 500 |
| $1 \times 10^6$ and $1.5 \times 10^9$ | 1 in 150 to 1 in 400 |
| $1 \times 10^6$ and $1.5 \times 10^9$ | 1 in 100 to 1 in 300 |
| $1 \times 10^6$ and $1.5 \times 10^9$ | 1 in 200 to 1 in 400 |
| $1 \times 10^6$ and $1.5 \times 10^9$ | 1 in 300 to 1 in 1,000 |
| $1 \times 10^6$ and $1.5 \times 10^9$ | 1 in 300 to 1 in 2,000 |
| $1 \times 10^6$ and $1.5 \times 10^9$ | 1 in 500 to 1 in 4,000 |
| $1 \times 10^7$ and $1.5 \times 10^9$ | 1 in 150 to 1 in 500 |
| $1 \times 10^7$ and $1.5 \times 10^9$ | 1 in 150 to 1 in 400 |
| $1 \times 10^7$ and $1.5 \times 10^9$ | 1 in 100 to 1 in 300 |
| $1 \times 10^7$ and $1.5 \times 10^9$ | 1 in 200 to 1 in 400 |
| $1 \times 10^7$ and $1.5 \times 10^9$ | 1 in 300 to 1 in 1,000 |
| $1 \times 10^7$ and $1.5 \times 10^9$ | 1 in 300 to 1 in 2,000 |
| $1 \times 10^7$ and $1.5 \times 10^9$ | 1 in 500 to 1 in 4,000 |
| $1 \times 10^7$ and $1.5 \times 10^{10}$ | 1 in 150 to 1 in 400 |
| $1 \times 10^7$ and $1.5 \times 10^{10}$ | 1 in 100 to 1 in 300 |
| $1 \times 10^8$ and $1.5 \times 10^{10}$ | 1 in 150 to 1 in 400 |
| $1 \times 10^8$ and $1.5 \times 10^{10}$ | 1 in 100 to 1 in 300 |
| $1 \times 10^8$ and $1.5 \times 10^{10}$ | 1 in 200 to 1 in 400 |
| $1 \times 10^8$ and $1.5 \times 10^{10}$ | 1 in 300 to 1 in 1,000 |
| $1 \times 10^8$ and $1.5 \times 10^{10}$ | 1 in 300 to 1 in 2,000 |
| $1 \times 10^8$ and $1.5 \times 10^{10}$ | 1 in 500 to 1 in 4,000 |
| $1 \times 10^9$ and $1.5 \times 10^{12}$ | 1 in 300 to 1 in 1,000 |
| $1 \times 10^9$ and $1.5 \times 10^{12}$ | 1 in 300 to 1 in 2,000 |
| $1 \times 10^9$ and $1.5 \times 10^{12}$ | 1 in 500 to 1 in 4,000 |

Nucleic acid molecules prepared and used in accordance with the invention may contain modified nucleic acid molecules including locked nucleic acids (LNA), peptide nucleic acids (PNA), and the like. A PNA is a polyamide type of DNA analog, and the monomeric units for A, G, T, U, and C are available commercially. Furthermore, nucleic acid molecules of the invention may comprise one or more modified bases selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethyl aminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 8-azaguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, wybutoxosine, pseudouracil, queosine, inosine, 2-thiocytosine, 5-methyl-2-thiouracil, 2-thiouracil, 4-thiouracil, 5-methyluracil, uracil-5-oxyacetic acid methylester, 5-methyl-2-thiouracil, 3-(3-amino-3-N-2-carboxypropyl)uracil, and 2,6-diaminopurine. The latter modified base can form three hydrogen bonds when base-paired with dT and can increase the $T^m$ of short nucleic acid molecules by as much as 1-2° C. per insertion. This effect, however, is complex and is dependent on sequence context.

2-Aminopurine can substitute for dA in a nucleic acid molecule. It is a naturally fluorescent base that is sensitive to the local environment making it a useful probe for monitoring the structure and dynamics of DNA hairpins and for detecting the base stacking state of a duplex. 2-aminopurine can be destabilizing and slightly lower the $T^m$. 5-Bromo-deoxyuridine is a photoreactive halogenated base that can be incorporated into nucleic acid molecules to crosslink them to DNA, RNA or proteins with exposure to UV light. Other modified bases such as inverted dT may be incorporated at the 3'-end of a nucleic acid molecule, leading to a 3'-3' linkage which inhibits both degradation by 3' exonucleases and extension by DNA polymerases. In another embodiment of the invention an inverted dideoxy-T may be placed at the 5' end of a nucleic acid molecule to prevent unwanted 5' ligations. A dideoxy-C (ddC) 3' chain terminator may be used to prevent 3' extension by DNA polymerases. 5-Methyl deoxy-C when substituted for dC will increase the $T^m$ by as much as 0.5° C. per insertion. In one embodiment the naturally occurring base deoxy-Inosine may be used which is less destabilizing than mismatches involving the four standard bases. Thus, the invention provides, in part, compositions and methods relating to the synthesis of modified nucleic acid molecules with novel properties and/or functions.

One modification of the plate format, shown in FIGS. 2 and 2B, is to use a "liquid cover" to the wells. One way this could be performed is for the wells to contain a bilayer. For example, the bottom portion of the well containing the solid support could contain an EGA. Above this could be a lower density, optionally non-miscible, fluid. The lower density fluid layer will prevent or retard the diffusion of acid out of the desired well and over to an undesired well. Further, the lower density fluid can be positioned to make conductive contact with an upper electrode. One example of a commercially available "liquid coverslip" is sold by Ventana Medical Systems, Inc (cat. no. 650-010). This product is a solution used as a barrier between the aqueous reagents and the air, which prevents evaporation, and is designed to provide a stable aqueous environment for applications such as immunohistochemistry and in situ hybridization reactions.

One exemplary protocol for practicing methods of the invention is as follows. Porous silane-coated magnetic beads (MyOne Beads, Dynal) with a uniform diameter of 1 micron are added to the chip surface by controlled or pulsed flow to ensure uniform distribution of the beads across the microwells (about 1.3 μm diameter) on the chip and to ensure that a maximum number of wells are loaded with one bead. Wells not containing a bead are identified by a pre-synthesis current check that delineate the resistance difference among empty wells and well that contain a conductive magnetic bead.

A variety of chemistries are possible in the preparation of the bead surface. For example, a number of layers of silane can be produced to impart greater functional surface area to the beads. The silane coating(s) is/are prepared so that there is stable attachment of the hydroxyl functional group; typically through a trimethoxy or triethoxy silane linker, of the silane core to the naked silica bead surface to expose a primary hydroxyl group through with the initial amidite synthetic step is coupled. The fundamental chemistry, developed for a planar array surface electrode, for initiation and coupling in DNA synthesis can be found in Maurer et al., *Electrochemically Generated Acid and Its Containment to 100 Micron Reaction Areas for the Production of DNA Microarrays, PLoS ONE* 1(1): e34. doi:10.1371/journal.pone.0000034 (2006).

Fabrication of the chip: Electrode materials such, as iridium metal up to 50 nm thick are produced on oxidized high-resistivity silicon selected for high conductivity and chemical stability under synthesis, reagent addition and deblocking conditions. Electrodes are connected by ultrasonic bonding to a printed circuit board to provide digitally controlled analogue integrated switch circuits activating electrodes chosen for deblocking a given well. Printed circuit boards are carefully aligned and bonded to the regular microwell structure to generate the synthesis chip. A cover plate providing and sealing the interior volume for reagents and a general complementary circuit electrode is bonded at the perimeter and over the upper surface of the microwell structure to complete the closed synthesis chip.

Conventional semiconductor or polymer material may be used for forming wells 200. For example, CMOS technology can be used to form wells of desired shape or size in the semiconductor material such as SiO or $SiO_2$. Depending on the desired application, electrodes 202 can be fabricated with wells 200 or separately.

Administration of nucleic acid synthesis (e.g., DNA synthesis) reagents to the chip can be performed by any number of means. For example, once the beads are loaded into the chip, a computing system controls a series of reagent additions and washings may be carried out to affect phosphoramidite DNA synthesis on the surface of the beads residing in the microwells of the chip. Processor-executable instructions may be employed which determine, for any given population of DNA sequences, the optimal order of DNA synthesis reagent additions and sequence of reagent additions and washing steps relative to volume/cost of reagents and time of a synthesis run. Furthermore, as mentioned above, controller or processor-controlled current to specific wells on the chip determine in which wells electrochemically generated acid may be produced and deprotection to activate the growing nucleic acid molecule on the bead in the well may be chemically prepared to couple the next amidite base added into the reaction vessel. A number of specific configurations of apparatus and components for administration of synthesis reagents and to ensure precise and controlled fluid administration are possible through an optimized development process. Phosphoramidite DNA synthesis steps, conditions and reagents using EGA to affect deprotection can be found in, for examples, Maurer et al., *Electrochemically Generated Acid and Its Containment to 100 Micron Reaction Areas for the Production of DNA Microarrays, PLoS ONE* 1(1): e34. doi:10.1371/journal.pone.0000034 (2006) and Egeland and Southern, *Electrochemically directed synthesis of oligonucleotides for DNA microarray fabrication, Nucleic Acids Research*, 33(14): e125 (2005).

While in many instances oligonucleotides may be produced using phosphoramidite synthesis chemistry, as well as variations thereof, other methods may also be used to produce oligonucleotides, including PCR, restriction enzyme digest, exonuclease treatment, or template-independent synthesis using a nucleotidyl transferase enzyme. Exemplary methods of template-independent synthesis using a nucleotidyl transferase enzyme are set out in U.S. Pat. No. 8,808,989. The nucleotidyl transferase enzyme (e.g., terminal deoxynucleotidyl transferase) is used to incorporate nucleotide analogs having an unmodified 3' hydroxyl and a cleavable protecting group. Because of the protecting group, synthesis pauses with the addition of each new base, whereupon the protecting group is cleaved, leaving a polynucleotide that is essentially identical to a naturally occurring nucleotide (i.e., is recognized by the enzyme as a substrate for further nucleotide addition). Thus, in certain embodiments, the invention includes methods in which oligonucleotides are produced by enzymatic reaction.

Nucleotide triphosphates (e.g., deoxynucleotide triphosphates) (NTPs) suitable for use with enzymatic oligonucleotide synthesis methods will have protecting groups that do not prevent the NTPs from being used by a nucleotidyl transferase as a substrate and can be efficiently removed to allow for addition to an oligonucleotide chain. Thus, in certain embodiments, the invention includes methods where nucleotide addition occurs via enzymatic reaction. In many instances, EGA will be generated as part of the deprotection process. Further, in certain instances, all or part of the oligonucleotide synthesis reaction may be performed in aqueous solutions.

One aspect of the present invention is the ability to the control the pH of the reaction environment. In certain embodiments, however, DNA degradation may occur due to the presence of strong acids, such as the EGA or PGA. It is known that the acid strength (which may be represented by the pKa value) has an effect on the depurination rate in that the lower the pKa (more acidic), the more significant the degradation of DNA by depurination. This may become obvious when comparing, for example, trichloroacetic acid (TCA) and dichloroacetic acid (DCA). Both TCA and DCA are used for DNA synthesis, but the depurination rate for 3% TCA (pKa=0.7) is about four times higher than the depurination rate for 3% DCA (pKa=1.5).

As disclosed herein, addition of a suitable molecule to act as a proton carrier may reduce the effect of DNA degradation by accepting protons from the EGA or PGA, thereby raising the pKa value of the solution. Any acceptable proton carrier may be used, including every electrochemically stable compound having a pKa ranging from about 0 to about 3. According to certain embodiments, the proton carrier may be at least one compound chosen from 2-chloro-6-methyl pyridine, diphenylamine, 2,2',2'-nitrilotriacetonitrile, pyridazine, urea, and malachite green. At the reaction site, the proton is released from the proton carrier with an optimized acid strength (pKa). This results in a reduction of DNA depurination, and consequently an increase in the quantity and/or quality of nucleic acid molecule synthesis.

Since a very weak acid may lead to long deprotection times, according to certain embodiments disclosed herein, the proton carrier may have a pKa of about 1. For example, 2-chloro-6-methylpyridine has a pKa value of about 0.72, and diphenylamine has a pKa value of about 0.78. By way of further examples, 2,2',2'-nitrilotriacetonitrile has a pKa value of about 1.1, pyridazine has a pKa value of about 2.1, urea has a pKa value of about 0.2, and malachite green has a pKa value of about 1.0.

In certain embodiments, the addition of a proton carrier, such as 2-chloro-6-methylpyridine, for example, may reduce the DNA degradation by at least about 15%, at least about 20%, or at least about 25%.

Using the above-disclosed proton carriers may result in a cost-efficient and simple method to enhance oligonucleotide quality and quantity for EGA-based and/or PGA-based methods.

In certain embodiments of the invention the nucleic acid molecule or a portion thereof may be subject to a sequence optimization process prior to synthesis. Different computational approaches for sequence modification are known in the art and may be employed to optimize a given nucleotide sequence in terms of 1) efficient assembly and/or 2) improved performance in a given host. To design a nucleotide sequence for optimal assembly, a full-length sequence may be broken down into a defined number of smaller fragments with optimal hybridization properties by means of an algorithm taking into account parameters such as melting temperature, overlap regions, self-hybridization, absence or presence of cloning sites and the like. In certain aspects of the invention, at least part of the desired nucleic acid sequence may encode a polypeptide or protein. In such cases, it may be desirable to optimize the open reading frame for improved performance in a given homologous or heterologous host, such as expression yield or solubility. An increase in gene expression may be achieved, for example, by replacing non-preferred or less preferred codons by preferred codons or by increasing the number of CpG dinucleotides in the open reading frame as described, for example, in U.S. Pat. Nos. 5,786,464 and 6,114,148 and U.S. Patent Publication No. 2009/0324546 AA, the disclosures of which are incorporated herein by reference.

In one specific embodiment, an optimized open reading frame may be combined with an algorithm to encrypt a secret message into the open reading frame as described in U.S. Patent Publication No. 2011/0119778 AA. Such message may allow the identification or tracking of certain synthetic nucleic acid molecules. In certain aspects of the invention, it may be desired to use an optimization strategy that takes into account multiple different parameters simultaneously including assembly—as well as expression-related sequence properties. One example of a comprehensive multiparameter approach that may be used in the current invention for optimized sequence design is the GENEOPTI-MIZER® technology described in U.S. Patent Publication No. 2007/0141557 AA, the disclosure of which is incorporated herein by reference. Thus, the invention provides in part aspects of optimal sequence design for downstream applications including assembly and expression strategies.

Module 2

After completion of a synthesis run on Module 1, support-associated (e.g., bead-associated) nucleic acid molecules may be subject to post-processing in Module 2. Processes performed in Module 2 may be performed manually or by computer directed automation controlling such steps as picking and pooling of a bead (e.g., a magnetic bead) from the synthesis microwell array and vapor-phase cleavage and deprotection to prepare the nucleic acid molecules for subsequent assembly steps, as appropriate.

To expose a microwell array of bead-attached nucleic acid molecules, the cover of the synthesis well, when present, may be removed. In one embodiment, the cover is removed by automatic means in a computer-controlled manner.

Depending on the application and the number of nucleic acid molecules to be assembled, all of the beads of the microwell array may be pooled or only a subset of the beads. When only a subset of the beads are pooled or when the total number of beads is limited, the number of beads pooled may vary widely and include from about 10 to about 50, from about 50 to about 100, from about 100 to about 1000, from about 50 to about 10,000, from about 100 to about 10,000, or from about 500 to about 10,000 individual beads. These beads may be deposited in any suitable container. One example of a container is the well of a microwell plate (e.g., a well of a 1536 microwell plate).

A. Magnetic Pooling Mechanisms

In instances where magnetic beads are used, a bead picking instrument comprising, for example a precision-controlled electro-micromagnet can be programmed and controlled to extract and pool individual beads harboring synthesized nucleic acid molecules.

Automation suitable use with the invention includes a precision-controlled electro-micromagnet picks up the first bead and deposits it into a pooling well (i.e., a well which contains multiple beads for collection of nucleic acid molecules sought to be used in combination). Alternatively, a precision-controlled electro-micromagnet can be used which picks up the first bead and then moves in the X-Y direction to the next position, lowers down in the Z direction to pick up the second bead, back up in the Z direction to get out of the magnetic field range, moves to the third well in the X-Y direction, etc. Thus, the magnet is left "on" and the set of beads (e.g., from about two to about fifty, from about ten to about fifty, from about two to about one hundred, from about ten to about one hundred, from about twenty to about eighty, etc.) is picked up and carried as a string of beads. As a set of beads is collected, this set is then deposited in simultaneously deposited into a pooling well. Of course, multiple sets of beads may be collected and deposited in a single pooling well.

In some instances, beads may be extracted and pooled using systems as described, for example, in U.S. Patent Publication Nos. 2008/0281466 AA or 2008/0113361 AA or in U.S. Pat. Nos. 6,887,431; 7,347,975 or 7,384,606, the disclosures of which are incorporated herein by reference. In other embodiments of the invention a bead picking instrument with at least one integrated precision-controlled electro-micromagnet may be used. Such a picking instrument may be controlled by a control unit which can be programmed to control the movement of the micromagnet to align with specific microwells. In a further embodiment, the control unit may provide means to control the adjustment of the distance between the micromagnet and the microwell. In a specific embodiment, the micromagnet may be controlled and activated by electric means to allow extraction of single magnetic beads carrying a specific nucleic acid sequence.

Electro-micromagnets used in aspects of the invention where magnetic beads are used may be hollow magnets or needle shaped and will often be of a size and dimension to focus the magnetic field at its tip to allow for specific targeting of individual beads. In a specific embodiment, the micromagnet may be composed of an electro-magnet and a permanent magnet wherein the activity of the permanent magnet can be controlled by the electro-magnet. Electro-micromagnet used in conjunction with the invention may be in any number or format and may, for example, comprise a single magnet or be arranged together with other micromagnets in a row.

In certain embodiments of the invention, an electro-micromagnet may be used to extract and pool all magnetic beads contained in the microwells of a single arrays. For this purpose, the electro-micromagnet may be allocated to each microwell to extract the bead-attached nucleic acid molecules in a step-wise manner in a pre-defined or random order. In one embodiment, all nucleic acid molecules required for the assembly of a full-length construct may be synthesized on a single array. According to the amount of nucleic acid molecules required to build a full-length construct, arrays of different sizes and dimensions can be used.

In another embodiment, the electro-micromagnet may be programmed to target only a portion of the microwells of a specific array to extract and pool a predefined selection of bead-attached nucleic acid molecules. The electro-micromagnet can be programmed to extract and pool beads from the microwells of two or more different plates. The picking may combine full extraction of all beads of a first plate with selective extraction of a portion of beads obtained from a second plate. The first and the second plate may vary in size and dimension.

Each magnetic bead extracted by the micromagnet may then be transferred to a pooling station by moveable means of the picking instrument. In one embodiment the pooling station may contain a chamber with a microwell plate. In one embodiment the microwell plate may be a 1536 microwell plate. However, microwell plates of other sizes and dimensions (e.g., standard 96 well plates) are known in the art and can be used in the current invention. Defined fractions of nucleic acid molecules can be pooled in individual wells of a microwell plate wherein one pooled fraction contains all nucleic acid molecules required to assemble at least a defined fragment of a full-length construct. In one embodiment, an individual nucleic acid molecule pool may contain all nucleic acid molecules required to assemble a full-length construct. Different nucleic acid molecule pools allocated to each well can be further identified using a machine readable identifier disposed on the microwell plates.

B. Non-Magnetic Pooling Mechanisms

Electrostatic forces may also be used to remove beads and other substrates from synthesis platforms. Using FIGS. 2A and 2B for purposes of illustration, oligonucleotide synthesis substrates (beads in this instance) may have an electrostatic charged and separated from association with a surface or well using an opposite charge. For example, if one or more beads shown in FIGS. 2A and 2B have a positive charge then the lower electrode may be used to generate a positive charge to repel the bead and force it from the well. Magnetic charges can also be used to achieve the same purpose. Residual magnetism may also be employed. In essence, residual magnetism is magnetism that remains in a material after being exposed to magnetic force. In many instances, magnetic substrates will be of small size. Thus, attraction of such substrates will typically not require strong magnetic fields. Residual magnetism may be present in the substrate a selection probe used to bind to the substrate or both. Further, charges may be used to selectively remove a subset of synthesis substrates from a synthesis platform.

Electrostatic forces for the removal of beads and other substrates from synthesis platforms can be readily calculated. Table 8 below assumes a relative homogeneous electrical field is present and that each bead acts as a single charge point. Nucleic acid molecules carry with them a charge which should be taken into consideration when charge is used to extrude a bead from a well. Further, charge need only be applied to wells that contain substrates with desired nucleic acid molecules (e.g., nucleic acid molecules for assembly into larger nucleic acid molecules.

TABLE 8

| Number of Strands | Charge per Strand (As) | Electrode Voltage (V) | Electrode Distance (m) |
|---|---|---|---|
| $1 \times 10^{11}$ | $1.6 \times 10^{-19}$ | 2 | $1.00 \times 10^{-5}$ |

| | | | Electrode Distance (μm) |
|---|---|---|---|
| | | | 10 |

| Point Charge (As) | Electric Field Strength (V/m) | Force N | |
|---|---|---|---|
| $1.6 \times 10^{-8}$ | 200000 | $3.2 \times 10^{-3}$ | |

| | Electric Field Strength (V/mm) | Force μN | |
|---|---|---|---|
| | 200 | 3200 | |

In another embodiment, a synthesis platform may contain a series of regions that separate from other regions of the synthesis platform. For example, a synthesis platform may contain 100 rows of synthesis areas in a square 10×10 arrangement. Further, the synthesis platform may be designed so that it is separable into ten rows of ten synthesis areas. For purposes of illustration, assume that one seeks to produce eight different assembled nucleic acid molecules and these assembled nucleic acid molecules are designed to be formed from the assembly of the following number of oligonucleotides:

TABLE 9

| Assembled Nucleic No. | No. of Oligos | Row No. | Assembled Molecule No. | No. of Oligos | Row No. |
|---|---|---|---|---|---|
| 1 | 7 | 1 | 5 | 9 | 5 |
| 2 | 8 | 2 | 6 | 10 | 6 |
| 3 | 8 | 3 | 7 | 13 | 7-8 |
| 4 | 9 | 4 | 8 | 15 | 9-10 |

Table 9 indicates the numerical designation of the various assembled nucleic acid molecules, the number of oligonucleotides that will be used to assemble the assembled nucleic acid molecules, and the rows in which the oligonucleotides are synthesized in. In this embodiment, rows 1-5 will each have at least one synthesis area in which no oligonucleotides will be produced.

After synthesis is completed, the separable rows may be separated and the synthesized nucleic acid molecules, collected/processed and assembled, for example, as described elsewhere herein.

Figure 18:
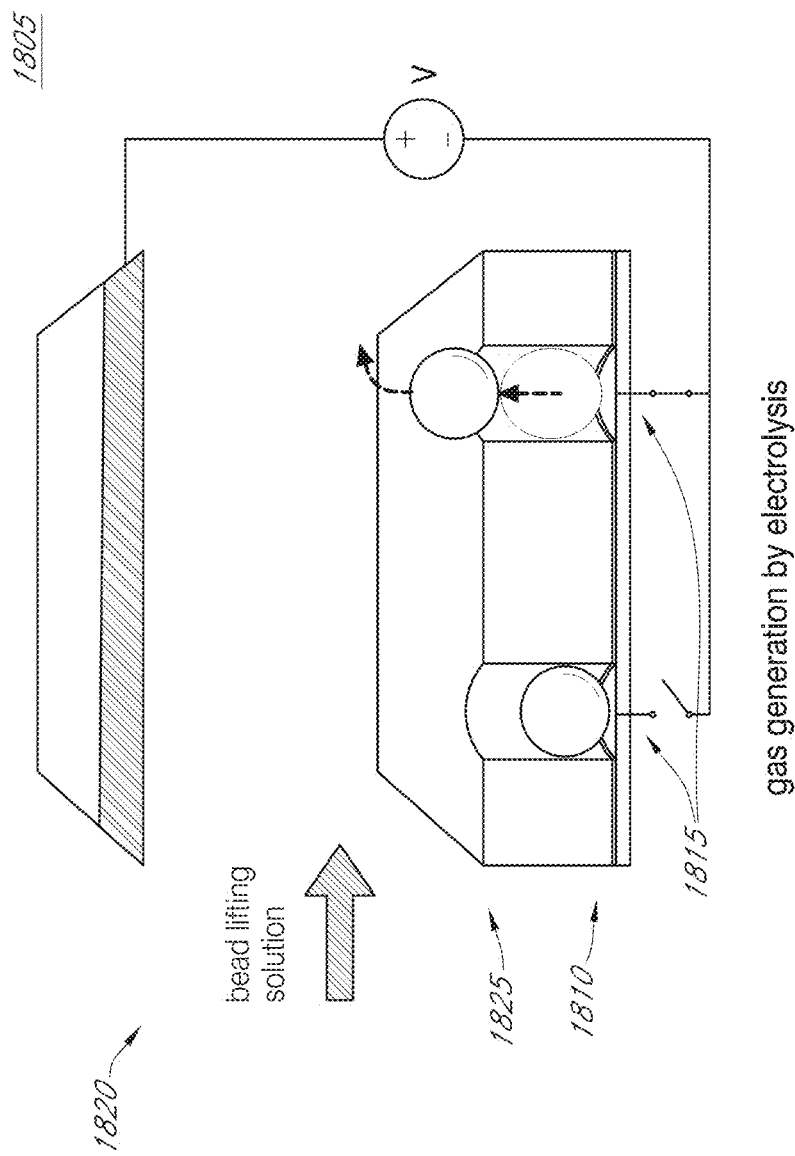
FIG. 18 shows a simplified example of a selective bead removal process from a synthesis chip using electrolysis according to methods of the invention.

In another aspect, electrolysis can be used to remove beads or other substrates from a synthesis platform. FIG. 18 shows a simplified example of a selective bead removal process from a synthesis chip 1805 using electrolysis according to the present teachings. For example, the synthesis chip 1805 can be a CMOS chip and can contain a plurality of microwells, such as microwell 1810. Each microwell also contains a first electrode 1815 (working electrode) formed at a bottom surface of the microwell and a second electrode 1820 (counter electrode). Each microwell is sized to accommodate a solid substrate, such as a bead 1825 and a volume of working fluid.

For example, electrode 1815 and 1820 can be similar to the electrodes that are discussed further below in relation to FIG. 9 and Table 11 and can be composed of any number of compounds, including platinum, palladium, copper, gold, aluminum, niobium, niobium oxide, tungsten, titanium, tantalum, molybdenum, nickel, platinum, silver, manganese, neodymium, carbon, and silicon, and an alloy material or a compound material containing one or more of the above-described elements, as well as other elements. A sufficiently high electrical potential difference is provided by a controller (not shown) between the electrode 1815 (working electrode) and electrode 1820 (counter electrode) to cause a current to flow in the fluid in the microwell and to produce an electrochemical reaction, e.g., electrolysis, resulting in the formation of one or more gas bubbles in the microwell.

For example, if the fluid is water, then about a 0.01V to about 10,000V, a 5V to about a 30V, or about 10V to about a 20V, or about a 15V to about a 30V, voltage can be applied to produce the electrochemical reaction. As the one or more gas bubbles expand and move toward the surface of the microwell 1810, the bead 1825 will also tend to rise. As a result, the volume of the fluid in the microwell 1810 is displaced and the bead 1825 is released from the microwell 1810 into a fluidic channel (not shown), for example in the direction indicated by the arrow in FIG. 18. A current controller, which could be the current controller discussed in relation to FIGS. 2A and 2B, can be used to control the amount of current applied to each electrode, which in turn can control the displacement of the beads from their respective wells. An increase of the current beyond a current threshold can result in potential loss of the bead during the bead removal process and/or heating of the fluid within each well. For example, current limit for one electrode can be multiplied by the number of active electrodes to yield the overall current limit that can be set by the current controller. The generation of the air bubbles generally occurs quickly, usually taking less than a second (although longer times may be used) for the bead to be displaced due to the rising of one or more gas bubbles, and is not dependent on the surface charge or other properties of the bead.

As noted herein, the generation of gas bubbles in microwell plates can be used as a method to remove beads from the respective well. Gas bubbles can be produced electrochemically in aqueous or non-aqueous buffers (e.g., water, NaCl dissolved in water and more complex non-aqueous buffers like 10 mL MeOH; 35 mL ACN; 1 M hydroquinone; 10 mM benzoquinone; 0.25M NEt4pTsO). The inherent properties of the buffer used can have significant implications on the efficiency or performance of the system. For example, the composition of the buffer can influence the surface tension of the bubbles produced. The surface tension is critical for the bubble movement in the well (retention potential). For an efficient removal of beads from a well it is desirable that both, beads and bubbles escape from the well (compared to the bubbles remaining in the well and disturbing the fluidic flow of the system). If the surface tension is too low, the generated bubbles will escape through the gap between well and bead without lifting the bead. If, however, the surface tension is too high, gas bubbles will stick tightly to the walls of the well, which may require additional treatment to remove the gas bubbles such as longer rinsing or rinsing with low surface tension solvents (such as e.g. methanol). Further, high surface tension may also result in beads sticking to gas bubble and not being released into the fluid stream. A favorable surface tension can be achieved by mixing organic solvents (e.g., acetonitrile, isopropanol) and aqueous solutions, preferable 50-90% organic solvents, more preferably, 60-70% organic solvent. The buffer can also be selected to avoid negative effects on the synthesis process. For example, acidic environment has the potential to damage the nascent oligonucleotide chain, and basic condition can promote premature cleavage of the oligonucleotide from the bead. Therefore, a buffered system can be used to avoid the generation of such an undesired condition. Although different buffer systems are available (e.g., HEPES, TRIS, carbonate or ammonium based buffers) a volatile buffer (e.g., ammonium sulfate) is preferred for the application in order to avoid undesired residues which might negatively influence other reaction steps.

In certain instances a lifting buffer may comprise water, tetraethylammonium-p-toluolsulfonat (NEt4pTsO), acetonitrile and methanol. In an exemplary embodiment a lifting buffer comprising 0.7 M (NEt4pTsO), 50% water, 30% methanol, and 20% acetonitrile can be used. This buffer has a high conductivity required for electrochemical generation of gas bubbles while its surface tension allows for efficient bead lifting and removal of bubbles from wells. Using this buffer, bead lifting can be achieved at a potential of >4.5 V. In certain embodiments a higher potential may be used for optimal bead lifting. For example, 8.5 V may be used without limiting the current. In a typical experiment a current of 20-60 mA may be observed for approximately 3,500 wells.

In certain embodiments, the displacement of one or more beads from the multiwell plate is controlled and programmed by computer directed automation. For example, when the synthesis chip 1805 is formed as the CMOS chip, each working electrode formed at the bottom of the microwells can be individually addressable, which allows the controller to selectively energize one or more working electrodes at a given time. Thus, one or more beads can be displaced from their respective microwells at the same time or about the same time to be subsequently collected for further processing and analysis.

For example, the synthesis chip 1805 can have a plurality of microwells, with each microwell having an associated working electrode. As discussed above, the number of wells in the multiwell plate may also vary widely and is limited by factors such as the amount of nucleic acid to be produced and technical factors such as manufacturability and mechanic factors related to use (e.g., the lower size limit of magnetic bead extractors).

The fluid in the microwell, as discussed further above in relation to the composition and concentration of EGA components, can include an aqueous or non-aqueous buffer solution. For example, the fluid can include relatively simple solutions, such as, water, NaCl dissolved in water, as well as more complex non-aqueous buffers like 10 mL methanol; 35 ml acetonitrile; 1 M hydroquinone; 10 mM benzoquinone; 0.25 M Net4pTsO).

Once the bead or other substrate is displaced from its corresponding microwell, the bead or other substrate can be collected by a bead collection device that can be programmed and controlled to extract and pool individual beads harboring synthesized nucleic acid molecules. Depending on the application and the number of nucleic acid molecules to be assembled, all of the beads of the microwell array may be pooled or only a subset of the beads.

Figures 19, 20:
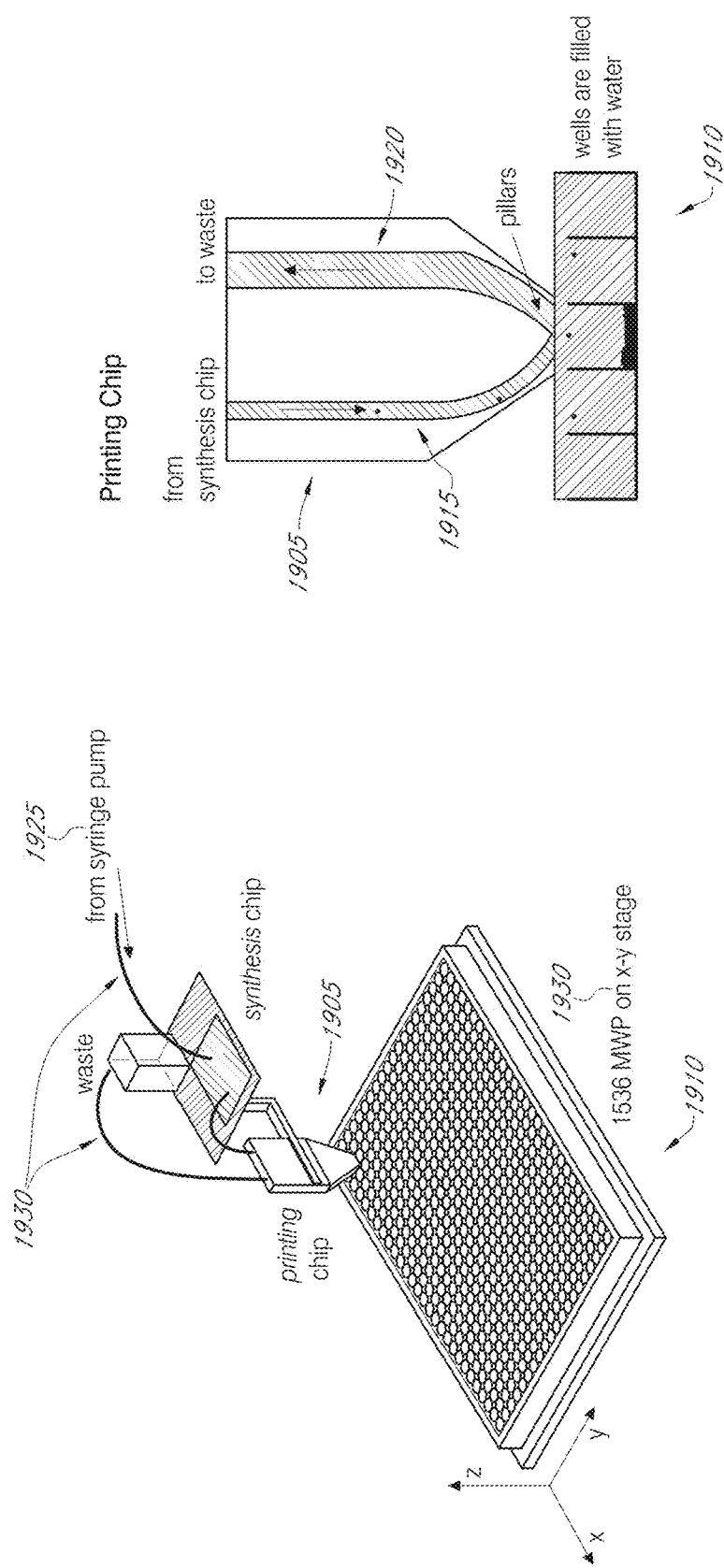
FIG. 19 shows an example bead collection process including a microfluidic or bead-collection device and a multiwell collection plate according to methods of the invention.
FIG. 20 shows the microfluidic or bead-collection device of FIG. 19 in greater detail.

By way of example, the bead or other substrate can be collected by a bead collection device 1905, as shown in FIG. 19, and in greater detail in FIG. 20, and placed into a multiwell plate 1910 or other suitable container for further processing and analysis. In this way, the bead collection device can be used to transfer one or more beads or other solid supports from the synthesis chip in an automated fashion to one or more wells of a multiwell collection plate or other suitable container for further processing. In addition, the bead collection device can be used to concentrate the beads or other substrates of similar sizes and dimensions (such as, e.g., vesicles or cells) into a smaller volume.

The bead collection device 1905 can include a first flow channel 1915 operable to allow the bead 1825 and associated fluid to flow in a first direction, e.g., downward, to be placed in a well of the multiwell plate 1910 or other suitable container. For example, due to gravity, the beads can fall into the selected well of the multiwell plate 1910 and be collected. The bead collection device 1905 can also include a second flow channel 1920 operable to allow fluid, e.g., waste fluid, to flow in a second direction, e.g., upward, opposite the first direction where it can be discarded. A pump 1925, e.g., a syringe pump, and associated tubing 1930 can be used to provide negative pressure, e.g. a vacuum, sufficient to cause the fluid to flow through the second flow channel 1920. The second flow channel 1920 may be equipped with a barrier or pillars to prevent beads from entering the second flow channel. In this way, the bead collection device can be used to collect and pool all of the beads from the synthesis platform having nucleic acid molecules that belong to one fragment. The pooled beads can be transferred to one or more wells of a multiwell plate or other suitable container for further processing, such as cleavage and deprotection to prepare the nucleic acid molecules for subsequent assembly steps as appropriate.

Each microwell of the multiwell plate 1910 can be sized to accommodate one or more beads. In one example, the multiwell plate 1910 can be supported by a moveable support structure 1930, e.g., a xyz stage, that is operable to be actuated in up to three degrees of freedom. This can allow the bead 1825 collected by the bead collection device to be transferred into a specific microwell on the multiwell plate 1910. Alternately, the bead collection device 1905 can be mounted on a moveable support structure that can allow the bead collection device 1905 to be actuated in up to three degrees of freedom. This process of using the bead collection device to transfer a bead or other substrate into a microwell plate can be performed manually or by computer directed automation.

In certain embodiments, the bead collection device 1905 can include an acoustic module and associated power and control circuitry (not shown) that can be operable to vibrate the bead collection device 1905 as a whole or selectively vibrate the first and/or second flow channels 1915, 1920 to facilitate the bead 1825 placement or the fluid removal. The bead collection device 1905 can also include a detector (not shown) operable to detect whether the oligo-bead 1825 has been removed from the bead collection device 1905.

Figure 21:
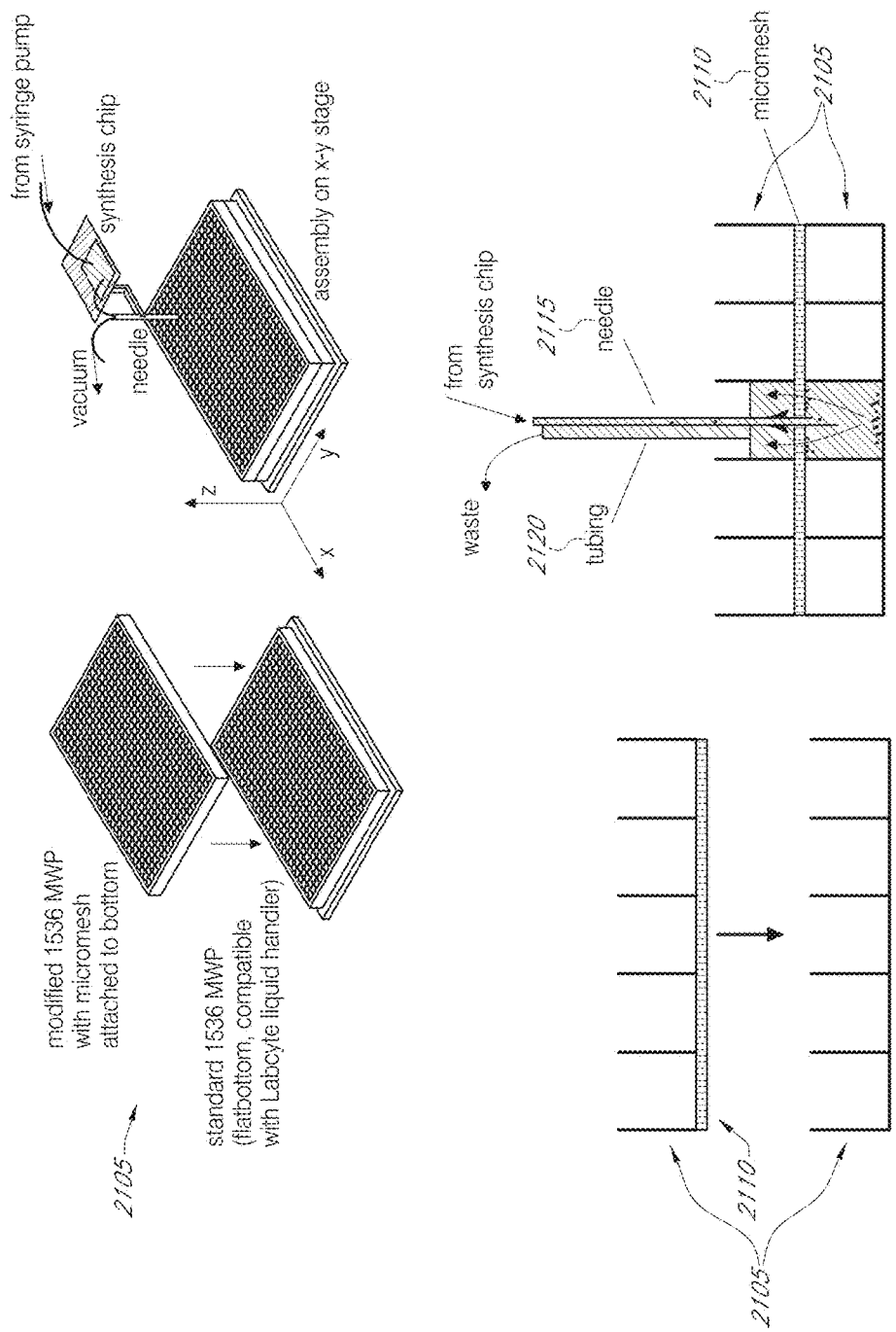
FIG. 21 shows another example multiwell collection plate according to the invention.

In one embodiment, the multiwell plate into which the bead is placed includes a fluid-permeable structure to facilitate bead placement into the multiwell plate and the concentration of the bead(s) into a smaller microwell volume. FIG. 21 shows another example multiwell plate 2105, according to the present teachings. The multiwell plate 2105 can include a fluid-permeable structure 2110 (such as, e.g., a micromesh) that can be attached, either permanently or non-permanently, to a top surface of the multiwell plate 2105. The fluid-permeable structure 2110 can be composed of a material that is permeable to fluid, and yet provides sufficient rigidity to hold one or more oligo-beads within a given well. The multiwell plate 2105 can also be composed of two multiwell plates separated by the fluid-permeable structure 2110. In one example, the multiwell plate is a standard 1536 well plate, as known in the art.

In the example of FIG. 21, a bead collection device, similar to the bead collection device 1905 as shown in FIG. 19, can include a needle or needle-like structure 2115 and associated tubing 2120 to place one or more beads in one or more wells of the multiwell plate 2105 as well to remove excess fluid from the multiwell plate 2105. The needle 2115 can be coupled to a moveable support structure, e.g., a xyz stage, to move the needle 2115 in one or more degrees of freedom to place the beads in the appropriate wells of the multiwell plate 2105. The needle 2115 can also have a needle-in-a-needle or needle-in-a-tube arrangement, such that a first needle is positioned inside a second needle or inside the tubing 2120. Alternatively, the first needle can be positioned adjacent to/parallel to a second needle or tubing 2120. For example, the first needle can be operable to deliver the beads to the multiwell plate 2105 and the second needle or tubing can be operable to remove excess fluid from the multiwell plate 2105. In such setting, the length of the first needle exceeds the length of the second needle or tubing such that in operation only the first needle gets into contact with the fluid-permeable membrane and the liquid volume contained between the fluid-permeable membrane and the bottom of the well, whereas the second needle or tubing gets in contact with the liquid volume contained between the fluid-permeable membrane and the top of the well. Also, the shape of the first and second needle may be the same or may be different. For example, the first needle may have a sharp or pointy end capable of puncturing through the fluid-permeable structure 2110, whereas the second needle or tubing may have a blunt end. Furthermore, the lumen of the first needle may be equal to or smaller than the lumen of the second needle or tubing. The lumen of the first needle should be of a dimension allowing one or more beads of a size as disclosed elsewhere herein and optionally loaded with oligonucleotides to smoothly pass through it into the well, whereas the lumen of the second needle or tubing should be of a dimension allowing excess liquid to be removed by vacuum from the well. Needles are available in a wide variety of outer diameters described by gauge numbers, wherein a smaller gauge number indicates a larger outer diameter. The inner diameter of a needle depends on both gauge and wall thickness. For purposes of illustration, the first needle may for example be a Hamilton® syringe with luer-lock and 25 or 26 gauge, whereas the second needle may be blunt with luer-lock and 17 gauge, 18 gauge or 19 gauge.

In operation, the needle 2115 can puncture through the fluid-permeable structure 2110 and beads that have been removed from the synthesis chip 1805 can be transferred into the multiwell plate 2105. The beads cannot escape the well of the multiwell plate 2105 because of the fluid-permeable structure 2110, while excess fluid can escape and is removed through the second needle or tubing by vacuum. This arrangement can reduce cross contamination between wells. If needed, the needle 2115 can now be washed and made ready for the next oligo-bead transport. After placing all of the beads into the multiwell plate 2105, a centrifugation step can be performed to ensure that the beads are at the bottom of the wells. Keeping the fluid-permeable structure 2110 on the top of the multiwell plate 2105 can also help with the gaseous deprotection of the nucleic acid molecules attached to the beads. After the deprotection, the multiwell plate 2105 can be opened and the bottom plate with the cleaved/deprotected nucleic acid molecule is ready for gene assembly reactions.

In other embodiments, rather than using a needle to puncture the fluid-permeable structure, pressure is applied to the top of a selected well in the multiwell collection plate, the pressure being sufficient to rupture the fluid-permeable structure and deliver one or more beads into the selected well of the multiwell collection plate. In certain embodiments, the pressure applied to rupture the fluid-permeable structure is between 0.1-50, 0.1-25, 0.1-20, 0.1-15, 0.1-10, 1-25, 1-20, 1-15, or 1-10 bar.

Figure 22:
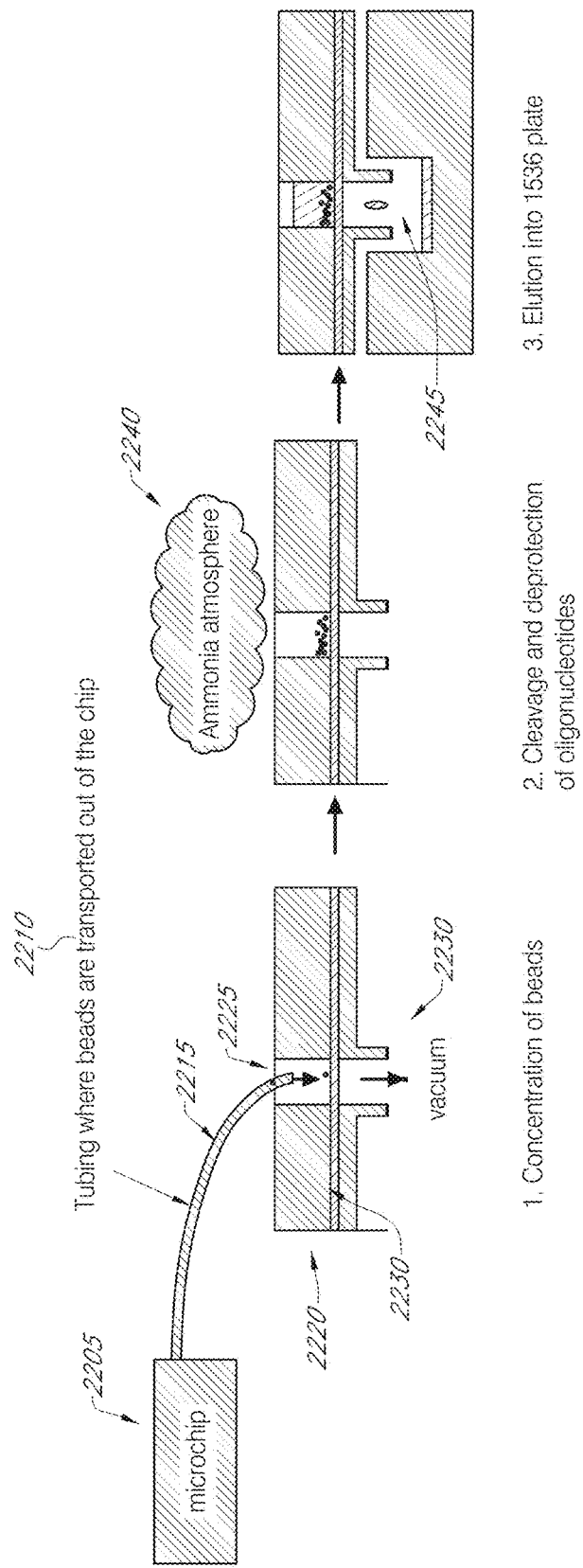
FIG. 22 shows an example process for bead removal from a synthesis chip, bead concentration in a multiwell collection plate comprising two tiers separated by a fluid-permeable structure, cleavage and deprotection of nucleic acids in the multiwell collection plate using, for example, ammonia atmosphere, and eluting the cleaved and deprotected nucleic acids into the bottom well of the multiwell collection plate using a system according to the invention.

In other embodiments, the oligonucleotides synthesized on the microchip can be pooled, concentrated, cleaved and deprotected on a fluid-permeable structure arranged on a top surface of or within a multiwell collection plate. The cleaved oligonucleotides can then be eluted into the well of a multiwell collection plate without having to puncture or otherwise rupture the fluid-permeable structure. FIG. 22 shows an exemplary system by which beads are collected from the synthesis microchip and pooled on a fluid-permeable structure arranged on a top surface of or within a multiwell collection plate. While the beads are retained on the fluid-permeable structure, the oligonucleotides on the beads are cleaved, deprotected, and eluted into a well of the microwell collection plate, in accordance with the present disclosure. Beads 2215 can be removed from the synthesis chip 2205 and collected, pooled, and concentrated, as shown at (1), into an individual well 2225 of the multiwell plate 2220, according to the various mechanisms discussed herein. A vacuum 2230 can be applied to direct the beads 2215 through one end of a fluid conduit 2210 into the well 2225 of the multiwell plate 2220. As discussed above in relation to FIG. 21, the multiwell plate 2220 can include a fluid-permeable structure 2230 either arranged on a top surface of or within the multiwell plate 2220. The fluid conduit 2210 can position the beads 2215 onto a top surface of the fluid-permeable structure 2230. Oligonucleotides can be cleaved from the beads 2215 and deprotected using, for example, an ammonia atmosphere 2240, as shown at (2). Once the oligonucleotides are cleaved and deprotected from the beads 2215, they can be eluted 2245 through the fluid-permeable structure 2230 and collected in the bottom of a well of the multiwell plate 2220, as shown at (3).

The frame of the multiwell collection plate 2220 can be composed of any suitable material, including, but not limited to, a polystyrene, polyethylene ("PE") or a polypropylene ("PP") material or cyclic olefin copolymer ("COC"), stainless steel, polytetrafluoroethylene ("PTFE") or polycarbonate, and can be solvent compatible. The multiwell collection plate 2220 can be covered on a top surface by a fluid-permeable structure 2230. The fluid-permeable structure 2230 can be composed of any suitable material, including, but not limited to, a polyethylene terephthalate ("PET"), polytetrafluoroethylene ("PTFE"), polypropylene ("PP") or a polyetheretherketone ("PEEK") material, that are fluid and gas permeable, but are able to hold the beads within the well 2225. For example, the fluid-permeable structure may be a polypropylene mesh. The mesh may be placed between two multiwell plates as indicated in FIG. 45B. To avoid lateral flow of liquids (and eluted oligonucleotides) between adjacent wells and/or fix the mesh within the multiwell plate, the mesh may be subject to heat treatment (e.g. on a hot plate) to melt and seal the material along the rim of the well protrusions of the upper and/or lower multiwell plate. The sealing process may be facilitated by applying pressure to the external surface of the upper and/or lower multiwell plate.

In one embodiment, a bead collection device may comprise a multiwell plate ("filter plate") with a fluid-permeable structure as discussed above and a coaxial needle assembly as shown in FIG. 45A. The needle assembly ensures fast pooling of beads into one or more wells of a filter plate. The needle or needle-like structure may be associated with tubing to place one or more beads in one or more wells of the filter plate. The needle can be coupled to a moveable support structure, e.g., a xyz stage, to move the needle in one or more degrees of freedom to place the beads in the appropriate wells of the filter plate. The needle can also have a needle-in-a-needle or needle-in-a-tube arrangement, such that a first needle is positioned inside a second needle or inside the tubing. Alternatively, the first needle can be positioned adjacent to/parallel to a second needle or tubing. For example, the first needle can be operable to deliver the beads to the filter plate and the second needle or tubing can be operable to provide a washing and/or elution buffer to rinse the beads collected in the filter plate and/or elute the oligonucleotides through the mesh. The needle assembly may be configured to allow for pooling and washing of beads at the same time. The chemical solution that is used for bead unloading by electrolysis preferably contains high concentrations of salt for high conductivity. The salt needs to be removed by washing with a suitable buffer (e.g. 50% acetonitrile, 50% water) before the nucleic acid molecules are cleaved and eluted from the beads. The simultaneous washing can be achieved by using, e.g., a needle-in-needle configuration wherein a first needle is connected with the microfluidic chip and configured to receive and place the beads into a pre-determined well of the microwell plate. The second needle can be connected with one or more reservoirs containing a washing and/or elution reagent and can be configured to transfer liquid from the reservoirs to the well containing pooled beads.

Once oligonucleotides have been cleaved from the beads and deprotected as described elsewhere herein, they can be eluted from the filter plate through the fluid-permeable mesh into a further multiwell plate arranged below the filter plate as illustrated by FIG. 45C. For this purpose, the filter plate may be moved (e.g., by means of an xyz-stage) from a first washing/purging position to a second elution position. The further multiwell plate may comprise wells of a size and dimension allowing alignment of a well of the filter plate with a well of the further multiwell plate such that oligonucleotides can be eluted simultaneously or subsequently from multiple wells of the filter plate into multiple aligned wells of the further multiwell plate. In certain instances, the protrusions of the lower filter plate may fit into the protrusions of the wells of the further multiwell plate. In other instances the protrusions of both plates may align exactly and be placed in contact with each other. The oligonucleotides may be eluted by centrifugal force or vacuum. For example the filter plate and further microwell plate may be arranged in a fixing device or frame holding both plates together during a centrifugation or vacuum step.

The multiwell collection plate, filter plate or further multiwell plate can comprise any appropriate number of wells. The most common multiwell plates have 96, 384, or 1536 wells. In certain embodiments, the multiwell collection plate has 1536 wells. The volume of each well in a 1536 well plate is about 12 µl with a working volume of about 3-10 µl. Each well of the multiwell collection plate can accommodate one or more beads from the synthesis chip. For example, in certain embodiments, each well of the multiwell collection plate comprises between 1-1,000, 1-500, 1-350, 1-250, 1-100, 1-50, 100-1,000, 100-500, 100-350, 100-250, 250-500, 250-350 or about 330 beads transferred from the synthesis chip. Further, the beads may occupy a specific volume of the well. For example, with a 1536 well plate, the beads may occupy up to about 90%, 80%, 70%, 60%, 50%, 40%, 30%, 20%, 10%, 1%, 0.5%, 0.1%, or 0.05% of the total well volume. In one embodiment, the beads occupy about 0.1% of the total well volume.

Other methods may also be used to collect and pool nucleic acid synthesis substrates, including (1) "grabbing", for example by the use of tweezers like devices which operate based upon mechanical (e.g., actual grabbing), optical, sonic, magnetic principles, (2) "destroying" structures surrounding nucleic acid synthesis substrates by methods such as chemical dissolution or through the use of lasers, (3) moving nucleic acid synthesis substrates by, for example, the use of thermal, electrostatic, magnetic, fluidic energy, (4) hybrid gripper which combine, for examples, (a) magnetic and fluidic flushing, (b) magnetic and piezoelectric methods, and (c) electrostatic lifting and fluidic flushing, (5) magnetic fixing/collecting using, for example, modulated permanent magnets, external coils, planar coils on synthesis substrates, etc., (6) electrostatic lifting & collecting, and (7) flux direction (e.g., the addition of fluid to the bottom of a well to lift substrates).

Additionally or alternatively, beads can be removed from the synthesis chip using other non-magnetic techniques, including, but not limited to, gravity-fed, dielectrophoresis, valving, or using a weir structure on the synthesis microchip. For example, if the bead contains a dielectric material, then a non-uniform electric field can be generated using, for example, the electrodes of the synthesis microchip, to produce a force (dielectrophoresis) that can be used to selectively remove beads from their respective wells on the synthesis microchip. By way of yet another example, the synthesis microchip can include a valving, weir, or barrier-like structure that can be used to alter the flow of the removed beads in a particular direction, such as to direct the beads to a particular well of the multiwell collection plate.

C. Electrochemically Generated Base Cleavage of Nucleic Acids

In certain embodiments disclosed herein, the synthesized nucleic acid molecules may be cleaved directly from the beads, or other suitable solid support, in the microchip and eluted into a suitable container, such as, for example a multiwell plate. In certain embodiments, the nucleic acid molecules can be cleaved from the one or more beads using an electrochemically generated base (EGB), as described herein. Nucleic acid molecules that belong to the same fragment can be pooled together at this stage as described herein. After cleavage, a concentration step may be performed, for example, using a reverse phase material or any other suitable resin, as described herein.

In certain embodiments disclosed herein, an EGB may be used to cleave the synthesized nucleic acid molecule from the bead, or other suitable solid support, directly in the well of the microchip. In a first step, protected nucleic acid molecules are synthesized according to methods disclosed herein and coupled to a bead via a base-cleavable linker, such as, for example, succinate. As used herein, a base-cleavable linker may be defined as any linker capable of being cleaved from a solid support by a base catalyzed reaction. The nucleic acid molecules are synthesized on a bead or other solid support in a microchip comprising at least one electrode, such as a platinum electrode, as disclosed herein. Next, a compound, such as azomethane, may be chemically reduced on the at least one electrode to yield an EGB. Other compounds that may be chemically reduced on the at least one electrode to yield an EBG include, for example, azobenzene, anthraquinone, aromatic halides (where the halide is iodine or bromine), and carbon disulfide. The EGB then acts to cleave the synthesized nucleic acid molecules from the beads or other suitable solid support.

Figure 25:
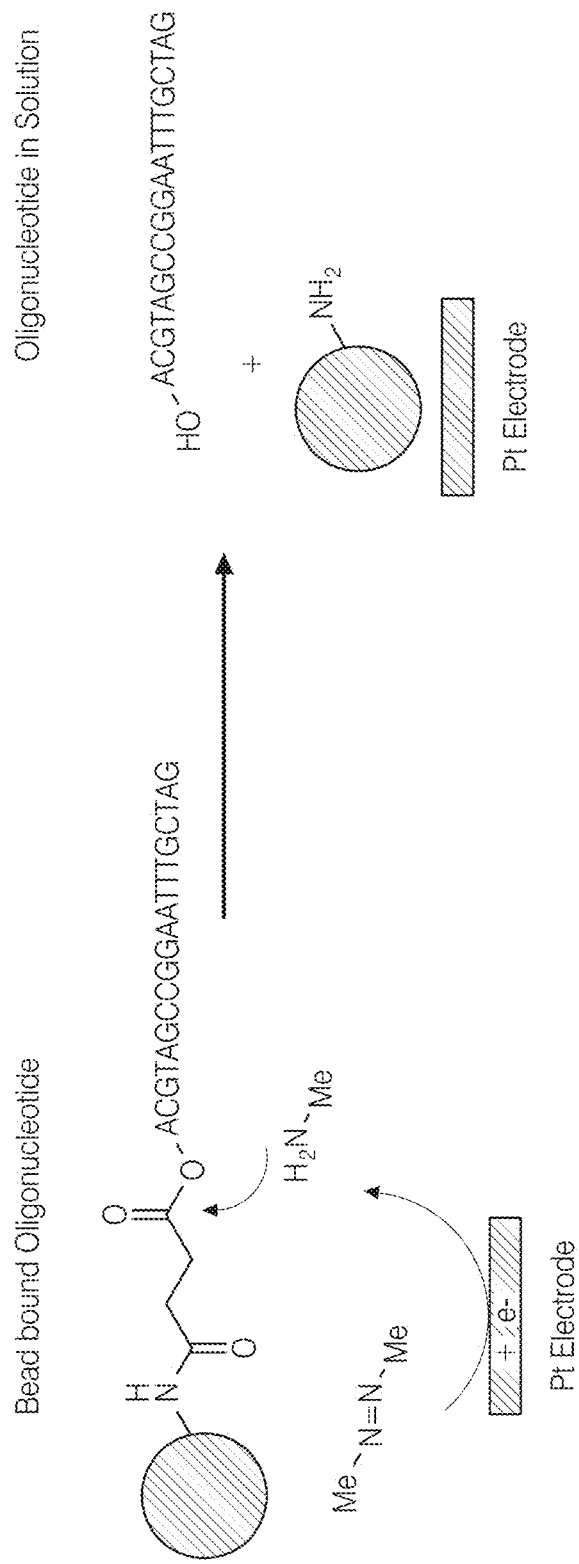
FIG. 25 illustrates an example cleavage reaction of a bead-bound nucleic acid molecule with an electrochemically generated base (SEQ ID NOS 23 and 23, respectively, in order of appearance).

As the EGB is only generated on activated electrodes, a site-selective cleavage of the desired nucleic acid molecules may be accomplished. The activation of the electrode causes the cleavage of the nucleic acid molecules that are linked to the bead with the base-cleavable linker, and the cleavage can be done in a highly selective manner so that only electrodes that are selected and activated have the nucleic acid molecules cleaved. The cleaved nucleic acid molecules are then free in solution and available for further processing. FIG. 25 shows an exemplary reaction wherein a nucleic acid molecule is bound to a bead via a base-cleavable linker. FIG. 25 shows electrons from the electrode acting to reduce azomethane to the base, methylamine. The methylamine then acts to cleave the nucleic acid molecule from the bead into the solution. In certain exemplary embodiments, an EGB may be generated from 1M dimethyldiazene, via activation of an electrode at about 7.5V for about 5 minutes.

D. Photolytic and Reductive Cleavage of Nucleic Acids

In certain other exemplary embodiments, the synthesized nucleic acid molecule may also be cleaved from the bead or other solid support by other cleavage means known in the art, such as photolytic cleavage and reductive cleavage. In certain embodiments, cleavage conditions may be generated in a site selective manner, such as in selected wells and/or on selected beads. In certain exemplary embodiments, a universal linker such as a UNYLINKER™ or a preloaded base is located between the synthesized nucleic acid molecules and the cleavable linker in order to prevent 3' phosphorylation of the desired nucleic acid molecules.

Figure 31:
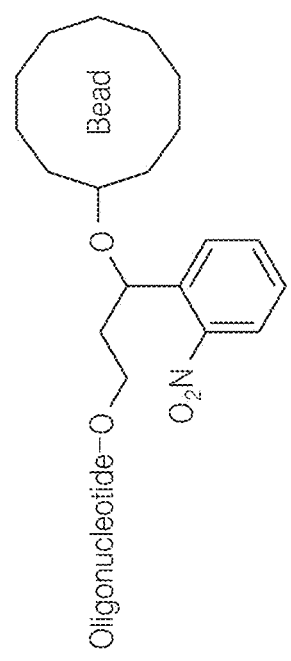
FIG. 31 shows an exemplary o-nitrobenzyl photocleavable linker linking a solid support bead to an oligonucleotide.

For photolytic cleavage, a photocleavage linker may be irradiated with lightwaves, such as UV lightwaves. The lightwaves trigger the cleavage of the nucleic acid molecules from the solid support (e.g., the bead). In certain embodiments, spatial control may be achieved with a light source, such as a mirror device like a digital micro mirror device. In certain exemplary embodiments, the light source illuminates selected synthesis positions (e.g., wells and/or beads), thereby cleaving selected nucleic acid molecules. FIG. 31 illustrates an exemplary embodiment wherein a photocleavable linker is bound to a bead and an oligonucleotide. Nonlimiting examples of photocleavable linkers that may be mentioned include, for example, o-nitrobenzyl, desyl, trans-o-cinnamoyl, m-nitrophenyl, and benzylsulfonyl groups.

Figure 32:
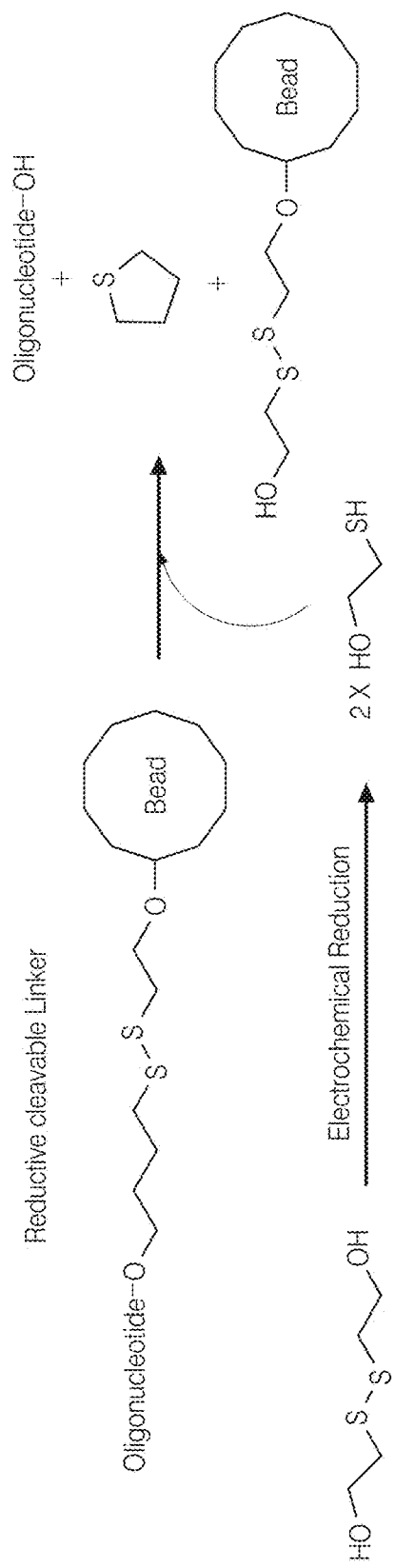
FIG. 32 shows an exemplary electrochemical reaction wherein reduction of 2,2'-disulfane diylbis(ethane-1-ol) to a monosulfide results in cleavage of an oligonucleotide and a disulfide reductive cleavable linker.

For reductive cleavage, a linker may be used that can be cleaved via an electrochemically reduced compound. In one exemplary embodiment, a disulfide linker may be used, as illustrated in FIG. 32. When a disulfide linker is used, for example and as shown in FIG. 32, 2-hydroxyethyl disulfide may be electrochemically reduced to generate 2-mercaptoethanol in situ on the desired synthesis positions. In certain embodiments, the reducing reagent, such as the 2-hydroxyethyl disulfide, is only reduced on the desired activated electrodes such that cleavage is site specific. The resulting monosulfide acts to cleave the desired oligonucleotide from the disulfide linker.

E. Enrichment of Nucleic Acids Using Solid Phase Materials

In certain embodiments, after the cleaved nucleic acid molecules are released into a solution, it may be desirable to perform a concentration step. For example, in certain embodiments the cleaved nucleic acid molecule volume may be concentrated so that the volume is compatible for use in certain multiwell plates for pooling as discussed herein, including, for example, 20 µL wells or a 1536 microwell plate (10 µL wells). Several exemplary embodiments are feasible for enrichment of the cleaved nucleic acid molecules.

In certain embodiments disclosed herein, a solid phase material may be used to absorb cleaved nucleic acid molecules, wherein the solid phase material is in a direct flow path following the cleavage step, such that cleaved nucleic acid molecules flow to the solid phase material, and then to an optional washing step, followed by an elution step, in a cycle of cleavage, absorption, optionally washing, and elution. Alternatively, in certain other exemplary embodiments, a solid phase material may be used in multiple positions of a multiwell plate, such that the cleavage, absorption, optional washing, and elution steps may occur one after each other, in parallel. Such parallel cleavage, absorption, and elution may be advantageous over cyclic cleavage, absorption, and elution, as it may in certain embodiments be more time efficient.

Absorption of the cleaved nucleic acid molecules may be performed by any means known in the art. For example, in certain embodiments, absorption of the cleaved nucleic acid molecule may be by a reverse phase resin material. When a reverse phase resin material is used to concentrate oligonucleotides that have been cleaved by an EGB, the cleavage reaction with the EGB may be carried out in an aqueous solution, or in certain embodiments, an aqueous solution comprising a small amount of at least one organic solvent, such as 20% acetonitrile. Subsequently, the nucleic acid molecule solution having a relatively low concentration of nucleic acid molecules may be pumped through a small amount of a reverse phase material. As used herein, reverse phase material refers to hydrophobic material having an affinity for hydrophobic compounds, thereby allowing hydrophilic compounds to elute in an aqueous solution. Reverse phase materials may include, for example, silica-based reverse phase materials, such as, for example, C18 modified silica or, in certain embodiments, polystyrene reverse phase materials. The protected nucleic acid molecules will remain on the reverse phase material, which may then be washed and dried, for example with nitrogen and/or air.

Next, the protected nucleic acid molecules may be eluted with an organic solution comprising at least an agent for removing a protecting group from a nucleic acid molecule, such as, for example, methylamine in a water/ethanol mixture. Any additional suitable organic solvents may be used, including, for example, at least one of acetonitrile, methanol, tetrahydrofuran, and isopropyl alcohol. In certain embodiments, the nucleic acid molecules may be eluted with 80% acetonitrile.

In certain embodiments, absorption of the cleaved nucleic acid molecule may be by a size exclusion material, such as cross-linked dextran gels (e.g., Sephadex®). The cleaved nucleic acid molecules may be retained in the size exclusion material and then eluted via gravity, such as in a centrifuge.

In certain other embodiments disclosed herein, absorption of the cleaved nucleic acid molecules may be by an anion exchange resin. Exemplary anion exchange resins may include, for example, resins comprising quaternary ammonium groups as the ion exchange groups, for example in styrene based resins such as crosslinked polystyrene or in acrylic resins. In certain embodiments, the absorption may occur at a relatively low anion concentration, such as about 1 mM. In certain exemplary embodiments, 1 mM $CF^-$ ions may be used. When an anion exchange resin is used, elution of the cleaved nucleic acid molecules may be performed with a relatively high anion concentration, such as about 1 M. In certain exemplary embodiments, 1 M $Cl^-$ ions may be used.

In certain other embodiments disclosed herein, absorption of the cleaved nucleic acids may occur on silica beads, such as those available from ThermoScientific and sold as the Silica Bead DNA Gel Extraction Kit. In this embodiment, the cleaved nucleic acids and at least one chaotropic salt are applied to the silica solid phase at a given pH. The presence of at least one chaotropic salt allows the cleaved nucleic acid to absorb to the silica. In certain embodiments, an optional washing step may be performed, followed by elution of the nucleic acids from the silica by an eluent. In certain embodiments, the cleaved nucleic acids may be absorbed to the silica at a given pH, such as an acidic pH, and then eluted from the silica as the pH gradient of the eluent changes, for example, increases to a more basic pH. In certain embodiments, the eluent may be water or a tris-EDTA buffer, such as a tris-acetate EDTA buffer or a tris-borate EDTA buffer.

In certain embodiments, the volume of the elution solution may be chosen to be low enough to enable dispensing the resulting solution in a multiwell plate, such as a 1536 microwell plate, with a fraction collector. The synthesized nucleic acid molecules may now be deprotected and pooled in the wells of a multiwell plate, preferably in volumes between 0.1 µL and 25 µL, 0.1 µL and 10 µL, 1 µL and 25 µL, 1 µL and 10 µL, 5 µL and 25 µL, 5 µL and 10 µL, or about 10 pt.

In certain embodiments, the solution comprising the synthesized nucleic acid molecules may then be evaporated, for example in a speedvac, before further processing. Optionally, in certain embodiments, an enzyme mix may be added to the dried nucleic acid molecule mixtures in order to start the gene assembly process or any other desired reaction.

In alternative embodiments, use may be made of a multiwell plate, such as a 1536 filter plate, that has been loaded with a solid phase resin, such as a reverse phase resin, a silica material, or an anion exchange resin. After the nucleic acid molecules are cleaved from the one or more beads by the EGB, as disclosed herein, the cleaved nucleic acid molecules may be rinsed in an individual well of the filter plate, wherein the nucleic acid molecules will bind to the solid phase resin. Next, the protection group on the nucleic acid molecules may be removed using known techniques, including, for example, gas phase or liquid deprotection. In certain embodiments, a washing step may be used to remove any free protecting groups and/or short truncated nucleic acid molecules.

Another method disclosed herein for the retrieval of nucleic acid molecules after synthesis is the use of a microfluidic chip for recovering nucleic acid molecules, such as nucleic acid molecules belonging to the same fragment from complex microarrays. The microfluidic chip used for retrieving the nucleic acid molecules may, for example, be similar to the microwell plates disclosed herein or may be similar to the microfluidic chip disclosed in Autebert, J. et al., *Hierarchical Hydrodynamic Flow Confinement: Efficient Use and Retrieval of Chemicals for Microscale Chemistry on Surfaces*, Langmuir 2014, 30(12) 3640-3645.

Disclosed herein are methods of retrieving nucleic acid molecules from a multiwell plate, a microfluidic chip or a microarray using micro-elution. It has been shown that hybridized nucleic acid molecules may be recovered by local denaturation from surface treatment with a NaOH solution, such as about 0.5M NaOH. Therefore, one method for retrieving nucleic acid molecules comprises preparation of two complementary sets of nucleic acid molecules on two microfluidic chips, wherein members of the first set of nucleic acid molecules can be hybridized to members of the second set of nucleic acid molecules and vice versa. In certain embodiments, the same type of microfluidic chip or microarray is used for the synthesis of both sets of nucleic acid molecules.

Synthesis of the complementary sets of nucleic acid molecules could be by any means known in the art, such as, for example, via inkjet or other techniques, including the synthetic techniques disclosed herein. In certain exemplary embodiments, the nucleic acid molecules may be synthesized on a bead, and the microfluidic chip may comprise a plurality of wells in which the beads may be located with each well having an associated working electrode that is individually addressable. The first and/or second sets of nucleic acid molecules may be prepared in one or more wells of a multiwell plate, a microfluidic chip or a microarray and may be prepared in an average amount of from about 1 attomole to about 1 picomole, from about 10 attomole to about 1 picomole, from about 10 attomole to about 100 picomole, from about 10 attomole to about 100 attomole etc.

As disclosed herein, a first set of nucleic acid molecules is synthesized on a first microfluidic chip, and a second set of nucleic acid molecules that is complementary to the first set is synthesized on a second microfluidic chip. In certain embodiments, the synthesized sets of nucleic acid molecules are synthesized such that nucleic acid molecules required for the assembly of a specific fragment are located in the same region on both of the chips. For example, if both sets of nucleic acid molecules are synthesized on identical microfluidic chips, then a subset of nucleic acid molecules associated with a fragment to be assembled from the first set nucleic acid molecules may be synthesized in a specific x-y location (e.g., region or wells) on the first chip. The same subset of nucleic acid molecules associated with the same fragment to be assembled from the second set of nucleic acid molecules may also be synthesized at the same x-y location on the second chip.

After synthesis, the nucleic acid molecules from the first chip are cleaved off and deprotected. The side protection groups of the nucleic acid molecules from the second chip are removed, but according to embodiments disclosed herein, the nucleic acid molecules on the second chip remain linked to the surface. To achieve this, for example the first and second sets of nucleic acid molecules may be attached to the surface (e.g. a bead in a well) via first and second types of linkers, respectively, wherein the first type of linker allows the first set of nucleic acid molecules to be cleaved off under deprotection conditions, and wherein the second type of linker allows the second set of nucleic acid molecules to remain linked to the surface under deprotection conditions. For example, the first type of linker may be a chemically-cleavable linker and the second type of linker may be a photocleavable or reductive cleavable linker as discussed elsewhere herein. Next, the second chip is contacted with the deprotected nucleic acid molecules from the first chip under hybridizing conditions such that the deprotected nucleic acid molecules from the first chip hybridize to nucleic acid molecules on the second chip. Optionally, at least one washing step may be performed to wash away non-bound nucleic acid molecules from the second chip.

Next, the nucleic acid molecules from the first chip that are hybridized to the second chip are denatured with a denaturing solution. In certain embodiments, the bound nucleic acid molecules may be chemically denatured with a basic solution, such as a NaOH solution. In certain embodiments, a 0.5M NaOH solution may be used to denature the nucleic acid molecules. The denatured nucleic acid molecules are then pooled and collected.

In certain embodiments, a microfluidic device may be used to add solutions (e.g., buffer or denaturing solution) or transfer the nucleic acid molecules cleaved from the first microfluidic chip to specific regions on the second microfluidic chip, such as wells in a multiwell plate. As will be appreciated by one skilled in the art, after cleavage and deprotection, a nucleic acid molecule synthesized in a specific x-y location of the first chip may be combined with the same nucleic acid molecule synthesized in the same x-y location of the second chip for the hybridization step. In this way, the same nucleic acid molecules may be combined physically in the same well on the second chip, without the presence of other nucleic acid molecules.

The microfluidic device may also be used to remove solutions (e.g., buffer or denaturing solution) and denatured nucleic acid molecules from specific locations, such as wells of a multiwell plate, where they may be collected, for example in a new multiwell plate or to a droplet making device for further processing, such as fragment assembly. In certain embodiments, the microfluidic device may be similar to the microfluidic probe disclosed in Autebert, J. et al., *Hierarchical Hydrodynamic Flow Confinement: Efficient Use and Retrieval of Chemicals for Microscale Chemistry on Surfaces*, Langmuir 2014, 30(12) 3640-3645.

Figure 26:
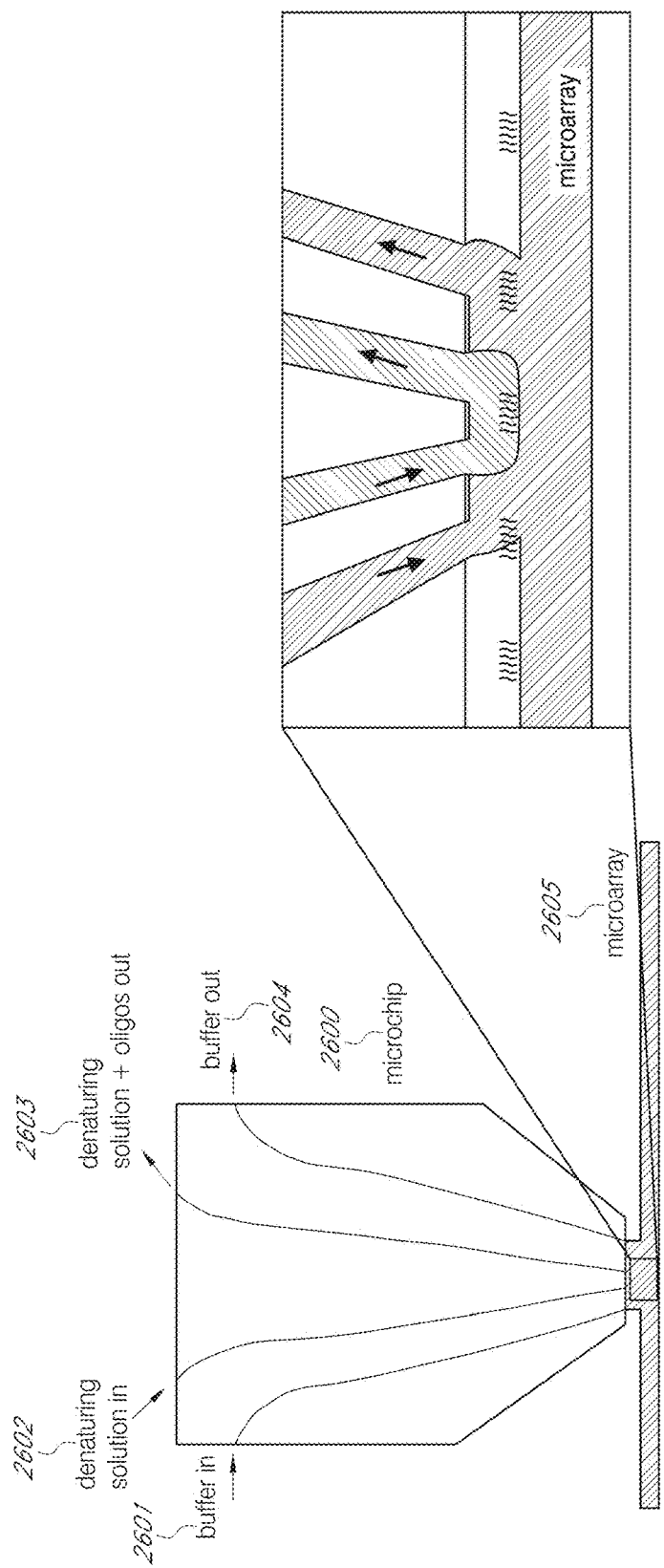
FIG. 26 illustrates an exemplary microfluidic chip for administering a nucleic acid molecule denaturing solution and optionally a buffer to a microarray of synthesized nucleic acid molecules.

FIG. 26 shows an exemplary microfluidic device according to certain embodiments disclosed herein. As shown in a FIG. 26, at least one buffer solution may be added to the second microfluidic chip 2605 via a first inlet channel 2601 in the microfluidic device 2600. Additionally, the denaturing solution and the first microarray's deprotected nucleic acid molecules may be added to the second microfluidic chip 2605 via a second inlet channel 2602 in the microfluidic device 2600. The at least one buffer solution may act to "nest" the denaturing solution and nucleic acid molecules, as shown in FIG. 26. The at least one buffer solution may then proceed out of the microfluidic device 2600 through a first outlet channel 2604, while the denaturing solution and nucleic acid molecules may proceed out of the microfluidic device 2600 through a second outlet channel 2603. The nucleic acid molecules from the second outlet channel 2603 may then be collected for further processing.

The above-described use of a microfluidic chip and microfluidic device for recovering nucleic acid molecules may have several advantages over using mixtures from multiwell plates. For example, the dilution of the nucleic acid molecules may be very low, as the microfluidic chip may contain only microliter or even nanoliter volumes. Additionally, nucleic acid molecules belonging to the same fragment can be combined physically, without the presence of other nucleic acid molecules. Other methods known in the art that amplify the desired nucleic acid molecules from a mixture by, for example, PCR may be more time consuming and have more contamination. Finally, the hybridization step adds an error correction step, because only nucleic acid molecule sequences with no or minor errors cleaved from the first microfluidic chip will hybridize to the second microfluidic chip. The hybridization step also adds a cleaning step, as very short nucleic acid molecules can be removed by optimizing the hybridization conditions.

Pooling stations used in the practice of the invention may further contain a microwell handling device which comprises controllable moveable means for moving the microwell plate from a first to at least a second position in X and/or Y and/or Z direction and can be programmed to perform liquid handling steps. Such pooling stations may further be equipped with a pipetting device and a suction apparatus allowing for controlled addition and removal of reagents. Alternatively the removal of liquid can be performed by vacuum means or using containers qualified for acoustic handling. The pipetting device may further be connected to reagent reservoirs and mixing means to mix and add defined amounts of reagents required for purification and subsequent processing and assembly steps. Integrated liquid handling devices combining the respective functions are known by those skilled in the art.

In a specific embodiment, the pooling station integrates means to allow for further combining of one or more nucleic acid molecule pools from first and second wells into a third well to yield a larger nucleic acid molecule pool. Such step-wise pooling may be required in cases where variants or libraries of full-length constructs are assembled from identical and variable sequence elements.

Pooling stations used in the practice of the invention may further contain a magnet located beneath the microwell plate. In a specific embodiment such a plate magnet may serve as counterpart to the micromagnet in order to trigger release of the extracted beads into the recipient microwell. Alternatively the electro-micromagnet may be a hollow magnet connected to a capillary that can be flushed with liquid to blow out the bound bead into the recipient well. Other means of bead release may also be employed.

With respect to pooling of nucleic acid molecules, this may be done any number of ways. For example, synthesis substrates may be collected and placed in a single container. Alternatively, nucleic acid molecules may be released from synthesis substrates and then contacted with each other. Further, nucleic acid molecules may be assembled by hybridization. This means that more than one assembly may occur in the same container. In other words, the invention includes methods by which assembly of more than one (e.g., two, three, four, five, six, etc.) nucleic acid molecule occurs from smaller, chemically synthesized nucleic acid molecules. One application where the assembly of more than one larger nucleic acid molecule (e.g., replicable nucleic acid molecules) may be useful is where the assembled nucleic acid molecules are intended for insertion into the same cell. Thus, one of the assembled nucleic acid molecules could be a chromosome and another could be a plasmid.

Once desired pools of nucleic acid molecules have been generated, bead-attached nucleic acid molecules will often be further processed, for example, to obtain functional nucleic acid molecules for downstream reactions. After chain synthesis the 5'-terminal 5'-hydroxy group is usually protected, for example, with a dimethoxytrityl (DMT) group; the internucleosidic phosphate or phosphorothioate moieties may also be protected, for example, with 2-cyanoethyl groups; and the exocyclic amino groups in all nucleic bases (except for T and U) may be protected, for example, with acyl protecting groups. Usually, the 5'-terminal DMT group is cleaved after the last synthesis cycle on the support before the bead-attached nucleic acid molecules are pooled. However, all protection groups have to be removed in a deprotection step before the nucleic acid molecules can be effectively used in subsequent processes.

In one embodiment of the invention, deprotection is performed, for example, without releasing the nucleic acid molecule form the bead. This can be carried out by choosing a base-stable, non-cleavable linker. Respective linkers are known by the skilled person.

In one embodiment, nucleic acid molecules are released from the beads prior to downstream assembly. If cleavage of nucleic acid molecule is required, cleavage and deprotection may be performed in a single step. Release of the nucleic acid molecules may be achieved by cleaving the linker attaching the 3'-end of the nucleic acid molecule to the bead (e.g., a magnetic bead) with a suitable reagent. Suitable reagents and conditions for cleavage depend on the nature of the linkage as described elsewhere herein and are known by those skilled in the art. In certain embodiments, nucleic acid molecules are released from the beads using, for example, an EGB, a photocleavable linker, or a reducing linker, as described herein.

In one embodiment of the invention, nucleic acid molecules are attached to the solid support (e.g., a magnetic or non-magnetic bead) via succinyl groups. In certain embodiments, a universal linker may be located between the succinyl group and the nucleic acid molecules. The succinyl linker may be cleaved by the use of, for example, concentrated aqueous ammonium hydroxide. The reaction is usually carried out at temperatures between 50° C. and 80° C. for at least one to about eight hours. In certain embodiments, the succinyl linker may be cleaved by the use of ammonia gas, using increased heat and pressure, such as, for example, a temperature of about 80° C., and a pressure of about 3 bar for a time of about 2 hours. Of course, cleavage conditions may vary depending on the protocol and the protecting groups used. In embodiments wherein aqueous ammonium hydroxide is used, the ammonia solution may then be removed by evaporation, leaving the nucleic acid molecules ready for purification.

In one embodiment, cleavage may be carried out by vapor-phase processing. In vapor-phase processing, nucleic acid molecules may be cleaved in a closed chamber in a gaseous environment comprising gaseous cleavage/deprotection reagent, such as gaseous ammonia or ammonium hydroxide vapors. Respective methods are set out, for example, in U.S. Pat. No. 5,514,789 or 5,738,829, the disclosures of which are incorporated herein by reference.

The above reaction will typically also triggers cleavage of other protecting groups including the cyanoethyl group and the group protecting the heterocyclic primary amine. Thus, a single cleavage reaction may be used, when appropriate, to remove all protecting groups present.

Linkers used in the practice of the invention may be cleaved using at least two approaches: (a) simultaneously under the same conditions as the deprotection step or (b) subsequently utilizing a different condition or reagent for linker cleavage after the completion of the deprotection step. Various methods to remove universal linkers from a nucleic acid molecule are described in the art such as, for example, U.S. Patent Publication No. 2002/0143166 A1, the disclosure of which is incorporated herein by reference.

For downstream applications, it may be required to purify the pooled and deprotected nucleic acid molecules to remove the cleaved groups, for example, by precipitation. It may further be required to separate the nucleic acid molecule mixture from the magnetic particles or other support. In one embodiment, a plate magnet located beneath the microwell plate can be used to immobilize the beads in the wells while the nucleic acid molecules can be eluted, for example, by suction. Alternatively, in the absence of a plate magnet, the beads may be automatically removed from the wells by magnetic means while the nucleic acid molecules would be retained in the well to obtain femtomoles of individual pools of high quality nucleic acid molecules at picomole concentration ready for further processing or use.

In some instances, nucleic acid molecules may be separated from solid support while the solid supports remain localized in the same or similar location as to where the nucleic acid molecules were synthesized. In such instances, typically after synthesis completion, oligonucleotide synthesis reagents may be removed from contact with synthesis supports, followed by the addition of one or more reagents for release of the constructed oligonucleotide, also referred to as cleavage reagents. These releasing reagents may be in forms such as liquid or gaseous. Gaseous reagents are referred to above.

In many instances, the cleavage reagent agent will be volatile (e.g., it can be removed via freeze drying) and non-ionic. The cleaved oligonucleotides may then be recovered by either removal from wells, when present, or by rinsing the synthesis substrate. When microwells are employed for synthesis, cleavage reagents in liquid form may be used. The synthesis substrate may be coated with such liquid reagents followed by either group removal of synthesized oligonucleotides or removal of individual oligonucleotides (less than all of oligonucleotides present). Removal of individual oligonucleotides may be achieved, for example, by limiting agitation of the substrate and site specific removal (e.g., with a pipette tip) of fluid containing individual oligonucleotides after cleavage has occurred. Such methods will be particularly useful when the substrate contains wells or cavities.

Optionally, synthesized nucleic acid molecules may be concentrated after pooling, cleavage and/or deprotection but prior to entering into Module 3 processes. One method of such concentration would be by an additional second binding, washing, and elution series of sets to reduce the final volume. This increased concentration will increase the concentration of synthesized nucleic acid molecules, resulting in accelerated hybridization of overlapping segments in sub-fragment generation as may be desired. Concentration to an increased concentration may also be used to "normalize" the concentration of multiple pools to a more constant range so that a limited set of, for example, assembly conditions need be employed in Module 3 processes (e.g., all Module 3 processes).

FIG. 13 shows two methods by which synthesized oligonucleotides may be separated from supports. In this figure, oligonucleotides have been synthesized on beads 1300 and released into the surrounding well of a microwell titer plate 1301. In each instance, wells containing oligonucleotides for collection are covered with fluid 1302 and pipette tips 1303 are used to collect that fluid. On the left side of the figure are two wells where the fluid is contained within the wells. Further to the right side of FIG. 13, a barrier 1304 extends above the wells to allow fluid to collect at a higher level. In both instances, the fluid may be there before the pipette tips are brought into close proximity or the fluid may be delivered by the pipette tips. Also, fluid surrounding the beads 1300 may be circulated to distribute released oligonucleotides by flow delivered by the pipette tips 1303.

In certain embodiments, the multiwell plate or other suitable container with the pooled beads is dried, for example, in a Speedvac to concentrate the beads in the multiwell plate or other suitable container. This can be followed by cleavage of the nucleic acid molecules from the bead and deprotection, as described herein, including, for example cleavage and deprotection in either vapor-phase phase processing or in liquid. Following cleavage and deprotection nucleic acid molecules can be eluted, preferably in a buffer used in assembly. The nucleic acid molecules can be transferred to the assembly stage in a buffer, as noted above, or dried.

Module 3

Once the chemical synthesis phase has been completed, the resulting nucleic acid molecules may be assembled, if desired, into larger nucleic acid molecules. Depending on the end purpose for which the final nucleic acid molecules are to be used, the "quality" (e.g., from a sequence fidelity perspective) of the chemically synthesized nucleic acid molecules may be too low for the intended application. As an example, if the chemically synthesized nucleic acid molecules are to be used as long probes, then they may be of sufficient quality for that purpose without further processing. However, consider the situation where one hundred nucleic acid segments are to be assembled, each nucleic acid segment is one hundred base pairs in length and there is one error per 200 base pairs. The net result is that there will be, on average, 50 sequence errors in each 10,000 base pair assembled nucleic acid molecule. If one intends, for example, to express one or more proteins from the assembled nucleic acid molecule, then the number of sequence errors would likely be considered to be too high. Also, while sequencing of individual nucleic acid molecules may be performed, this is time consuming and involves additional cost. Thus, in many instances, an error removal step may be performed. Typically, this will be performed after a first round of assembly. Thus, in one aspect, methods of the invention involve the following (in this order or different orders):

1. Fragment Amplification and Assembly (e.g., PCR/in vitro assembly).
2. Error Correction.
3. Final Assembly (e.g., in vivo assembly).

In various embodiments of the present disclosure, error removal steps may also be implemented by executing processor-executable instructions. The invention thus includes software based instructions for performing mechanical functions associated with error removal processes, as well as other aspects of the invention.

Any number of methods may be used for fragment amplification and assembly. One exemplary method is described in Yang et al., *Nucleic Acids Research,* 21:1889-1893 (1993) and U.S. Pat. No. 5,580,759, the disclosure of which is incorporated herein by reference.

In the process described in the Yang et al. paper, a linear vector is mixed with double stranded nucleic acid molecules which share sequence homology at the termini. An enzyme with exonuclease activity (i.e., T4 DNA polymerase, T5 exonuclease, T7 exonuclease, etc.) is added which peels back one strand of all termini present in the mixture. The "peeled back" nucleic acid molecules are then annealed incubated with a DNA polymerase and deoxynucleotide triphosphates under condition which allow for the filling in of single-stranded gaps. Nicks in the resulting nucleic acid molecules may be repaired by introduction of the molecule into a cell or by the addition of ligase. Of course, depending on the application and work flow, the vector may be omitted. Further, the resulting nucleic acid molecules, or sub-portions thereof, may be amplified by polymerase chain reaction.

Other methods of nucleic acid assembly include those described in U.S. Patent Publication Nos. 2010/0062495 A1; 2007/0292954 A1; 2003/0152984 AA; and 2006/0115850 AA and in U.S. Pat. Nos. 6,083,726; 6,110,668; 5,624,827; 6,521,427; 5,869,644; and 6,495,318, the disclosures of which are incorporated herein by reference.

A method for the isothermal assembly of nucleic acid molecules is set out in U.S. Patent Publication No. 2012/0053087, the disclosure of which is incorporated herein by reference. In one aspect of this method, nucleic acid molecules for assembly are contacted with a thermolabile protein with exonuclease activity (e.g., T5 polymerase) a thermostable polymerase, and a thermostable ligase under conditions where the exonuclease activity decreases with time (e.g., 50° C.). The exonuclease "chews back" one strand of the nucleic acid molecules and, if there is sequence complementarity, nucleic acid molecule will anneal with each other. The thermostable polymerase fills in gaps and the thermostable ligase seals nicks. Methods like this may be used in conjunction with equipment of FIG. 16. Further, more than one nucleic acid molecule may be stored with other suitable reagents in the individual storage units of 1609 and these storage units may be set to a temperature of, for example, of 50° C. for assembling the stored molecules.

One commercially available kit which may be used to assemble nucleic acid molecules of the invention, as well as for the insertion of such nucleic acid molecules into vectors is the GENEART® Seamless Cloning and Assembly Kit (cat. no. A13288), available from Life Technologies Corp., Carlsbad, Calif.

Single-stranded binding proteins such as T4 gene 32 protein and RecA, as well as other nucleic acid binding or recombination proteins known in the art, may be included, for example, to facilitate nucleic acid molecules annealing.

In some instances, nucleic acid molecules may be amplified on solid supports. Thus, the invention includes methods where nucleic acid molecules are synthesized but are not cleaved from solid supports they are synthesized on. In such instances, the amplified nucleic acid molecules may be used directed (e.g., as probes) or assembled as described elsewhere herein.

Figure 3:
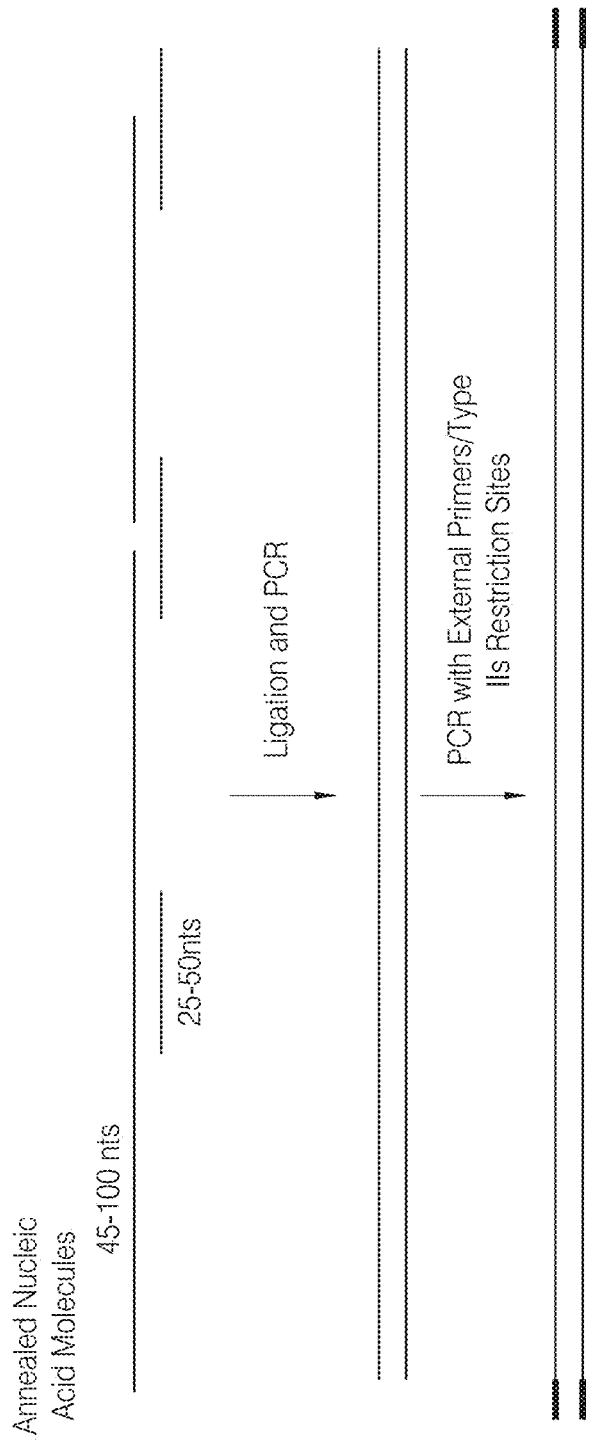
FIG. 3 shows a nucleic acid assembly scheme. The thick ends on the assembled nucleic acid molecule shown at the bottom of the figure represent regions added by external primers, also referred to as terminal primers.

One method for assembling nucleic acid molecules (FIG. 3) involves starting with overlapping nucleic acid molecules which are "stitched" together using PCR. In many instances, the stitched nucleic acid molecules will be chemically synthesized and will be less than 100 nucleotides in length (e.g., from about 40 to 100, from about 50 to 100, from about 60 to 100, from about 40 to 90, from about 40 to 80, from about 40 to 75, from about 50 to 85, etc. nucleotides). A process similar to that shown in FIG. 3 is set out in U.S. Pat. No. 6,472,184, the disclosure of which is incorporated herein by reference. Primers may also be used which contain restriction sites for instances where insertion into a cloning vector is desired. One suitable cloning system is referred to as Golden Gate which is set out in various forms in U.S. Patent Publication No. 2010/0291633 A1 and PCT Publication WO 2010/040531, the disclosures of which are incorporated herein by reference. Thus, where desirable, assembled nucleic acid molecules may be directly inserted into vectors and host cells. This may be appropriate when the desired construct is fairly small (e.g., less than 5 kilobases). Type IIs restriction site mediated assembly may be used to assemble multiple fragments (e.g., two, three, five, eight, ten, etc.) when larger constructs are desired (e.g., 5 to 100 kilobases).

An alternative method for PCR-based assembly of nucleic acid molecules (e.g., chemically synthesized nucleic acid molecules) is based on the direct ligation of overlapping pairs of 5'-phosphorylated nucleic acid molecules ("ligation-based assembly"). In this process, single-stranded nucleic acid molecules are synthesized, phosphorylated and annealed to form double-stranded molecules with complementary overhangs (e.g., overhangs of four nucleotides). The individual double stranded molecules are then ligated to each other to form larger constructs. In certain embodiments this method may be desirable over PCR methods in particular where highly repetitive sequences, such as GC stretches are to be assembled. This method may be used to assemble from about two to about forty nucleic acid molecules (e.g., from about two to about forty, from about three to about forty, from about five to about forty, from about eight to about forty, from about two to about thirty, from about two to about twenty, from about two to about ten, etc. nucleic acid molecules). A related method is described in U.S. Pat. No. 4,652,639, the disclosure of which is incorporated herein by reference.

In many instances when ligation-based assembly is employed using chemically synthesized nucleic acid molecules, the molecules will be less than 100 base pairs in length. Also, the complementary overlaps may be used for joining the nucleic acid molecules will generally be between two and ten (e.g., from about two to about ten, from about four to about ten, from about five to about ten, from about two to about eight, from about three to about seven, etc. nucleotides in length) (FIG. 4).

One process that may be used to assemble nucleic acid molecules is Red/ET recombination. This process employs *E. coli* based homologous recombination mediated by phage protein pairs, such as RecE/RecT or Redα/Redβ. This process is not limited by nucleic acid size and is independent of restriction sites. Essentially any DNA molecule in *E. coli* of almost any size can be engineered at any site using Red/ET recombination. In essence, Red/ET recombination involves three steps/conditions. The first step or condition is the presence of homology arms (e.g., arms of 50 base pairs in length) in linear DNA. The second step or condition is the insertion or presence of the linear DNA in an *E. coli* cell. The third step or condition is the expression or presence of any appropriate phage pair (e.g., RecE/RecT or Redα/Redβ) in the *E. coli* cell. Red/ET recombination is set out in U.S. Pat. Nos. 6,355,412 and 6,509,156, the disclosures of which are incorporated herein by reference.

Figure 4:
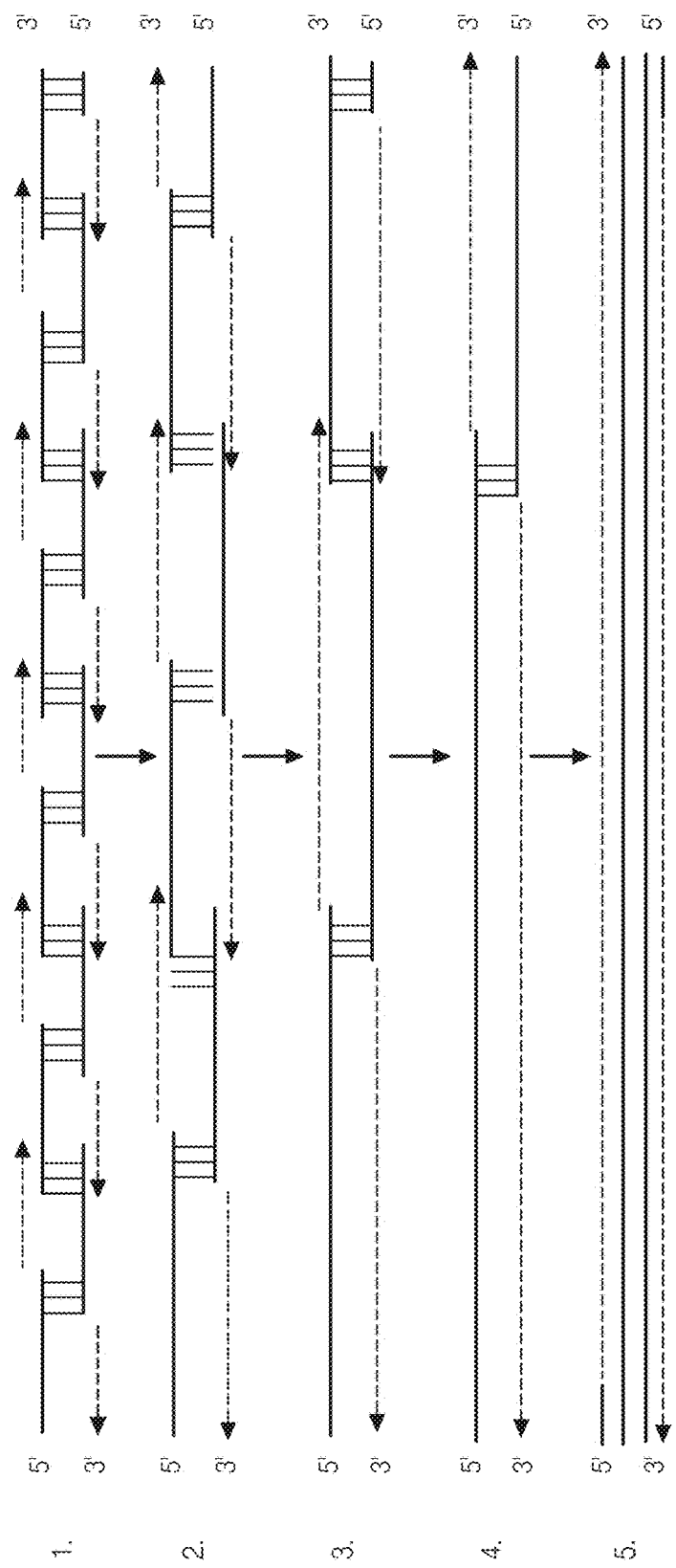
FIG. 4 shows a second nucleic acid assembly scheme. Dotted lines with arrows show PCR based synthesis direction and area.

Further, as shown in FIG. 4, multiple rounds of polymerase chain reactions may be used to generate successively larger nucleic acid molecules.

In most instances, regardless of the method by which a larger nucleic acid molecule is generated from chemically synthesized nucleic acid molecules, errors from the chemical synthesis process will be present. Thus, in many instances, error correction will be desirable. Error correction can be achieved by any number of means. One method is by individually sequencing chemically synthesized nucleic acid molecules. Sequence-verified nucleic acid molecules can then be retrieved by various means. One way of selecting nucleic acid molecules of correct sequence is referred to as "laser catapulting" and relies on the use of high-speed laser pulses to eject selected clonal nucleic acid populations from a sequencing plate. This method is described, for example, in U.S. Patent Publication No. 2014/0155297 the disclosure of which is incorporated herein by reference.

Figure 6:
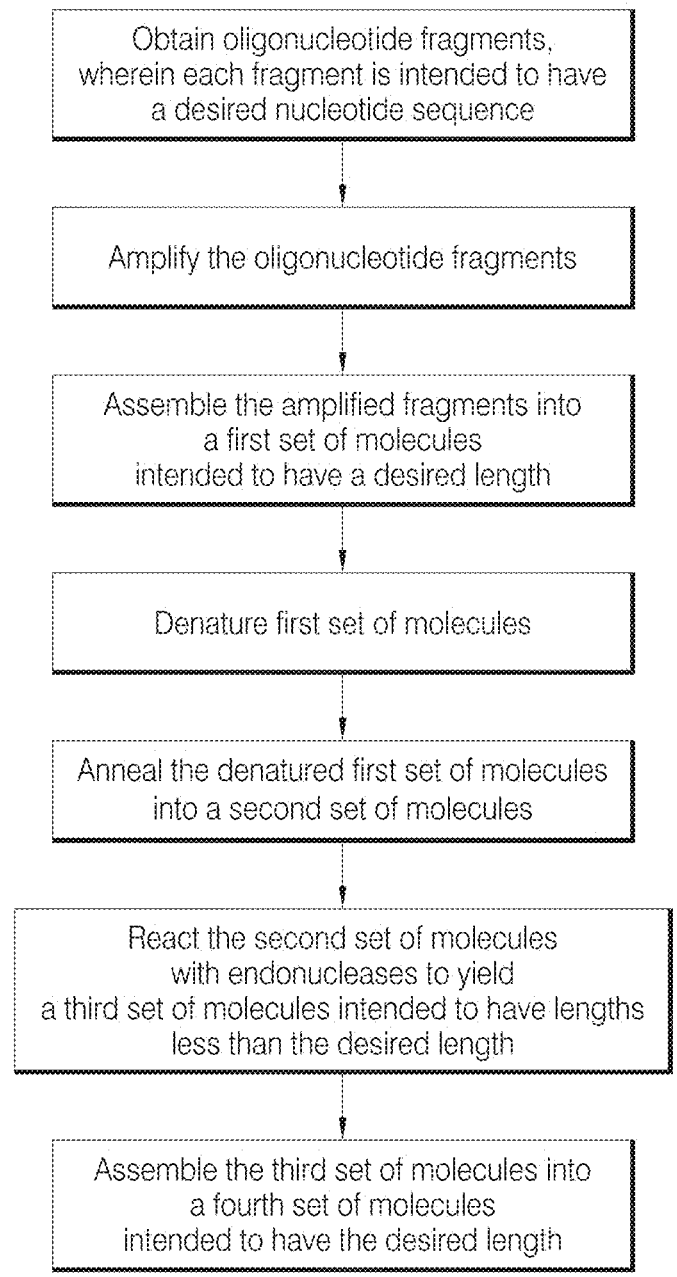
FIG. 6 is a flow chart of an exemplary process for synthesis of error-minimized nucleic acid molecules.

Another method of error correction is set out in FIG. 6. FIG. 6 is a flow chart of an exemplary process for synthesis of error-minimized nucleic acid molecules. In the first step, nucleic acid molecules of a length smaller than that of the full-length desired nucleotide sequence (i.e., "nucleic acid molecule fragments" of the full-length desired nucleotide sequence) are obtained. Each nucleic acid molecule is intended to have a desired nucleotide sequence that comprises a part of the full length desired nucleotide sequence. Each nucleic acid molecule may also be intended to have a desired nucleotide sequence that comprises an adapter primer for PCR amplification of the nucleic acid molecule, a tethering sequence for attachment of the nucleic acid molecule to a DNA microchip, or any other nucleotide sequence determined by any experimental purpose or other intention. The nucleic acid molecules may be obtained in any of one or more ways, for example, through synthesis, purchase, etc.

In the optional second step, the nucleic acid molecules are amplified to obtain more of each nucleic acid molecule. In many instances, however, sufficient numbers of nucleic acid molecules will be produced so that amplification is not necessary. When employed, amplification may be accomplished by any method known in the art, for example, by PCR, Rolling Circle Amplification (RCA), Loop Mediated Isothermal Amplification (LAMP), Nucleic Acid Sequence Based Amplification (NASBA), Strand Displacement Amplification (SDA), Ligase Chain Reaction (LCR), Self Sustained Sequence Replication (3SR) or solid phase PCR reactions (SP-PCR) such as Bridge PCR etc. (see e.g. Fakruddin et al., J Pharm Bioallied Sci. 2013; 5(4): 245-252 for an overview of the various amplification techniques). Introduction of additional errors into the nucleotide sequences of any of the nucleic acid molecules may occur during amplification. In certain instances it may be favorable to avoid amplification following synthesis. The optional amplification step may be omitted where nucleic acid molecules have been produced at sufficient yield in the first step. This may be achieved by using improved compositions and methods of the invention such as e.g. optimized bead formats as described elsewhere herein, designed to allow synthesis of nucleic acid molecules at sufficient yield and quality.

In the third step, the optionally amplified nucleic acid molecules are assembled into a first set of molecules intended to have a desired length, which may be the intended full length of the desired nucleotide sequence. Assembly of amplified nucleic acid molecules into full-length molecules may be accomplished in any way, for example, by using a PCR-based method.

In the fourth step, the first set of full-length molecules is denatured. Denaturation renders single-stranded molecules from double-stranded molecules. Denaturation may be accomplished by any means. In some embodiments, denaturation is accomplished by heating the molecules.

In the fifth step, the denatured molecules are annealed. Annealing renders a second set of full-length, double-stranded molecules from single-stranded molecules. Annealing may be accomplished by any means. In some embodiments, annealing is accomplished by cooling the molecules. Some of the annealed molecules may contain one or more mismatches indicating sites of sequence error.

In the sixth step, the second set of full-length molecules are reacted with one or more mismatch cleaving endonucleases to yield a third set of molecules intended to have lengths less than the length of the complete desired gene sequence. The endonucleases cut one or more of the molecules in the second set into shorter molecules. The cuts may be accomplished by any means. Cuts at the sites of any nucleotide sequence errors are particularly desirable, in that assembly of pieces of one or more molecules that have been cut at error sites offers the possibility of removal of the cut errors in the final step of the process. In an exemplary embodiment, the molecules are cut with T7 endonuclease I, E. coli endonuclease V, and Mung Bean endonuclease in the presence of manganese. In this embodiment, the endonucleases are intended to introduce cuts in the molecules at the sites of any sequence errors, as well as at random sites where there is no sequence error. In another exemplary embodiment, the molecules are cut only with one endonuclease (such as T7 endonuclease I or another endonuclease of similar functionality).

In the seventh step, the third set of molecules is assembled into a fourth set of molecules, whose length is intended to be the full length of the desired nucleotide sequence. Because of the late-stage error correction enabled by the provided method, the set of molecules is expected to have many fewer nucleotide sequence errors than can be provided by methods in the prior art. Optionally, steps four to seven may be repeated one or several times to further increase the efficiency of error reduction.

The process set out above and in FIG. 6 is also set out in U.S. Pat. No. 7,704,690, the disclosure of which is incorporated herein by reference. Furthermore, the process described above may be encoded onto a computer-readable medium as processor-executable instructions.

Another process for effectuating error correction in chemically synthesized nucleic acid molecules is by a commercial process referred to as ERRASE™ (Novici Biotech). Error correction methods and reagent suitable for use in error correction processes are set out in U.S. Pat. Nos. 7,838,210 and 7,833,759, U.S. Patent Publication No. 2008/0145913 A1 (mismatch endonucleases), and PCT Publication WO 2011/102802 A1, the disclosures of which are incorporated herein by reference.

Exemplary mismatch binding and/or cleaving enzymes include endonuclease VII (encoded by the T4 gene 49), RES I endonuclease, CEL I endonuclease, and SP endonuclease or an endonuclease containing enzyme complex. For example, the MutHLS complex constitutes a bacterial mismatch repair system, wherein MutS has mismatch detection and mismatch binding activity, MutH has nuclease activity and MutL directs MutH to MutS-bound mismatch sites. The skilled person will recognize that other methods of error correction may be practiced in certain embodiments of the invention such as those described, for example, in U.S. Patent Publication Nos. 2006/0127920 AA, 2007/0231805 AA, 2010/0216648 A1, 2011/0124049 A1 or U.S. Pat. No. 7,820,412, the disclosures of which are incorporated herein by reference.

Figure 7:
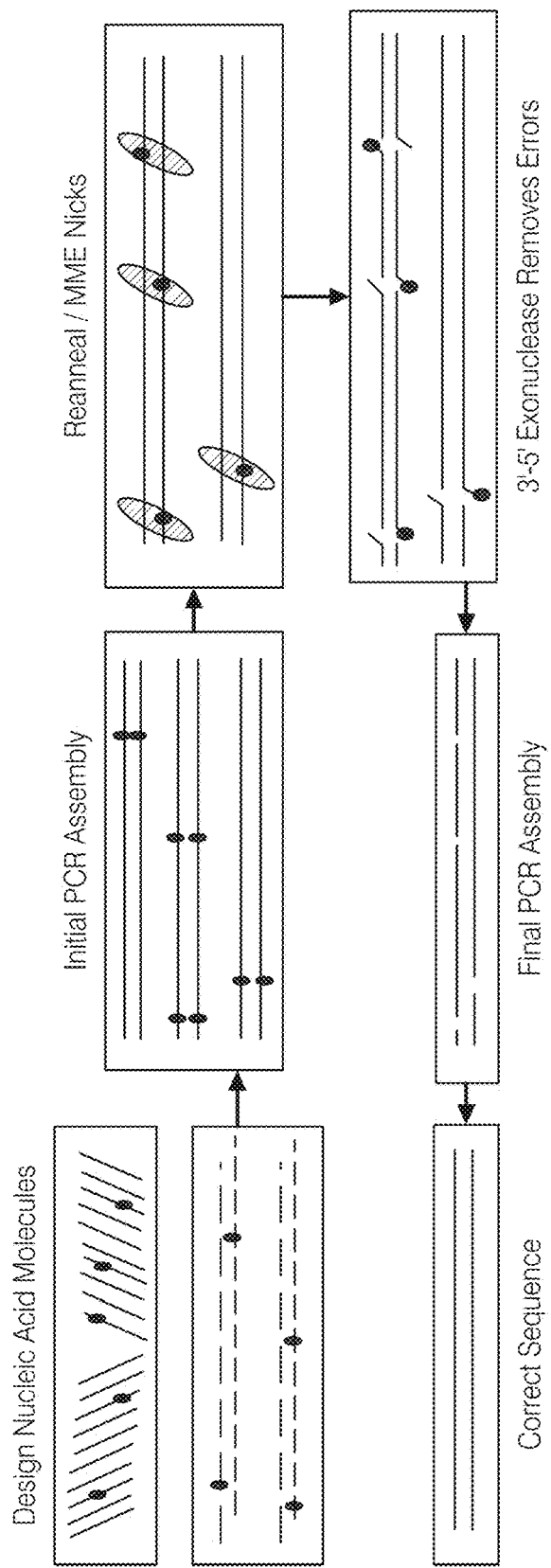
FIG. 7 is a work flow chart of an exemplary process for synthesis of error-minimized nucleic acid molecules. Different strands of a double-stranded nucleic acid molecule are represented by thicker and thinner line. "MME" refers to mis-match endonuclease. Small circles represent sequence errors.

Another schematic of an error correction method is shown in FIG. 7.

Synthetically generate nucleic acid molecules typically have error rate of about 1 base in 300-500 bases. As noted above in many instances, conditions can be adjusted so that synthesis errors are substantially lower than 1 base in 300-500 bases. Further, in many instances, greater than 80% of errors are single base frameshift deletions and insertions. Also, less than 2% of errors result from the action of polymerases when high fidelity PCR amplification is employed. In many instances, mismatch endonuclease (MME) correction will be performed using fixed protein: DNA ratio.

One error correction methods involves the following steps. The first step is to denature DNA contained in a reaction buffer (e.g., 200 mM Tris-HCl (pH 8.3), 250 mM KCl, 100 mM $MgCl_2$, 5 mM NAD, and 0.1% TRITON® X-100) at 98° C. for 2 minutes, followed by cooling to 4° C. for 5 minutes, then warming the solution to 37° C. for 5 minutes, followed by storage at 4° C. At a later time, T7 endonuclease I and DNA ligase are added the solution 37° C. for 1 hour. The reaction is stopped by the addition EDTA. A similar process is set out in Huang et al., *Electrophoresis* 33:788-796 (2012).

The generation of nucleic acid molecules that closely match an intended nucleotide sequence can be achieved in a number of ways. One way is to chemically synthesize nucleic acid molecules (e.g., oligonucleotides) with high sequence fidelity. Another way is to select chemically synthesized nucleic acid molecules that have the desired sequence out a population of individual molecules, some of which are not of the correct nucleotide sequence. Yet another way is to correct sequence error in populations of nucleic acid molecules believed to contain "errors". Methods related to the above are set out elsewhere herein. Methods of the invention include any one, two or all three of the ways of generating nucleic acid molecules that have few variations (e.g., errors) from an intended nucleotide sequence. For example, nucleic acid molecules could be synthesized with high sequence fidelity, followed by error correction, followed by selection members of the population that have a desired nucleotide sequence. By "intended nucleotide sequence" is meant that a nucleotide sequence is known and there is a desire to obtain a nucleic acid molecule with that sequence. Deviations from an intended nucleotide sequence are essentially what are referred to herein as errors.

One method for the correcting errors in nucleic acid molecules is set out diagrammatically in FIG. 6. In the second to last step of the process set out in FIG. 6, annealed nucleic acid molecules are reacted with one or more endonucleases as part of the error correction process. Variations of this process are as follows. First, two or more (e.g., two, three, four, five, six, etc.) rounds of error correction may be performed. Second, more than one endonuclease may be used in one or more rounds of error correction. For example, T7 endonuclease I and Cel II may be used in each round of error correction. Third, different endonucleases may be used in different error correction rounds. For example, T7 endonuclease I and Cel II may be used in a first round of error correction and Cel II may be used alone in a second round of error correction.

Table 10 shows the results of error correction using two different enzymes separately and together with the sequencing of over two million base pairs of DNA. Using the enzyme mixture T7 endonuclease and Cel II for purposes of illustration, after first, second and third rounds of error correction, the number of errors present are, respectively, 1 in 4363, 1 in 16,115, and 1 in 36,293. The large standard deviations seen in some of the data is believed to be at least partly due to the small number of errors present.

Table 10 also shows that certain types of error are preferentially reduced via error correction. For example, insertion/deletion error (indels) are substantially eliminated after multiple rounds of error correction. A to G and C to T substitutions are more refractory to correction. Using the data of the T7N1 rows from Rounds 0 and 3, the number of such substitutions are, respectively, 7 per 62,192 (1 in 8,884) and 21 per 933,716 (1 in 44,463) base pairs sequenced. This represents roughly 5 fold a reduction in A to G and C to T substitutions.

In many instances, a ligase may be present in reaction during error correction. It is believed that some endonucleases used in error correction processes have nickase activity. The inclusion of one or more ligase is believed to seal nicks caused by such enzymes and increase the yield of error corrected nucleic acid molecules after amplification. Exemplary ligases that may be used are T4 DNA ligase, Taq ligase, and PBCV-1 DNA ligase. Ligases used in the practice of the invention may be thermolabile or thermostabile (e.g., Taq ligase). If a thermoloabile ligase is employed, it will typically need to be readded to a reaction mixture for each error correction cycle. Thermostabile ligases will typically not need to be readded during each cycle, so long as the temperature is kept below their denaturation point.

Figure 36:
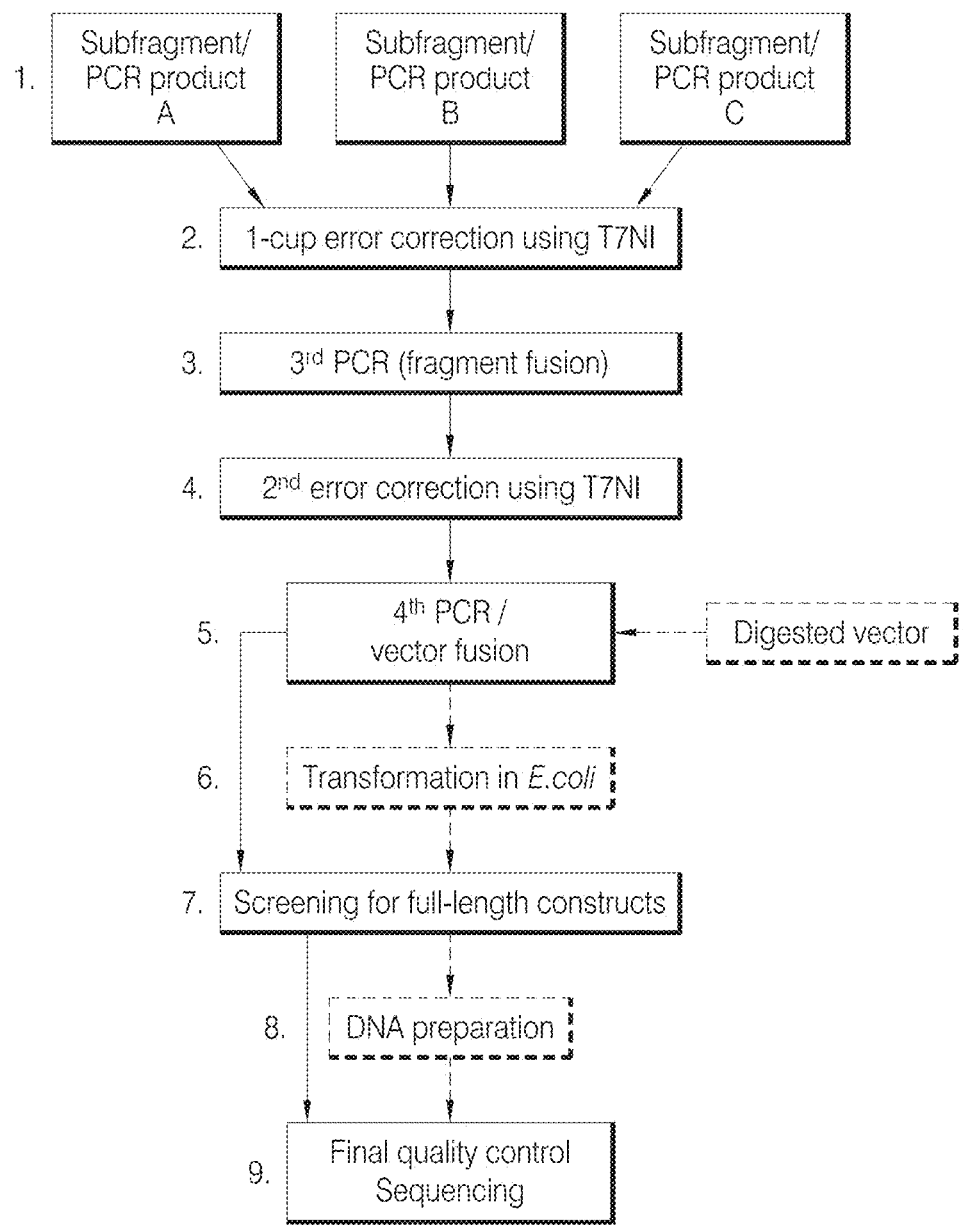
FIG. 36 shows a workflow schematic for the assembly of oligonucleotides and double error correction. Nine line numbers are labeled in the workflow for reference in the specification.

A representative workflow of the invention is set out in FIG. 36. In this workflow, three nucleic acid segments (referred to as "Subfragments") are pooled and subjected to error correction using the enzyme T7 endonuclease I ("T7NI") (Line 2). The three nucleic acid segments are then assembled by PCR (Line 3) and then subjected to a second round of error correction (Line 4). After another round of PCR (Line 5), the resulting nucleic acid molecules are then screened for those that are full length (Line 7). These nucleic acid molecules may then be screened for remaining errors by, for example, sequencing.

Figure 42A:
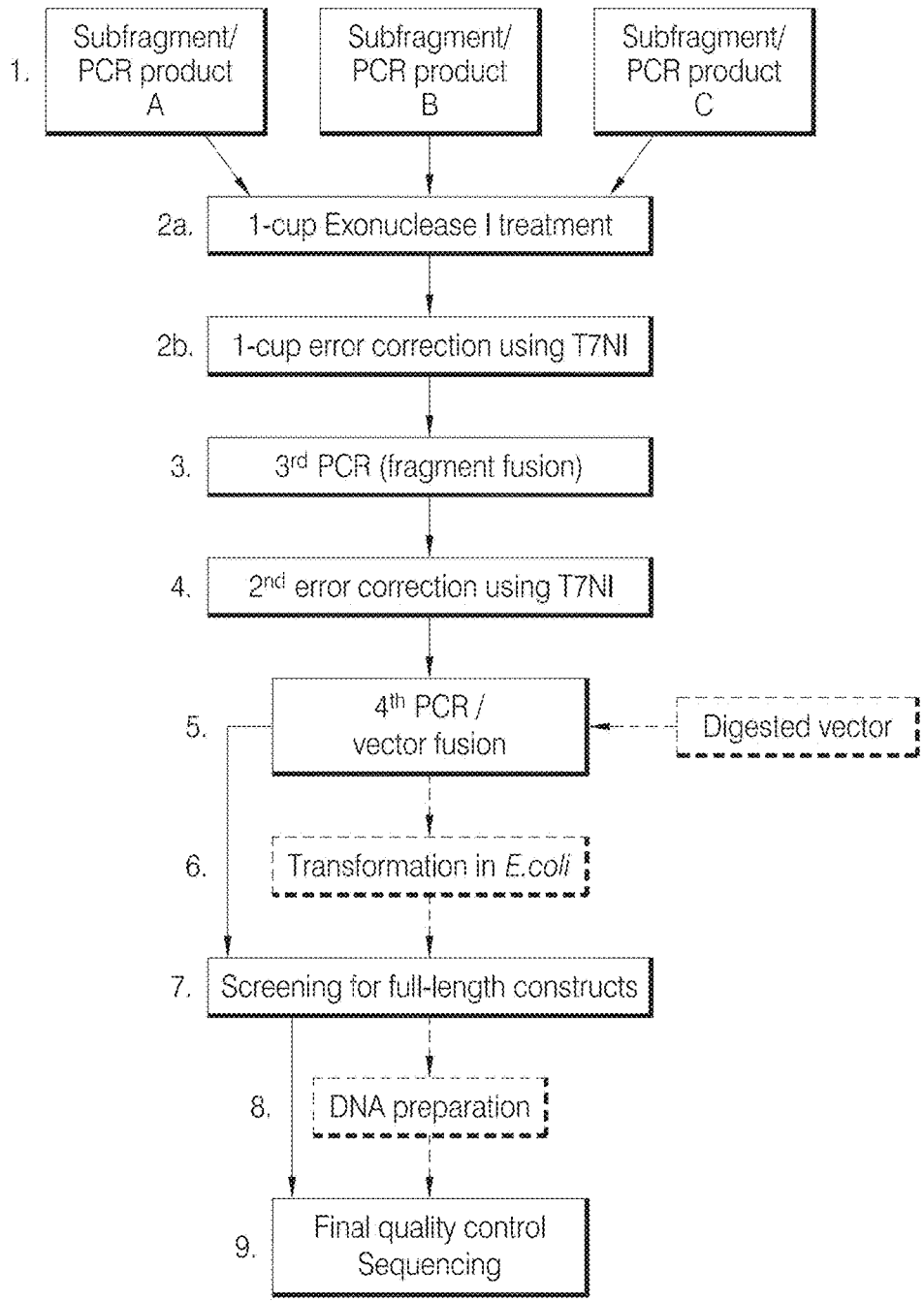
FIGS. 42A and 42B show alternative workflow schematics for the assembly of oligonucleotides comprising Exonuclease I treatment. In a first variation, double error correction is performed using one type of endonuclease (workflow on the left). In a second variation, double error correction is performed using one or more endonucleases in the first round and a mismatch binding protein in the second round (workflow on the right). Nine line numbers are labeled in the workflow for reference in the specification.
Figure 42B:
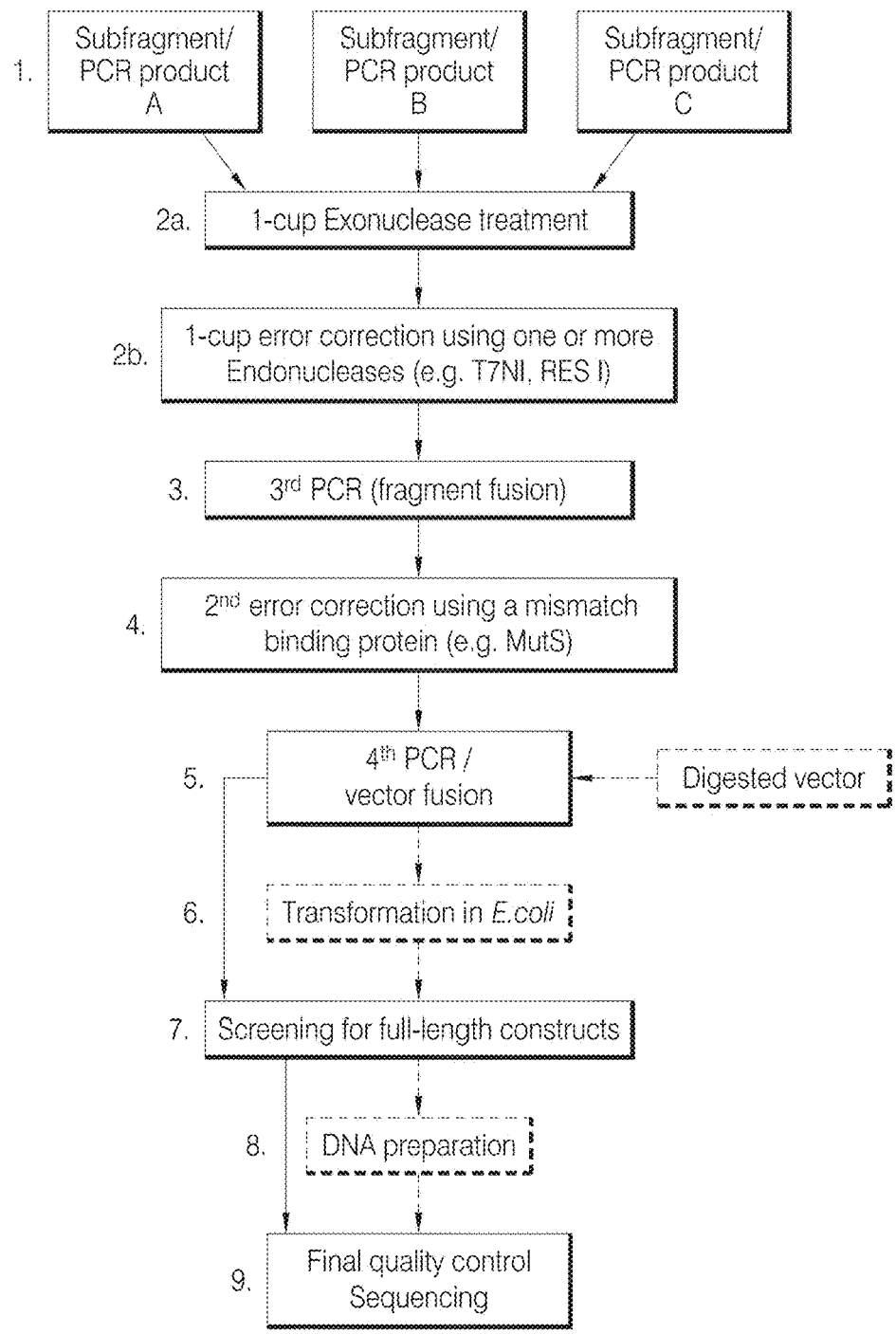

A first variation of the workflow of FIG. 36 is outlined in FIGS. 42A and 42B, workflow on the left. In this embodiment, the subfragments (Line 1) are pooled and treated with an exonuclease (such as, e.g., Exonuclease I; Line 2a) before they are subjected to the double error correction process an (Lines 2b and 4). The exonuclease eliminates single stranded primer molecules left over in the PCR reaction product that may interfere with subsequent PCR reactions (Line 3) and generate unspecific amplification products. In a second variation of the workflow, the first error correction step may use more than one endonuclease such as, e.g., T7NI combined with RES I (FIGS. 42A and 42B, workflow on the right, Line 2b). Optionally, the workflow may comprise a third error correction step to eliminate remaining mismatches after segment assembly PCR (Line 3). Such third error correction step may be conducted with a mismatch binding protein such as, e.g., MutS (Line 4). The skilled person will understand that various orders and combinations of first, second and/or third and possibly further error correction cycles may be applied to further decrease the error rate of assembled nucleic acid molecules.

Figure 37:
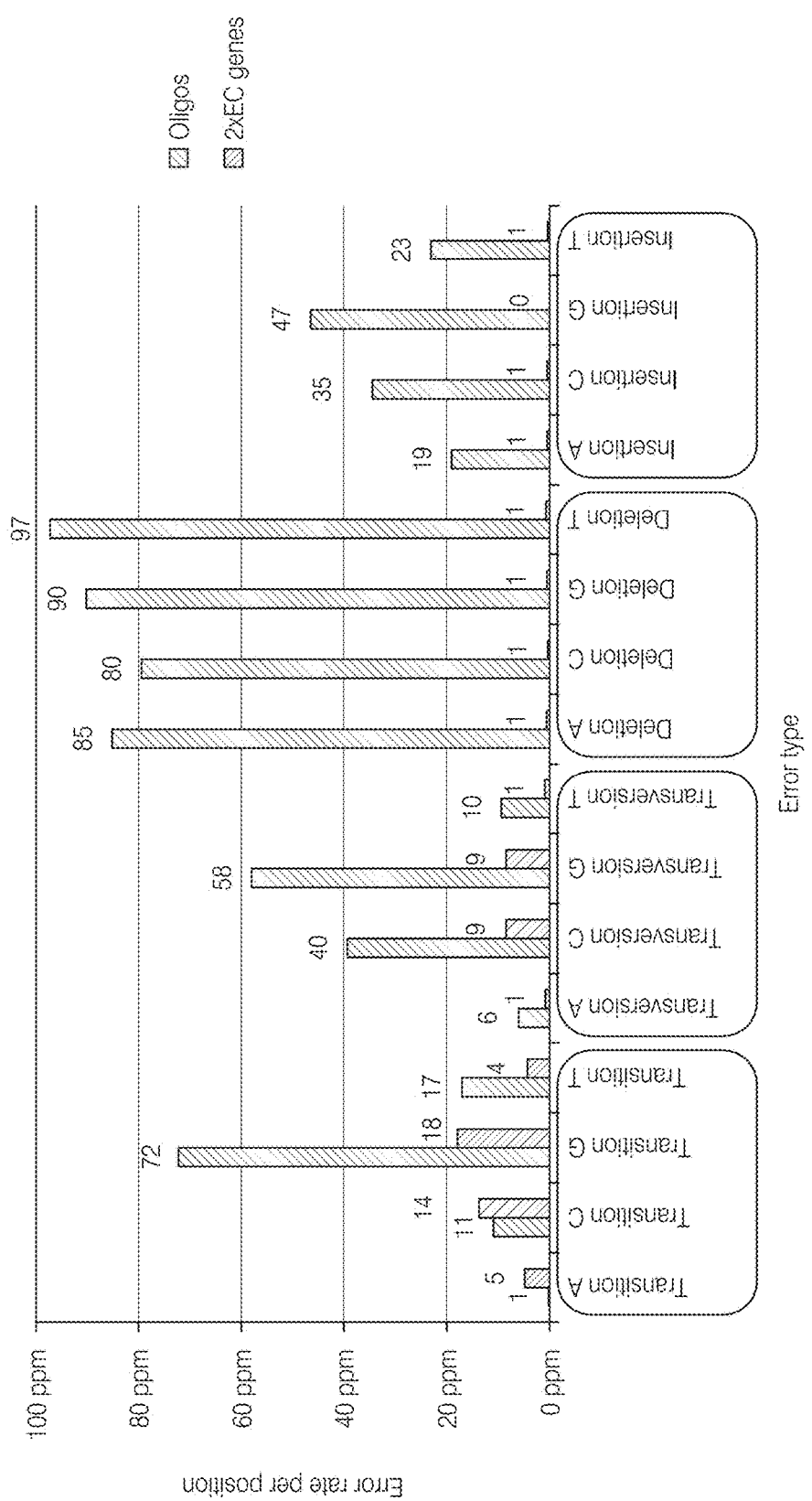
FIG. 37 shows a table of error types and rates found in chemically synthesized oligonucleotides prior to error correction and after two rounds of error corrections using T7 endonuclease I. These data were generated as set out in Example 9.

FIG. 37 shows individual and comparative frequencies of nucleotide sequence errors in chemically synthesized nucleic acid molecules both before and after error correction. As can be seen from the data, insertions and deletions are effectively removed by T7 endonuclease I mediated error correction.

Figure 38:
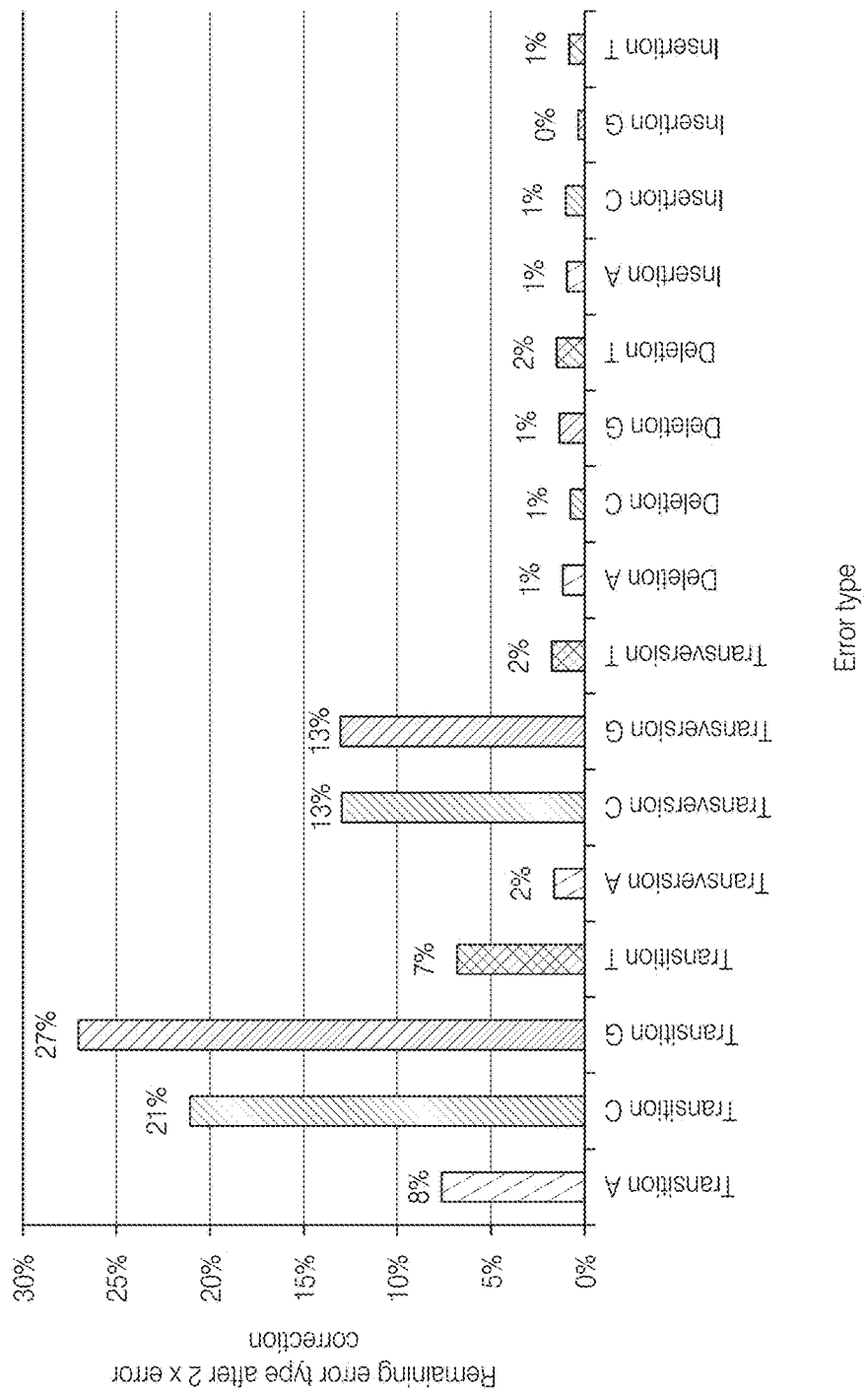
FIG. 38 shows the remaining errors, by type, found in chemically synthesized oligonucleotides after two rounds of error corrections using T7 endonuclease I. These data were generated as set out in Example 9.

FIG. 38 shows errors remaining by percentage of total errors after two rounds of error correction. About 63% of remaining errors are transitions and about 30% of remaining errors transversions. Thus, 93% of the remaining errors are transitions and transversions. Further, as can be seen in FIG. 37, error corrected nucleic acid molecules appear to have more C transitions than uncorrected chemically synthesized nucleic acid molecules. As explained in Example 9, this may result from substitutions that occur during PCR.

The invention thus provides methods for removing indels from nucleic acid molecules. In many instances, such methods result in the reduction of indels of greater than 95%. In some instances, all indels are removed from error corrected nucleic acid molecules. Indel removal is important because such alterations have a significant potential for adversely affecting the function of nucleic acid molecules. When an indel is present within a protein coding regions of a nucleic acid molecule, the result is often a frameshift. The invention thus includes methods for removing indels from nucleic acid molecules, wherein greater than 90% (e.g., from about 90% to about 99.9%, from about 93% to about 99.9%, from about 95% to about 99.9%, from about 98% to about 99.9%, from about 95% to about 99%, etc.) indels are removed.

The invention also provides methods for removing all types of errors from nucleic acid molecules. As can be seen from the data shown in FIG. 37, transition rate were decreased from about 101 ppm to about 41 ppm, transversions from about 114 ppm to about 20 ppm, thus, overall substitutions from about 215 ppm to about 61 ppm (a 72% reduction).

The invention also provides methods for the removal of errors in nucleic acid molecules that result in the elimination of greater than 95%, greater than 97%, greater than 98%, greater than 99%, greater than 99.5%, or greater than 99.8% of all errors introduced during chemical synthesis. In other words, errors may be introduced into nucleic acid molecules that are the subject of the invention in several ways. One way is by synthesis errors that occur during chemical synthesis of oligonucleotides (chemical synthesis errors). Another way is through the polymerase chain reaction (PCR) process. One way to reduce non-chemical synthesis errors is by limiting the number of error introduction manipulations that the nucleic acid molecules are subjected to after chemical synthesis. Further, in some instances, errors may be removed during chemical synthesis of oligonucleotides and additional errors may be introduced in later processes.

Using errors potentially introduced into nucleic acid molecule during PCR as an example, a number of methods may be used to reduce such errors. Polymerase errors are known to be strongly dependent on the nucleotide sequence of molecules being replicated. Further, the more rounds of PCR used, the more potential for the introduction of errors. Also, different polymerases have been shown to have different error rates (see, e.g., McInerney et al., "*Error Rate Comparison during Polymerase Chain Reaction by DNA Polymerase*", Molecular Biology International, Volume 2014, Article ID 287430). Thus, polymerase introduced errors may be reduced by several methods including (1) a reduction or elimination of polymerase mediated application steps, (2) the choice of polymerase used, and (3) adjustment of the sequence being amplified.

A number of studies have been performed on polymerase error rates. One such study is set out in McInerney et al., Molecular Biology International, Volume 2014, Article ID 287430. In this study, the following error rates were found Taq polymerase (Fermentas)—$3.0 \times 10^{-5}$, $5.6 \times 10^{-5}$ (two experiments), ACCUPRIME™-Taq (Life Technologies Corp.)—$1.0 \times 10^{-5}$, KOD Hot Start (Novagen)—$7.6 \times 10^{-6}$, Cloned Pfu polymerase (Agilent)—$2.8 \times 10^{-6}$, PHUSION® Hot Start (Finnzymes)—$2.6 \times 10^{-6}$, and Pwo polymerase (Roche)—$2.4 \times 10^{-6}$. Thus, McInerney et al., estimates that error rates for the enzymes tested range from about $1.0 \times 10^{-5}$ to about $7.6 \times 10^{-6}$.

It should be noted that Accuprime-Taq is an enzyme mixture with one of the enzymes being recombinant Taq DNA polymerase and another being *Pyrococcus* species GB-D polymerase. *Pyrococcus* species GB-D polymerase is a proofreading enzyme that possesses a 3' →5' exonuclease activity. Mixture of this enzyme with Taq DNA polymerase is believed to increase fidelity.

McInerney et al., Molecular Biology International, Volume 2014, Article ID 287430 also sets out the type of errors introduced by polymerases. The number of indels were so low that their number were not statistically meaningful. Thus, what appear to be total number for all polymerases tested are as follows: 155 transitions, 9 transversions, and 4 indels.

Hence, indels appear to be readily removed by methods of the invention and may be introduced at relatively low frequency into polymerase amplified nucleic acid molecules.

The invention thus includes methods for generating nucleic acid molecules that closely match an intended nucleotide sequence. These methods may employ one or more of the following: high fidelity nucleic acid synthesis, correction of errors introduced into nucleic acid molecules during the synthesis process, minimization of the number of rounds of PCR that nucleic molecules designed to have an intended nucleotide sequence are subjected to, the use of high fidelity polymerases and/or mixtures of polymerases, the use of one or more error correction process at one or more step in the generation of nucleic acid molecules, and the use of one or more error correction process late in the process of generating the nucleic acid molecules (e.g., to remove polymerase introduced errors and to limit the number of new polymerase introduced errors).

The invention also includes methods in which the total number of amplification reactions is less than twenty (e.g., from about 4 to about 20, from about 6 to about 20, from about 8 to about 20, from about 10 to about 20, from about 12 to about 20, from about 14 to about 20, etc.) The invention further includes methods in which the total number of amplification reactions after error correction, which includes amplification associated with the error correction process as being "error correction", is less than ten (e.g., from about 0 to about 10, from about 1 to about 10, from about 2 to about 10, from about 4 to about 10, from about 5 to about 20, from about 11 to about 5, etc.).

TABLE 10

| | | | Gene (size) | | | | | |
|---|---|---|---|---|---|---|---|---|
| Rounds | Enzyme Mix | Feature | A (1288 bp) | B1aB1b (1478 bp) | B2a (776 bp) | B2b (766 bp) | Rate (−1) Average | ST DEV |
| 0 | T7N1 | bp sequenced | 62192 | 0 | 0 | 0 | | |
| | | # error | 53 | 0 | 0 | 0 | | |
| | | Error Rate (−1) | 1173 | 0 | 0 | 0 | 1173 | N/A |
| 1 | T7N1 | bp sequenced | 130398 | 0 | 0 | 0 | | |
| | | # errors | 15 | 0 | 0 | 0 | | |
| | | Error Rate (−1) | 8693 | 0 | 0 | 0 | 8693 | N/A |
| | T7N1 | bp sequenced | 10304 | 14780 | 6208 | 5362 | | |
| | | # errors | 1 | 1 | 4 | 5 | | |
| | | Error Rate (−1) | 10304 | 14780 | 1552 | 1072 | 6927 | 6739 |
| | Cel2 | bp sequenced | 12880 | 11824 | 7760 | 6128 | | |
| | | #errors | 3 | 4 | 6 | 5 | | |
| | | Error Rate (−1) | 4293 | 2956 | 1293 | 1226 | 2442 | 1471 |
| | T7N1/Cel2 | bp sequenced | 10304 | 13302 | 7760 | 12256 | | |
| | | # errros | 2 | 2 | 3 | 4 | | |
| | | Error Rate (−1) | 5152 | 6651 | 2587 | 3064 | 4363 | 1889 |
| 2 | T7N1 | bp sequenced | 91504 | 0 | 0 | 0 | | |
| | | # errors | 6 | 0 | 0 | 0 | | |
| | | Error Rate (−1) | 15251 | 0 | 0 | 0 | 15251 | N/A |

TABLE 10-continued

| | | | | | | | |
|---|---|---|---|---|---|---|---|
| | T7N1 | bp sequenced | 25760 | 28082 | 15520 | 15320 | | |
| | | # errors | 2 | 2 | 4 | 0 | | |
| | | Error Rate (−1) | 12880 | 14041 | 3880 | 15320 | 11530 | 5197 |
| | T7N1/Cel2 | bp sequenced | 25760 | 29560 | 14744 | 14554 | | |
| | | # errors | 2 | 1 | 1 | 2 | | |
| | | Error Rate (−1) | 12880 | 29560 | 14744 | 7277 | 16115 | 9508 |
| 3 | T7N1 | bp sequenced | 269423 | 222270 | 108367 | 159280 | | |
| | | # errors | 7 | 12 | 15 | 13 | | |
| | | Error Rate (−1) | 38489 | 18522.5 | 7224 | 12252 | 19122 | 18713 |
| | T7N1/Cel2 | bp sequenced | 371409 | 328610 | 104117 | 129580 | | |
| | | # errors | 6 | 7 | 10 | 5 | | |
| | | Error Rate (−1) | 61902 | 46944 | 10412 | 25916 | 36293 | 22707 |

| | | | | Error Break Down | | | | |
|---|---|---|---|---|---|---|---|---|
| Rounds | Enzyme Mix | Feature | Total bp seq | A<>G + C<>T | A<>C + G<>T | C<>G | A<>T | Indels | Total No. |
| 0 | T7N1 | bp sequenced # error Error Rate (−1) | 62192 | 7 | 2 | 1 | 0 | 43 | 53 |
| 1 | T7N1 | bp sequenced # errors Error Rate (−1) | 130398 | 10 | 0 | 0 | 0 | 5 | 15 |
| | T7N1 | bp sequenced # errors Error Rate (−1) | 36654 | 6 | 0 | 0 | 1 | 4 | 11 |
| | Cel2 | bp sequenced #errors Error Rate (−1) | 38592 | 7 | 1 | 0 | 0 | 10 | 18 |
| | T7N1/Cel2 | bp sequenced # errros Error Rate (−1) | 43622 | 5 | 0 | 2 | 1 | 3 | 11 |
| 2 | T7N1 | bp sequenced # errors Error Rate (−1) | 91504 | 6 | 0 | 0 | 0 | 0 | 6 |
| | T7N1 | bp sequenced # errors Error Rate (−1) | 84682 | 3 | 0 | 0 | 4 | 1 | 8 |
| | T7N1/Cel2 | bp sequenced # errors Error Rate (−1) | 84618 | 3 | 0 | 0 | 1 | 2 | 6 |
| 3 | T7N1 | bp sequenced # errors Error Rate (−1) | 759340 | 34 | 8 | 3 | 2 | 0 | 47 |
| | T7N1/Cel2 | bp sequenced # errors Error Rate (−1) | 933716 | 21 | 6 | 0 | 1 | 0 | 28 |

Another method for removal of error from chemically synthesized nucleic acid molecules is by selection of nucleic acid molecules having correct nucleotide sequences. This may be done by the selection of a single nucleic acid molecule for amplification, then sequencing of the amplification products to determine if any errors are present. Thus, the invention also includes selection methods for the reduction of sequence errors. Methods for amplifying and sequence verifying nucleic acid molecules are set out in U.S. Pat. No. 8,173,368, the disclosure of which is incorporated herein by reference. Similar methods are set out in Matzas et al., *Nature Biotechnology*, 28:1291-1294 (2010). Selection of sequence-verified nucleic acid molecules can be accomplished by various means including methods using laser pulses as described elsewhere herein.

Methods according to this aspect of the invention may include the following steps: (a) providing a mixture of nucleic acid molecules synthesized to have the same nucleotide sequence, (b) separating nucleic acid molecules in the mixture such that amplification results in progeny nucleic acid molecules being derived from a single starting nucleic acid molecule, (c) sequencing more than one amplified nucleic acid molecule generated in step (b), and (d) identifying at least one individual nucleic acid with the desired sequence from the nucleic acid molecules sequenced in step (c). The nucleic acid molecule identified in step (d) may then be used as one nucleic acid molecule in an assembly process, as described elsewhere herein.

The invention also includes compositions and methods for the isolation of nucleic acid molecules that have a desired nucleotide sequence present in a population of nucleic acid molecules that do not have the desired sequence (e.g., have "errors"). This may be done using methods in which nucleic acid molecules containing errors are physically separated from nucleic acid molecules that have the "correct" nucleotide sequence. The invention further includes compositions and methods by which nucleic acid molecules are not subjected to in vitro amplification steps, or other steps, that may introduce errors. Thus, as part of, for example, the error correction process, nucleic acid molecules having correct sequences may be physically separated from those that do not have the correct sequence. One means by which to do this involves the use of agents that bind nucleic acid molecules that contain mismatches.

As an example, a protein that has been shown to bind double-stranded nucleic acid molecules containing mismatches is *E. coli* MutS (Wagner et al., *Nucleic Acids Res.*, 23:3944-3948 (1995)). Wan et al., *Nucleic Acids Res.*, 42:e102 (2014) demonstrated that chemically synthesized nucleic acid molecules containing errors can be retained on a MutS-immobilized cellulose column with nucleic acid molecules not containing errors not being so retained.

The invention thus includes methods, as well as associated compositions, in which nucleic acid molecules are denatured, followed by reannealing, followed by the separation of reannealed nucleic acid molecules containing mismatches. In some aspects, the mismatch binding protein used is MutS (e.g., *E. coli* MutS).

Further, mixtures of mismatch repair binding proteins may be used in the practice of the invention. It has been found that different mismatch repair binding proteins have different activities with respect to the types of mismatches they bind to. For example, *Thermus aquaticus* MutS has been shown to effectively remove insertion/deletion errors but is less effective in removing substitution errors than *E. coli* MutS. Further, a combination the two MutS homologs was shown to further improve the efficiency of the error correction with respect to the removal of both substitution and insertion/deletion errors, and also reduced the influence of biased binding. The invention thus includes mixtures of two or more (e.g., from about two to about ten, from about three to about ten, from about four to about ten, from about two to about five, from about three to about five, from about four to about six, from about three to about seven, etc.) mismatch repair binding proteins.

The invention further includes the use of multiple rounds (e.g., from about two to about ten, from about three to about ten, from about four to about ten, from about two to about five, from about three to about five, from about four to about six, from about three to about seven, etc.) of error correction using mismatch repair binding proteins. One or more of these rounds of error correction may employ the use of two or more mismatch repair binding proteins. Alternatively, a single mismatch repair binding protein may be used in a first round of error correction whereas the same or another mismatch binding protein may be used in a second round of error correction.

Using the workflow set out in FIG. 36 for purposes of illustration, nucleic acid molecules containing errors may be removed at one or more steps. For example, "mismatched" nucleic acid molecules may be removed between steps 1 and 2 in FIG. 36. This would result in the treatment of a "preselected" population of nucleic acid molecules with a mismatch repair endonuclease. Further, two error corrections such as these may be merged. As an example, nucleic acid molecules may be denatured, then reannealed, followed by removal of nucleic acid molecules with mismatches through binding with immobilized MutS, then followed by contacting the nucleic acid molecules that are not separated by MutS binding with a mismatch repair endonuclease without intervening denaturation and reannealing steps.

While not wishing to be bound by theory, it is believed that amplification of nucleic acid molecules introduces errors into the molecules being amplified. One means of avoiding the introduction of amplification mediated errors and/or for the removal of such errors is by the selection of nucleic acid molecules with correct sequences after most or all amplification steps have been performed. Again using the workflow set out in FIG. 36 for purposes of illustration, nucleic acid molecules with mismatches may be separated from those without mismatches after step 5. Alternatively, mismatch-containing molecules may be removed after step 3 as shown in FIGS. 42A and 42B, workflow on the right.

Nucleic acid molecules with mismatches may be separated from those without mismatches by binding with a mismatch binding agent in a number of ways. For example, mixtures of nucleic acid molecules, some having mismatches, may be (1) passed through a column containing a bound mismatch binding protein or (2) contacted with a surface (e.g., a bead (such as a magnetic bead), plate surface, etc.) to which a mismatch binding protein is bound.

Exemplary formats and associated methods involve those using beads to which a mismatch binding protein is bound. For example, a solution of nucleic acid molecules may be contacted with beads to which is bound a mismatch binding protein. Nucleic acid molecules that are bound to the mismatch binding protein are then linked to the surface and not easily removed or transferred from the solution.

Figure 39:
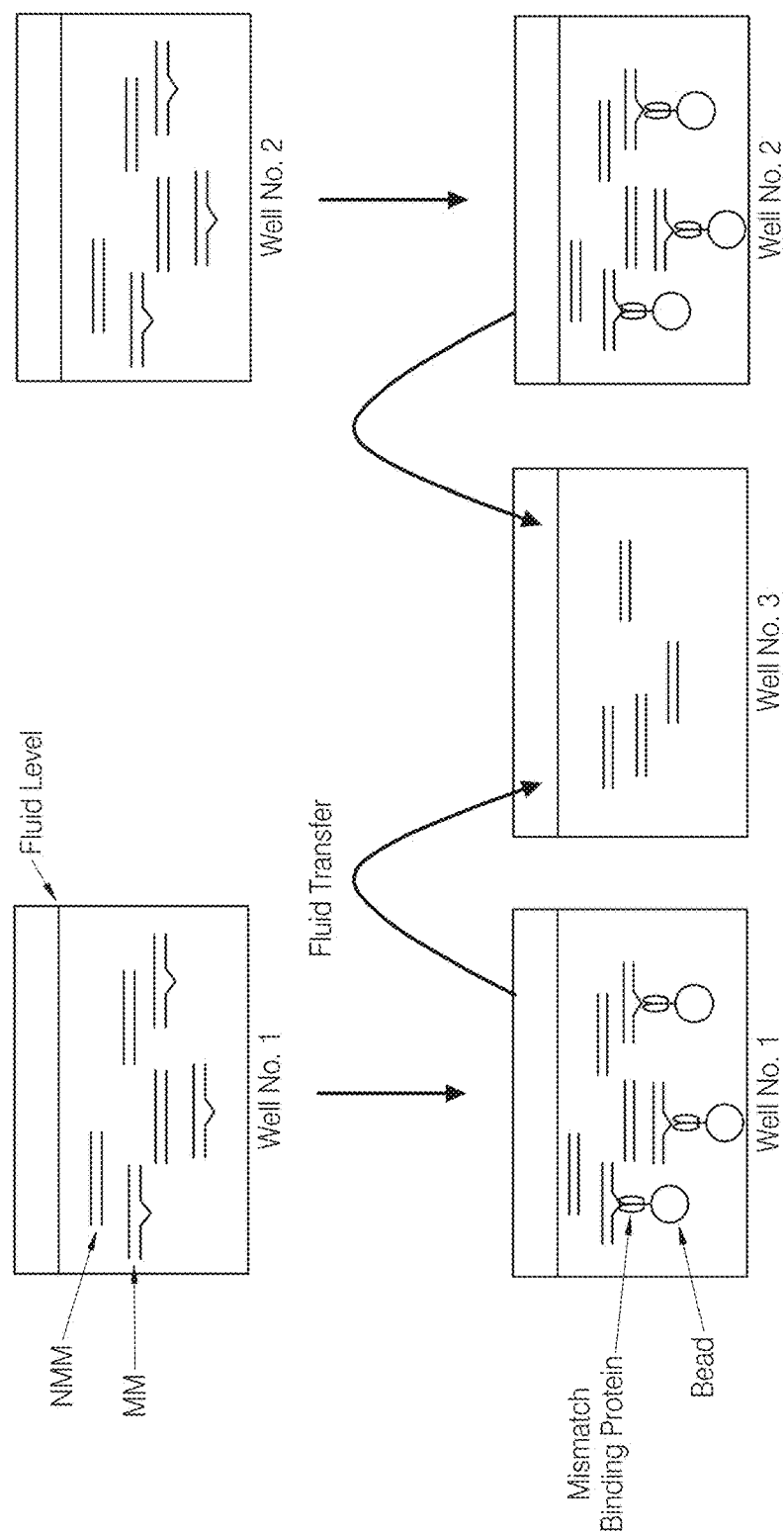
FIG. 39 shows a schematic representation of a workflow employing bead bound mismatch repair binding proteins for the separation of nucleic acid molecules that contains mismatches from those that do not contain mismatches. NMM refers to a non-mismatched nucleic acid molecule and MM refers to a mismatched nucleic acid molecule.
Figure 40A:
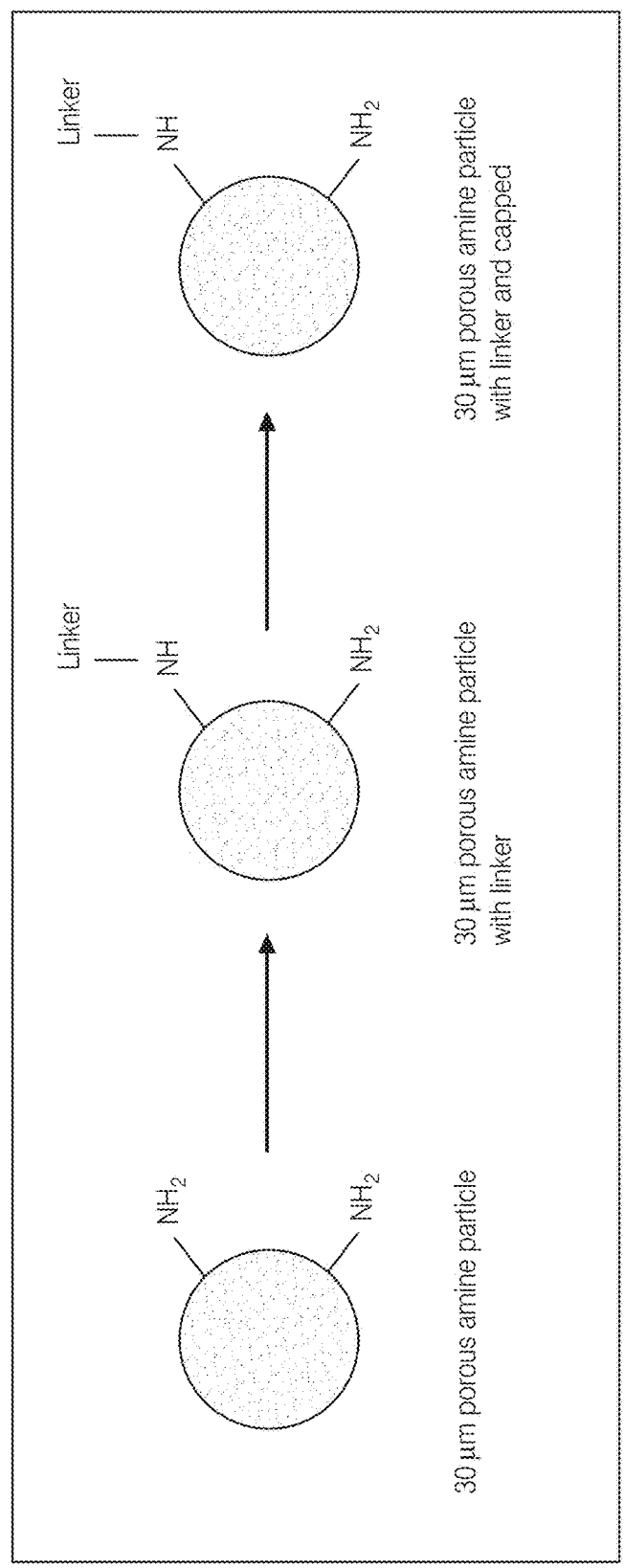
FIGS. 40A and 40B show the modification of porous amine functionalized particles with linker molecules.
Figure 40B:
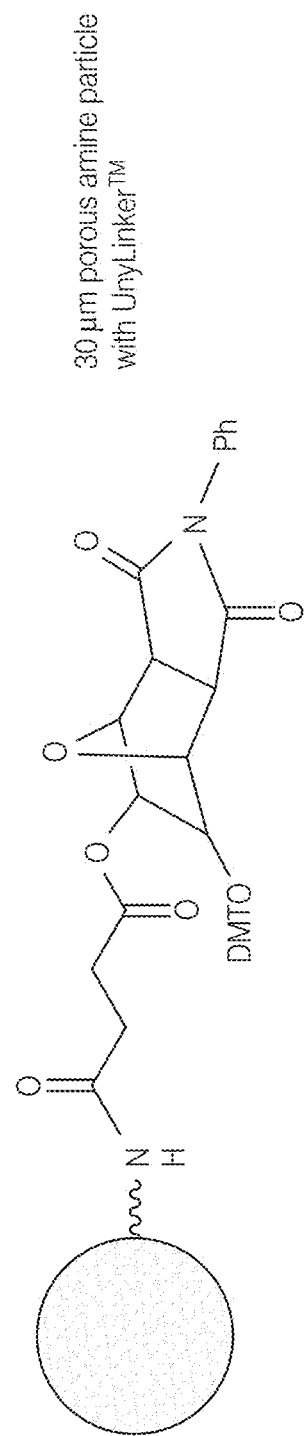
Figure 41A:
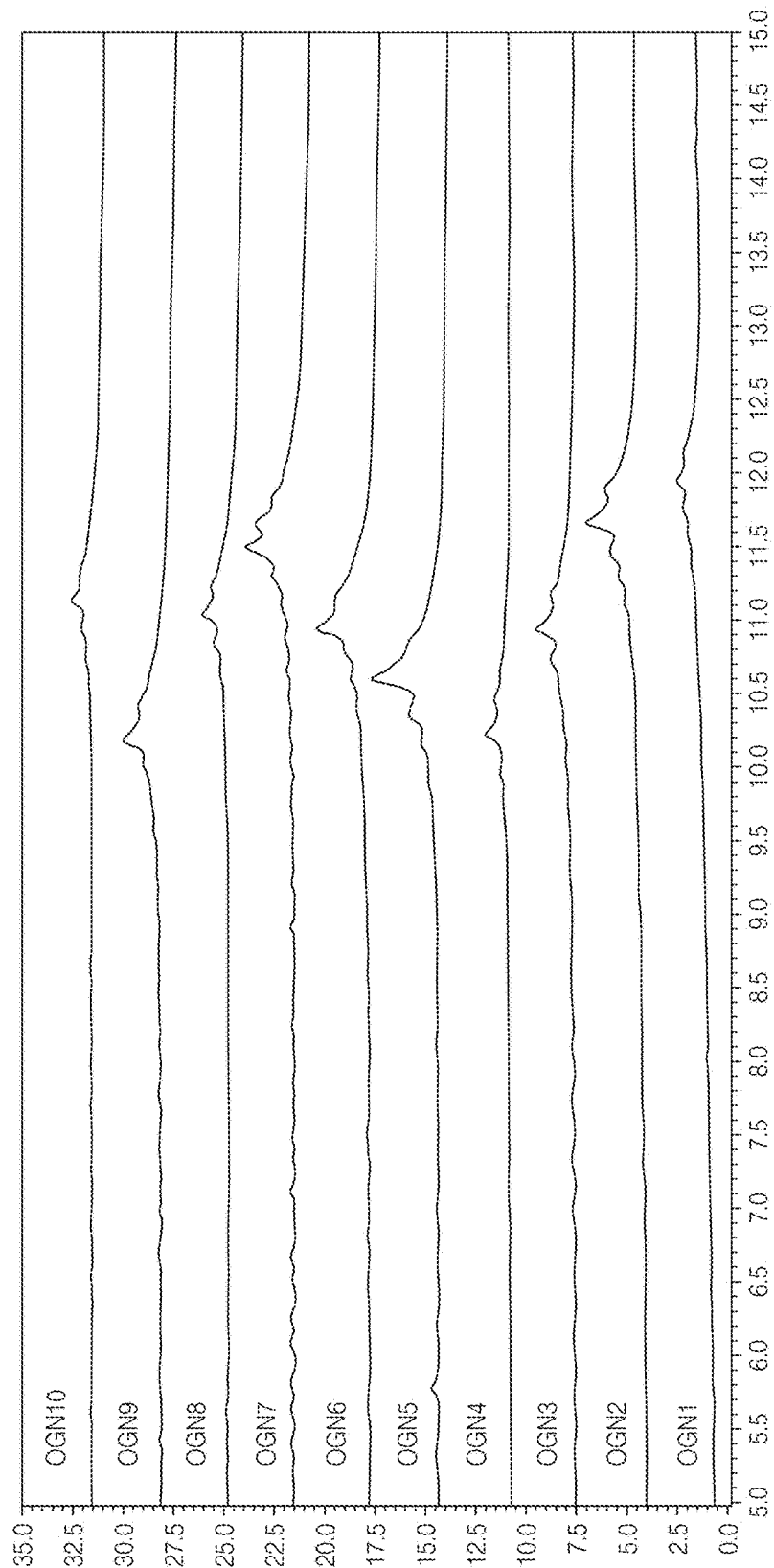
FIGS. 41A and 41B show the oligonucleotides used for assembly of a lacZ gene.
Figure 41B:
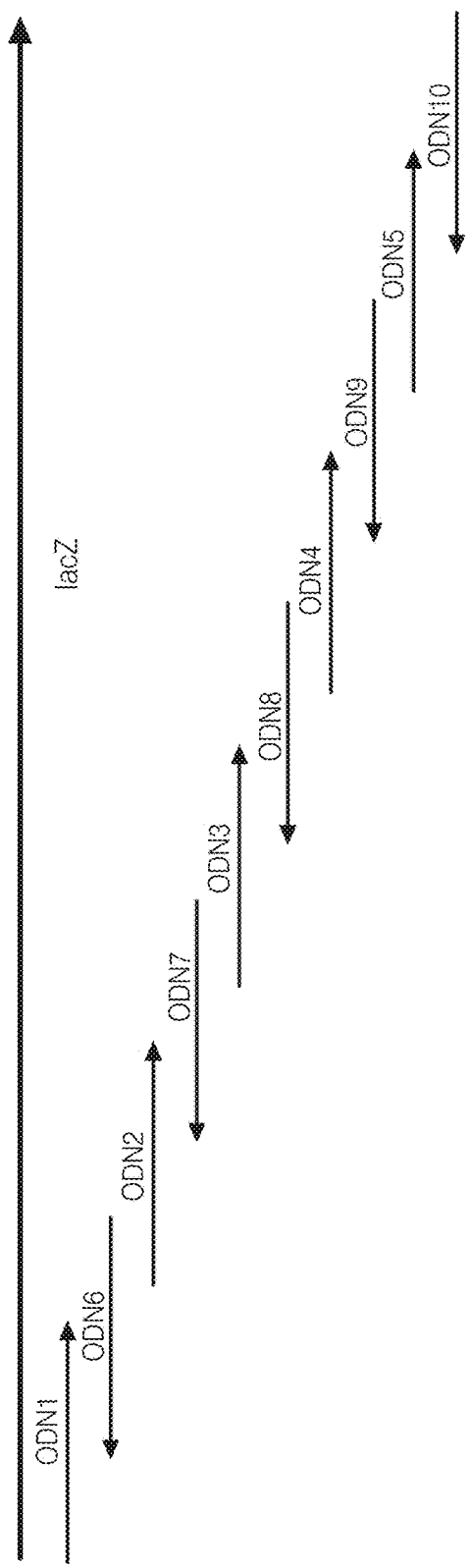

In a specific format set out in FIG. 39, beads with a bound mismatch binding protein may be placed in a vessel (e.g., a well of a multi-well plate) with nucleic acid molecules present in solution, under conditions that allow for the binding of nucleic acid molecules with mismatches to the mismatch binding protein (e.g., 5 mM $MgCl_2$, 100 mM KCl, 20 mM Tris-HCl (pH 7.6), 1 mM DTT, 25° C. for 10 minutes). Fluid may then be transferred to another vessel (e.g., a well of a multi-well plate) without transferring of the beads and/or mismatched nucleic acid molecules.

Any number of methods may be used for transferring fluids containing nucleic acid molecules. For example, a micropipette may be used. Further, a magnetic field may be used to hold magnetic beads to which mismatched nucleic acid molecules are bound in place, for examples, during pipetting or while the fluid to be transferred is otherwise removed. As another example, a solid object (e.g., a glass or metal rod) may be introduced into a first vessel containing nucleic acid to be transferred, followed by dipping the solid object into fluid present in a second vessel. Fluid adhering to the solid object, and nucleic acid molecules associated with the solid object, would be transferred from the first vessel into the second vessel. Acoustic fluid transfer (described elsewhere herein) may also be employed. Acoustic liquid transfer may be used to transfer fluid from the surface of one vessel (e.g., Well No. 1 and/or Well No. 2 in FIG. 39), where beads are located at the bottom of the first vessel, to a second vessel (e.g., Well No. 3 in FIG. 39). Thus, bead bound nucleic acid molecules containing mismatches will not be in close proximity to fluid being transferred. In instances where no magnetic field is applied to hold beads coated with mismatch-binding protein in place, it may be required to adjust the concentration of beads in a well such that no beads will be transferred together with a predetermined volume of transferred liquid. The lower the concentration of beads in a well from which liquid is to be transferred, the more volume can be transferred without co-transferring non-immobilized beads from that well. For example, a bead concentration within a range of from about 100 µg/µl to about 1 mg/µl may be used to transfer from about 0.1 µl to about 5 µl of liquid comprising error-corrected nucleic acid molecules from a well of a multiwell plate by acoustic fluid transfer.

At the same time, the concentration of beads should be high enough to ensure that sufficient amounts of MutS will be provided on the beads to efficiently capture mismatch containing nucleic acid molecules in the sample. For example where mismatch containing fragments have a length of about 300 to 500 bp, beads (such as, e.g., Magnetic Mismatch Binding Beads (M2B2), MAGDETECT™; United States Biological, Salem, Mass.; provided at a stock solution of 10 mg/ml) may be used at a concentration that equals a concentration of about 0.5 to about 2 µg/µl of MutS protein.

Further beads may be separated from a solution containing nucleic acid molecules that have not bound to the beads. This results in the separation of nucleic acid molecules containing mismatches from those that do not contain mismatches. In some embodiments, the mismatch binding properties of certain proteins such as MutS may be used to remove nucleic acid molecules that still contain errors after an error-correction step performed with one or more endonucleases as described above. Thus, methods of removing errors may comprise a combination of (i) endonuclease-based repair and (ii) mismatch binding protein-mediated removal of error-containing nucleic acid molecules. In some workflows, step (i) may be followed by step (ii) as illustrated by FIGS. 42A and 42B, right flow chart. In other embodiments step (ii) may be followed by step (i). Step (i) may for example be conducted by T7NI and step (ii) may be conducted by MutS. In some instances the combination of steps (i) and (ii) may lead to an overall error reduction rate by factors of between 1.5 and 3, 3 and 20 (e.g., from about 4 to about 20, from about 5 to about 20, from about 7 to about 20, from about 10 to about 20, from about 12 to about 20, from about 4 to about 17, from about 4 to about 15, from about 8 to about 15, etc.).

The invention thus includes methods for preparing compositions that have an increased number of nucleic acid molecules with a desired sequence, as compared to composition that have fewer nucleic acid molecules with a desired sequence. This may be done by sequestration of nucleic acid molecules that do not have the desired sequence, followed by separating these nucleic acid molecules from nucleic acid molecules that do have the desired sequence. Further, the nucleic acid molecules that have the desired sequence may be a final end product or may be combined with other nucleic acid molecules (e.g., other chemically synthesized nucleic acid molecules or a vector).

Once nucleic acid molecules that have the desired sequence have been obtained, they may be treated in a manner that limits the number of alterations that may be introduced into them. For example, nucleic acid molecules may be designed such that they are assembled and or amplified upon introduction into a cell (e.g., a yeast cell). Intracellular assembly and amplification makes use of cellular machinery and with that comes error correction processes that can be employed to result in low numbers of new errors being introduced into nucleic acid molecules.

In specific embodiments, the invention includes compositions and methods for the production, assembly, and correction of errors in oligonucleotides and nucleic acid molecules fully or partially assembled from oligonucleotides. For example, methods of the invention include (1) chemical synthesis of multiple oligonucleotides, (2) partial assembly of the multiple oligonucleotides to form two or more partially assembled nucleic acid molecules, (3) performing one or more round of error correction on each of the two or more partially assembled nucleic acid molecules, (4) assembly of the two or more error corrected partially assembled nucleic acid molecules generated in step (3) to form a larger nucleic acid molecule, and (6) performing one or more round of error correction on the larger nucleic acid molecule generated in step (5), wherein the error correction methods are performed by denaturing and reannealing nucleic acid molecules, followed by contacting the reannealed nucleic acid molecules with (a) a mismatch repair endonuclease under conditions suitable for the cleavage of nucleic acid molecules that contain mismatches, (b) a mismatch repair binding protein under conditions where nucleic acid molecules that contain mismatches are sequestered, or (c) both (a) and (b) simultaneously or in different steps.

Further, when error correction is performed using a mismatch endonuclease, one or more ligase (such as Taq ligase) may be present in the reaction mixture. This is especially desirable when the mismatch endonuclease has nickase activity. The one or more ligase may be omitted but this may result in lower yields of nucleic acid molecules especially when an amplification step is used after endonuclease digestion.

According to various embodiments described herein, a computer-readable medium may be encoded with processor-executable instructions for: (a) providing a mixture of nucleic acid molecules synthesized to have the same nucleotide sequence, (b) separating nucleic acid molecules in the mixture such that amplification results in progeny nucleic acid molecules being derived from a single starting nucleic acid molecule, (c) sequencing more than one amplified nucleic acid molecule generated in step (b), and (d) identifying at least one individual nucleic acid with the desired sequence from the nucleic acid molecules sequenced in step (c). The nucleic acid molecule identified in step (d) may then be used as one nucleic acid molecule in an assembly process, as described elsewhere herein. In various embodiments, the computer-readable medium may be included in a system configured to reduce error from chemically synthesized nucleic acid molecules by selection of nucleic acid molecules having correct nucleotide sequences.

Sequence errors in nucleic acid molecules may be referenced in a number of ways. As examples, there is the error rate associated with the synthesis nucleic acid molecules, the error rate associated with nucleic acid molecules after error correct and/or the selection, and the error rate associated with end product nucleic acid molecules (e.g., error rates of (1) a synthetic nucleic acid molecules that have either been selected for the correct sequence or (2) assembled chemically synthesized nucleic acid molecules). These errors may come from the chemical synthesis process, assembly processes, and/or amplifications processes. Errors may be removed or prevent by methods, such as, the selection of nucleic acid molecules having correct sequences, error correct, and/or improved chemical synthesis methods.

In some instances, methods of the invention will combine error removal and prevention methods to produce nucleic acid molecules with relative low numbers of errors. Thus, assembled nucleic acid molecules produced by methods of the invention may have error rates from about 1 base in 2,000 to about 1 base in 30,000, from about 1 base in 4,000 to about 1 base in 30,000, from about 1 base in 8,000 to about 1 base in 30,000, from about 1 base in 10,000 to about 1 base in 30,000, from about 1 base in 15,000 to about 1 base in 30,000, from about 1 base in 10,000 to about 1 base in 20,000, etc.

Some error correction processes suitable for use in methods of the invention are as follows. Two µl of nucleic acid (~150 ng) is mixed with 1 µl of 10× Assay Buffer (Tris 200 mM, KCl 250 mM, $MgCl_2$ 200 mM, NAD 5 mM, X-100 0.1% pH 8.3+/−0.05 at room temperature) and 5 µl of water. The nucleic acid is then denatured and re-annealed as follows: 98° C. for 2 minutes, 4° C. for 5 minutes, 37° C. for 5 minutes, then maintain at 4° C. One µl T7N1/Tth ligase mix (1782 µL Storage Buffer (Tris 10 mM, EDTA 0.1 mM, KCl 50 mM, X-100 0.15%, BSA 0.2 µg/mL, Glycerol 50% pH 7.4+/−0.05 @4 C), 12 µL, T7N1 (1:150) (stock 0.92 mg total protein/mL) (6.1 ng total protein/µL after dilution), and 6 µL, Tth Ligase (1:300) (Stock 1 mg total protein/mL) (3.3 ng total protein/uL after dilution). The amount and proportion of enzymes to be included in the mix are determined by titrating them using a mismatched substrate in the context of the Surveyor Assay (Transgenomic Inc.). The right amount and proportion is that one that digests 50% of the template.) and 1 µl of Cel II (Transgenomic Inc., Surveyor kit component "SURVEYOR Nuclease S") are added to the nucleic acid and mixed. In some embodiments, the reaction mixture may comprise 2 µl of nucleic acid, 1 µL, Taq Ligase NEB 40 units, 1 µl T7E1 NEB 10 units, 1 µL, of 10× Taq ligase buffer in 10 µl total volume.

The mixture is then incubated at 45° C. for 20 minutes without heating the lid cover. Two µl of error-corrected sample is then transferred to a PCR mix and PCR is performed. The PCR product is purified and an aliquot is cloned into a zero-blunt TOPO vector for sequencing. After a second round of error correction, the resulting PCR product is purified using a PureLink PCR column purification kit and then subjected to error correction as described above. For the third round of error correction, the resulting PCR product is purified and subjected to error correction again. The resulting PCR product is purified for subsequent cloning and sequencing.

Large nucleic acid molecules are relatively fragile and, thus, shear, readily. One method for stabilizing such molecules is by maintaining them intracellularly. Thus, in some aspects, the invention involves the assembly and/or maintenance of large nucleic acid molecules in host cells.

One group of organisms known to perform homologous recombination fairly efficient is yeasts. Thus, host cells used in the practice of the invention may be yeast cells (e.g., *Saccharomyces cerevisiae, Schizosaccharomyces pombe, Pichia, pastoris*, etc.).

Yeast hosts are particularly suitable for manipulation of donor genomic material because of their unique set of genetic manipulation tools. The natural capacities of yeast cells, and decades of research have created a rich set of tools for manipulating DNA in yeast. These advantages are well known in the art. For example, yeast, with their rich genetic systems, can assemble and re-assemble nucleotide sequences by homologous recombination, a capability not shared by many readily available organisms. Yeast cells can be used to clone larger pieces of DNA, for example, entire cellular, organelle, and viral genomes that are not able to be cloned in other organisms. Thus, in some embodiments, the invention employs the enormous capacity of yeast genetics generate large nucleic acid molecules (e.g., synthetic genomics) by using yeast as host cells for assembly and maintenance.

The mating capacity of yeast is favorable for modifying genomes and other large nucleic acids. Yeast recombination machinery, when activated during yeast mating, can be used to generate libraries, e.g., combinatorial libraries containing variants of cloned genomes or nucleic acids. For example, Yeast Artificial Chromosome (YAC) libraries have been constructed for several different bacteria (Azevedo et al., *PNAS USA* 90, 6047 (1993); Heuer et al., *Electrophoresis* 19, 486 (1998); Kuspa et al., *PNAS USA* 86, 8917 (1989). Large prokaryotic DNA segments can be cloned in yeast using the universal genetic code. Toxic gene expression typically is not a barrier to cloning nucleic acids in yeast. Studies with bacterial and archeal genomes, for example, indicate that because eukaryotes use different protein expression machinery than these bacteria, there is little risk of harm to yeast hosts by proteins expressed from the cloned genomes. Thus, the invention further includes methods for the generation of nucleic acid molecules (e.g., synthetic genomes) which confer a toxic phenotype when introduced into non-yeast cell (e.g., bacterial cells).

Nucleic acid molecules may be assembled from natural or synthetic fragments together with yeast vectors prior to transformation into yeast cells or simultaneously co-transformed into yeast cells. New organisms may created by transferring these genomes or other nucleic acid molecules, which have been optionally manipulated as desired, into compatible recipient cells. Thus, one embodiment provides suitable techniques for transferring genomes and other nucleic acid molecules to yeast host cells, modifying the genomes within host cells while maintaining their stability and integrity, and transplanting the cloned and manipulated genomes from yeast host cells back into recipient cells that more closely resemble original donors (e.g., organisms from which the nucleotides sequences were obtained), thus creating.

A commercially available product for the assembly of nucleic acid molecules in yeast cells is the GENEART® High-Order Genetic Assembly Systems (Life Technology, Cat. No. A13286). This is a kit for the simultaneous and seamless assembly of up to 10 DNA fragments, totaling up to 110 kilobases in length, into vectors. The system uses the ability of yeast to take up and recombine DNA fragments with high efficiency. This greatly reduces the in vitro handling of DNA and eliminates the need for enzymatic treatments, such as restriction and ligation, while allowing for precise fusions of DNA sequences. The kit contains materials for the transformation and purification from yeast, including yeast selective media, and competent *E. coli* for plasmid amplification of correct clones.

Assembly and maintenance of nucleic acid molecules in will often involve either the generation of or the insertion into cells nucleic acid molecule which contain elements such as one or more origin of replication (e.g., two origins of replication which are functional in different cell types) and one or selection marker (e.g., one or more positive selection marker and/or one of more negative selection marker).

Nucleic acid molecules introduced into cells for assembly will normally have certain features which allow them to be assembled in a particular order. One feature is terminal sequence homology between nucleic acid molecules being assembled.

Assembled nucleic acid molecules may be introduced into other nucleic acid molecules located within a cell (e.g., a viral genome, a nuclear genome, an organelle genome, a bacterial chromosome, etc.). In such instances, functional elements such as origins of replication, centromeres, etc. will generally be present in the other nucleic acid molecules located within the cell. Thus, the invention provides, in part, compositions and methods relating to the assembly of nucleic acid molecules and the insertion of the resulting assembly into other nucleic acid molecules.

In some instances, standard ligase based joining of partially and fully assembled nucleic acid molecules may be employed. For example, fully assembled nucleic acid molecule may be generated with restriction enzyme sites near their termini. These nucleic acid molecules may then be treated with one of more suitably restrictions enzymes to generate, for example, either one or two "sticky ends". These sticky end molecules may then be introduced into a vector by standard restriction enzyme-ligase methods. In instances where the inert nucleic acid molecules have only one sticky end, ligases may be used for blunt end ligation of the "non-sticky" terminus.

Assembled nucleic acid molecules may also include functional elements which confer desirable properties (e.g., origins of replication, selectable markers, etc.). In many instances, the assembled nucleic acid molecules will be assembled from multiple individual nucleic acid segments with one of the segments being a vector (e.g., a linear vector).

Figure 8:
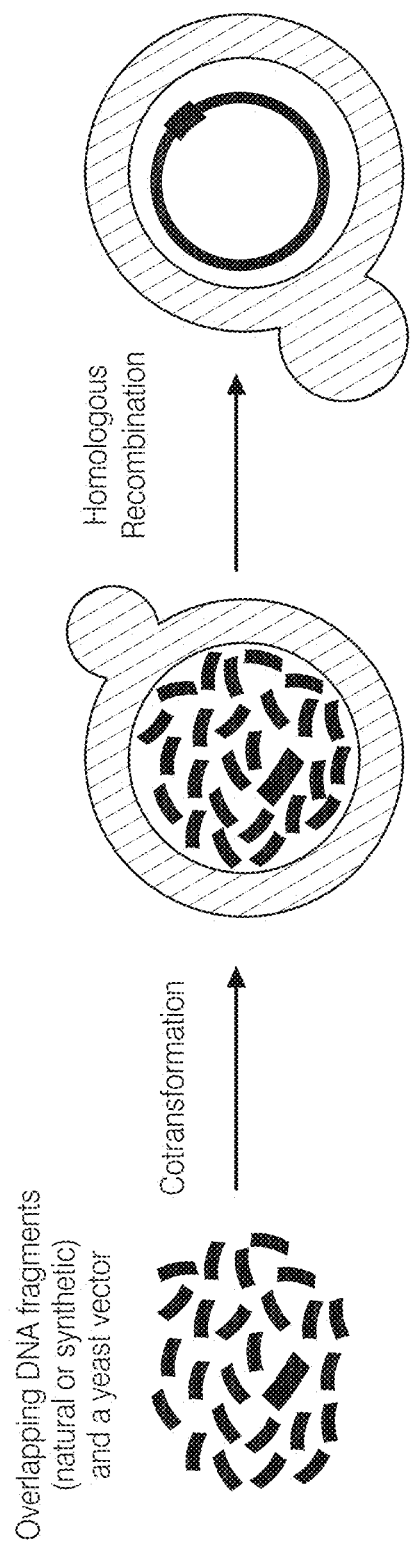
FIG. 8 generally illustrates methods for assembly and cloning of nucleic acid segments in yeast. In some embodiments of the invention, a number of nucleic acid segments (one of which is a vector) are co-transforming the fragments into a yeast host cell, where they are assembled by homologous recombination to form, for example, a closed, circular nucleic acid molecule.

Using the schematic of FIG. 8 for purposes of illustration, this approach may be carried out by co-transforming into the host cell, along with the host vector, a plurality (e.g., two, three, five, eight, ten, fifteen, twenty, thirty, etc.) of "overlapping" nucleic acid fragments for which assembly is desired. In this instance, each of the fragments contains are two regions of homology to regions of other nucleic acid segments introduced into the host cell. The nucleic acid segments after transformation into the host cell, for example by homologous recombination through regions of homology. In the instance shown in FIG. 8, the result is an assembled, closed circular nucleic acid molecule.

In one variation of the illustrative example shown in FIG. 8, overlapping fragments of a circular bacterial genome are co-transformed into a yeast host cell along with a linear yeast vector. Again, the yeast vector contains regions of homology at its termini to portions of the bacterial genome. Upon introduction of the genome fragments and yeast host vector into the host cell, the fragments and vector recombine, thereby joining the genome fragments and host vector.

The process shown in FIG. 8 relies, in part, on selection for the assembly of a closed, circular, replicable nucleic acid molecule. As similar selection mechanisms is set out in U.S. Patent Publication No. 2004/0219516 A1 (see, e.g., FIG. 20 of this application), the disclosure of which is incorporated herein by reference. Of course, nucleic acid molecules assembled by methods of the invention need not always generate a closed circular nucleic acid molecules. Other nucleic acid molecules which may be generated by methods of the invention include linear plasmids (e.g., plasmids which can replicate in linear form) and chromosomes.

In vivo assembly systems of the type shown in FIG. 8 may be composed of two core components: (1) Nucleic acid segments for assembly and (2) a suitable host cell. In certain embodiments where desired functional elements (e.g., origins of replication, selectable markers, etc.) are not represented in the nucleic acid segments for assembly, a vector may be included as an additional nucleic acid segment.

Fragments to be assembled will generally contain sequences that are overlapping at their termini. In one embodiment, the overlaps are approximately 10 bp; in other embodiments, the overlaps may be 15, 25, 50, 60, 70, 80 or 100 base pairs, etc. (e.g., from about 10 to about 120, from about 15 to about 120, from about 20 to about 120, from about 25 to about 120, from about 30 to about 120, from about 40 to about 120, from about 10 to about 40, from about 15 to about 50, from about 40 to about 80, from about 60 to about 90, from about 20 to about 50, etc. base pairs). In order to avoid misassembly, individual overlaps that should not be duplicated or closely match amongst the fragments. Since homologous recombination does not require 100% sequence identity between the participating nucleic acid molecules or regions, each terminus should be sufficiently different to prevent misassembly. Further, termini intended to undergo homologous recombination with each other should share at least 90%, 93%, 95%, or 98% sequence identity.

In in vivo assembly methods, a mixture of all of the fragments to be assembled is used to transfect the host recombination and assembly cell using standard transfection techniques. The ratio of the number of molecules of fragments in the mixture to the number of cells in the culture to be transfected should be high enough to permit at least some of the cells to take up more molecules of fragments than there are different fragments in the mixture. Thus, in most instances, the higher the efficiency of transfection, the larger number of cells will be present which contain all of the nucleic acid segments required to form the final desired assembled nucleic acid molecule. Technical parameters along these lines are set out in U.S. Patent Publication No. 2009/0275086 A1, the disclosure of which is incorporated herein by reference.

Figure 5:
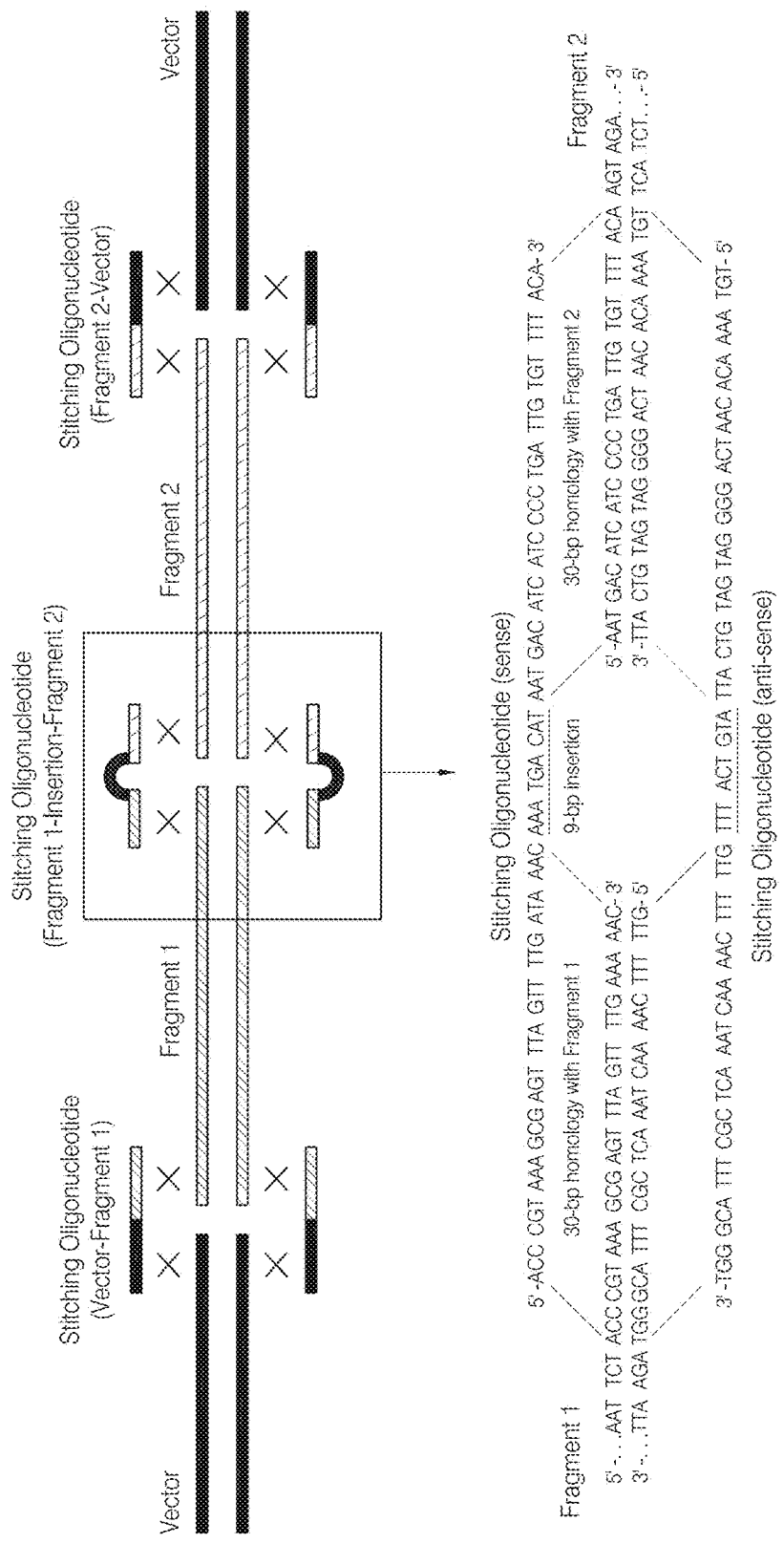
FIG. 5 shows the assembly of two DNA fragments that do not share any homology into a vector using stitching nucleic acid molecules. The 69 base pair double-stranded stitching nucleic acid molecules (SEQ ID NO: 14), shown in bold in the lower portion of the figure, share 30-bp homology with each adjacent fragment (Fragments 1 (SEQ ID NO: 15) and 2 (SEQ ID NO: 16)). These stitching nucleic acid molecules are used to insert 9 bp at the junction of the adjacent fragments. The insertion bases are shown underlined.

One example of an assembly method which for joining double-stranded nucleic acid molecules which do not share terminal sequence homology is shown in FIG. 5. In this embodiment, two double-stranded fragments are introduced into a linear vector using singe-stranded "stitching nucleic acid molecules". In a sense, this is an assembling of five nucleic acid segments, wherein one of the segments is the vector, two of the segments are the two stitching nucleic acid molecules, and final two segments are the segments are labeled Fragment 1 and Fragment 2. In addition to facilitating the joining of other nucleic acid molecules, the stitching nucleic acid molecules introduced short insertion (e.g., nine base pairs) into the assembled nucleic acid molecule. A commercially available product which contains these features is the GENEART® High-Order Genetic Assembly Systems (Life Technology, Cat. No. A13286).

Assembly methods, in addition to other methods described herein, are capable of being miniaturized and/or automated. In fact, in many instances, miniaturization will be desirable when the nucleic acid molecules being assembled and/or introduced into vectors are present in lower total numbers. One means by which micro-mixing can be accomplished for assembly and processes such as insertion of nucleic acid molecules into vectors is by electrowetting, for example, as described elsewhere herein. In some workflows, oligonucleotides differing in nucleotide sequence are mixed and assembled. As an example, wells of a microwell plate may contain mixture of oligonucleotides that are to be assembled and fluid from each of these wells may be removed for mixture in an assembly chamber (e.g., a well of a microwell plate). In many instances, fluid amounts employed will be too small for convenient pipetting (e.g., in the nanoliter range). One means for transferring fluids is to use acoustic energy.

One form of acoustic energy liquid transfer is referred to as acoustic droplet ejection. Acoustic droplet ejection uses a pulse of ultrasound to move small volumes (e.g., nanoliters or picoliters) of fluids (typically) without making physical contact with the fluids themselves. This technology works by focusing acoustic energy into a fluid sample in order to eject droplets as small as a picoliter. Acoustic droplet ejection technology has been shown to not significantly damage biological molecules and thus can be used to transfer proteins, high molecular weight DNA and live cells without appreciable damage or loss of viability. This technology tends to work best with fluid vessels that have flat bottoms.

In acoustic energy liquid transfer methods, sound waves eject droplets from a source location (e.g., a well of a microwell plate) onto a surface above the source location (e.g., a well of another microwell plate). Acoustic energy liquid transfer systems (e.g., acoustic droplet ejection systems) are available from Labcyte Inc. (Sunnyvale, Calif., 94089). Technology related to acoustic energy liquid transfer is set out in U.S. Pat. No. 6,612,686.

The invention thus also includes a method for the assembly of a nucleic acid molecule from oligonucleotides, the method comprising:

(a) synthesizing oligonucleotides;

(b) collecting the synthesized oligonucleotides in two or more primary reactions vessels (e.g., wells or a microwell plate);

(c) performing a first polymerase chain reaction (PCR) (or series of PCR reactions) or other thermocycling based method in the two or more primary reactions vessels to generate two or more sub-assemblies of the nucleic acid molecule;

(d) transferring fluid (e.g., by acoustic energy liquid transfer) from each of the two or more primary reaction vessels to one or more secondary reaction vessels; and (e) performing a second polymerase chain reactions or other thermocycling based method in the one or more secondary reactions vessels to generate the nucleic acid molecule.

For purposes of illustration, thirty oligonucleotides of 40 nucleotides each may be generated in step (a) above. Fifteen each of these thirty oligonucleotides may be transferred to two different primary reactions vessels to generate by, for example, a first PCR reaction (step (c)) two double-stranded sub-assemblies of 700 base pairs. Fluid containing these two sub-assemblies may then be transferred to the secondary reaction vessel by acoustic energy liquid transfer, followed by, for example, a second PCR reaction (step (e)) to generate a nucleic acid molecule that is 1360 base pairs in length.

The invention thus includes work flows in which acoustic energy liquid transfer is used to move fluids from one location to another. These fluids may contain, for example, a single oligonucleotide, mixtures of oligonucleotides, partially assembled nucleic acid molecules, etc.

The workflow exemplified above is typical for many other complex molecular biology workflows which integrate the following steps: (1) a first liquid handling step to combine one or more molecules and one or more reagents, (2) a first thermal incubation or thermocycling reaction to assemble, amplify or modify the molecules, (3) a second liquid handling step to combine assembled, modified or amplified molecules obtained from step (2) and to add further reagents as required, and optionally (4) a second thermal incubation or thermocycling reaction to further process the combined, assembled, or modified molecules. In certain instances, alternating steps of liquid handling and thermal incubation may be repeated one or several times.

In an embodiment where larger double stranded nucleic acid molecules are assembled from shorter single stranded nucleic acid molecules, such workflow may comprise the steps of (1) liquid handling to combine a plurality of single stranded nucleic acid molecules with one or more enzymes and amplification reagents, (2) a first thermocycling reaction for enzymatic assembly of the single stranded nucleic acid molecules into double stranded subfragments, (3) a second liquid handling step to combine various subfragments obtained from step (2) and to add reagents for error correction and amplification, (4) a second thermal incubation comprising an error correction and subfragment assembly step, and optionally wherein steps (3) and/or (4) are repeated at least once.

Figure 49A:
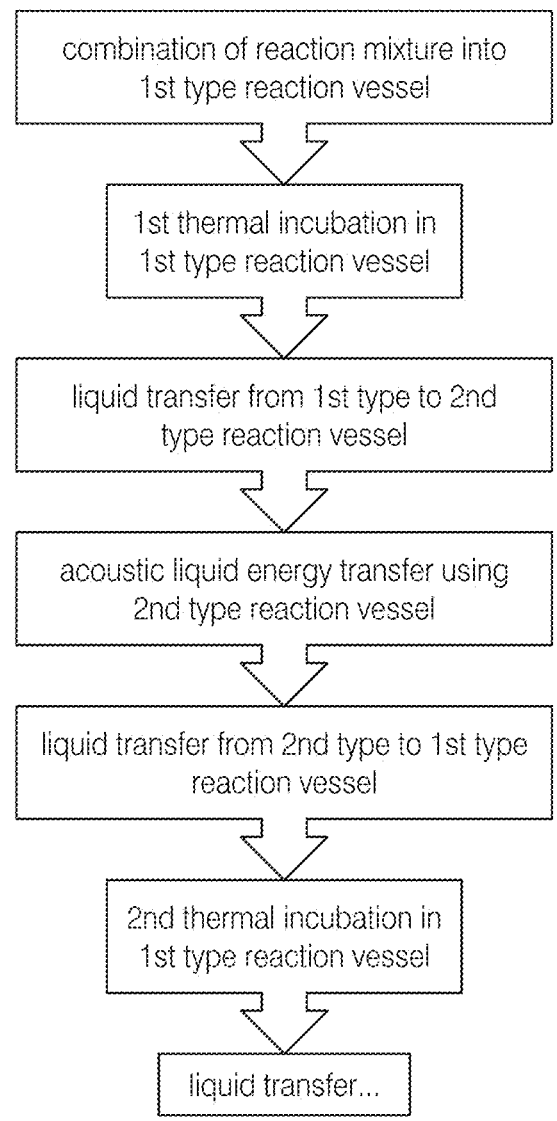
FIGS. 49A and 49B show in improved seamless workflow for micro-processing of biological samples comprising alternate steps of liquid handling and thermocycling.
Figure 49B:
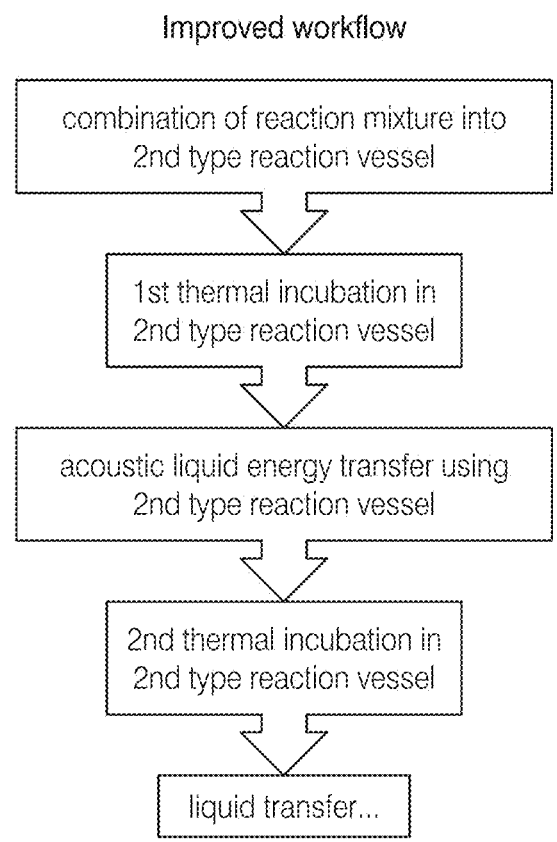

In workflows where small volumes are to be transferred, one or more of the liquid handling steps may be conducted using acoustic liquid energy transfer as described above. Commercial platforms for acoustic liquid energy transfer (such as e.g. Echo® Liquid Handler, Labcyte Inc., Sunnyvale, Calif.) typically use types of reaction vessels or multiwell plates that may have different specifications than the types of reaction vessels or multiwell plates used for thermocycling. For example, a multiwell plate used in a standard PCR cycler may require thin walls with high conductivity, whereas acoustic liquid energy transfer may require flatbottom multiwell plates with rather low conductivity. Therefore, alternating steps of liquid handling (using acoustic liquid energy transfer) and thermocycling cannot be performed in the same type of reaction vessel or multiwell plate. Once liquid has been transferred by acoustic ejection from a "source plate" to a "destination plate" the reaction mixture needs to be transferred from the destination plate to another type of vessel or plate as the flatbottom destination plate is not compatible with a regular PCR cycler. Such regular workflow is illustrated in FIGS. 49A and 49B (left flow chart). The inventors have found that such additional liquid transfer from a destination vessel or plate to a thermocycling compatible vessel or plate can be avoided when a flat bottom destination plate is used in a flatbed cycler that is configured to operate with a flat thermal block as described in Example 12B (such as, e.g, a PROFLEX™ PCR System, Thermo Fisher Scientific, Waltham Mass.). Such improved workflow as illustrated in FIGS. 49A and 49B, right flow chart, allows for the use of one type of reaction vessel or plate (e.g., a flat bottom 384- or 1536-well plate) for both, acoustic liquid transfer and subsequent thermal incubation leading to saving of time, material and reagents. Such improved configuration may be applied to any workflow where subsequent or alternating steps of liquid handling and thermal incubation are used including any type of assembly reactions, traditional restriction/ligation based cloning, error correction, sample prep reactions for capillary electrophoresis sequencing, emulsion PCR etc. Scalability of such workflows is typically limited by the ability to handle large numbers or volumes of samples individually in parallel. In addition, such workflows often have cost limitations due to the volume at which typical liquid handling solutions operate. Providing a solution which enables users to efficiently combine liquid handling and thermal incubation/cycling in microscale, automation-friendly format as described above thus provides significant opportunities to improve these workflows.

Figure 16:
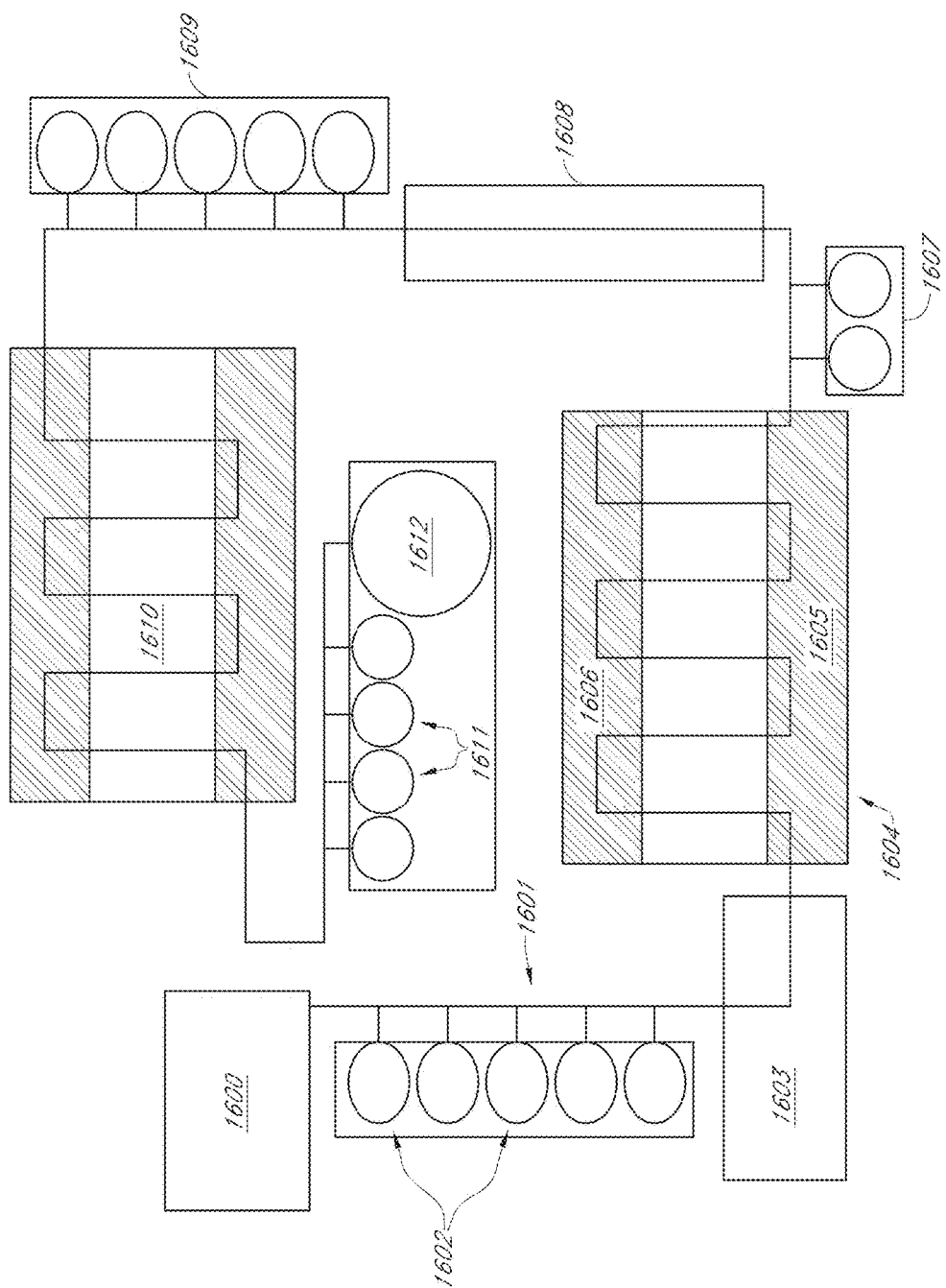
FIG. 16 is a schematic of automated system for performing methods of the invention.

FIG. 16 is a block diagram of one embodiment of an instrument for processing nucleic acid molecules of the invention. On the upper left of this figure is a carrier oil reservoir 1600 and a tube 1601 for transporting oil from this reservoir. Carrier oil is transported past a series of additional reservoirs 1602 that contain reagents. The circular structures represent individual reagents reservoirs. Exemplary reagents are nucleic acid molecules, PCR enzymes, primers, and vectors, as well as, for example, other Module 3 related components. The reagents will typically be in the form of aqueous vesicles transported between oil barriers.

The reagents transported by the carrier oil are then transported to a mixing chamber 1603 where mixing occurs. The reagents then move on to a digital PCR station 1604. The tube 1601 travels between a heating block 1605 where denaturation occurs followed by a cooling block 1606 where annealing and PCR occurs. Each time a vesicle travels to the cooling block 1606 after the first time, a PCR amplification occurs.

After exiting the digital PCR station 1604, the vesicles move past additional reagent reservoirs 1607 for the optional addition of more reagents, (e.g., buffers, error correction components, etc.), then on to another optional mixing chamber 1608. The vesicle then move on to an optional storage location 1609. In instances where more than one nucleic acid molecule is to be assembled into a larger molecule, the individual nucleic acid molecules for assembly will often arrive at the storage location 1609 at different times and will need to be sequestered for a period of time until other components arrive.

The nucleic acid molecules then move on to another digital PCR station 1610 and again cycle between cooling and heating blocks. Error correction reaction may occur in digital PCR station 1610. Finally, assembled nucleic acid molecules are transported to interface outlets 1611 for collection and waste materials (e.g., carrier oil) is collection in a waste reservoir 1612.

Systems of the type represented in FIG. 16 can process multiple samples at the same time. These samples can be sequestered between carrier oil and sent through the system in series. The FIG. 16 block diagram does not show a computer system, optical components, valves and other components related to system automation. Optical elements, as well as other elements (e.g., electrical elements) can be used to keep track of the location and identification of reagent vesicles and various points in the flow system. These reagent vesicles will generally contain nucleic acid molecules of a predetermined sequence. Thus, the invention include methods for the simultaneous processing (e.g., sequential processing) of multiple samples Module 4

Following isolation and treatment, the assembled nucleic acid molecules can be further transplanted into recipient cells using methods described herein or known in the art. Methods which may be used include protoplast and spheroplast fusion, conjugal transfer (e.g., bacterial conjugation), viral infection, electroporation and Sendai virus mediated cell fusion. Thus, the invention includes methods for transferring synthesized and/or assembled nucleic acid molecules to cells.

One method for generating yeast protoplast fusions in set out in Nakazawa and Iwano, *Efficient selection of hybrids by protoplast fusion using drug resistance markers and reporter genes in Saccharomyces cerevisiae, J. Biosci. Bioeng.* 98:353-358 (2004). Further, methods have been developed for the fusion or prokaryotic and eukaryotic cells. (See, e.g., Gyuris and Duda, *High-efficiency transformation of Saccharomyces cerevisiae cells by bacterial minicell protoplast fusion, Mol. Cell. Biol.* 6:3295-3297 (1986). Methods such as these may be used in the practice of the invention to transfer nucleic acid molecules between cells without exposing the nucleic acid molecules to an extracellular environment. Other methods which may be used include natural competence, biolistic gun, electroporation, Baculovirus mediated transduction, and Type III secretion systems.

An exemplary transplantation protocol is described in PCT Publication WO 2011/109031. One method used to transplant *Mycoplasma* genomes from donors to *Mycoplasma* recipients is described by Lartigue et al., *Genome transplantation in bacteria: changing one species to another, Science* 317:632 (2007). This work related to the complete replacement of the genome of a bacterial cell with a genome from another species by genome transplantation as naked DNA using polyethylene glycol-mediated transformation. The resulting recipient cells were phenotypically identical to the donor strain. Such methods can be used to transfer assembled nucleic acid molecules constructed by methods of the invention to recipient cells.

Recipient cells typically will be chosen based on their ability to support gene expression from the assembled nucleic acid molecules. For example, after a bacterial genome has been assembled in a eukaryotic host cell having a suitable genetic manipulation system (e.g., yeast), then it may be necessary or desirable to transplant the genome back into a bacterial recipient cell. Differences in translation and transcription and different codon usage, among other factors, can prevent expression of the donor gene products within the host cell. The recipient cell, therefore, may be of the same species or a similar species as a donor cell or organism. In many cases, the recipient cells will be of the same order or kingdom as the donor. However, in cases where expression in unrelated cell types is required, the initial gene design may include codon and sequence optimization strategies to allow for expression in different recipient cells.

Additional Applications

As one skilled in the art would understand, nucleic acid molecules produced in microscale quantities (e.g., femtomoles to nanomoles quantities, such as from about 0.001 femptomole to about 1.0 nanomole, from about 0.01 femptomole to about 1.0 nanomole, from about 0.1 femptomole to about 1.0 nanomole, from about 0.001 femptomole to about 0.1 nanomole, from about 0.001 femptomole to about 0.01 nanomole, from about 0.001 femptomole to about 0.001 nanomole, from about 1.0 femptomole to about 1.0 nanomole, from about 1.0 femptomole to about 0.1 nanomole, from about 1.0 femptomole to about 0.01 nanomole, from about 1.0 femptomole to about 0.001 nanomole, from about 10 femtomoles to about 1.0 nanomole, from about 10 femtomoles to about 0.001 nanomole, from about 20 femtomoles to about 1.0 nanomole, from about 100 femtomoles to about 1.0 nanomole, from about 500 femtomoles to about 1.0 nanomole, from about 1 nanomole to about 800 nanomoles, from about 40 nanomoles to about 800 nanomoles, from about 100 nanomoles to about 800 nanomoles, from about 200 nanomoles to about 800 nanomoles, from about 500 nanomoles to about 800 nanomoles, from about 100 nanomoles to about 1,000 nanomoles, etc.).

The invention may be used to prepare microarrays. Such microarrays may be generated in multiple ways including by the depositing of nucleic acid molecules on a support (e.g., a solid support such as a planar sold support) or by synthesis of nucleic acid directly on the support. In one embodiment, the plate shown in FIGS. 2A and 2B can be modified so that the base/bottom is designed for the synthesis of nucleic acid on its surface. Optionally, the base could be structured to be removable to yield, for example, a planar microarray. In most such instances, the bead shown in FIGS. 2A and 2B would be omitted during nucleic acid synthesis. Thus, the invention includes methods for the generation of microarrays.

Methods for printing microarrays are set out in U.S. Pat. Nos. 5,807,522 and 7,211,148, the disclosure of which is incorporated herein by reference. Such methods may be used in the practice of the invention to produce, for example, microarrays by the deposition of nucleic acid molecules produced as described herein.

One advantage of methods described herein is their modularity. As an example, nucleic acid molecules which form sub-portions of different larger nucleic acid molecules may be produced on the same plate to array. Thus, methods of the invention allow for the simultaneous production of nucleic acid molecules, followed by selection of individual synthesized nucleic acid molecules for later processes (e.g., pooling, cleavage deprotection, and assembly). Thus, methods of the invention include those where nucleic acid molecules are simultaneously produced (e.g., chemically synthesized), followed by assembly into two or more (e.g., two to ten, three to ten, four to ten, five to ten, two to thirty, five to thirty, ten to thirty, five to fifty, etc.) larger nucleic acid molecules.

In certain embodiments, nucleic acid molecules or plurality of nucleic acid molecules synthesized by the methods of the present invention may be primers and/or probes. Primers and/or probes can be generated in microquantity using, for example, a solid support as described herein. Primers prime nucleic acid extension reactions that can be part of an amplification reaction. Probes are used to detect a target nucleic acid sequence. Accordingly, probes are used in detection methods to directly or indirectly detect a target nucleic acid sequence. Primers and probes typically have a predetermined nucleotide sequence that hybridize with or otherwise bind to a target nucleic acid sequence. Probes in illustrative embodiments include a label, such as a fluorescent label. For example, a control mechanism may be connected to a solid support or an array of solid supports used in the methods of the present invention, wherein a target nucleotide sequence is input into the control mechanism. The control mechanism may be used to direct the sequence of addition of reactants for nucleic acid synthesis, such that a nucleic acid molecule having the target nucleotide sequence is synthesized.

Probes and primers hybridize with or otherwise bind to a target nucleic acid sequence because of sequence identity they share with the target nucleic acid sequence. For example, a primer or probe can share 80, 85, 90, 95, 96, 97, 98, 99, 99.5, or 100% contiguous sequence identity with a target nucleic acid sequence. Primers and probes hybridize with their target nucleic acid sequence under stringent and typically highly stringent conditions, as are known in the art.

A label can be attached to the 5' terminal nucleotide, the 3' terminal nucleotide, or any internal nucleotide of the primers and/or probes of the present invention. The label in certain illustrative embodiments, is a fluorophore. A vast array of fluorophores are known to those of skill in the art and can be included in the methods and compositions of the present invention. See, for example, Cardullo et al, *Proc. Natl. Acad. Sci. USA* 85:8790-8794 (1988); Dexter, D. L, *J. of Chemical Physics* 21:836-850 (1953); Hochstrasser et al., *Biophysical Chemistry* 45:133-141 (1992); Selvin, R, *Methods in Enzymology* 246:300-334 (1995); Steinberg, I., *Ann. Rev. Biochem,* 40:83-114 (1971); Stryer, L., *Ann. Rev. Biochem,* 47:819-846 (1978); Wang et al., *Tetrahedron Letters* 31:6493-6496 (1990); Wang et al., Anal. Chem. 67:1197-1203 (1995). For example, the fluorophore can be Biosearch Blue, FAM, TET, a CAL Fluor dye, JOE, VIC, HEX, a Quasar dye, a Cy dye, NED, TAMRA, ROX, Texas Red, or a Pulsar dye. These dyes and nucleic acid synthesis reactants that include these dyes are commercially available, for example, from Biosearch Technologies, Inc., Glen Research, or Life Technologies.

In illustrative embodiments, primers synthesized by methods provided herein, are PCR primers. In certain embodiments, primers are labeled with a label on their 5' end or 3' end. For example, primers can be LUX primers, Scorpion primers, Amplifluor primers, and/or Plexor primers.

In certain embodiments, the present invention provides a method for synthesizing a plurality of primer and probe sets (e.g., pairs). The primer and probe sets (e.g., pairs) can be generated in microquantity using a plate described herein (e.g., a plate of the general format shown in FIGS. 2A and 2B). A primer and probe set (e.g., pair) includes one or more primers that prime an extension reaction that generates a nucleic acid extension product that is a target nucleic acid sequence for one or more probes of the primer and probe set (e.g., pair). In other words, in a primer and probe set (e.g., pair), the probe typically binds to the amplification product generated by the primer(s). In illustrative embodiments, the primer and probe set (e.g., pair) include a pair of PCR primers and a probe that binds to an amplification product generated by an amplification reaction that uses the pair of primers. For example, the primer and probe set (e.g., pair) can include two PCR primers and one 5' nuclease probe or one Molecular Beacons probe that binds to the amplification product generated when the PCR primers are used in a PCR reaction.

As noted above, methods of the present invention can generate an array of nucleic acid molecules, such as primers, probes, and/or primer and probe sets (e.g., pairs). For example, nucleic acid molecules can be synthesized in an array of positions such that each position includes one or a plurality of nucleic acid molecules such as primers, probes, and/or primer and probe sets (e.g., pairs). Array can include primers, probes, and primer and probe sets (e.g., pairs) at a density of 100, 200, 250, 500, 1000, 10,000, 100,000, 1,000,000, or 10,000,000 per $cm^2$. The total number of nucleic acid molecules in an array of nucleic acid molecules generated using methods of the present invention can include, for example, 100, 200, 250, 500, 1000, 10,000, 100,000, 1,000,000, 10,000,000, 100,000,000, 1,000,000, 000, or 10,000,000,000 primer, probes, and/or primer and probe sets (e.g., pairs). More than one primer and probe set (e.g., pair) can be included in an array position such that the primer and probe set (e.g., pair) are designed to perform a multiplex reaction, such as a multiplex PCR reaction.

Probes of the invention can be labeled with a single dye, such as a single fluorophore. Probes of the invention can be FISH probes.

Probes of the invention can be probes used in amplification reactions. For example, these probes can be dual-labeled probes. Dual-labeled probes in certain illustrative embodiments include labels that are donor-acceptor energy transfer pairs, such as FRET pairs. When the donor (fluorophore) is a component of a probe that utilizes donor-acceptor energy transfer, the donor fluorescent moiety and the quencher (acceptor) of the invention are preferably selected so that the donor and acceptor moieties exhibit donor-acceptor energy transfer when the donor moiety is excited. One factor to be considered in choosing the fluorophore-quencher pair is the efficiency of donor-acceptor energy transfer between them. In many instances, the efficiency of FRET between the donor and acceptor moieties is at least 10%, at least 50%, or at least 80%. The efficiency of FRET can easily be empirically tested using the methods both described herein and known in the art.

In some instances, the donor-acceptor pair may include a fluorophore and a quencher. The quencher can be a dark quencher. As such, probes of the present invention can include a BHQ dye or a DQ dye (Epoch) as the quencher. The quencher in other embodiments may be DABCYL or TAMRA.

Primers and probes synthesized using methods and systems of the present invention can include can include moieties that stabilize hybridization of nucleic acids (e.g., intercalators, minor groove binding moieties, bases modified with a stabilizing moiety (e.g., alkynyl moieties, and fluoroalkyl moieties)), and conformational stabilizing moieties, such as those disclosed in U.S. Patent Application Publication No. 2007/0059752, the disclosure of which is incorporated herein by reference. The primers and probes can include intercalating agents such as acridine. In other embodiment, primers and probes synthesized using methods and systems of the present invention can be locked nucleic acid (LNA) probes, or peptide nucleic acid (PNA) probes.

Dual-labeled probes synthesized using methods and systems of the present invention can be used in amplification reactions such as real-time PCR reactions. The dual-labeled probes in illustrative examples are hydrolysis probes, such as 5' nuclease probes (see e.g., Livak et al, PCR Methods Appl., 4:357-562 (1995); and U.S. Pat. No. 5,538,848), molecular beacons (see e.g., Mhlanga, Methods, 25:463-472 (2001)), scorpions (see e.g., Saha, J. Virol. Methods, 93:33-42 (2001)), or hybridizing probes (see e.g., U.S. Pat. No. 7,670,832). In certain embodiments the primers and probes of the present invention are used in digital amplification reactions such as digital PCR reactions.

Primers synthesized by methods of the present invention can be between 5 and 50 nucleotides in length and are typically between 10 and 30 and more typically 15 and 30 nucleotides in length. Probes of the present invention can be between 5 and 100, 10 and 50, 10 and 30, or 15 and 30 nucleotides in length.

Methods of the present invention can utilize general chemistries and chemical methods known in the art for synthesizing nucleic acid molecules that include one, two, or more labels, such as a fluorescent labels. For example, such methods can utilize phosphoramidites and/or solid supports that are modified to include such labels. Exemplary solid supports, for example, can include at least one quencher bound through a linker to the solid support. Additional exemplary embodiments can utilize a solid support or a phosphoramidite functionalized moiety that stabilizes a duplex, triplex or higher order aggregation (e.g., hybridization) of a nucleic acid molecule synthesized according to the present invention with a target nucleic acid molecule.

In certain embodiments, the primers and/or probes of the present invention are used in real-time PCR assays such as gene expression assays or genotyping assays, for example SNP genotyping assays. The probes can be generated using methods provided herein, at a concentration, for example, of between 1 nM and 1 M, 1 mM and 1 M. An exemplary concentration can be 100 mM. The probes and/or especially the primers generated by methods provided herein can be lyophilized. For example, 1-1,000,000 picomole of primer can be lyophilized in a reaction vessel, such as a tube, or a well, or can be dried on a spot of an array of positions.

In one embodiment, the present invention provides a method for nucleic acid synthesis that includes combining nucleic acid synthesis reactants inside a microwell and generating the nucleic acid molecule inside the microwell. The microwell can be linked to a controller, such as a computer processor, wherein a nucleotide sequence for one or more nucleic acid molecules is input into the controller or otherwise present in a computer memory of the controller. The controller can be connected to or otherwise in communication with a nucleic acid molecule design and ordering functionality that can be provided over a wide-area network. For example, nucleic acid molecule design and ordering functionality can be provided over the Internet.

In certain embodiments, methods of the present invention include an HPLC-purification step. In addition, methods of the present invention can be performed under ISO and/or GMP-certified conditions. In some embodiment, nucleic acid molecule synthesis is performed using a microwell plate.

Methods and apparatus of the invention may also be used for the preparation of libraries. These libraries may contain one or more point mutations or highly divergent molecules (e.g., nucleic acid molecules which encode proteins with different functional activities). Along these lines, the invention includes methods for the generation of libraries where all or some of the library members are chemical synthesized and thus not generated from cellular nucleic acid. Library types which may be generated by methods of the invention include cDNA libraries, genomic libraries, combinatorial libraries, point mutation libraries, and combinations of one or more of such libraries.

Figure 11:
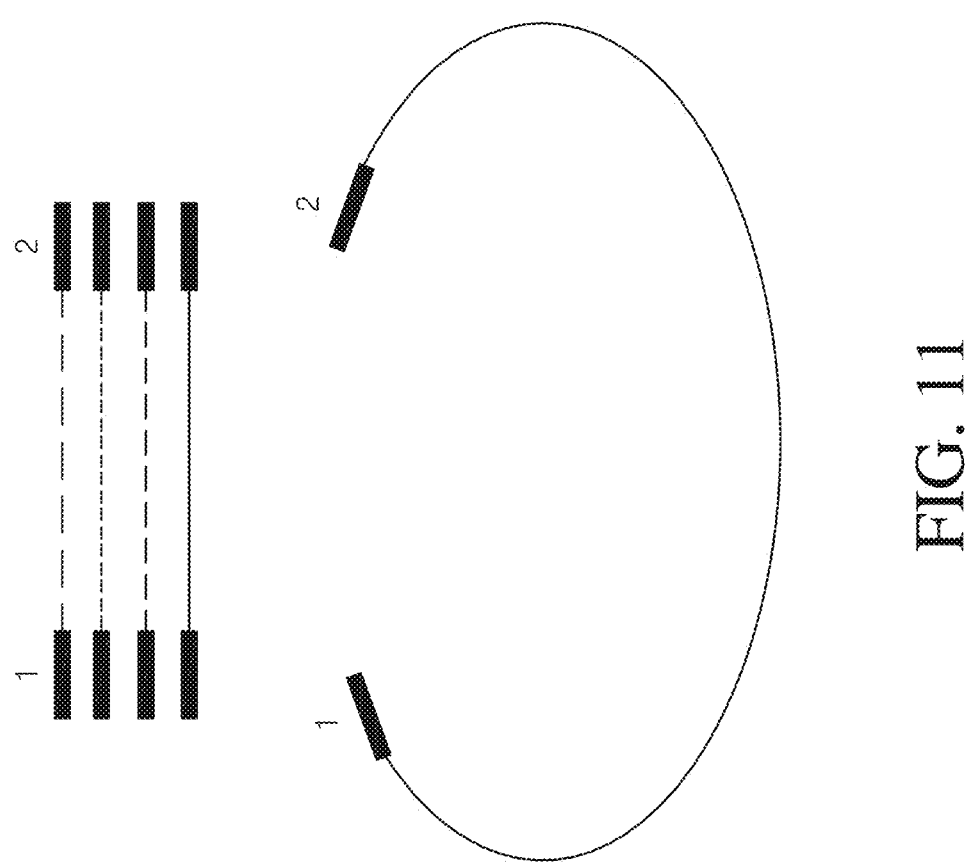
FIG. 11 shows a library of linear, nucleic acid molecules (top) generated by methods of the invention and a vector (bottom) designed to accept library members. The upper portion of the figure shows a series of lines representing four members of the library. The lower open circular line represents a vector. The blocks on each end of the nucleic acid molecule represent nucleic acid segments which facilitate joining (e.g., GATEWAY® sites, regions of homology, etc.). The numbers and the termini of the nucleic acid molecules indicate compatible ends.
Figure 14A:
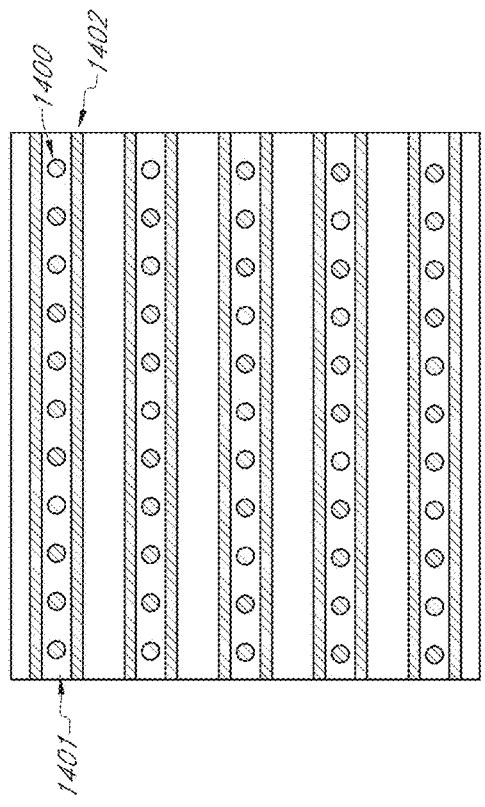
FIGS. 14A and 14B shows two different views of a nucleic acid molecules synthesis platform designed to generate identical nucleic acid molecules in each row 1401.
Figure 14B:
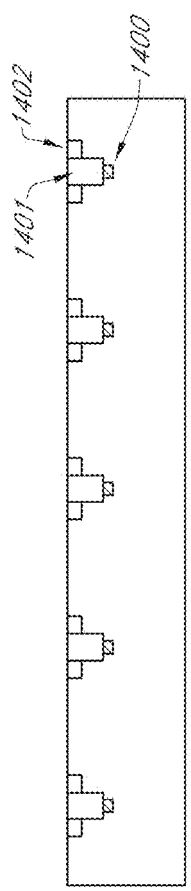

As noted above, in some embodiments, the invention includes methods or producing cDNA library equivalents generated, as well as the libraries themselves, using bioinformatic information. Using the schematic shown in FIG. 11 for purposes of illustration, a library may be synthesized and, if necessary, assembled according to methods described herein. The library members may then be inserted into a non-library nucleic acid molecule (e.g., a vector, a cellular chromosome, etc.). Insertion may be facilitated by any number of means such as ligation (e.g., "sticky end" ligation).

The invention includes methods for generating library, as well as the libraries themselves. Some of these libraries are of types which are difficult or impossible to produce by standard library production methods. One such type is a partial cDNA library. Partial cDNA libraries (also referred to as "cDNA equivalent" libraries) may be generated by bioinformatically selecting specific cDNAs for inclusion in the library. Nucleic acid molecules may then be synthesized and, if necessary, assembled to form the library.

cDNA libraries typically contain DNA molecules which correspond to RNA transcripts within a cell. In many cases, such libraries are biased towards transcripts which contain polyA tails. mRNAs represented in such libraries typically contain multiple cDNAs corresponding to individual coding regions. This is true when splice variants of a genomics coding region are generated by splicing events. The present invention allows for the production of cDNA libraries (as well as genomic libraries) with "exclusive" representation. For example, since nucleic acid molecules are selected for inclusion, as compared to exclusion, the DNA molecules corresponding to the following may be excluded from libraries: ribosomal RNAs, globin RNAs, tRNAs, and specified mRNAs. Thus, the invention includes methods for producing member biased and exclusive member inclusion cDNA and genomic libraries, as well as the libraries themselves.

Further, libraries of the invention include those which contain specified nucleic acid molecules. For example, the invention includes methods for producing cDNA libraries containing a subset of member represented in cDNA libraries generated by standard methods. For purposes of illustration, assume that a particular mammalian cell type has on average 15,000 different mRNA transcripts including splice variants and one seeks to use a cDNA library which contains 125 cDNA molecules corresponding to all of the known splice variants of transcripts corresponding to 35 different kinases. In another instance, one seeks to screen a collection of nucleic acid molecules that encode variants of the same wild-type coding sequence. Using FIG. 12A for purposes of illustration, amino acids 85 through 95, and the coding sequence of a wild-type cDNA is shown at the top of the figure. Amino acids 88 through 91 represent a region which is predicted to be a flexible linker connecting two functional domains. In this instance, a collection of nucleic acid molecules is produced encoding proteins with different, but specified, amino acids at positions 88 through 91 (the linker region). Collections of nucleic acid molecules such as those shown in FIG. 12A may be generated in number of ways.

One way will generally be over inclusive in that additional nucleic acid molecules will normally be generated.

This method employs "dirty bottle" synthesis. To generate variant molecules such as those shown in FIG. 12A reagents for the addition of bases at particular positions are mixed. Thus, when the base at the first and second positions of codon 88 are to be added, a mixture of reagents for addition of a C and G could be used. The ratio of these reagents may be adjusted to favor either C or G addition or the ratio may be adjusted so that equal amounts of C and G are introduced. In a portion of the population, the codon CGT (arginine) would also be generated.

Another method by which collections of nucleic acid molecules such as those shown in FIG. 12A may be generated is by synthesizing the individual variant sequences as separate nucleic acid segments. This allows for the generation of only nucleic acid molecules (except for synthesis errors) which encode the desired variant population members.

The invention also includes individual and collections of nucleic acid molecules with codon alterations as compared to wild-type molecules, as well as methods for producing such molecules. In some aspects, a codon altered library is generated where some or all (in many cases all or most) of the nucleic acid molecules in the collection are codon altered as compared to naturally wild-type coding sequences. This shows one substantial advantage of methods of the invention over standard library construction methods. With standard library construction methods, libraries are built from naturally occurring nucleic acid molecules (e.g., genomic DNA, mRNA, etc.). Methods of the invention allow for efficient construction of libraries using bioinformatic information. The result being that individual nucleic acid molecules in any collection generated can be generated with "tailored" nucleotide sequences.

Using FIG. 12B for purposes of illustration, a collection of nucleic acid molecules that contain different codons for the same coding sequence may be generated and then screened for desired features (e.g., increased or decreased expressions levels). Decreased expression levels may be desired when over expression of a protein is delirious to cells or host organisms that the protein is produced in. Thus, codon selection can be used as an expression regulation mechanism.

Methods of the invention may also be used to generate large numbers of primers for multiplex amplification (e.g., PCR). Typically such primers will be between 15 and 100 (e.g., from 15 to 90, from 25 to 90, from 25 to 80, from 25 to 70, from 25 to 60, from 25 to 50, from 30 to 90, from 30 to 60, etc.) nucleotides in length. Further, primers may also contain bar codes to allow for the tagging of amplified nucleic acid molecules for, for example, later identification as well as tracking of primers and primer pairs during and subsequent to synthesis runs.

In some instances, between 500 and 50,000, between 1,000 and 50,000, between 2,000 and 50,000, between 5,000 and 50,000, between 5,000 and 40,000, between 5,000 and 30,000, between 5,000 and 100,000, between 5,000 and 300,000, between 5,000 and 500,000, between 5,000 and 1,000,000, between 5,000 and 5,000,000, between 10,000 and 100,000, between 10,000 and 500,000, between 10,000 and 800,000, between 20,000 and 100,000, between 20,000 and 500,000, etc. primers pairs will be generated.

The invention includes the preparation of primers which may be used in processes such as Life Technology Corporation's AMPLISEQ™ products (see, e.g., cat. no. 4472395). Products such as this employ multiplex PCR for the amplification of specific nucleic acid molecules. The amplified nucleic acid molecules may then be used in downstream processes such as sequencing to identify nucleic acids present in a starting sample. In some cases, modified nucleic acid bases and/or natural bases not typically associated with DNA (e.g., deoxyuridine) are synthetically incorporated into the primer sequences as a "fifth (or greater) bottle" to impart particular properties into the individual primer(s) and/or primer set to facilitate downstream processing of the amplified products prior to sequencing or to further impart encoding of the individual primer(s) and/or primer set in the manner of barcoding to facilitate and resolve complex sequence analysis typically from a mixture of samples.

The invention thus provides methods for producing primer pools, as well as the primer pools themselves. Primer pools may be used to amplify RNA and/or DNA populations or subpopulation. As an example, primer pools may be produced that allow for the amplification of genomic DNA representing the entire nuclear genome of a cell, a single nuclear chromosome, a set of nuclear genes or regions (e.g., a set of chromosomal loci), a mitochondrial genome, or a chloroplast genome, as well as combinations thereof. The invention thus includes the bioinformatic design of primers for specific applications (e.g., the applications set out immediately above).

The invention also provides methods for producing primer pools for the amplification of specific RNA populations. In one embodiment of the invention, a primer pool is designed to amplify all mRNA molecules or a subpopulation of mRNA molecules (e.g., mRNAs encoding kinases, phosphatases, etc.) produced by a cell but, optionally, not other RNA molecules (e.g., tRNA, rRNA, hnRNA, etc.). Such primer pools may then be used for expression analysis (e.g., measuring the level of expression under various conditions). Expression analysis may be performed using, for example, microarrays or sequencing platforms. The invention thus includes expression analysis methods. In some embodiments, such methods include one or more of the following steps: (a) designing bioinformatically a primer pool, (b) synthesizing primer pairs of the primer pool, (c) contacting the primer pool to a sample derived from a cell containing nucleic acids (e.g., mRNA), (d) amplifying nucleic acid molecules in the sample corresponding to the primer pairs, and (e) analyzing the resulting amplified nucleic acid molecules.

The reduction or elimination of nucleic acid molecules corresponding to rDNA is desirable in many expression analysis applications because of the abundance of rRNA in many samples. Other rRNA amplification reduction methods are set out in U.S. Patent Publication No. 2008/0187969, the disclosure of which is incorporated herein by reference.

The invention also includes variations of the above for additional applications such as multiplex methods of the identification of mutations in genomic nucleic acid. Thus, the invention further includes methods and compositions for the identification of mutations, including cancer screens.

The invention includes methods for producing various numbers of primers (in many instances in primer pairs). The number of primers which may be prepared by methods of the invention as separate entities and/or in mixed populations range from five to 500,000, from 500 to 500,000, from 1,000 to 500,000, from 5,000 to 500,000, from 10,000 to 500,000, from 20,000 to 500,000, from 30,000 to 500,000, from 5,000 to 250,000, from 5,000 to 100,000, from five to 5,000, from five to 50,000, from 5,000 to 800,000, from 5,000 to 1,000,000, from 5,000 to 2,000,000, from 10,000 to 2,000,000, from 20,000 to 1,000,000, from 30,000 to 2,000,000, etc.

The invention thus provides methods for the rapid design, configuration and synthesis of defined sets of primers for the specifically determining genetic compositions and characterization of regions for a wide variety of analyses, sample sets and experimental designs. This aspect of the invention partially flows from the use of bioinformatics in conjunction with nucleic acid molecule synthesis methods described herein. In particular, the complete sequences of a considerable number of genomes have been sequenced. This sequence information, combined with nucleic acid synthesis methods (as well as other methods) described herein allow for detailed genome and transcriptome analyses. Multiplex methods, such as those set out above, provide one means for performing such analyses.

Representative Embodiments

Numerous variations of the invention are feasible and may be employed to achieve the desired results. Many such variations may be directed to design features. In some instances, such design features may be used for operator convenience and/or cost savings (e.g., decreased reagent usage).

Figure 9:
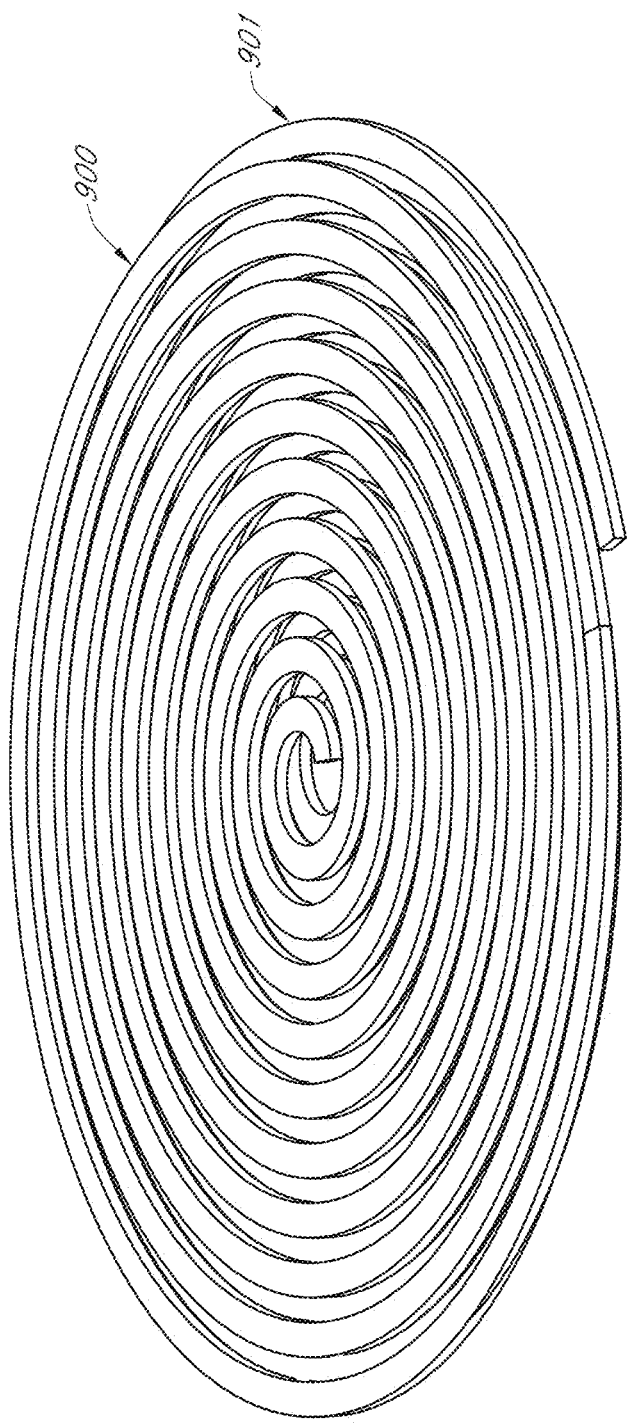
FIG. 9 is a drawing of an electrical coil that may be used in the practice of the invention.

FIG. 9 shows one embodiment of an electrical coil that may be used in specific embodiments of the invention. Numerous variations of such coils, a number of which are described elsewhere herein, may be used with the invention.

An electrical coil such as that shown in FIG. 9 may be designed with the following exemplary structural an operation parameters: Maximum current density 3 Amps/mm$^2$, double layer flat coil, wire cross section 5×2 µm, 10 turns, inner diameter (Di) ~10 µm, outer diameter (Da) ~180 µm, and wire length ~6 mm.

TABLE 11

| current (A) | Mag. Field Strength (A/m) (approx. short coil) |
|---|---|
| 0.00003 | 6.314390318 |

| current (µA) | Mag. Flux Density (T) |
|---|---|
| 30 | 7.9349E−06 |

FIG. 9 and Table 11 show exemplary specifications of a flat double layer coil that can be build up on a wafer. A coil such as that shown in FIG. 9 may be designed such that contact is made with each well in a synthesis platform. Further, the generation of a magnetic field may be used to lift beads from synthesis sites (e.g., wells). Exemplary magnetic field strength/flux density figures are shown in Table 11. A FEM-program like Comsol (www.comsol.com) may be used to calculate parameters for specific systems and formats.

Several materials, and properties associated with these materials, that may be used in electrodes used in various aspects of the invention are set out in Table 12. The selection of electrode materials will be determined by numerous factors including costs and various design specifications and power requirements.

TABLE 12

| Material | Specific Resistance (($\Omega$*mm$^2$)/m) | Coil Resistance ($\Omega$) | DC Power (µW) | Voltage (V) |
|---|---|---|---|---|
| Copper | 1.68E−02 | 10.068 | 0.009061 | 0.000302 |
| Aluminum | 2.65E−02 | 15.9 | 0.01431 | 0.000477 |
| Gold | 2.21E−02 | 13.284 | 0.011956 | 0.000399 |

Electrodes (e.g., electrical coils) used in the practice of the invention will be designed so as to meet the particular applications for which they are used. As an example, when electrodes are used to generate EGA, they will generally be designed with the following in mind: (1) The application (e.g., local application) of sufficient current to allow for the generation of an effective amount of EGA within a specified time period, (2) limitation of heating associated with the application of current. Thus, it will generally be desirable to limit the amount of current used to reach a local pH of 1.0 with the addition of little excess current. Table 13 provides calculations for achieving this with specific well parameters. Further, the generation of pH 1 in a well as set out below will require that 1 µA of current be applied for about 1 second. This results in a current density of 1 mA/mm$^2$ on the working electrode.

TABLE 13

Current/pH generation for a cylindrical well using a 35 µm bead

| Well Diameter (µm) | 40 | Well Vol. (µm$^3$) | 62831 |
|---|---|---|---|
| Well Height (µm) | 50 | Current Density WE (mA/mm$^2$) | 1 |
| Desired pH | 1 | Charge (µAs) | 1 |
| Area (µm$^2$) | 1256 | | |

The shape of an electrode may vary greatly and may be a coil as shown in FIG. 9, a disk, a thin film, etc. Further, electrodes used in the practice of the invention may be composed of any number of compounds, including platinum, palladium, copper, gold, aluminum, niobium, niobium oxide, tungsten, titanium, tantalum, molybdenum, nickel, platinum, silver, manganese, neodymium, carbon, and silicon, and an alloy material or a compound material containing one or more of the above-described elements, as well as other elements.

Figure 10:
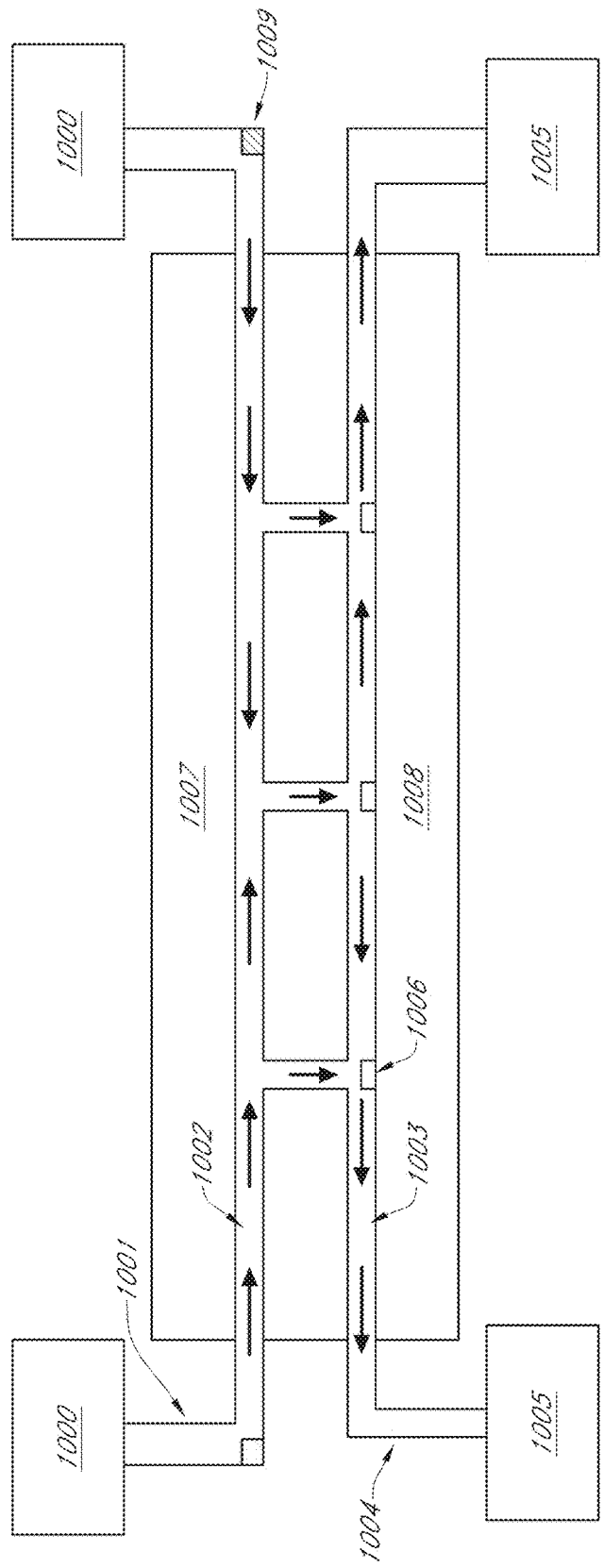
FIG. 10 is cross-sectional view of one embodiment of a fluid reagent delivery system suitable for use with the invention.

FIG. 10 shows an exemplary apparatus format of the invention. This figure shows two pumps 1000 that deliver fluids, as well as gases when appropriate, through tubes 1001 to fluidic channels 1002, which is bounded at the top by a plate 1007. Fluids delivered to the apparatus are removed through drainage channels 1003 to drainage tubes 1004 which lead to waste collection 1005. The pumps 1000 are connected to fluid reservoirs (not shown), or gas reservoirs when appropriate, and a control device (not shown) that regulate what fluid or gas is delivered to the apparatus.

The control device also regulates the length of time that fluids or gasses contact nucleic acid synthesis "chips" 1006. Three nucleic acid synthesis "chips" 1006 are visible in FIG. 10 resting on an electrode 1008. Fluids and/or gases are put in contact with the chips and current passes through particular locations on the chips where it is desirable for chemical reactions to occur. As described elsewhere herein, any number of reagents and washing materials may be used in the practice of the invention. In many instances, the reagents and materials used will be those which allow for the production of nucleic acid molecules.

The lower electrode 1008, as shown in FIG. 9, covers the entire base of the apparatus. This need not be the case and one or more electrodes may be associated with one end of each well or more than one well. Opposite this electrode (shown as a lower electrode 1008 in FIG. 10), there will typically be one or more second electrodes (not shown in FIG. 10) that allows for current to flow through entire chips or through wells of the chips. In many instances, these second electrodes will be positioned over individual wells of the chip to allow for current to be directed through the wells on an individual basis (see FIGS. 2A and 2B).

Fluid channel 1002 can be formed in a surface layer, such as a well. The surface layer can be formed of a polymeric material, inorganic material, or a combination thereof. For example, the surface layer can be formed of a polymeric material. An exemplary polymeric material includes acrylic, fluoropolymer, ethylene vinyl acetate (EVA), or any combination thereof. In an example, the polymeric material is a fluoropolymer. An exemplary fluoropolymer includes polyvinylidene fluoride (PVDF), polyvinyl fluoride (PVF), fluorinated ethylene propylene (FEP) copolymer, ethylene chlorotrifluoroethylene (ECTFE) copolymer, a copolymer of tetrafluoroethylene, hexafluoropropylene, and vinylidene fluoride (THV), a copolymer of tetrafluoroethylene and perfluoro methylvinylether (PFA or MFA), a fluoropolymer having a fluorinated oxolane in its backbone, perfluoroether, or any combination thereof. In particular, the fluoropolymer can be a fluoropolymer having fluorinated oxolane in its backbone, for example, Cytop. Further, the polymer coating can be amorphous, exhibiting little or no crystallinity. In another example, the surface layer is formed of an inorganic insulator. For example, the inorganic insulator can include an oxide of silicon, aluminum, hafnium, tantalum, zirconium, or any combination thereof, can include tetraorthosilicate, can include a nitride of silicon, or can include any combination thereof. In an example, the inorganic insulator can include an oxide of silicon. In another example, the inorganic insulator includes a nitride of silicon.

An exemplary microchip for synthesizing nucleic acids may in certain embodiments be a microchip (e.g., CMOS chip) comprising multiple wells, such as about 20,000 to about 40,000 wells, or about 35,000 wells, or 35,440 wells. Each well may be operably connected to at least one electrode, and each well is configured to accommodate a monodisperse bead, such as a monodisperse polystyrene bead having a diameter ranging from about 30 µm to about 40 µm, wherein the monodisperse bead may be preloaded with a universal linker, such as a UnyLinker™, for the synthesis of nucleic acid molecules. The microchip may further comprise microfluidic channels for the introduction and removal of fluids or gases, such as reagents and waste. The microchip may further be operably connected to a control device that regulates what fluid or gas is delivered to the apparatus and for what length of time, as well as the amount of current and length of time that current is applied to the individual electrodes, which may be used, for example for electrolysis as disclosed herein and/or for the generation of an electrogenerated acid or electrogenerated base. In certain embodiments, the microchip disclosed herein may be configured such that select monodisperse beads from multiple wells of the microchip may be pooled together into selected wells of a suitable collection container, such as a 1536 microwell plate for further processing and assembly. The pooling of the monodisperse beads from the microchip of this embodiment may be performed by any means known in the art, including the means disclosed herein.

Figure 23A:
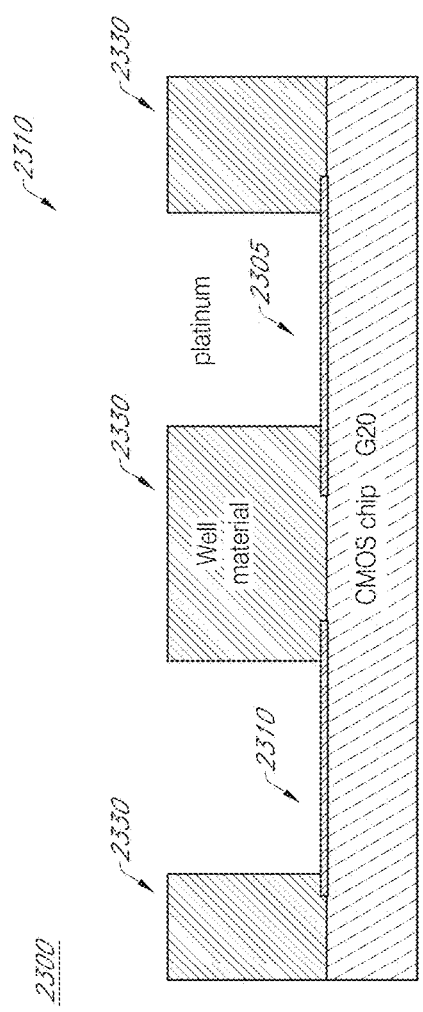
FIGS. 23A and 23B show another example of an oligonucleotide synthesis microchip according to the invention.
Figure 23B:
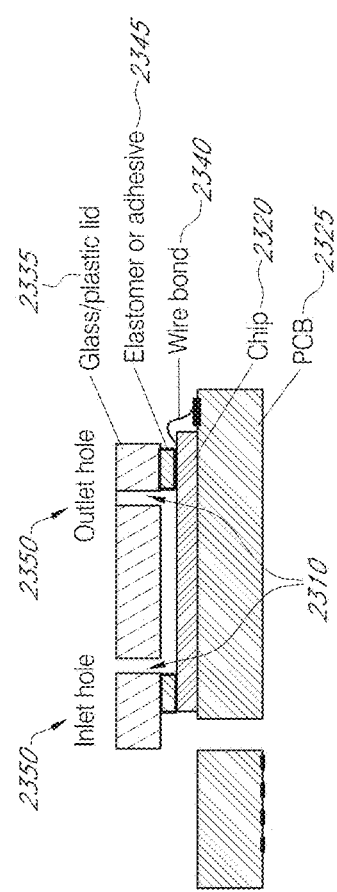

FIGS. 23A and 23B show an example of a nucleic acid synthesis microchip 2300 according to the present disclosure. Microchip 2300 includes several layers, each with a specific purpose, as discussed below. As one example, the result of these layers is that on an 18 mm by 18 mm square chip, about 35,000 electrodes can be switched individually. Because of the built-in logic of the chip, only a few (10-20) electrical connections have to be made to an outside control instrument (not shown).

Microchip 2300 includes a CMOS chip 2320 bonded to a printed circuit board ("PCB") 2325 and can be electrically connected thereto by appropriate electrical connections, such as wire bonds 2340. For example, CMOS chip 2320 can be bonded to PCB 2325 using conventional chip-on-board technology where wirebonds are used to connect the small contact pads of the chip that may then be encapsulated with an adhesive, such as glue. The CMOS chip 2320 can have a silicon base with circuitry embedded therein to route externally generated electrical signals to the desired one or more electrodes. By using the CMOS design, each of the electrodes can be addressed individually.

The electrodes 2305 are formed between the CMOS chip 2320 and one or more layers of well material 2330 such that the central portion of the electrode 2305 is exposed within a microwell 2310 to provide for electrochemistry processes and the edges of the electrode 2305 are covered by being bounded on one side by the CMOS chip 2320 and on another side by the well material 2330 to prevent detachment of the electrodes 2305 by the electrochemical processes. The electrodes 2305 can be made of platinum or other similarly electrically conductive materials that are known in the art. In the example where the electrodes 2305 are made of platinum, the platinum can be between about 10 nm and 500 nm or about 100 nm and about 300 nm in thickness. Other thicknesses of the electrodes 2305 can be used depending on the particular material used for the electrodes, the particular fluid to be used in the electrochemistry process, and the particular arrangement of the microchip 2300.

Figure 43A:
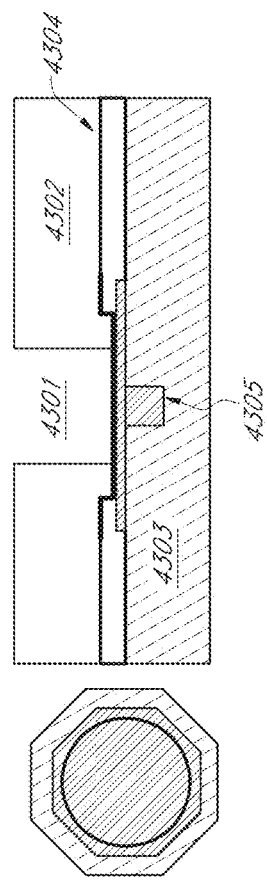
FIGS. 43A, 43B and 43C show exemplary embodiments of how a metal layer of an electrode may be connected to the top metal of the CMOS part of a microfluidic chip.

Different arrangements may be used to connect the one or more metal layers of an electrode 4305 (such as, e.g., a platinum layer 4302) to a top metal layer of the CMOS part 4303. In some instances, the electrodes 4305 may be arranged in a central or shifted position (with regard to the center of a well) as indicated respectively in FIGS. 43A and 43B. In these exemplary embodiments, the passivation layer of the CMOS chip 4303 may be opened at the end of the CMOS run (together with the bond pads) to access the top metal layer of the CMOS chip 4303. In FIG. 43A, the platinum is directly deposited onto a large opening in the passivation layer thereby creating a large-area contact between the platinum and the CMOS metal. In certain instances, the opening may have a diameter that is larger than the diameter of a well 4301 having well walls 4302. For example, where a 40-µm well is provided, the opening may be at least 45 µm in diameter. The edges of the opening in the passivation layer and the platinum layer may be covered or sealed by the well layer.

Figure 43B:
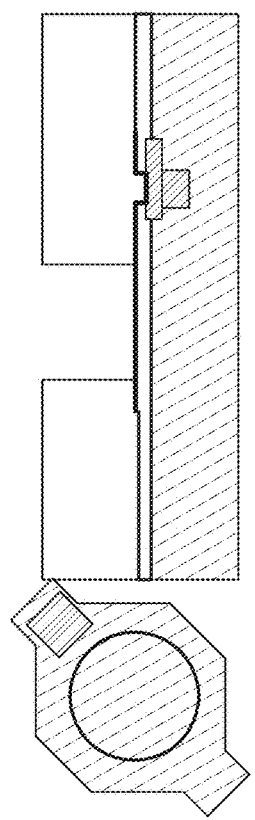

For certain applications a shifted configuration like the one shown in FIG. 43B may be used. In this configuration, the connection between the platinum and the CMOS metal is shifted sideways beneath the well layer. Such arrangement may protect the connection from degradation by reactive solvents, washing agents or chemicals that may contact the well layer during a microfluidic workflow.

Figure 43C:
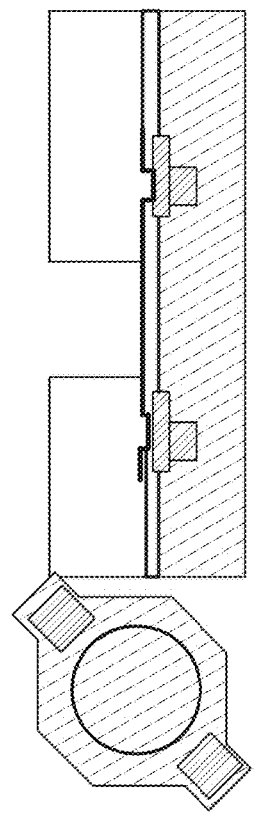

In some embodiments, an electrode may have more than one contact. For example, a second contact may be arranged in a certain distance to or opposite the first contact (for example, at the opposite end of the platinum pad, as illustrated in FIG. 43C). In a setting where two (or more) contacts are provided, they may be used together with the according circuitry in the CMOS part. Such arrangement may be useful to determine or measure certain parameters that may be critical for the functionality of a chip, such as, e.g., whether there is a complete circuit between the one or more contacts. For example, the arrangement of FIG. 43C may be used to measure if the pad is correctly deposited and connected and/or whether the platinum layer is undamaged to allow the passing of current between the first and second contact using the platinum base across the bottom of the well as a current channel. Such functionality testing may be performed at the wafer level to determine whether a particular chip meets pre-defined quality criteria required for a specific application (such as, e.g., the use in oligonucleotide synthesis). By way of example, such test may be set up to distinguish functional from non-functional electrodes wherein chip positions having non-functional electrodes may be avoided or excluded in a microfluidic workflow.

In certain embodiments, each microwell 2310 can accommodate a porous microbead 2315. The microchip comprises multiple wells such as about 20,000 to about 40,000 wells, or about 35,000 wells, or 35,440 wells. The microwell 2310 can have a height of between about 50-100 μm or 50-60 μm and a width of a size sufficient to accommodate a microbead of the size of about 10 μm to 50 μm, about 20 μm to 50 μm, about 25 μm to about 40 μm, about 30 μm to 50 μm, about 25 μm to 50 μm, about 30 μm to 40 μm, or about 35 μm.

In one embodiment, the well material 2330 can include a high-aspect ratio photoresist material, such as SU-8 (epoxy based resist) and its variants that are known in the art. SU-8 is a viscous polymer that can be spun or spread over a thickness ranging from below about 1 μm up to above about 300 μm and can be processed with standard contact lithography. SU-8 is resistant against many chemicals used in the present disclosure. Also other high aspect-ratio photoresists that are sold as laminate films can be used, such as TMMF (by Tok) and SUEX (by DJDevcorp). Other examples of the well materials 2330 are glass, ceramics, and silicon, which can provide greater chemical resistance than SU-8 material and can be micro-machined with standard techniques available to MEMS manufacturing, like dry or wet etching, such that the glass/silicon is about 25 μm to 100 μm, about 25 μm to 75 μm, about 30 μm to 60 μm, or about 50 μm and is bonded to an CMOS chip or a whole CMOS wafer, for example in an 8 inch format.

A fluidic lid 2335 can be formed and/or removably bonded by bonding materials, such as using a polymer, e.g., an elastomer or adhesive structure 2345, on a top surface of the well material 2330 to provide for a flow chamber 2350 that distributes the synthesis chemicals as evenly as possible to the wells and to provide the counter-electrode ("CE") for the electrochemical reactions (EGA and bubble generation). In certain embodiments, the flow chamber can be about 150 μm to about 250 μm high, which results in a chamber volume of about 10 μl to about 30 μl. In certain embodiments, the chamber volume may be about 10-100 μl, including, for example, about 13 μl, 26 μl, or 52 μl. As discussed above with regard to the electrodes 2305, the CE can be made from platinum and can be structured to enable visual inspection of the chip. The fluidic lid 2335 can be slightly larger than the CMOS chip 2320 to make electrical connections to the CE.

FIGS. 24A, 24B and 24C illustrate three examples of the fluidic lid 2335 of FIG. 23B, shown in cross-section. In one example shown in FIG. 24A, the fluidic lid 2335 can be a reusable lid comprising an electrode 2410, e.g., the second electrode made of an electrical conductive material such as platinum, formed between a polymer layer 2405, e.g., an elastomer, and a glass layer 2415. The fluidic lid 2335 can include one or more fluid channels 2420. The fluidic lid 2335 can be affixed firmly onto the chip 2320 to provide a tight seal and provide a flow path for fluids to be delivered to and from the wells.

In another example shown in FIG. 24B, the fluidic lid 2335 can be a permanent glass lid comprising an electrode 2410, e.g., the second electrode made of an electrical conductive material such as platinum, formed on a surface of the glass layer 2415 and bonded to the chip 2320 with an adhesive layer 2425. The fluidic lid 2335 can include one or more fluid channels 2420. Again, the fluidic lid 2335 can be affixed firmly onto chip 2320 to provide a tight seal and provide a flow path for fluids to be delivered to and from the wells.

In yet another example shown in FIG. 24C, the fluidic lid 2335 can be a permanent plastic lid comprising an electrode 2410, e.g., the second electrode made of an electrical conductive material such as platinum, formed on a surface of COC (cyclic olefin copolymer) layer 2430 and bonded to the chip 2320 with an adhesive layer 2425. The fluidic lid 2335 can include one or more fluid channels 2420. Again, the fluidic lid 2335 can be affixed firmly onto the chip 2320 to provide a tight seal and provide a flow path for fluids to be delivered to and from the wells. FIG. 24D shows a top view of the examples of FIG. 24A, 24B, or 24C showing the electrical connections 2435, fluidic connections 2440, seal 2445, flowchamber with electrode 2450 (i.e., platinum electrode) can be made with the chip 2320 or other controllers or computer systems, disclosed herein, to facilitate the practice of the various disclosed examples.

Figure 46:
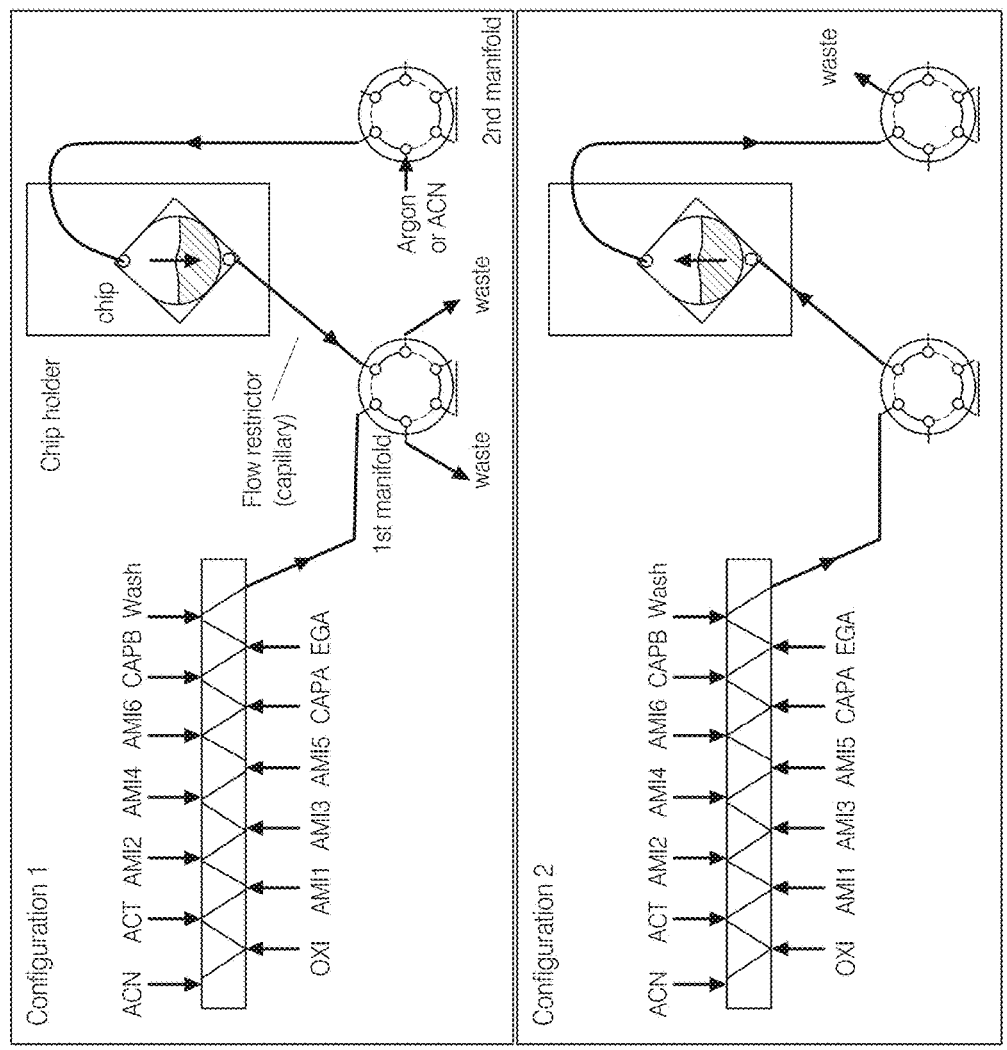
FIG. 46 shows representative embodiments of alternative fluidics configurations used in an oligonucleotide synthesis instrument.

Another example of how fluidic transport may be regulated in an oligonucleotide synthesis system is shown in FIG. 46. The system may comprise a microfluidic chip arranged in a holder. The chip and/or the holder may be arranged in various positions. In instances, where gas is passively generated within the fluidic system (e.g., by degassing of solvents) or wherein gas is actively generated within one or more wells of the chip to displace synthesis beads from the wells as described elsewhere herein, the chip may be used in a vertical position to facilitate removal of the generated gas from the chip. The chip in this exemplary system is in fluid communication with reagents required for oligonucleotide synthesis (such as acetonitrile (ACN), activator (ACT), phosphoramidites (AMI), oxidizer (OXI), capping reagents (CAP A and CAP B) and EGA). The reagents may be stored in reservoirs and may be arranged in a reagent cabinet further equipped with pressure and flow sensors, regulators, valves and manifolds for fluidic control. Fluidic transport in this system may be pressure-driven and manifolds comprising zero dead-volume valves (as, e.g., described in U.S. Pat. No. 4,558,845 the disclosure of which is incorporated herein by reference) can be used to trigger entry of selected chemicals or solvents into the main fluid path. In the example of FIG. 46, a first manifold may connect the chip with reagent reservoirs and may further connect the chip and the reagent reservoir with waste collection. A second manifold may connect the chip with a gas reservoir and waste collection. Two possible configurations are illustrated in FIG. 46. In configuration 1, the valves are set to allow for washing and priming of the first manifold, and draining of the chip (using for example a gas or a solvent), wherein both flow paths are connected with the waste collection of the first manifold. Accordingly, the washing and priming of the first manifold and the draining of the chip may be conducted simultaneously.

In configuration 2, the valves are set to allow filling of the emptied chip with synthesis reagent wherein the flow path is connected with the waste collection of the second manifold.

The skilled person will recognize that other configurations or valve/manifold arrangements may be used to fill and drain the chip during oligonucleotide synthesis.

In instances, where the chip is arranged in a vertical position as illustrated in FIG. 46, it may be emptied or drained by purging a gas or a solvent in a direction from a top inlet/outlet of the chip to a bottom inlet/outlet of the chip to efficiently remove reagents or gas through the bottom inlet/outlet of the chip. Thus, the invention may comprise workflows, where a microfluidic chip is filled with synthesis reagents in a first flow direction through a first inlet/outlet of the chip and is washed or emptied in a second flow direction that is different from the first flow direction through a second inlet/outlet of the chip. Reagents suitable for emptying or purging a chip may for example comprise heavy gases (such as e.g., argon) or certain solvents with low density. A suitable solvent may have a density that is lower than the density of the used synthesis reagents (such as, e.g., AMI, ACT, OXI, CAP A, CAP B and/or EGA). One exemplary solvent that may be used to purge the chip is acetonitrile (ACN). Different solvents with similar properties are known to those skilled in the art and can be selected by the skilled person depending on the used reagents and flow configurations of the system.

In certain embodiments, the system may be equipped with a flow restrictor device (such as a capillary) to allow controlling of the flow rates of liquid or gas through the fluidic channels. For example, whereas the washing and priming of the manifold in configuration 1 may occur at higher flow rates of at least about 1 mL/min, filling of the chip at configuration 2 should occur at flow rates of less than 1 mL/min. The complete emptying of the chip and refilling allows for very fast fluid exchange, without the need to adjust for the different density of the fluids. The flowrate at which liquid is transferred through the flowcell of a microfluidic synthesis chip may be critical in terms of (i) allowing equal distribution of reagent within the flowcell and sufficient reaction time at all synthesis positions (assuming that flow rates are different in the middle path and the edges of the flowcell), (ii) avoiding displacement of beads contained in one or more wells of the chip when fluid is passed through the chip at high velocity and (iii) the overall time required to synthesize oligonucleotides on a chip. In an exemplary embodiment, flow rates used to transfer liquid through a 40-μl flowcell of a microfluidic chip may be adjusted to be within a range of about 100 μl/min to about 1.5 mL/min. In many instances, the flow velocity may not exceed a predetermined value as higher velocities may displace beads from the wells applied for longer times. For example, where a 40-μl flowcell is used, the flow velocity may not exceed 2 meters/min.

Individual wells used in the practice of the invention may be of any number of shapes and sizes. One example of well parameters is set out in Table 14. Of course, well volume and other factors will change with well dimensions.

TABLE 14

Exemplary cylindrical well parameters

| Well Diameter | 40 μm | Well Volume | 62,831 μm³ |
|---|---|---|---|
| Well Height | 50 μm | Charge | 1 μAs |
| pH | 1 | Current Density/Well | 1 mA/mm |
| Area/Well | 1,256 μm² | | |

TABLE 15

| Number of Oligos/Bead | $1.0 \times 10^{11}$ | Required Buffer Vol. (μl) | 2.5 |
|---|---|---|---|
| Oligonucleotide Concentration (μmol/l) | 0.20 | Bead Vol. (pl) | 22 |
| Bead Diameter (μm) | 35 | | |

Table 15 shows some bead parameters and estimate buffer volume and concentration for a particular bead size.

After completion of nucleic acid molecules production steps, the substrates (e.g., beads) containing the nucleic acid molecules may be collected, separated from the synthesis substrates, and further processed.

An exemplary work flow is one such as the following: (1) Beads are prepared with functional (hydroxyl or amine) groups, (2) the beads are derivatized in batch off-line forming amide with pre-synthesized universal primers with rare type IIs restriction site for enzymatic cleavage of synthesized nucleic acid molecules off the beads, (3) the beads are loaded by flowing suspension into chip, gravity or centrifugation secures beads in wells, (4) the loaded beads are in or near physical contact with an anode and EGA is generated at anode and on the bead surface for deprotection, (5) synthesis steps as described herein are performed, (6) after synthesis, digitally electro-eject of desired beads from well is accomplished by reversing the current, as an alternative, gas bubble ejection may be employed, (7) ejected beads are collected and pooled from the liquid flow out of chip.

Figure 27:
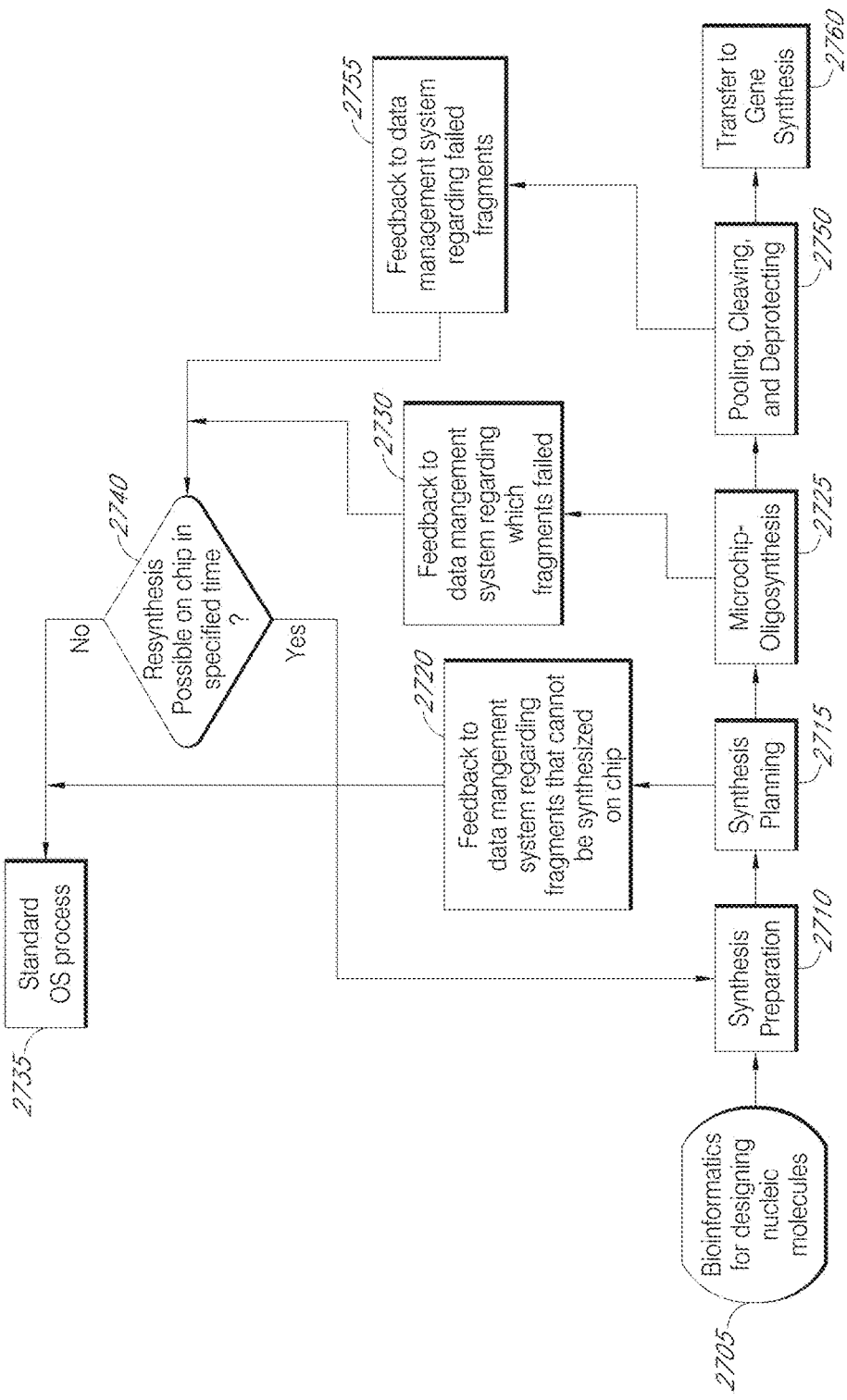
FIG. 27 shows an example work flow diagram of the nucleic acid synthesis (Module 1) and the pooling, cleavage and deprotection steps (Module 2).

FIG. 27 provides an example work flow diagram of the nucleic acid synthesis (Module 1) and the pooling, cleavage and deprotection steps (Module 2) ("Module 1/2 work flow"). The work flow begins by using bioinformatics to inform decisions about which nucleic acid molecules to synthesize 2705. Bioinformatics is an interdisciplinary field that combines software, computer science, statistics, and mathematics to help understand, analyze, and manipulate biological data. For the synthesis of nucleic acid molecules, the biological data can include information to optimize the yield of synthetic nucleic acid molecules or genes and/or maximize expression of synthetic nucleic acid molecules or genes (or the proteins encoded thereby) in different expression systems.

When designing nucleic acid molecule to optimize yield or maximize expression bioinformatics can be used, for example, to 1) adjust codon usage, 2) remove unwanted repeat sequences, 3) remove unwanted splice sequences, 4) optimize GC (guanine/cytosine) content, 5) avoid unwanted secondary structures in RNA molecules, 6) remove unwanted restriction enzyme recognition sequences, 7) adjust length of synthesized nucleic acid molecule (as sequence length increases, eventually yield and sequence fidelity decrease), 8) calculate the fragmentation of a gene or other nucleic acid molecule of interest into smaller overlapping oligonucleotides, which are chemically synthesized on the microchip, and later assembled into the gene or nucleic acid of interest, or 9) design the sequences at the termini of the synthesized nucleic acid molecules to facilitate assembly of the nucleic acid molecules, for example, through amplification reactions. Bioinformatics may also be to define rules to calculate the difficulty of synthesizing a particular nucleic acid molecule and to use this data to inform decisions about what sequences can or cannot be synthesized.

It maybe desirable, for example, to use bioinformatics to modify one or more codon sequences in a nucleic acid molecule to improve the translation of the nucleic acid sequence and expression of the resulting protein is optimized for a particular expression system. A nucleic acid sequence that has been adjusted to optimize the codon sequences encodes the same protein as a non-optimized parental sequence upon which the codon-optimized nucleic acid sequence is based. For example, the one or more codons of a nucleic acid sequence may be adjusted to optimize for expression in mammalian cells (e.g., CHO cells, human cells, mouse cells etc.), bacterial cells (e.g., *E. coli*), insect cells, yeast cells or plant cells.

One example of a comprehensive multiparameter approach that may be used in the current invention for optimized sequence design is the GENEOPTIMIZER® technology described in U.S. Patent Publication No. 2007/0141557, the disclosure of which is incorporated herein by reference. Thus, the invention provides in part aspects of optimal sequence design for downstream applications including assembly and expression strategies.

Figure 28A:
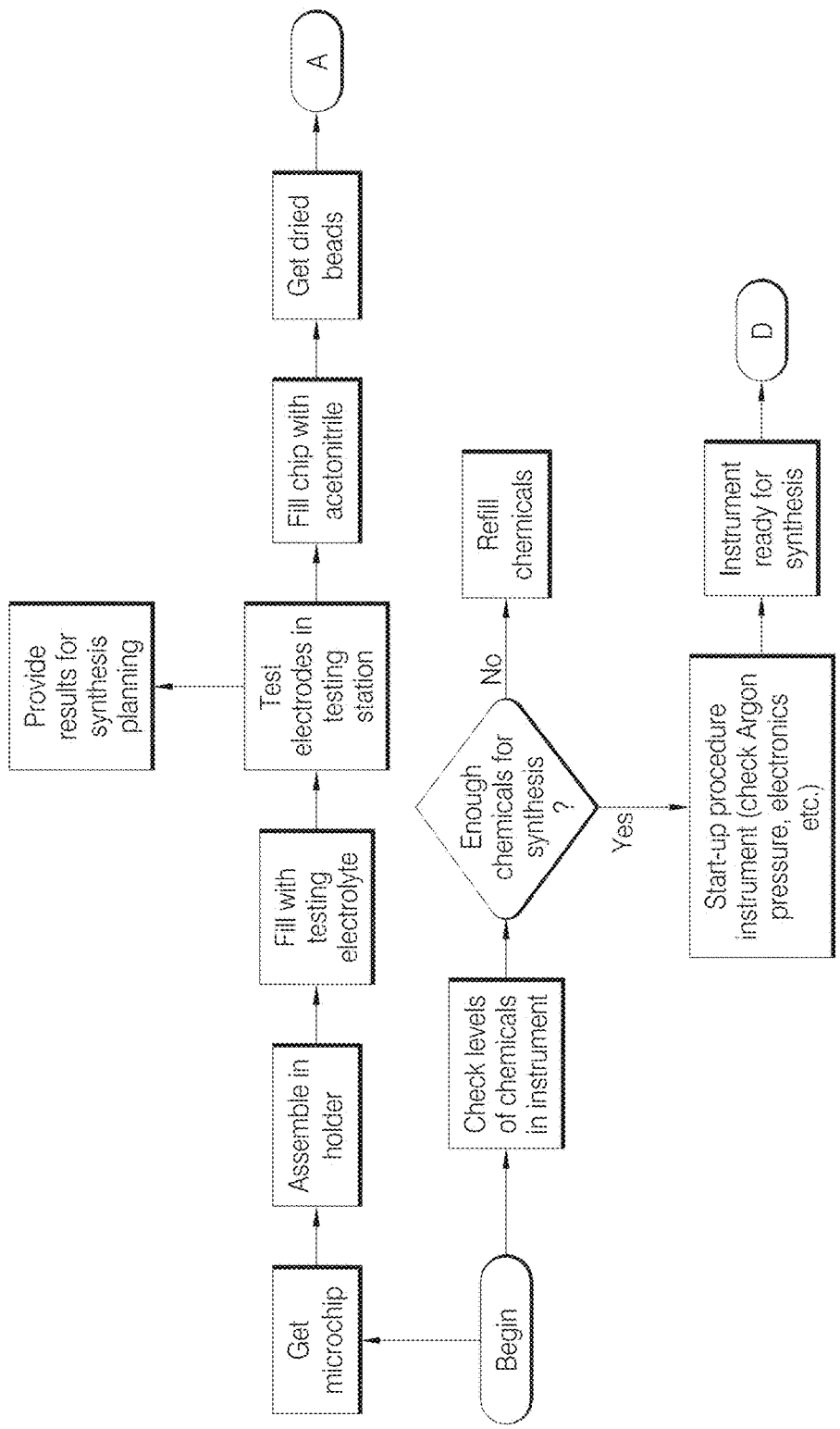
FIGS. 28A, 28B and 28C show an example work flow diagram of synthesis preparation.
Figure 28B:
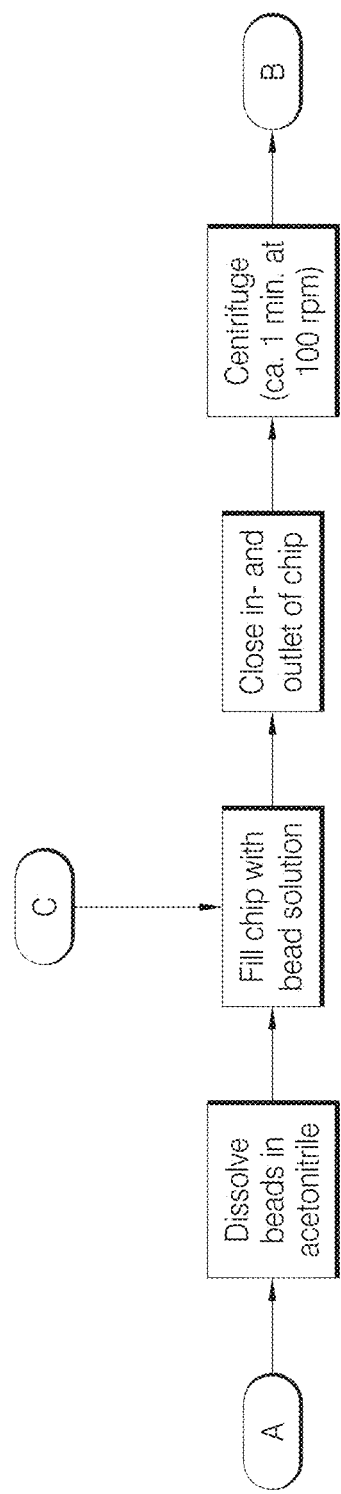
Figure 28C:
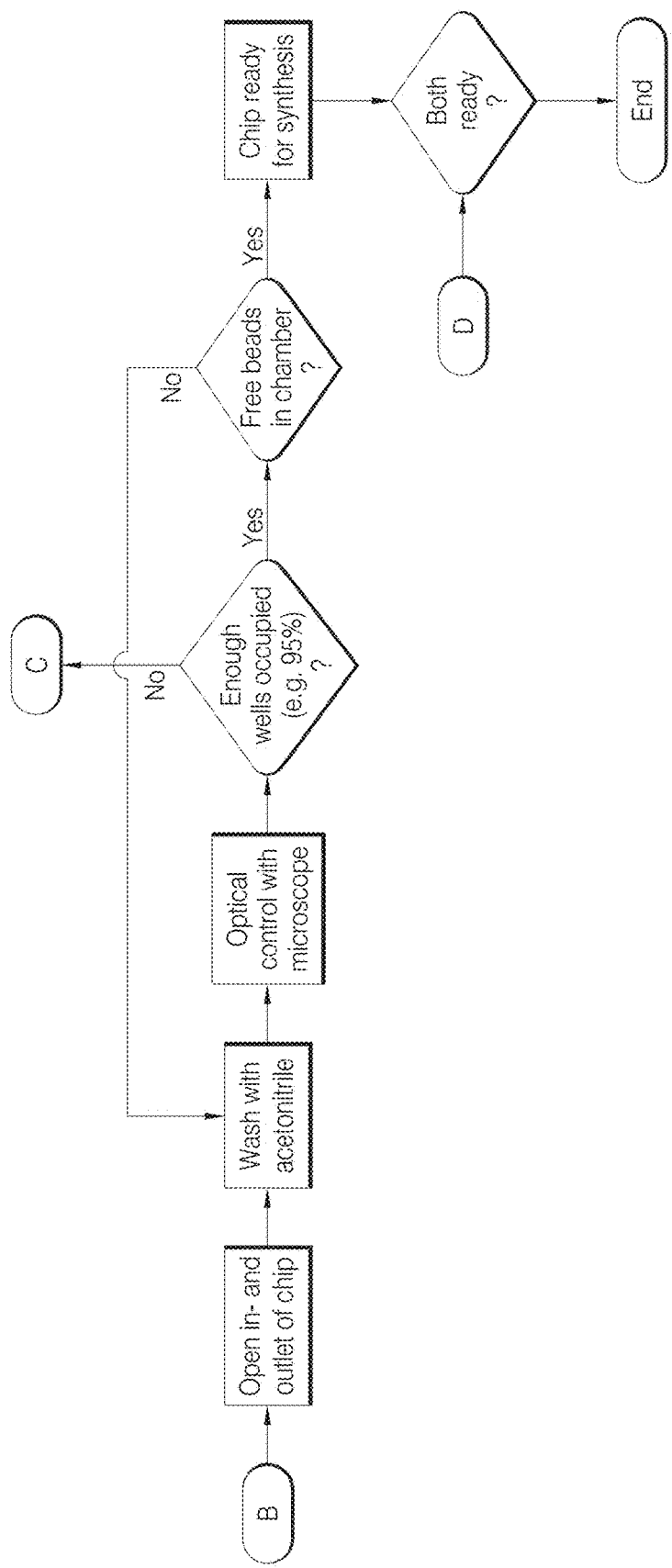

The next step of the Module 1/2 work flow involves synthesis preparations 2710, which are performed before the actual nucleic acid synthesis. For example, the microchip for synthesizing nucleic acid molecules can be tested for functionality, by measuring the current flow at each electrode with an electrolyte present in the chip. If any nonfunctional electrodes are identified, they are saved in a file and their non-functionality is taken into account in the synthesis planning step to either remove the microchip with one or more non-functional electrodes or ensure that any well associated with a non-functional electrode will not be used in the synthesis step. Synthesis preparation also involves filling the beads or other substrate in a sufficient quantity into the microchip. To maximize efficiency, it is preferable to fill the microchip to near capacity, e.g., 95% or greater. Synthesis preparation can also include starting the instrument housing the reagents used in the synthesis step and checking and optionally refilling the reagents stored in the instrument. An example work flow of the synthesis preparation step 2710 is set forth in FIGS. 28A, 28B and 28C.

The next step in the Module 1/2 example work flow is synthesis planning 2715. As part of the synthesis planning step, feedback is sent to a computerized data management system regarding nucleic acid molecules that have been identified through bioinformatics as being poor choices for synthesis on the microchip 2720. In certain instances, it may be necessary to synthesize specific nucleic acid molecules on different synthetic platforms, particularly for nucleic acid molecules that are difficult to synthesize on a microchip platform or need to be produced in higher concentrations to obtain sufficient yield of a full length nucleic acid product. Nucleic acids having increased GC content may be more difficult to synthesize and/or need to be synthesized in higher concentrations. In certain instances, when a higher concentration of a nucleic acid molecule is desired, it will be possible to increase the concentration of the nucleic acid molecule by assigning the nucleic acid molecule to more wells in the synthetic microchip so that more copies of the nucleic acid molecule are produced during the synthesis step. Thus, by way of example, a nucleic acid molecule that is identified as being "easy" to synthesize may be assigned to some number of wells for synthesis, e.g., 5, 6, 7, 8, 9, or 10, while a nucleic acid molecule that is "difficult" to synthesize would be assigned to more wells than the "easy" nucleic acid molecule. In a specific embodiment, the "easy" nucleic acid molecule is synthesized in 6 wells while the "difficult" nucleic acid molecule is synthesized in 14 wells. Assigning the "difficult" nucleic acid molecule to more wells than the "easy" nucleic acid molecule, will increase the amount of the "difficult" nucleic acid molecule synthesized and allow both the "difficult" and the "easy" nucleic acid molecules to be present at about the same concentration during the assembly step (Module 3).

Figure 29A:
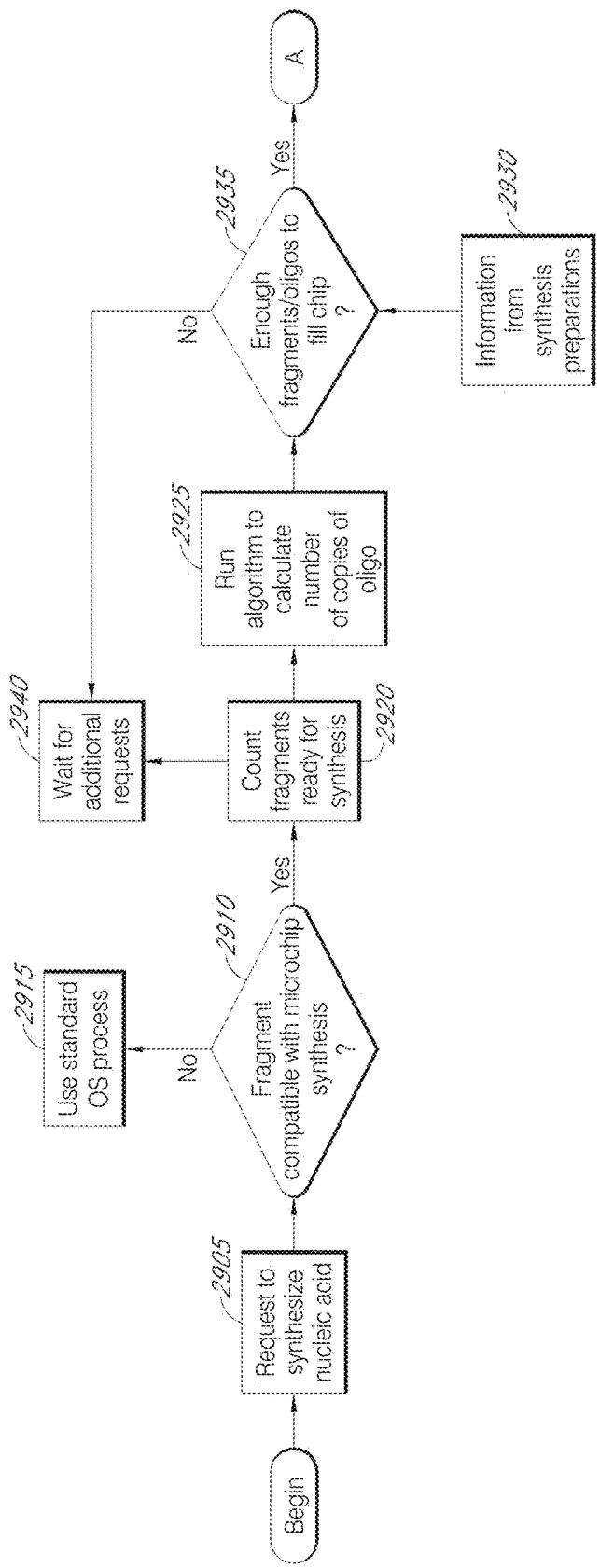
FIGS. 29A and 29B shows an example work flow diagram of synthesis planning.
Figure 29B:
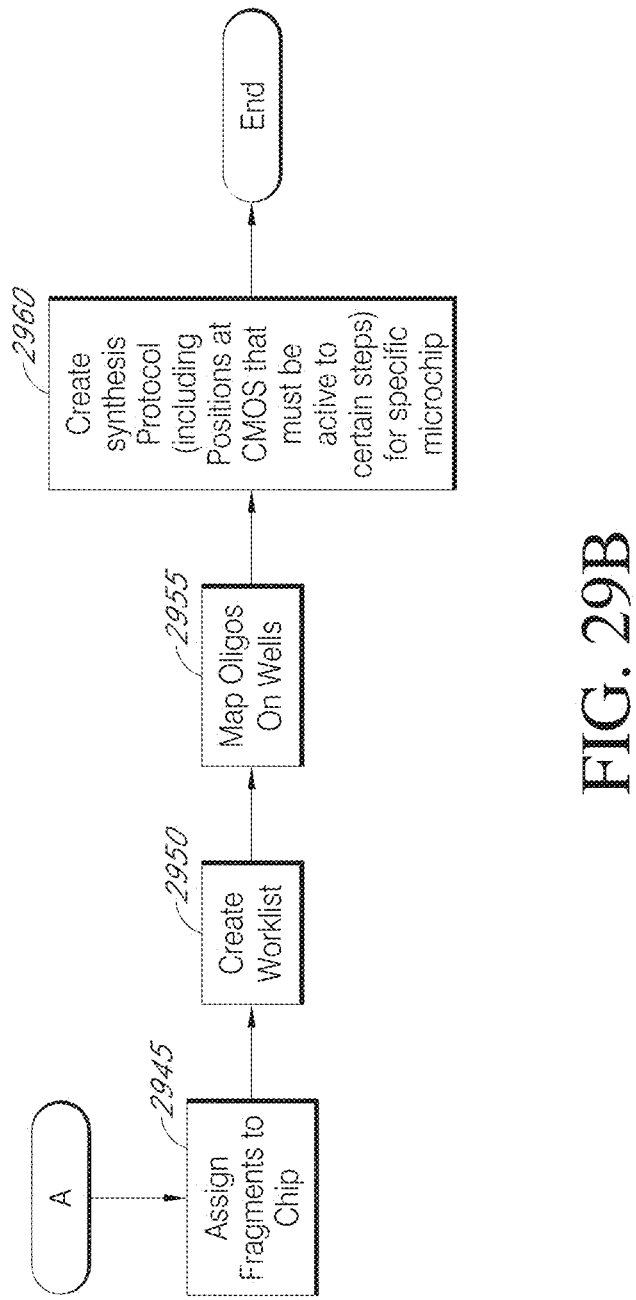

An example work flow of the synthesis planning step 2715 is set forth in FIG. 29A. A request to synthesize a nucleic acid is received 2905. If the fragments designed for assembling the requested nucleic acid are not compatible with the microchip synthesis 2910, feedback is sent to the computerized data management system regarding nucleic acid molecules that have been identified as being incompatible for synthesis on the microchip 2915. If the fragments designed for assembling the requested nucleic acid are compatible with the microchip synthesis 2910, the number of fragments ready for synthesis are counted 2920. Next an algorithm is run to calculate the number of copies of each nucleic acid molecule that should be synthesized 2925.

Using synthesis preparation information 2930, a determination is made whether there are a sufficient number of nucleic acid molecules to fill the microchip 2935. As discussed above, this may depend on the number of wells in the microchip. Of course, the number of wells used for the synthesis of a specific oligonucleotide sequence in the microchip can be adjusted based on the number of nucleic acid molecules that are in queue for synthesis at any given time. If there are not enough nucleic acid molecules to fill the chip, it is possible to wait until receiving additional requests to synthesize nucleic acids 2940. Alternatively, a chip with fewer wells can be used or the same nucleic acid molecule can be synthesized in a higher quantity to fill the chip. If there are enough nucleic acid molecules to fill the microchip, the fragments for assembling the requested nucleic acid are assigned to the microchip 2945 and a worklist is created 2950. The nucleic acid molecules are then mapped to individual wells on the microchip 2955. After all of the nucleic acid molecules have been mapped on the microchip, a synthetic protocol can be generated in which the positions of the electrodes that need to be activated (to generate an EGA) or light sources that need to be activated (to generate a PGA) for each cycle of amidite are identified 2960. The protocol can be and saved or stored on a computer system and used during the subsequent synthesis step to direct the synthesis of the nucleic acid molecules on the microchip.

The next step in the example Module 1/2 work flow is synthesis of the nucleic acid molecules on the microchip 2725 (corresponding to Module 1 of FIG. 1). As described herein, the synthetic steps will vary, but in certain embodiments, a plurality of nucleic acid molecules are synthesized on the microchip. This step includes a feedback mechanism to collect and send data about nucleic acid molecules that failed to synthesize to the computerized data management system 2730. The collected data is stored in a computer system 2735 used to make decisions (2740) about whether to continue from the synthetic step from which the data were obtained or return to the synthesis preparation step. The collected data about nucleic acid molecules that failed to synthesize can also be added to the bioinformatics database and used to help optimize the yield of other synthetic processes.

The activation of an electrode to create an EGA or a light source to generate a PGA allows for the selective deprotection of a desired amidite. In this way, the addition of amidites can be done in a highly selective manner so that only electrodes or light sources that are selected and activated generate EGA or PGA, respectively, that deprotects the desired amidite and allows the amidite to be added to the nucleic acid molecule attached to the solid support. This also permits the nucleic acid molecules to be synthesized in a highly automated fashion that does not require the pipetting of amidites into different positions or wells of a multiwell plate.

In certain embodiments, the amidite and catalyst, such as tetrazole or 4,5 dicyanoimidazole, are flushed over the whole microchip at once. It is not critical that certain wells contain an amidite and catalyst, even though they are not designated to add the specific amidite, because as long as the electrode or light source in that well is not activated, no EGA or PGA will form and the amidite will not be added to the nucleic acid molecule attached to the bead or other suitable substrate in the well. This stands in sharp contrast to other methods that require the pipetting of the amidites into only the desired positions or wells.

Thus, by way of example, in the synthetic step, the wells of the microchip are filled with an EGA reagent (e.g., solution containing hydroquinone or benzoquinone or derivative thereof) or PGA reagent. Next, an EGA (or PGA) is selectively generated only in wells where the first amidite (e.g., Adenosine) should be added. The EGA (or PGA) deprotects the exposed sugar group of the terminal nucleotide attached to the bead or other suitable solid support in the well. The microchip is washed with a suitable reagent (e.g., acetonitrile) before pumping a capping agent (e.g., acetic anhydride or N-methylimidazole) through the microchip to cap the deprotected sugar group of any unreacted terminal nucleotide. This is followed by another washing step before pumping an oxidizing agent (e.g., iodine-containing reagent) throughout the microchip to oxidize the phosphite triester to the more stable phosphate triester. Next, the microchip is washed again with a suitable reagent (e.g., acetonitrile) before filling the wells of the microchip with the EGA or PGA reagent and starting the same cycle again for the next amidite (e.g., A, C, G, T, or U). This cycle is repeated as needed until all of the desired nucleic acid molecules have been synthesized and are ready for cleavage from the bead or other suitable solid support.

Figure 30:
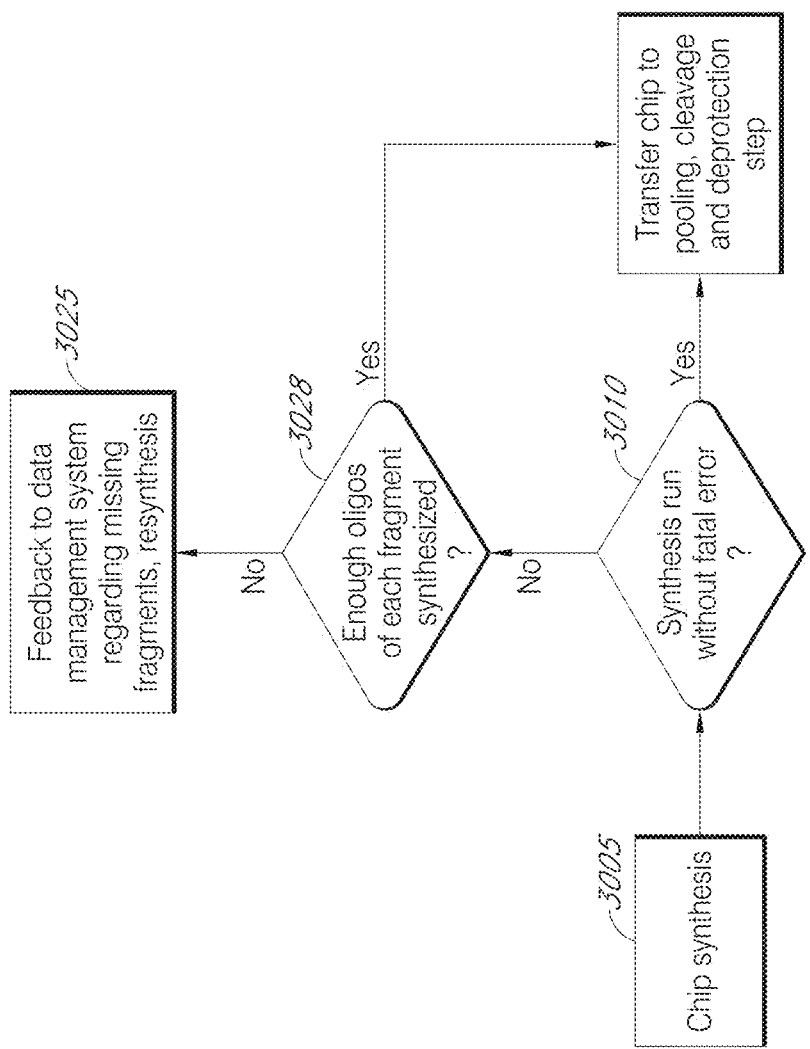
FIG. 30 shows an example work flow diagram of microchip synthesis.

An example work flow of the synthetic step is set forth in FIG. 30. The plurality of nucleic acid molecules are synthesized on the microchip 3005. Data are analyzed to determine whether the synthesis step was completed without any errors 3010. If so, the microchip is ready for the pooling, cleaving, and deprotecting steps. If not, the microchip is further analyzed to determine whether, notwithstanding the errors, a sufficient amount of nucleic acid molecules of each fragment was synthesized 3020. If so, the microchip is ready for the pooling, cleaving, and deprotecting steps. If not, data about the nucleic acid molecules that were not synthesized or were synthesized in amounts that were not sufficient for subsequent assembly are sent to the computerized data management system 3025. The data can be used to make decisions about resynthesizing nucleic acid molecules that were not synthesized or were synthesized in amounts that were not sufficient for subsequent assembly. The data can also be added to the bioinformatics database to help in the future design of synthetic nucleic acid molecules.

After synthesizing the nucleic acid molecules on individual solid supports (e.g., beads) inside the microchip, the nucleic acid molecules need to removed from the microchip and pooled for further processing. The next step in the example Module 1/2 work flow is pooling of the solid supports (e.g., beads), cleaving of the nucleic acid molecules from the solid supports, and deprotecting of the cleaved nucleic acid molecules 2750 (corresponding to Module 2 in FIG. 1). This step also has a feedback mechanism to collect and send data about nucleic acid molecules that failed to synthesize to the computerized data management system 2755. The collected data is stored within a computer system and used to make decisions about whether to continue the pooling/cleaving/deprotecting step from which the data were obtained. For example, if there is sufficient time and space on the microchip, the pooling/cleaving/deprotecting step can be aborted and the microchip returned to synthesis preparation step 2710 where software integrated with the computer system takes into account the nucleic acid molecule(s) that failed to synthesize and proposes alternative synthetic strategies 2740. The collected data about nucleic acid molecules that failed to synthesize can also be added to the bioinformatics database and used to help optimize the yield of other synthetic processes.

The final step in the example Module 1/2 work flow is transfer of the nucleic acid molecules to the gene synthesis stage 2760. The gene synthesis stage can include amplification and assembly of the synthesized nucleic acid molecules, error correction, and final assembly (corresponding to Module 3 in FIG. 1). In certain embodiments, the nucleic acid molecules are transferred to the gene synthesis stage in a multiwell plate (e.g., a 1536 well plate).

During the different steps of the gene synthesis stage (e.g., amplification, assembly, error correction, final assembly), different solutions can be added to and removed from the multiwell plate. There are numerous liquid handling devices that can be used to transfer small volumes of solution, including, but not limited to peristaltic pump based bulk dispensers, fixed-tip transfer devices, changeable-tip transfer devices, pintool transfer devices, piezoelectric devices, solenoid based devices, and acoustic devices. Using these various liquid handling devices, it is possible to accurately transfer small volumes of solution, such as about 1-100 µL, 1 µL to 500 nL, or 500 nL or less.

In certain embodiments, the multiwell plate can be qualified for acoustic liquid handling, which provides accurate, precise transfer of small volumes or droplets. Acoustic liquid handling uses a pulse of focused sound energy to transfer a droplet of precise volume from a source, such as a multiwell plate, to any destination position, which can also be a different multiwell plate. Droplets can have a volume that is less than or equal to about 10 µL, 1 µL, 500 nL, 100 nL, 50 nL, 10 nL, or 1 nL. Acoustic liquid handling dispenses with the need to use pipettes and disposable tips that can result in cross contamination. Nothing physically touches the fluid with acoustic liquid handling, minimizing or eliminating the risk of cross contamination.

Those skilled in the art will recognize that the operations of the various embodiments may be implemented using hardware, software, firmware, or combinations thereof, as appropriate. For example, some processes can be carried out using processors or other digital circuitry under the control of software, firmware, or hard-wired logic. (The term "logic" herein refers to fixed hardware, programmable logic and/or an appropriate combination thereof, as would be recognized by one skilled in the art to carry out the recited functions.) Software and firmware can be stored on computer-readable media. Some other processes can be implemented using analog circuitry, as is well known to one of ordinary skill in the art. Additionally, memory or other storage, as well as communication components, may be employed in embodiments of the invention.

FIG. 15 is a block diagram that illustrates a computer system 1500 that may be employed to carry out processing functionality, according to various embodiments, upon which embodiments of a thermal cycler system may utilize. Computing system 1500 can include one or more processors or controllers, such as a processor 1504. Processor 1504 can be implemented using a general or special purpose processing engine such as, for example, a microprocessor, controller or other control logic. In this example, processor 1504 is connected to a bus 1502 or other communication medium. For example, processor 1504 may be a current controller as described above with reference to FIGS. 2A and 2B.

Further, it should be appreciated that a computing system 1500 of FIG. 15 may be embodied in any of a number of forms, such as a rack-mounted computer, mainframe, supercomputer, server, client, a desktop computer, a laptop computer, a tablet computer, hand-held computing device (e.g., PDA, cell phone, smart phone, palmtop, etc.), cluster grid, netbook, embedded systems, or any other type of special or general purpose computing device as may be desirable or appropriate for a given application or environment. Additionally, a computing system 1500 can include a conventional network system including a client/server environment and one or more database servers, or integration with LIS/LIMS infrastructure. A number of conventional network systems, including a local area network (LAN) or a wide area network (WAN), and including wireless and/or wired components, are known in the art. Additionally, client/server environments, database servers, and networks are well documented in the art.

Computing system 1500 may include bus 1502 or other communication mechanism for communicating information, and processor 1504 coupled with bus 1502 for processing information.

Computing system 1500 also includes a memory 1506, which can be a random access memory (RAM) or other dynamic memory, coupled to bus 1502 for storing instructions to be executed by processor 1504. Memory 1506 also may be used for storing temporary variables or other intermediate information during execution of instructions to be executed by processor 1504. Computing system 1500 further includes a read only memory (ROM) 1508 or other static storage device coupled to bus 1502 for storing static information and instructions for processor 1504.

Computing system 1500 may also include a non-transitory storage device 1510, such as a magnetic disk, optical disk, or solid state drive (SSD) is provided and coupled to bus 1502 for storing information and instructions. Storage device 1510 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having stored there in particular computer software, instructions, or data.

In alternative embodiments, storage device 1510 may include other similar instrumentalities for allowing computer programs or other instructions or data to be loaded into computing system 1500. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 1510 to computing system 1500.

Computing system 1500 can also include a communications interface 1518. Communications interface 1518 can be used to allow software and data to be transferred between computing system 1500 and external devices. Examples of communications interface 1518 can include a modem, a network interface (such as an Ethernet or other NIC card), a communications port (such as for example, a USB port, a RS-232C serial port), a PCMCIA slot and card, Bluetooth, etc. Software and data transferred via communications interface 1518 are in the form of signals which can be electronic, electromagnetic, optical or other signals capable of being received by communications interface 1518. These signals may be transmitted and received by communications interface 1518 via a channel such as a wireless medium, wire or cable, fiber optics, or other communications medium. Some examples of a channel include a phone line, a cellular phone link, an RF link, a network interface, a local or wide area network, and other communications channels.

Computing system 1500 may be coupled via bus 1502 to a display 1512, such as a cathode ray tube (CRT) or liquid crystal display (LCD), for displaying information to a computer user. An input device 1514, including alphanumeric and other keys, is coupled to bus 1502 for communicating information and command selections to processor 1504, for example. An input device may also be a display, such as an LCD display, configured with touch screen input capabilities. Another type of user input device is cursor control 1516, such as a mouse, a trackball or cursor direction keys for communicating direction information and command selections to processor 1504 and for controlling cursor movement on display 1512. This input device typically has two degrees of freedom in two axes, a first axis (e.g., x) and a second axis (e.g., y), that allows the device to specify positions in a plane. A computing system 1500 provides data processing and provides a level of confidence for such data. Consistent with certain implementations of embodiments of the present teachings, data processing and confidence values are provided by computing system 1500 in response to processor 1504 executing one or more sequences of one or more instructions contained in memory 1506. Such instructions may be read into memory 1506 from another computer-readable medium, such as storage device 1510. Execution of the sequences of instructions contained in memory 1506 causes processor 1504 to perform the process states described herein. Alternatively hard-wired circuitry may be used in place of or in combination with software instructions to implement embodiments of the present teachings. Thus implementations of embodiments of the present teachings are not limited to any specific combination of hardware circuitry and software.

The term "computer-readable medium" and "computer program product" as used herein generally refers to any media that is involved in providing one or more sequences or one or more instructions to processor 1504 for execution. Such instructions, generally referred to as "computer program code" (which may be grouped in the form of computer programs or other groupings), when executed, enable the computing system 1500 to perform features or functions of embodiments of the present invention. These and other forms of computer-readable media may take many forms, including but not limited to, non-volatile media, volatile media, and transmission media. Non-volatile media includes, for example, solid state, optical or magnetic disks, such as storage device 1510. Volatile media includes dynamic memory, such as memory 1506. Transmission media includes coaxial cables, copper wire, and fiber optics, including the wires that comprise bus 1502.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 1504 for execution. For example, the instructions may initially be carried on magnetic disk of a remote computer. The remote computer can load the instructions into its dynamic memory and send the instructions over a telephone line using a modem. A modem local to computing system 1500 can receive the data on the telephone line and use an infra-red transmitter to convert the data to an infra-red signal. An infra-red detector coupled to bus 1502 can receive the data carried in the infra-red signal and place the data on bus 1502. Bus 1502 carries the data to memory 1506, from which processor 1504 retrieves and executes the instructions. The instructions received by memory 1506 may optionally be stored on storage device 1510 either before or after execution by processor 1504.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

EXAMPLES

Example 1A: Crosslinked Porous Polystyrene Particles Containing Amine Functionality, 32 μm, 4 Mole % Aminostyrene 1,380 g of water, 179 g of bis(2-ethylhexyl)adipate, 230 g of acetone and 7 g of sodium dodecyl sulphate (SDS) were emulsified for 5 minutes by using an ULTRA TURRAX® mixer and homogenized in a two stage Manton Gaulin homogenizer at 400 kg/cm³ in the first stage and 100 kg/cm³ in the second stage for 5-8 minutes.

After homogenization, 275 g of the emulsion was charged with a seed suspension of monodisperse oligomeric styrene particles having a particle diameter of 5 μm. 75 g of seed suspension containing 7 g of oligomeric particles and 68 g of water were used.

After stirring at 45° C. for 1 day, 59.5 g of the seed suspension containing activated seed particles was charged with 1,467.4 g of an emulsion containing 1,063.9 g of water, 1.6 g of METHOCEL™ K-100 (Dow Chemical Co.), 0.6 g of sodium dodecyl sulphate (SDS), 56.5 g of divinylbenzene (DVB) (i.e., 80% by weight DVB, 20% by weight ethyl vinyl benzene and other byproducts in DVB production), 66.9 g of styrene, 5.3 g of aminostyrene, 190.9 g of toluene, 74.6 g of heptane and 7.1 g of 2,2'-azobis(2-methylbutyronitrile). The mixture was emulsified for 5 minutes by using an ULTRA TURRAX® mixer and homogenized at 400 kg/cm² in the first stage and 100 kg/cm² in the second stage for 16-20 min.

After swelling at 27° C. for 1 hour, 476.5 g of water and 3.2 g of METHOCEL™ K-100 were charged to the reactor. The dispersion was then polymerized for 1 hour at 60° C. and 10 hours at 70° C., yielding a suspension of particles having a diameter of 32 μm.

The particles were separated from the liquid phase by flotation and the liquid phase was discharged. The particles were then cleaned with 2 liters of 2 g/L SDS solution (aq) by stirring for 30 min. followed by flotation and removal of the liquid. This was repeated a minimum of two times. Methanol (2 liters) was then added and the particle suspension was stirred for 30 min. followed by sedimentation. The supernatant was removed and fresh methanol added, and the washing was repeated a minimum of two times. Finally, the particles were drained and sieved through a 100 μm sieving cloth. Particle diameter was measured on particles dispersed in aqueous electrolyte solution containing 1% NaCl and 0.01% SYNPERONIC™ All by Coulter Counter principle on a Beckman Coulter MULTISIZER™ 4.

Example 1B: Crosslinked Porous Polystyrene Particles Containing Amine Functionality, 32 μm, 11 Mole % Aminostyrene 1,380 g of water, 179 g of bis(2-ethylhexyl)adipate, 230 g of acetone and 7 g of sodium dodecyl sulphate (SDS) were emulsified for 5 minutes by using an ULTRA TURRAX® mixer and homogenized in a two stage Manton Gaulin homogenizer at 400 kg/cm³ in the first stage and 100 kg/cm³ in the second stage for 5-8 minutes.

After homogenization, 275 g of the emulsion was charged with a seed suspension of monodisperse oligomeric styrene particles having a particle diameter of 5 μm. 75 g of seed suspension containing 7 g of oligomeric particles and 68 g of water were used.

After stirring at 45° C. for 1 day, 59.5 g of the seed suspension containing activated seed particles was charged with 1,453.3 g of an emulsion containing 986.7 g of water, 1.6 g of METHOCEL™ K-100 (Dow Chemical Co.), 0.6 g of sodium dodecyl sulphate (SDS), 56.3 g of divinylbenzene (DVB) (i.e., 80% by weight DVB, 20% by weight ethyl vinyl benzene and other byproducts in DVB production), 58.4 g of styrene, 15.1 g of aminostyrene, 190.4 g of toluene, 74.4 g of heptane and 7.1 g of 2,2'-azobis(2-methylbutyronitrile). The mixture was emulsified for 5 minutes by using an ULTRA TURRAX® mixer and homogenized at 400 kg/cm² in the first stage and 100 kg/cm² in the second stage for 16-20 min.

After swelling at 27° C. for 1 hour, 476.5 g of water and 3.2 g of METHOCEL™ K-100 were charged to the reactor. The dispersion was then polymerized for 1 hour at 60° C. and 10 hours at 70° C., yielding a suspension of particles having a diameter of 32 μm.

The particles were separated from the liquid phase by flotation and the liquid phase was discharged. The particles were then cleaned with 2 liters of 2 g/L SDS solution (aq) by stirring for 30 min. followed by flotation and removal of the liquid. This was repeated a minimum of two times. Methanol (2 liters) was then added and the particle suspension was stirred for 30 min followed by sedimentation. The supernatant was removed and fresh methanol added, and the washing was repeated a minimum of two times. Finally, the particles were drained and sieved through a 100 μm sieving cloth. Particle diameter was measured on particles dispersed in aqueous electrolyte solution containing 1% NaCl and 0.01% SYNPERONIC™ All by Coulter Counter principle on a Beckman Coulter MULTISIZER™ 4.

Example 2

Conjugation of UnyLinker™ to Amine Functionalized Particles 24 g of the particles described in Example 1 in 406 g of toluene were charged to a reactor equipped with a stirrer and heating jacket. Under stirring, 1.8 g of N,N'-diisopropylcarbodiimide (DIC) was added. After 5 minutes, 5.6 g of UnyLinker™ (ChemGenes, Wilmington, Mass.) succinate triethylammonium salt dissolved in 50 g of toluene was also introduced and the reaction stirred at 25° C. for 20 hours.

Upon completion, the particles were allowed to settle and the supernatant was removed. This was followed by addition of 0.5 liters of toluene and the suspension was stirred for 30 minutes. This washing process was repeated twice and then three more times using 0.5 liters of tetrahydrofuran (THF) instead of toluene.

The linker loading of the particles was confirmed to be within a range of 15-100 μmol/g by cleavage of the DMT protecting group from the UnyLinker™ using trichloroacetic acid and subsequent analysis by ultraviolet-visible spectroscopy according to the following protocol: 10-20 mg of dry particles were weighed in a glass vial. 2 mL of 3 w % trichloroacetic acid (TCA) in dichloromethane (DCM) was added and the vial shaken gently for 5 min. 200 μL of the solution was transferred to a 2 mL vial containing 1.8 mL of 0.1 M p-toluenesulfonic acid in acetonitrile. The 2 mL vial was shaken for 10 seconds and centrifuged to sediment the polymer. 100 μL was transferred to a new 2 mL vial containing 900 μL 0.1 M p-toluenesulfonic acid in acetonitrile. UV absorbance was measured in a cuvette at a wavelength of 498 nm and confirmed a UnyLinker™ loading of 53 μmol per gram of particles according to the method described below.

$$L = 2*10^8 * \frac{A}{l*\varepsilon*m}$$

where L is the loading in μmol/g, A is the absorption at 498 nm, l is the cell length in cm, ε=68,700 L/(mol*cm) and m is the sample mass in mg.

Example 3: Capping of UnyLinker™ Functionalized Particles 24 g of particles in tetrahydrofuran (THF) containing UnyLinker™ as described in Example 2 were allowed to settle and as much of the solvent removed by suction as possible. 480 g of CAP B was added and the particles re-suspended. The solution was subsequently charged to a glass jacketed reactor equipped with a stirrer and condenser and 480 g of CAP A was added under stirring. The reaction was heated to 60° C. and left for 4 hours at that temperature.

When finished, the polymer was allowed to settle and the supernatant was removed. This was followed by addition of 0.5 liters of tetrahydrofuran (THF) and stirring for 30 minutes. The washing process was repeated three times and then four more times using 0.5 liters methanol instead of THF. Upon completion of the final wash, the particles were re-suspended in 0.5 liters of THF and concentrated in vacuo on a rotary evaporator.

Example 4: Simultaneous Synthesis of 10 Different Oligonucleotides on a Microfluidic Chip A microfluidic synthesis chip was assembled in a flowcell and connected to an ABI392 DNA Synthesizer (Applied Biosystems, Thermo Fisher Scientific Inc., Waltham, Mass.) serving as reagent manifold. The glass flow restrictor was replaced by a 10 cm long PEEK™ Tubing, (0.006"×1/16, IDEX Health & Science, Oak Harbor, Wash.) to adjust the maximal flow rate to approx. 900 μL/min. The microfluidic synthesis chip, loaded with 32 μm porous polystyrene beads (60 μmol/g UnyLinker™, 70% porosity, Thermo Fisher Scientific Inc., Waltham, Mass.) prepared according to Examples 1 through 3, was used to simultaneously synthesize 10 different oligonucleotide sequences (Table 16) using methods described herein.

TABLE 16

| Oligo-nucleotide | Sequence | SEQ ID NO: |
|---|---|---|
| OGN1 | 5'-ATGACCATGATTACGCCAAGCTTGGCCGTCGTTTTACAACG-3' | 2 |
| OGN2 | 5'-GGGAAAACCCTGGCGTTACCCAACTTAATCGCCTTGCAGCA-3' | 3 |
| OGN3 | 5'-GCCAGCTGGCGTAATAGCGAAGAGGCCCGCACCGATCG-3' | 4 |
| OGN4 | 5'-GTTGCGCAGCCTGAATGGCGAATGGCGCCTGATGCG-3' | 5 |
| OGN5 | 5'-TTCTCCTTACGCATCTGTGCGGTATTTCACACCGCA-3' | 6 |
| OGN6 | 5'-CGCCAGGGTTTTCCCAGTCACGACGTTGTAAAACGACGGC-3' | 7 |
| OGN7 | 5'-TTACGCCAGCTGGCGAAAGGGGGATGTGCTGCAAGGCGATT-3' | 8 |
| OGN8 | 5'-TCAGGCTGCGCAACTGTTGGGAAGGGCGATCGGTGCGGG-3' | 9 |
| OGN9 | 5'-ACAGATGCGTAAGGAGAAAATACCGCATCAGGCGCC-3' | 10 |
| OGN10 | 5'-ATTGTACTGAGAGTGCACCATATGCGGTGTGAAATACCG-3' | 11 |

The synthesis positions of the microfluidic synthesis chip were divided into 10 areas. The areas were electronically connected using several platinum electrodes on the bottom layer of the microfluidic synthesis chip to connect the 10 areas as individually addressable working electrode bundles. The platinum counter electrode was attached to the lid, covering the upper side of the synthesis chamber.

The relay 1 of the ABI392 DNA Synthesizer was connected to SCB-68A Connector Block (National Instruments Corp., Austin, Tex.). The SCB-68A Connector Block was further connected to the working electrode bundles of the microfluidic synthesis chip. Closing the relay 1 on the ABI392 triggered electrochemical acid generation on the different synthesis positions. The sequence on the different synthesis positions was controlled using LabView (National Instruments Corp., Austin, Tex.). ODN1 was synthesized on area 1 on the microfluidic synthesis chip. ODN2 was synthesized on area 2 on the microfluidic synthesis chip. ODN3 was synthesized on area 3 on the microfluidic synthesis chip. ODN4 was synthesized on area 4 on the microfluidic synthesis chip. ODN5 was synthesized on area 5 on the microfluidic synthesis chip. ODN6 was synthesized on area 6 on the microfluidic synthesis chip. ODN7 was synthesized on area 7 on the microfluidic synthesis chip. ODN8 was synthesized on area 8 on the microfluidic synthesis chip. ODN9 was synthesized on area 9 on the microfluidic synthesis chip, and ODN10 was synthesized on area 10 on the microfluidic synthesis chip.

The synthesis was done using standard chemistry (coupling, capping and oxidation) as described elsewhere herein, except for deblocking, which was achieved by electrochemical generation of acid according to the protocol in Table 17. Following reagents were used for the DNA synthesis: acetonitrile (anhydrous for DNA Synthesis, Fisher Bioreagents), dicyanoimidazole as activator (Sigma Aldrich), DMT-dA(bz)phosphoramidite (Sigma Aldrich), DMT-dG (ib) phosphoramidite (Sigma Aldrich), DMT-dC(bz) phosphoramidite (Sigma Aldrich), DMT-dT phosphoramidite (Sigma Aldrich), CAP A (Sigma Aldrich), CAP B (Sigma Aldrich), oxidizer 0.1 M (Sigma Aldrich). The mixture for electrochemical acid generation together with suitable electrochemical conditions were described previous elsewhere (Maurer K, Cooper J, Caraballo M, Crye, J, Suciu D, et al (2006) Electrochemically Generated Acid and Its Containment to 100 Micron Reaction Areas for the Production of DNA Microarrays. PLoS ONE 1(1): e34. doi:10.1371/journal.pone.0000034).

TABLE 17

| STEP | FUNCTION | TIME (sec.) |
|---|---|---|
| 1) | Begin | |
| 2) | 18 (Acetonitrile) to Waste | 3.0 |
| 3) | 18 (Acetonitrile) to Column | 30.0 |
| 4) | Reverse Flush | 25.0 |
| 5) | Block Flush | 3.0 |
| 6) | Phosporamidite Prep | 3.0 |
| 7) | Column 1 On | |
| 8) | Block Vent | 2.0 |
| 9) | Activator to Waste | 1.7 |
| 10) | Phosporamidite + Activator to Column | 25.0 |
| 11) | Wait | 20.0 |
| 12) | Phosporamidite + Activator to Column | 10.0 |
| 13) | Wait | 20.0 |
| 14) | Phosporamidite + Activator to Column | 10.0 |
| 15) | Column 1 Off | |
| 16) | Column 2 On | |
| 17) | 18 (Acetonitrile) to Waste | 4.0 |
| 18) | Block Flush | 3.0 |
| 19) | Block Vent | 2.0 |
| 20) | Activator to Waste | 1.7 |
| 21) | Phosporamidite + Activator to Column | 25.0 |
| 22) | Wait | 20.0 |
| 23) | Phosporamidite + Activator to Column | 10.0 |
| 24) | Wait | 20.0 |
| 25) | Phosporamidite + Activator to Column | 10.0 |
| 26) | Column 2 Off | |
| 27) | Wait | 25.0 |
| 28) | Cap Prep | 3.0 |
| 29) | 18 (Acetonitrile) to Waste | 4.0 |
| 30) | Reverse Flush | 25.0 |
| 31) | Block Flush | 3.0 |
| 32) | Cap to Column | 25.0 |
| 33) | Wait | 5.0 |
| 34) | Cap to Column | 5.0 |
| 35) | Wait | 5.0 |
| 36) | 18 (Acetonitrile) to Waste | 4.0 |
| 37) | Reverse Flush | 25.0 |
| 38) | Block Flush | 3.0 |
| 39) | 15 (Oxidizer)to Column | 25.0 |
| 40) | Wait | 10.0 |
| 41) | 15 (Oxidizer)to Column | 10.0 |
| 42) | 18 (Acetonitrile) to Waste | 4.0 |
| 43) | Wait | 5.0 |
| 44) | Reverse Flush | 25.0 |
| 45) | Block Flush | 3.0 |
| 46) | 18 (Acetonitrile) to Column | 25.0 |
| 47) | Reverse Flush | 25.0 |
| 48) | Block Flush | 3.0 |
| 49) | 18 (Acetonitrile) to Waste | 4.0 |
| 50) | 18 (Acetonitrile) to Column | 25.0 |
| 51) | Reverse Flush | 25.0 |
| 52) | Block Flush | 3.0 |
| 53) | Start Detrityl | |
| 54) | 18 (Acetonitrile) to Waste | 4.0 |
| 55) | 18 (Acetonitrile) to Column | 25.0 |
| 56) | Reverse Flush | 25.0 |
| 57) | Block Flush | 3.0 |
| 58) | 14 (EGA Buffer) to Column | 25.0 |
| 59) | Relay 1 On | |
| 60) | 14 (EGA Buffer)to Column | 3.0 |
| 61) | Relay 1 Off | |
| 62) | 14 (EGA Buffer)to Column | 90.0 |
| 63) | Reverse Flush | 25.0 |
| 64) | Block Flush 1 | 3.0 |
| 65) | 18 (Acetonitrile) to Column | 25.0 |
| 66) | Waste - Bottle | |
| 67) | Reverse Flush | 25.0 |
| 68) | Block Flush | 4.0 |
| 69) | 18 (Acetonitrile) to Column | 25.0 |
| 70) | End | |

After oligonucleotide synthesis the microfluidic chip was flushed with electrolyte solution (0.7 M Tetraethylammonium p-toluenesulfonate, 50% water, 30% methanol, 20% acetonitrile). The beads corresponding to one oligonucleotide sequence where pooled by applying 7.5 V to the related synthesis positions using the electrodes under the beads as anodes. This allows electrochemical production of gas bubbles under the beads of a specific oligonucleotide sequence. Those gas bubbles lifted the beads of one specific oligonucleotide sequence out of a synthesis position. Those beads were flushed out of the microfluidic chip and collected in a filter. This procedure was repeated until the beads with ODN1 to ODN10 were collected in 10 different filters. The oligonucleotides were cleaved using gaseous ammonia (2 bar, 2 h), eluted in water (see FIG. 22) and analyzed using rpHPLC.

Example 5: Synthesis of 40-mer Test Oligonucleotide

A 40-mer test oligonucleotide was synthesized using an exemplary synthesis chip. 35 µm beads preloaded with dG (80 µmol/g) were used in the synthesis chip having 55 µm deep wells with a diameter of 38 µm (SU8) and Pt electrodes on the bottom of the wells. EGA was generated in the wells of the synthesis chip using 1M hydroquinone, 0.01M benzoquinone, and 0.25M tetraethylammonium p-toluenesulfonate in a mixture of 80% acetonitrile and 20% methanol. To generate the acid, 6.5 V with a current limit of 0.3 µA were applied for 3 seconds to the desired wells. The EGA was used to remove the DMT protecting group before the next amidite was added to the growing nucleic acid molecule attached to the bead. This process was repeated until the desired 40-mer oligonucleotide had been synthesized on the bead.

Figure 34:
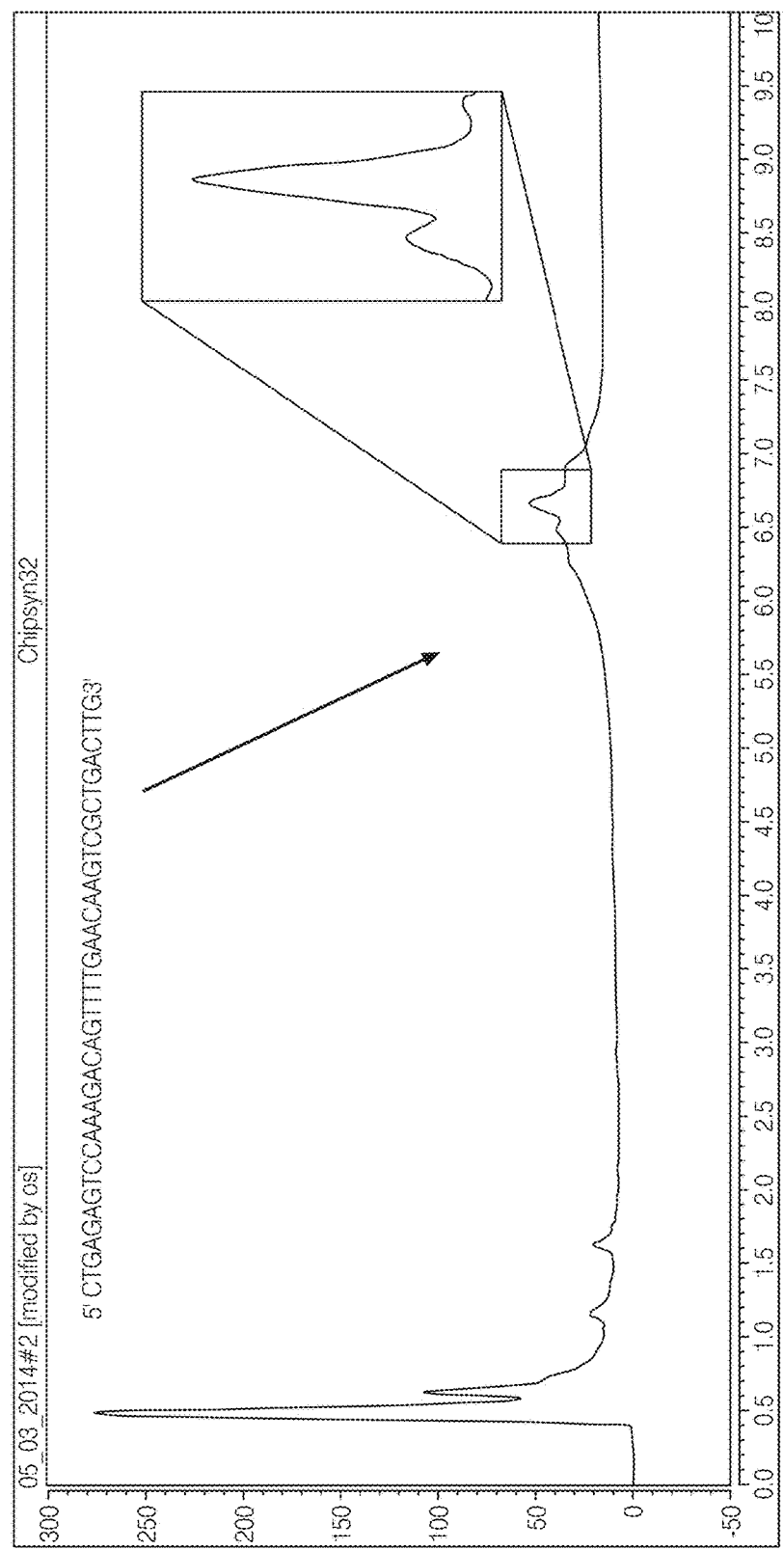
FIG. 34 shows a chromatogram of a 40-mer test oligonucleotide synthesized according to the invention (SEQ ID NO: 24).

Next, the oligonucleotide was cleaved and deprotected in the synthesis chip using a 1:1 mixture of methylamine in water and ammonia in water. The oligonucleotide was dried in vacuum, dissolved in water and injected on a reverse phase HPLC without further purification. The buffers for HPLC were 0.1M n-hexylammonium acetate with 10% (vol) acetonitrile and 0.1M n-hexylammonium acetate with 50% (vol.) acetonitrile. The HPLC column was packed with polystyrene. A chromatogram of the 40-mer test oligonucleotide synthesized on the microchip using EGA is shown in FIG. 34. The x axis shows the retention time in minutes and the y axis shows the intensity of the UV signal at 260 nm in mAU.

Example 6: Selective Removal of Beads from Synthesis Chip Using Electrolysis

Figures 33A, 33B, 33C:
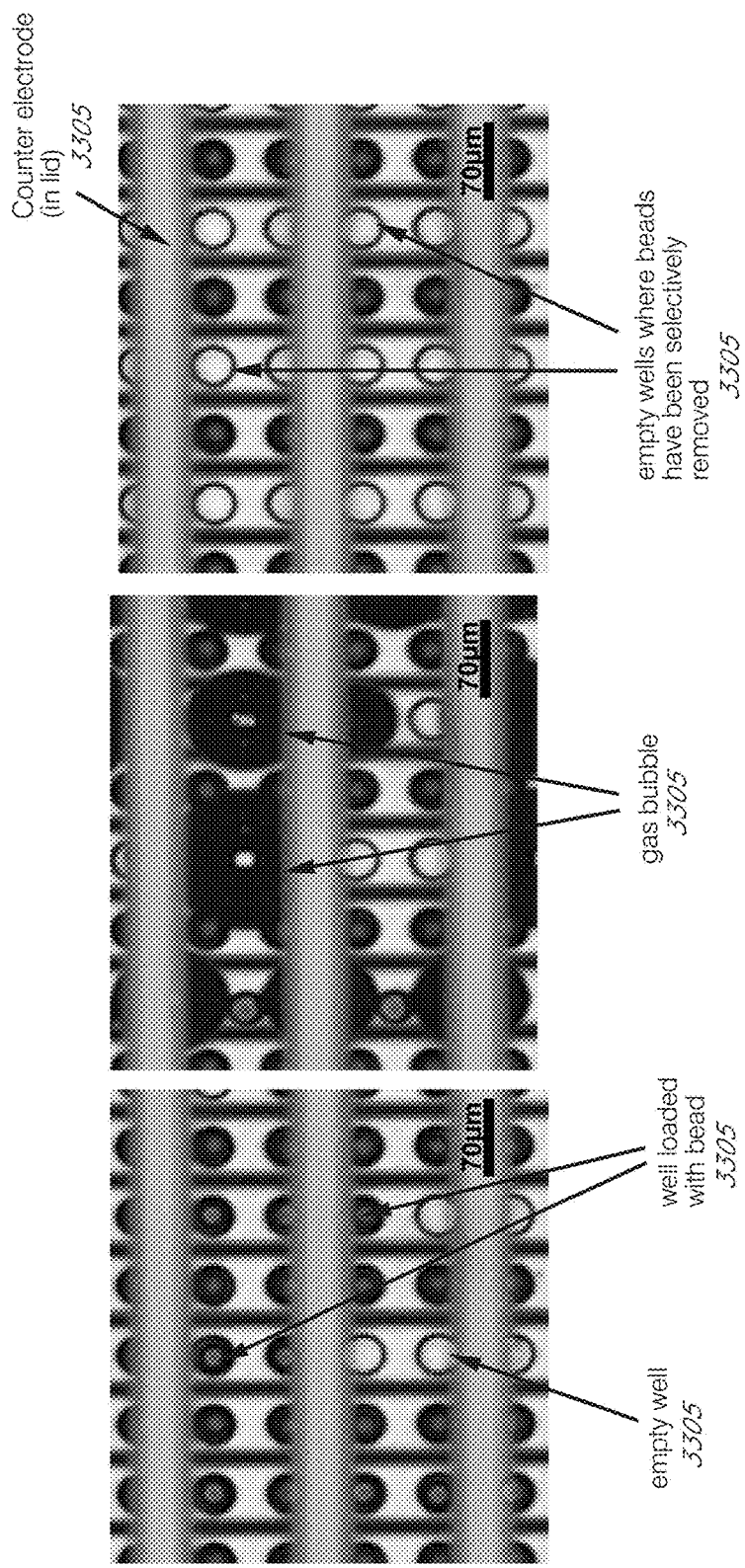
FIGS. 33A, 33B, and 33C shows an example time series of images depicting the selective removal of beads from a multiwell synthesis chip using electro-generated gas according to the invention.

Beads were selectively removed from an exemplary, multiwell, synthetic microchip using gas bubbles generated by electrolysis. FIGS. 33A, 33B and 33C show a time series of images depicting the bead removal process according to an exemplary embodiment of the present invention. As shown in FIG. 33A, 35 μm polystyrene beads were loaded in 55 μm deep wells made from SU8 resist, as denoted at 3310, with some wells left empty (i.e., no beads), as denoted at 3305. Although not shown in FIG. 33A, but illustrated and described in relation to FIGS. 18, and 24A, 24B and 24C, an electrode was located at the bottom of each well. As shown in FIG. 33C, a counter electrode 3325 in the lid was used in conjunction with the electrode at the bottom of each well to produce the electrical potential to cause electrolysis of the solvent and generate the gas bubble(s), as discussed herein. As shown in FIG. 33B, applying a voltage in selected wells caused electrolysis of the solvent (e.g., acetonitrile, hydroquinone, benzoquinone and tetraethylammonium p-toluenesulfonate) in the selected wells, which in turn produced a gas bubble 3315 that expanded in milliseconds and lifted the bead to the top of the well, where the fluid flow transported the bead away from the well. Thus, this example demonstrates the selective removal of beads from the wells of a synthetic microchip using electrolysis of a solvent. After applying a washing step, the well can be reused. In cases where the bead is not removed in the first gas generation pulse, more gas generation cycles could follow.

Example 7: Selective Removal of Beads from Synthesis Chip Using Electrolysis

Figure 44:
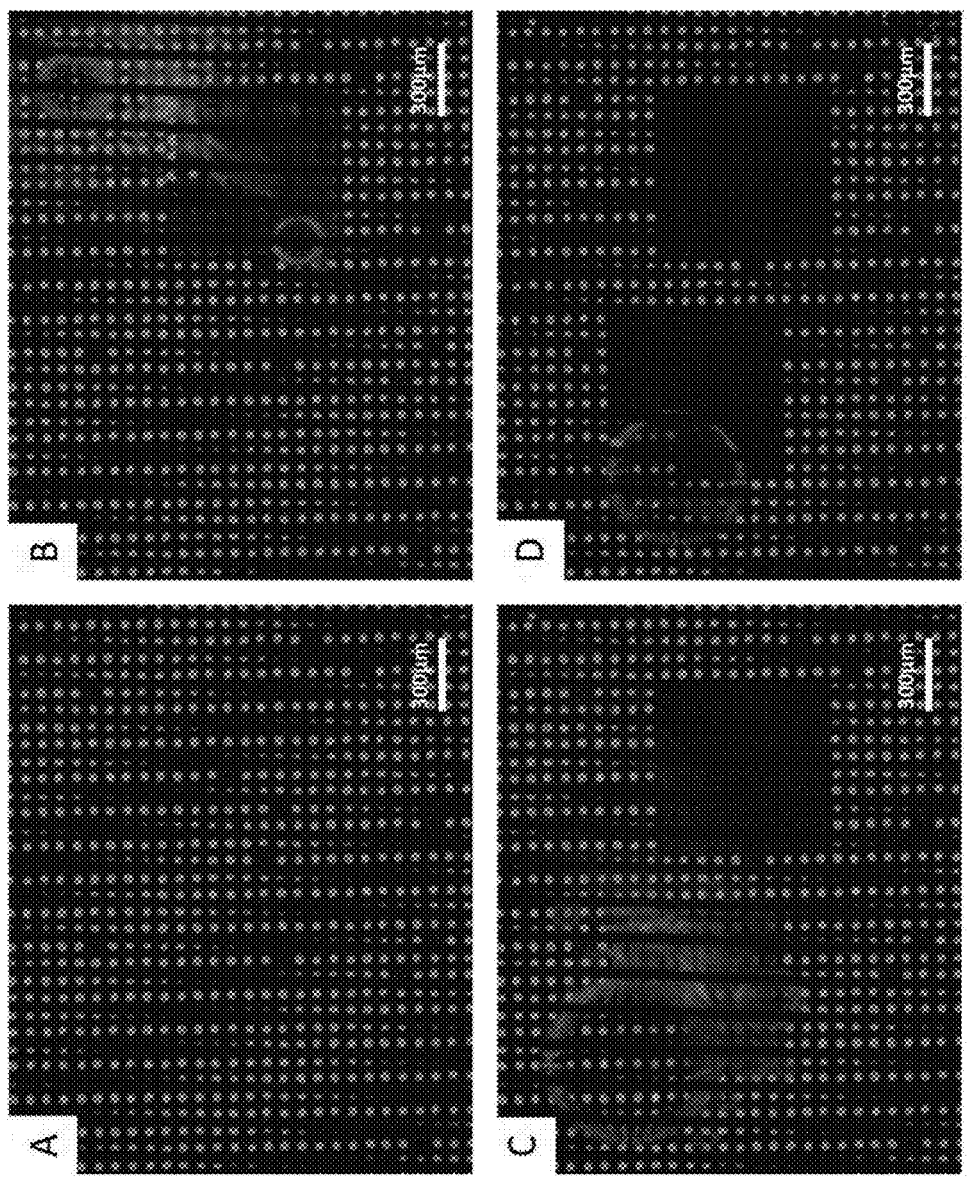
FIG. 44 (Panels A, B, C and D) show the selective removal of beads from a microfluidic synthesis chip using electrolysis as described in Example 6.

Beads produced as described in Examples 1 to 4 were loaded with oligonucleotides comprising a fluorescently labeled base and were filled into the wells of a microfluidic chip, so that ~99% of all wells were occupied (FIG. 44, Panel A). (Not all of the wells are visible in the microscopic images of FIG. 44, Panels A through D, due to the counter electrode present in the fluidic lid (stripes of platinum)). A solution suitable for electrolysis (0.7 M tetraethylammonium p-toluenesulfonate (TEAPTS), 50% $H_2O$, 30% MeOH, 20% acetonitrile (ACN)) was then flushed through the chip, at a flow rate of 500 μl/min and a voltage of 8.5 V was applied to a subset of 100 electrodes (10 by 10) for 5 sec. The applied voltage led to electrolysis within the selected wells (FIG. 44B), which removed the beads from the wells. Beads were flushed out of the chip at a flow rate of 500 μl/min. The process was then repeated for another subset of electrodes using the same parameters (FIGS. 44C and 44D). The process illustrated by FIGS. 44A through 44D takes less than 30 seconds. This example demonstrates that beads can be efficiently removed from pre-selected wells by inducing electrolysis at the respective electrodes using methods described herein.

Example 8: Collection of Beads Using a Mesh Puncture Collection Device

A synthesis microchip with 25,000 wells was filled with differently labeled beads that were associated with different electrodes (e.g., Cy3-labeled beads were loaded into wells of electrode 1, Cy5-labeled beads were loaded into wells of electrode 2, etc.). In this example, 2,500 wells were connected as bundles to one working electrode. The outlet of the synthesis microchip was connected to a needle and the inlet of the synthesis chip was connected to a switching valve, which was connected to the lifting buffer (comprising (i) a volatile compound selected from the group consisting of ammonium bicarbonate, formiate, acetate, substituted ammonium salt such as, e.g., triethylammonium acetate and (ii) a solvent such as water, acetonitrile, tetrahydrofuran (THF) or alcohol) and acetonitrile for washing.

The synthesis microchip and the needle were placed on a movable z-stage, while a multiwell collection plate assembly was on a plate that was movable in x-y direction. The multiwell collection plate assembly included an unmodified 1536 cyclic olefin copolymer (COC) plate, a fluid-permeable micromesh made from PEEK (Polyetheretherketone), and a modified 1536 COC plate where the bottom of the wells was removed. The modified plate was used to clamp the mesh on top of the unmodified plate. To begin transferring the beads to the multiwell collection plate assembly, the needle was punched through the micromesh layer into the first well of the bottom plate (unmodified). The lifting solvent was flushed through the chip and the needle, and electrode 1 (Cy3-labeled beads) was activated to remove beads by electrolysis from the selected wells. After 3 pulses, the valve was switched and acetonitrile was flushed to wash the chip and the first well of the multiwell collection plate assembly. The flow was then stopped, the needle was moved to the second well of the multiwell collection plate assembly and the process was repeated for electrode 2 (Cy5-labeled beads). This was repeated for several electrodes, while always alternating the beads. After selectively transferring the beads, the multiwell collection plate assembly was centrifuged, dried, disassembled and investigated under a fluorescent microscope. Little to no cross contamination could be seen for most wells of the bottom plate (unmodified) of the multiwell collection plate assembly, while almost all beads were transferred from the chip to the wells of the multiwell collection plate assembly (i.e., no beads were lost in needle or tubing).

Example 9: Error Correction Process

Sequences of interest are divided into subfragments of up to 1.2 kbp in length (Line 1 in FIG. 36) having 30 bp homologous regions to adjacent vector or subfragments, respectively. Subfragment sequences again are split up into shorter oligonucleotides. Subfragments are assembled from oligonucleotides using PCR. These linear DNA fragments or any other PCR products are purified using a size exclusion purification method (AcroPrep™ Advance Filter Plate with Omega 30K MWCO from PALL Life Sciences).

For error correction of one fragment (Line 2 in FIG. 36), 10-30 ng of purified PCR product contained in 10 mM Tris-Cl, is denatured and reannealed in order to form heteroduplexes (98° C. for 2 min; 4° C. for 5 min; 37° C. for 5 min; followed by 4° C.). In the case of longer fragments (e.g., fragments greater than 1.1 kbp in length), subfragments (15-45 ng of each subfragment) are pooled, denatured and reannealed as described before. T7 endonuclease I (40 U) and Taq Ligase (1 U) are added and errors are corrected (45° C. for 20 min). Nucleic acid present in the digestion mixture are amplified (98° C. for 2 min; 15 cycles including the following three incubation steps: 98° C. for 20 sec; 65° C.-57.5° C. for 30 sec; 72° C. for 90 sec; 25° C.) and terminal primers are added to select and amplify full-length fragments (Line 3 in FIG. 36) (98° C. for 20 sec; 58° C. for 30 sec; 72° C. for 90 sec (20 cycles of the preceding three steps); 72° C. for 5 min; 4° C.).

To further improve the correctness of fragments, a second round of error correction is carried out (Line 4 in FIG. 36). In brief, PCR products (referred to in FIG. 36 as $3^{rd}$ PCR) from the first error correction round are purified from solution again using size exclusion purification method as set out above. 50-120 ng of purified PCR products in 10 mM Tris-Cl are used to generate heteroduplexes (98° C. for 2 min; 4° C. for 5 min; 37° C. for 5 min; 4° C.), enzymes are added (40 U T7 endonuclease I and 1 U Taq Ligase) and incubated for 20 min at 45° C.

To generate full-length fragments (Line 5 in FIG. 36), another round of amplification is done (95° C. for 4 min; 95° C. for 30 sec; 70-43° C.* for 30 sec (*touchdown −0.9° C. per cycle); 72° C. for 6 min (30 cycles last three steps); 4° C.). In the case of direct assembly with a vector, a linearized plasmid containing 29 bp homologous regions to terminal ends of the fragment is added in a PCR amplification step. Afterwards, screening for full-length fragments is either carried out via (i) size check on agarose gel (for linear fragments) or (ii) colony PCRs (for cloned fragments) (Line 7 in FIG. 36). Finally, full-length fragments are further analyzed via Sanger and next generation sequencing in order to verify sequence correctness (Line 9 in FIG. 36).

Oligonucleotides used for fragment assembly have a specific inherent rate of errors, namely insertions, deletions and substitutions. In the case of substitutions, transitions and transversions were distinguished. In a study sequencing a total of 9 million base pairs of untreated oligonucleotides produced on oligonucleotide synthesizers using standard phosphoramidite chemistry, an average frequency of an error per position (error rate) of 692 ppm (1 error in 1445 bp) was determined.

The most common error type found was single-nucleotide deletions, with equal frequency of A-, C-, G- and T-positions (see FIG. 37). The next most common error type found was single-nucleotide insertions. The least common error type found was single-nucleotide substitutions. After two rounds of error correction using T7 endonuclease I, as described above, an average total error rate of 66 ppm (1 error in 15,132 bp, 35 million base pairs from 9 fragments were analyzed) was achieved, including all types of errors. 92% of remaining errors were substitutions and only 8% were insertions or deletions.

Regarding the specific error types, mainly transitions were found (62%), more precisely primarily G and C, with less common A and T, transitions found.

This could be explained by deamination of G into Xanthine, which pairs with T, ultimately leading to a G-C→A-T transition. In addition, 30% of errors found were transversions, mainly affecting positions that are normally occupied Cs and Gs. Residual errors are deletions (5%) and insertions (3%). Taken together, deletions and insertions are recognized and eliminated by T7 endonuclease I quite well, leaving substitutions as the dominant remaining error type after two rounds of error correction, with 74% of all substitutions affect G/C-positions.

Further, the ratio of transitions:transversions is about 2:1 in error corrected nucleic acid molecules prepared as set out above (FIG. 38). This distribution is typical of substitutions introduced by PCR. Oligonucleotides not subjected to error correction typically have a statistical ratio of transitions: transversions being about 1:2. Further, deletions and insertions are almost completely eliminated by the above error correction protocol and A and C transitions actually increase after two rounds of error correction (see FIG. 38). Based upon this, it can be concluded that it is unlikely that T7 endonuclease I specifically misses these G/C substitutions during error correction but they are rather introduced by the PCR step following T7 endonuclease I treatment.

Example 10: Assembly of a lacZ Gene Using Chip-Synthesized Oligonucleotides

Oligonucleotides OGN1-OGN10 simultaneously synthesized on the microfluidic synthesis chip as described in Example 4 and containing complementary terminal overlaps to allow PCR-based assembly as illustrated in FIG. 4, were used to construct a 251-bp lacZ gene. The concentration of all oligonucleotides was determined using a 96-well plate reader (Tecan Group Ltd., Maennedorf, Switzerland) and each oligonucleotide was used at an average concentration of 0.15 µM in the oligonucleotide assembly reaction.

Oligonucleotide assembly was performed in a reaction volume of 1.23 µl (PCR master mix: 0.2 mM dNTPs (Thermo Fisher Scientific Inc., Waltham, Mass.), 1 unit of TRUESCRIPT™ polymerase (PAN Biotech, Aidenbach, Germany), 60 mM Tris-HCl, 6 mM $(NH_4)_2SO_4$, 10 mM KCl, and 2 mM $MgSO_4$) in a 384-well plate (MICROAMP® ENDURAPLATE™ Optical 384-Well, Thermo Fisher Scientific Inc., Waltham, Mass.) using a PROFLEX™ Thermal Cycler (Thermo Fisher Scientific Inc., Waltham, Mass.) using cycling conditions according to Table 18.

TABLE 18

| Oligonucleotide assembly PCR | | |
|---|---|---|
| 95° C. | 4 min | |
| 95° C. | 30 sec | |
| 60° C.* | 30 sec | 30x |
| 72° C. | 1 min | |
| 72° C. | 4 min | |
| 4° C. | ∞ | |

*touch down −0.8° C./cycle

The oligonucleotide assembly PCR was followed by a second PCR reaction conducted in the presence of terminal primers to amplify the assembled full-length gene. This amplification reaction was conducted in a reaction volume of 10 µl in the same well of the 384-well plate by adding TRUESCRIPT™ PCR master mix and 0.8 µM forward (5'-ATGACCATGATTACGCCAAGCTTGG-3' (SEQ ID NO: 1)) and reverse (5'-ATTGTACTGAGAGTGCAC-CATATGC-3' (SEQ ID NO: 13)) primers using cycling conditions as specified in Table 19.

TABLE 19

| Amplification PCR with terminal primers | |
|---|---|
| 98° C. | 30 sec |
| 98° C. | 30 sec |

TABLE 19-continued

Amplification PCR with terminal primers

| 58° C. | 30 sec | 30 x |
|---|---|---|
| 72° C. | 1 min | |
| 72° C. | 4 min | |
| 4° C. | ∞ | |

After the second PCR, the complete reaction mixture was transferred to a 384-well LDV Labcyte plate (Labcyte Inc., Sunnyvale, Calif.). From this plate 0.0396 µl PCR product were transferred into a new 384-well ENDURAPLATE™ by using the Labcyte ECHO® 555 (Labcyte Inc., Sunnyvale, Calif.) and 0.132 units of Exonuclease I (Thermo Fisher Scientific Inc., Waltham, Mass.) were added and incubated at 37° C. for 15 minutes to remove excess primers and any extraneous single-stranded DNA from the PCR product that may interfere with downstream reactions.

Following Exonuclease I treatment, the purified DNA fragments were denatured and re-hybridized according to the conditions indicated in Table 20 to inactivate Exonuclease I and allow the formation of mismatches at sites of sequence error for subsequent error correction.

TABLE 20

Exonuclease treatment and Denaturation-rehybridization reaction

| 37° C. | 15 min |
|---|---|
| 98° C. | 10 min |
| 4° C. | 5 min |
| 37° C. | 5 min |
| 4° C. | ∞ |

The denaturated-rehybridized DNA was then mixed with Ampligase Puffer, 0.04 µl (0.4 units) T7 Endonuclease I (NEB) and 0.04 µl (1.6 units) Taq ligase (NEB) in a volume of 0.4 µl and the mixture was incubated at 45° C. for 20 minutes for error correction.

After error correction a fusion PCR reaction (3rd PCR; FIG. 36 or 42) was performed in the same 384-well by adding the PCR master mix to the error correction mix. The fusion PCR mix contained: 0.16 units PHUSION® polymerase (Thermo Fisher Scientific Inc., Waltham, Mass.), 200 µM dNTPs, 0.25 µM forward and reverse primer, 25 mM TAPS-HCl (pH 9.3 at 25° C.), 50 mM KCl, 2 mM MgCl$_2$, 1 mM β-mercaptoethanol. The reaction was cycled according to the protocol indicated in Table 21.

TABLE 21 fragment fusion PCR

| 98° C. | 4 min | |
|---|---|---|
| 98° C. | 30 sec | |
| 65° C. | 30 sec | 15 x |
| 72° C. | 90 sec | |
| 25° C. | pause | add forward and reverse primers |
| 4° C. | ∞ | |
| 98° C. | 30 sec | |
| 58° C. | 30 sec | 20 x |
| 72° C. | 90 sec | |
| 72° C. | 5 min | |
| 4° C. | ∞ | |

* touch down −0.5° C./cycle

Successful assembly of a functional lacZ gene was demonstrated by blue white screening. For this purpose, the assembled genes were cloned into Hind/III/NdeI-cut pUC19 vector via seamless cloning and transformed into E. coli.

Figure 48A:
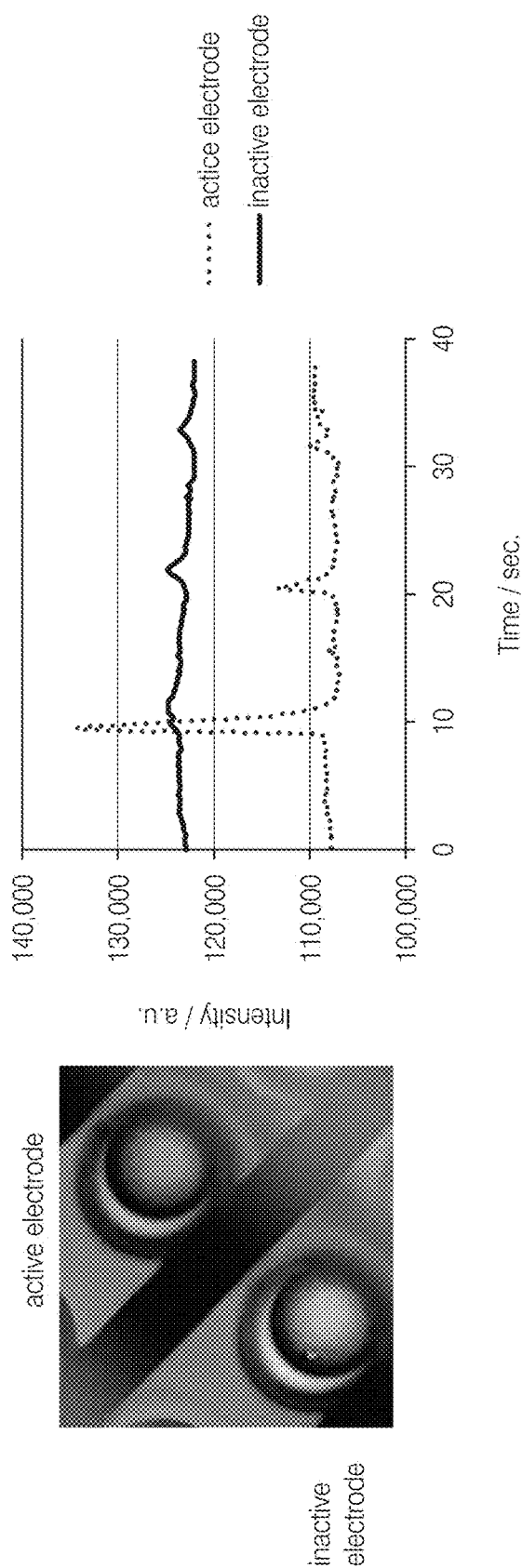
FIGS. 48A and 48B show examples of how base-coated scavenger beads can be used to protect synthesis positions in the vicinity of a reaction side with acidic conditions. A 32-μm porous synthesis support was loaded into each well. The experiment of FIG. 48A was performed in the absence of scavenger beads, whereas the experiment of FIG. 48B was performed in the presence of smaller scavenger beads filled into each well.

Example 11: Protection of Inactive Synthesis Sites from Proton Contamination Using Base-Coated Scavenger Beads 40-µm wells of a microfluidic chip having platinum electrodes at the bottom of the wells were loaded with 32-µm porous polystryrene beads ("synthesis support"; dG S80, GE Healthcare). Protons to remove the temporary DMT protecting group on the nucleic acid molecules were generated via an electrochemical reaction using the conditions as set forth in Example 5. In a first setting, a first electrode was activated three times with a delay of 10 seconds to produce electrochemical acid in the respective well (FIG. 48A). The synthesis well turned red, since released DMT-cation has a strong red color. However, in this setting the adjacent well having an inactive electrode turned slightly red as well, since no proton scavenger was present that could prevent the generated protons from diffusing to neighboring wells. The change in color intensity over time as measured in one active and one inactive synthesis well (illustrated by the microscopic picture on the left), is represented by the plot on the right.

Figure 48B:
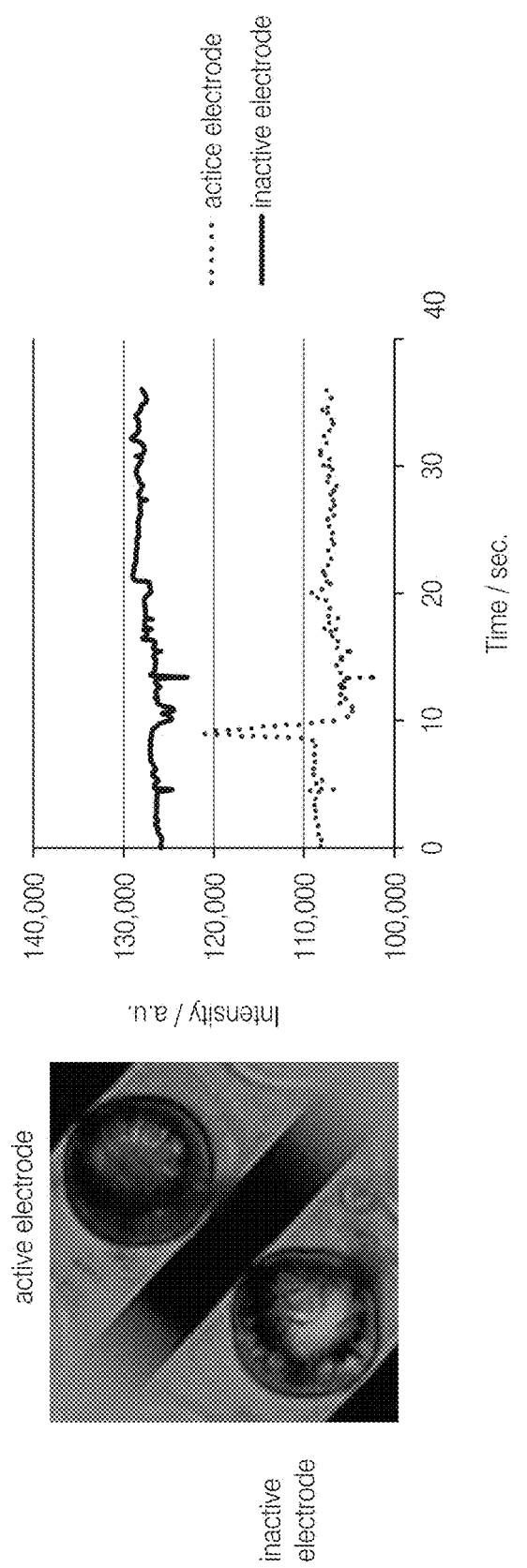

In a second setting, the synthesis wells each containing a synthesis support were filled with smaller beads coated with basic amine groups (7 µm, NUCLEOGEN 60-7 DEAE, Macherey Nagel) (as reflected by the irregular well structure of the microscopic image of FIG. 48B and the background noise of the respective plot curves). The electrode was activated three times with a delay of 10 seconds. As in the previous experiment, the well with the active electrode turned red indicating that the presence of the scavenger beads did not prevent efficient removal of the DMT protective groups. However, in contrast to the first setting, the well with the inactive electrode showed no change in color as reflected by the plot on the right. This clearly demonstrates that the used solid proton scavenger beads are capable of protecting neighboring inactive sites from proton contamination without compromising the efficiency of deprotection at the active site.

Example 12A: Gene Fragment Assembly Workflow in 384-Well Plate Format Comprising Alternating Steps of Liquid Handling and PCR Cycling This example describes a microscale workflow for the assembly of an error-corrected gene fragment from oligonucleotides using one type of multiwell plate for alternating steps of liquid handling and thermal incubation. For subfragment assembly PCR (first PCR), 1 µl of a PCR master mix comprising PCR buffer, dNTPs and polymerase were predispensed into wells of a 384-well plate (MICROAMP® ENDURAPLATE™ Optical 384-Well; Thermo Fisher Scientific, Waltham, Mass.) using a Nano Dispenser (MULTIDROP™ Combi nL Reagent Dispenser, Thermo Scientific, Waltham, Mass.). 0.25 µl of a mixture of pooled oligonucleotides synthesized on a chip (comprising overlapping complementary ends and together representing a gene subfragment) were added to the 384-well plate using a Labcyte ECHO® 555 Liquid Handler (Labcyte Inc., Sunnyvale, Calif.). The 384-well plate was then placed into a ProFlex™ PCR cycler (Thermo Fisher Scientific, Waltham Mass.) and the reaction mixture was cycled. For amplification PCR (second PCR), the first PCR product was supplemented with 1.75 µl of a mixture comprising forward and reverse primers using ECHO® 555 and 7 µl of a PCR master mix comprising buffer, dNTPs and polymerase using the Nano Dispenser. The 384-well plate was then placed into the PROFLEX™ cycler and the subfragments were amplified in the presence of the terminal primers. 10 µl of the second PCR product was then transferred to a 384-well LDV Labcyte plate (Labcyte Inc., Sunnyvale, Calif.) using a TECAN Liquid Handler (Tecan Group Ltd., Maennedorf, Switzerland).

For a first purification step, 0.04 µl of the second PCR product and 0.1 µl of Exonuclease I (Thermo Fisher Scientific Inc., Waltham, Mass.) were transferred into a further 384-well microamp Endura plate using the ECHO® 555 and the mixture was incubated in the PROFLEX™ 384-well cycler to remove residual primers and allow melting and reannealing of the subfragments. 0.2 µl of an error correction enzyme mixture comprising ampligase buffer, T7NI and Taq Ligase were then added to the re-annealed subfragments using ECHO® 555 and further incubated in the PROFLEX™ cycler to remove mismatches in a first error correction step. 9.1 µl of a PCR master mix was then added to the first error correction product using the Nano dispenser, and 0.5 µl of a mixture comprising forward and reverse primers were added to the 384 well plate using ECHO® 555. A fusion PCR (third PCR) was then conducted in the PROFLEX™ cycler to assemble the error-corrected subfragments into full-length fragments.

For a second purification step, 10 µl of the third PCR product was transferred to a 384-well LDV Labcyte plate using the Tecan Liquid Handler. 0.8 µl of the third PCR product and 0.35 µl of Exonuclease I were then transferred to a 96-well plate (SuperPlate PCR Plate, 96-well, Thermo Fisher Scientific, Waltham, Mass.) using ECHO® 555 and the mixture was incubated in an Eppendorf PCR Cycler (Mastercycler Pro S, Eppendorf AG, Hamburg, Germany) to remove residual primers and allow melting and re-annealing of the subfragments. The purified re-annealed fragments were then supplemented with 1 µl of error correction mix comprising ampligase buffer, T7NI and Taq Ligase using the ECHO® 555, and the reaction mixture was further incubated in the Eppendorf PCR cycler to remove mismatches in a second error correction step. 45.5 µl of a of a PHUSION® PCR master mix (New England Biolabs, Ipswich, Mass.) was then added to the 96-well plate using the Nano dispenser and the reaction mixture was transferred to the Eppendorf PCR cycler to conduct a further fusion PCR (fourth PCR) to amplify the full-length fragments in the presence of terminal primers. Alternatively, were assembled fragments have sizes of up to 1 kb or about 1 kb, the fourth PCR may be performed in the presence of a linearized target vector to allow for direct insertion of the fragments into the target vector via overlapping complementary ends in a fusion PCR reaction. The resulting vector containing the inserted fragment may then be transformed into competent *E. coli*.

Example 12B: Gene Subfragment Assembly Workflow in 1536-Well Plate Format Comprising Alternating Steps of Liquid Handling and PCR Cycling This example describes a microscale workflow for the assembly of an error-corrected gene fragment from oligonucleotides using one type of multiwell plate for alternating steps of liquid handling and thermal incubation. For subfragment assembly PCR (first PCR), 2 µl of a PCR master mix comprising PCR buffer, dNTPs and polymerase were predispensed into wells of a 1536 flatbottom well (1536 LDV plate, Labcyte Inc., Sunnyvale, Calif.) plate using a Nano dispenser (MULTIDROP™ Combi nL Reagent Dispenser, Thermo Scientific, Waltham, Mass.). 0.5 µl of a mixture of pooled oligonucleotides synthesized on a chip (comprising overlapping complementary ends and together representing a gene subfragment) were added to the 1536-well plate using a Labcyte ECHO® 555 Liquid Handler (Labcyte Inc., Sunnyvale, Calif.). The 1536-well plate was then placed into a PROFLEX™ PCR cycler (Thermo Fisher Scientific, Waltham Mass.) comprising a flatbottom thermal block and the reaction mixture was cycled for 3 hours. For amplification PCR (second PCR), 0.4 µl of the first PCR product and 0.5 µl of a mixture comprising forward and reverse primers were transferred into a further 1536-well plate using Labcyte ECHO® 555 and 2 µl of a PCR master mix comprising buffer, dNTPs and polymerase were added to the 1536-well plate using the Nano dispenser. The 1536-well plate was then placed into the PROFLEX™ cycler and the subfragments were amplified in the presence of the terminal primers.

For a first purification step, 0.25 µl of the second PCR product and 0.6 µl of Exonuclease I (Thermo Fisher Scientific Inc., Waltham, Mass.) were transferred into a further 1536-well plate using the Labcyte ECHO® 555 and the mixture was incubated in the PROFLEX™ cycler to remove residual primers. The purified subfragments were then supplemented with 0.25 µl of ampligase buffer and incubated in the PROFLEX™ cycler to allow melting and reannealing of the subfragments before 1.5 µl of an error correction enzyme mixture comprising T7NI and Taq Ligase was added to the re-annealed subfragments using ECHO® 555 and further incubated in the PROFLEX™ cycler for removal of mismatches in a first error correction step. 2.75 µl of a PCR master mix was predispensed into a further 1536-well plate using the Nano dispenser, and 0.15 µl of the first error correction product and 0.15 µl of a mixture comprising forward and reverse primers were added to the 1536-well plate using ECHO® 555. A fusion PCR (third PCR) was then conducted in the PROFLEX™ cycler to amplify error-corrected full-length subfragments.

For a second purification step, 0.4 µl of the third PCR product and 1.1 µl of Exonuclease I were transferred into a further 1536-well plate using ECHO® 555 and the mixture was incubated in the PROFLEX™ cycler to remove residual primers. The purified subfragments were then supplemented with 0.45 µl of ampligase buffer and incubated in the PROFLEX™ cycler to allow melting and reannealing of the subfragments before 1.8 µl of error correction enzyme mixture was added to the re-annealed subfragments using ECHO® 555 and further incubated in the PROFLEX™ cycler for removal of mismatches in a second error correction step. 2.5 µl of the second error correction product was then transferred to a 96-well plate (SuperPlate PCR Plate, 96-well, Thermo Fisher Scientific, Waltham, Mass.) using ECHO® 555 and 45 µl of a PHUSION® PCR master mix (New England Biolabs, Ipswich, Mass.) was added using the Nano dispenser. After 15 cycles 2.5 µl of a mixture of forward and reverse primers for fusion PCR mix were added. Finally, the 96-well plate was transferred to an Eppendorf PCR Cycler (MASTERCYCLER™ Pro S, Eppendorf AG, Hamburg, Germany) to conduct a further fusion PCR (fourth PCR) to re-assemble and amplify the full-length subfragments.

All publications, patents and patent applications mentioned in this Specification are indicative of the level of skill of those of ordinary skill in the art and are herein incorporated by reference to the same extent as if each individual publication, patent, or patent applications was specifically and individually indicated to be incorporated by reference.

The invention being thus described, one skilled in the art would recognize that the invention may be varied in many ways. Such variations are not to be regarded as a departure from the spirit and scope of the invention, and all such modifications as would be obvious to one of ordinary skill in the art are intended to be included within the scope of the following claims.

The invention is further represented by the following clauses:

1. A method for removing a bead from a fluid-filled well of a microchip for synthesizing nucleic acid molecules, wherein a nucleic acid molecule is attached to the bead, the method comprising: providing a voltage between a first electrode that is arranged at a bottom of the fluid-filled well and a second electrode, wherein the voltage is sufficient to cause fluid in the fluid-filled well to undergo electrolysis producing one or more bubbles in the fluid to rise to a top of the fluid-filled well along with the bead.

2. The method according to clause 1, further comprising collecting the bead that has risen to the top of the fluid-filled well with a bead-collection device.

3. The method according to clause 1 or 2, further comprising transferring the bead that was collected to a well of a first multiwell collection plate.

4. The method according to any of clauses 1-3, wherein the fluid comprises an aqueous or a non-aqueous buffer solution.

5. The method according to any of clauses 1-4, wherein the fluid comprises water, NaCl dissolved in water, methanol, acetonitrile, hydroquinone, benzoquinone, and Net4pTsO.

6. The method according to any of clauses 1-5, wherein the first electrode is composed of platinum and the voltage is about 0.1 to about 100 volts.

7. The method according to any of clauses 1-6, wherein the second electrode is arranged above the first electrode.

8. The method according to any of clauses 1-7, wherein the microchip comprises a lid operable to be formed on a top surface of the microchip and operable to provide a fluid flow path over the well.

9. The method according to any of clauses 1-8, wherein the second electrode is formed in the lid.

10. The method according to any of clauses 1-9, wherein each well of the microchip and is individually addressable by a controller.

11. The method according to any of clauses 1-10, wherein the microchip is a complementation metal-oxide-semiconductor ("CMOS") chip.

12. The method according to any of clauses 1-11, wherein the bead is composed of: a synthetic polymer, a modified naturally occurring polymer, glass, controlled pore glass, magnetic controlled pore glass, magnetic beads, ceramics, or one or more metals.

13. The method according to any of clauses 1-12, further comprising collecting the bead that has risen to the top of the fluid-filled well with a bead-collection device, wherein the bead collection device is in fluid communication with the fluid flow path and comprises a first channel to allow for the bead to move a first direction and a second channel to allow for fluid to move in a second direction different than the first direction.

14. The method according to any of clauses 2-13, wherein the bead collection device comprises an acoustic module that is controllable by a controller to facilitate movement of the bead in the first channel, the fluid in the second channel, or both.

15. The method according to any of clauses 2-14, wherein the first multiwell collection plate comprises a plurality of well structures and a fluid-permeable structure formed on a top surface of or within the plurality of well structures.

16. The method according to any of clauses 3-15, wherein the first multiwell collection plate comprises a plurality of well structures and further comprising a second multiwell collection plate, wherein the second multiwell collection plate comprises a plurality of well structures and a fluid-permeable structure formed on a bottom surface of the plurality of well structures, wherein the second multiwell collection plate is placed on top of the first multiwell collection plate such that the plurality of well structures in the second multiwell collection plate are aligned with the plurality of well structures in the first multiwell collection plate.

17. The method according to any of clauses 2-16, wherein the bead collection device comprises a needle structure that is operable to 1) place the bead from the nucleic acid molecule synthesis microchip into a well of the first multiwell collection plate by puncturing the fluid-permeable structure, and/or 2) remove fluid from the well of the first multiwell collection plate in which the bead was placed.

18. The method of clause 17, wherein the needle structure comprises a first lumen that is operable to place the bead from the nucleic acid molecule synthesis microchip into a well of the first multiwell collection plate by puncturing the fluid-permeable structure and a second lumen that is operable to remove fluid from the well of the first multiwell collection plate in which the bead was placed.

19. The method according to any of clauses 3-18, further comprising moving the bead collection device in one or more degrees of freedom to deliver the beads that are collected in the bead collection device into the plurality of wells of the first multiwell collection plate.

20. The method of any of clauses 3-19, wherein the microchip is programmed to extract the bead from a specific well of interest in the microchip and deliver the bead via the bead collection device to an addressable well in the plurality of wells in the first multiwell collection plate.

21. The method according to any of clauses 3-20, wherein the total volume of each well of the first multiwell collection plate is between 1 and 25 µl.

22. A system for synthesis of a nucleic acid molecule, the system comprising: a microchip comprising a plurality of well structures formed thereon, each well of the plurality of well structures sized to accommodate a bead for synthesis of the nucleic acid molecule, wherein each well has formed therein a first electrode at a bottom of the well that is individually controllable by a controller; and a lid member arranged on top of the microchip and comprising a fluidic channel formed therein to provide fluid path for the bead, wherein the lid member comprises a second electrode, wherein the controller is operable to provide a voltage between the first electrode and the second electrode that is sufficient to cause fluid in the well to undergo electrolysis producing one or more bubbles in the fluid to rise to a top of the well along with the bead.

23. The system according to clause 22, further comprising a bead-collection device operable to collect the bead that is removed from the well.

24. The system according to clause 22 or 23, further comprising a first multiwell collection plate operable to receive the bead that is collected from the bead-collection device.

25. The system according to any one of clauses 22-24, wherein the fluid comprises an aqueous or a non-aqueous buffer solution.

26. The system according to any one of clauses 22-25, wherein the fluid comprises water, NaCl dissolved in water, methanol, acetonitrile, hydroquinone, benzoquinone, and Net4pTsO.

27. The system according to any one of clauses 22-26, wherein the first electrode is composed of platinum and the voltage is about 0.1 to about 100 volts.

28. The system according to any one of clauses 22-27, wherein the second electrode is arranged above the first electrode.

29. The system according to any one of clauses 22-28, wherein each well of the microchip has a depth between about 40 and about 60 µm.

30. The system according to any one of clauses 22-29, wherein the microchip is a complementation metal-oxide-semiconductor ("CMOS") chip.

31. The system according to any one of clauses 22-30, wherein the bead is composed of: a synthetic polymer, a modified naturally occurring polymer, glass, controlled pore glass, magnetic controlled pore glass, magnetic beads, ceramics, or one or more metals.

32. The system according to any one of clauses 23-31, wherein the bead collection device is in fluid communication with the fluid path and comprises a first channel to allow for the bead to move a first direction and a second channel to allow for fluid to move in a second direction different than the first direction.

33. The system according to any one of clauses 23-32, wherein the bead collection device comprises an acoustic module that is controllable by a controller to facilitate movement of the bead in the first channel, the fluid in the second channel, or both.

34. The system according to any one of clauses 24-33, wherein the first multiwell collection plate comprises a plate comprising a plurality of well structures and a fluid-permeable structure formed on a top surface of or within the plurality of well structures.

35. The system according to any one of clauses 24-34, wherein the first multiwell collection plate comprises a plurality of well structures and further comprising a second multiwell collection plate, wherein the second multiwell collection plate comprises a plurality of well structures and a fluid-permeable structure formed on a bottom surface of the plurality of well structures, wherein the second multiwell collection plate is placed on top of the first multiwell collection plate such that the plurality of well structures in the second multiwell collection plate are aligned with the plurality of well structures in the first multiwell collection plate.

36. The system according to any one of clauses 23-35, wherein the bead collection device comprises a needle structure that is operable to 1) place the bead from the nucleic acid molecule synthesis microchip into a well of the first multiwell collection plate by puncturing the fluid-permeable structure, and 2) remove fluid from the well in which the bead was placed.

37. The system of clause 36, wherein the needle structure comprises a first lumen that is operable to place the bead from the nucleic acid molecule synthesis microchip into a well of the multiwell collection plate by puncturing the fluid-permeable structure and a second lumen that is operable to remove fluid from the well in which the bead was placed.

38. The system according to any one of clauses 23-37, further comprising a controller that is operable to move the bead collection device in one or more degrees of freedom to deliver the beads that are collected in the bead collection device into the plurality of wells of the first multiwell collection plate.

39. The system of any one of clauses 23-38, wherein the microchip is programmed to extract the bead from a specific well of interest in the microchip and deliver the bead via the bead collection device to an addressable well in the plurality of wells in the first multiwell collection plate.

40. The system according to any one of clauses 24-39, wherein the total volume of each well of the first multiwell collection plate is between 1 µl and 25 µl.

41. A non-transitory computer-readable storage medium encoded with instructions, executable by a processor, for removing a bead from a fluid-filled well of a microchip for synthesizing nucleic acid molecules, wherein a nucleic acid molecule is attached to the bead, the instructions comprising instructions for: providing a voltage between a first electrode that is arranged at a bottom of the fluid-filled well and a second electrode, wherein the voltage is sufficient to cause fluid in the fluid-filled well to undergo electrolysis produces one or more bubbles in the fluid to rise to a top of the fluid-filled well along with the bead.

42. A system for removing a bead from a fluid-filled well of a microchip for synthesizing nucleic acid molecules, wherein a nucleic acid molecule is attached to the bead, the system comprising: a processor; and a memory encoded with processor-executable instructions for: providing a voltage between a first electrode that is arranged at a bottom of the fluid-filled well and a second electrode, wherein the voltage is sufficient to cause fluid in the fluid-filled well to undergo electrolysis producing one or more bubbles in the fluid to rise to a top of the fluid-filled well along with the bead.

43. A method for selectively removing one or more beads from a microchip for synthesizing nucleic acid molecules having a plurality of fluid-filled wells, wherein each of the plurality of wells comprises an electrode formed at the bottom of the well and each bead of the one or more beads occupies a single well on the microchip, the method comprising: identifying one or more wells that contain one or more beads to be removed from the microchip; providing a voltage between a first electrode in the one or more wells that have been identified and a second electrode, wherein the voltage is sufficient to cause fluid in the one or more fluid-filled wells to undergo electrolysis and produce one or more bubbles in the fluid to rise to a top of the one or more fluid-filled wells along with the one or more beads contained within the one or more wells; collecting the one or more beads that have risen to the top of the one or more fluid-filled well with by a bead-collection device; and transferring the one or more beads that were collected to one or more wells of a multiwell collection plate.

44. A system for synthesis of a nucleic acid molecule, the system comprising: a microchip comprising a plurality of well structures formed thereon, each well of the plurality of well structures sized to accommodate a monodisperse bead for synthesis of the nucleic acid molecule, wherein each well has formed therein a first electrode at a bottom of the well that is individually controllable by a controller, and wherein the diameter of the monodisperse bead is smaller than the diameter of each well by about 5% to about 20%; and a lid member arranged on top of the microchip and comprising a fluidic channel formed therein to provide fluid path for the bead, wherein the lid member comprises a second electrode, wherein the controller is operable to provide a voltage between the first electrode and the second electrode that is sufficient to cause fluid in the well to undergo electrolysis producing one or more bubbles in the fluid to rise to a top of the well along with the bead.

45. The system of clause 44, wherein the diameter of the monodisperse bead varies less than 10%.

46. The system of clause 44 or 45, wherein the monodisperse bead is smaller than the diameter of each well by about 12.5%.

47. The system according to any one of clauses 44-46, wherein the diameter of the monodisperse bead is about 35 μm, the diameter of each well is about 40 μl, and the depth of each well is about 55 μl.

48. The system according to any one of clauses 44-47, wherein the monodisperse bead has a linker loading capacity of the oligonucleotide synthesis substrate within a range of 30 to 100 μmol/g.

49. The system according to any one of clauses 44-48, further comprising a bead-collection device operable to collect the monodisperse bead that is removed from the well of the microchip.

50. The system according to any of clauses 44-49, further comprising a first multiwell collection plate operable to receive the monodisperse bead that is collected from the bead-collection device.

51. A multiwell plate for non-template directed synthesis of nucleic acid molecules, the plate comprising: a bead located in each of a plurality of wells of the plate, and a photogenerated acid being present in one or more wells of the plurality of wells, wherein the bead is between 1.0 μm and 100 μm in diameter.

52. The multiwell plate of clause 51, wherein the number of wells in the plate is between 10 and 2,000,000.

53. The multiwell plate of clause 51 or 52, wherein the total volume of each well is between 6.3×10-6 μl and 6.3×10-4 μl.

54. The multiwell plate according to any one of clauses 51-53, wherein each well is operably connected to a light source.

55. The multiwell plate according to any one of clauses 51-54, wherein the wells of the plate are connected to one or more microfluidic channels for the introduction and removal of reagents.

56. A method for the generation of an assembled nucleic acid molecule, the method comprising: a) synthesizing a plurality of nucleic acid molecules, wherein each nucleic acid molecule is prepared in a well of a plate in an average amount of from about 50 femtomoles to about 15,000 femtomoles, wherein the well is operably connected to a light source for the production of a photogenerated acid; b) combining the nucleic acid molecules generated in (a) to produce a pool; c) joining some or all of the nucleic acid molecules present in the pool formed in (b) to form a plurality of larger nucleic acid molecules; d) eliminating nucleic acid molecules which contain sequence errors from the plurality of larger nucleic acid molecules formed in (c) to produce an error corrected nucleic acid molecule pool; and e) assembling the nucleic acid molecules in the error corrected nucleic acid molecule pool to form the assembled nucleic acid molecule.

57. The method of clause 56, wherein the joining in (c) is mediated by polymerase chain reaction and/or ligases.

58. The method of clause 56 or 57, wherein the assembled nucleic acid molecule is composed of at least five nucleic acid molecules.

59. The method according to any one of clauses 56-58, wherein the assembled nucleic acid molecule is composed of between five and five thousand nucleic acid molecules.

60. The method according to any one of clauses 56-59, wherein the assembled nucleic acid molecule is at least 20 kilobases.

61. The method according to any one of clauses 56-60, wherein the assembled nucleic acid molecule is between 10 kilobases and 1 megabase.

62. The method according to any one of clauses 56-61, wherein the assembled nucleic acid molecule is closed, circular.

63. The method of clause 62, wherein the assembled nucleic acid molecule is a plasmid.

64. The method according to any one of clauses 56-63, wherein two or more assembled nucleic acid molecule are simultaneously formed.

65. The method according to any one of clauses 56-64, wherein assembly of the nucleic acid molecules in the error corrected nucleic acid molecule pool occurs in a fungal cell.

66. The method according to any one of clauses 56-65, wherein the assembled nucleic acid molecule generated in either one or both of (c) or (e) are assembled and introduced into a cloning vector.

67. The method according to any one of clauses 56-66, wherein the well of the plate comprises at least one proton carrier to reduce degradation of the nucleic acid molecules exposed to the photogenerated acid.

68. The method of clause 67, wherein the at least one proton carrier is chosen from 2-chloro-6-methylpyridine and diphenylamine.

69. A non-transitory computer-readable storage medium encoded with instructions, executable by a processor, for the generation of an assembled nucleic acid molecule, the instructions comprising instructions for: a) synthesizing a plurality of nucleic acid molecules, wherein each nucleic acid molecule is prepared in a well of a plate in an average amount of from about 50 femtomoles to about 15,000 femtomoles, wherein the well is operably connected to a light source for the production of a photogenerated acid; b) combining the nucleic acid molecules generated in (a) to produce a pool; c) joining some or all of the nucleic acid molecules present in the pool formed in (b) to form a plurality of larger nucleic acid molecules; d) eliminating nucleic acid molecules which contain sequence errors from the plurality of larger nucleic acid molecules formed in (c) to produce an error corrected nucleic acid molecule pool; and e) assembling the nucleic acid molecules in the error corrected nucleic acid molecule pool to form the assembled nucleic acid molecule.

70. A system for the generation of an assembled nucleic acid molecule, the system comprising: a processor; and a memory encoded with processor-executable instructions for: a) synthesizing a plurality of nucleic acid molecules, wherein each nucleic acid molecule is prepared in a well of a plate in an average amount of from about 50 femtomoles to about 15,000 femtomoles, wherein the well is operably connected to a light source for the production of a photogenerated acid; b) combining the nucleic acid molecules generated in (a) to produce a pool; c) joining some or all of the nucleic acid molecules present in the pool formed in (b) to form a plurality of larger nucleic acid molecules; d) eliminating nucleic acid molecules which contain sequence errors from the plurality of larger nucleic acid molecules formed in (c) to produce an error corrected nucleic acid molecule pool; and e) assembling the nucleic acid molecules in the error corrected nucleic acid molecule pool to form the assembled nucleic acid molecule.

71. A method for the generation of an assembled nucleic acid molecule, the method comprising: a) synthesizing a plurality of nucleic acid molecules, wherein each nucleic acid molecule is prepared in a well of a plate in an average amount of from about 50 femtomoles to about 15,000 femtomoles, wherein the well comprises at least one acid for the deprotection of the nucleic acid molecules and at least one proton carrier to reduce degradation of the nucleic acid molecules exposed to the at least one acid; b) combining the nucleic acid molecules generated in (a) to produce a pool; c) joining some or all of the nucleic acid molecules present in the pool formed in (b) to form a plurality of larger nucleic acid molecules; d) eliminating nucleic acid molecules which contain sequence errors from the plurality of larger nucleic acid molecules formed in (c) to produce an error corrected nucleic acid molecule pool; and e) assembling the nucleic acid molecules in the error corrected nucleic acid molecule pool to form the assembled nucleic acid molecule.

72. The method of clause 71, wherein the at least one proton carrier is chosen from 2-chloro-6-methylpyridine and diphenylamine.

73. The method of clause 71 or 72, wherein the at least one acid is chosen from an electrochemically generated acid and a photogenerated acid.

74. A non-transitory computer-readable storage medium encoded with instructions, executable by a processor, for the generation of an assembled nucleic acid molecule, the instructions comprising instructions for: a) synthesizing a plurality of nucleic acid molecules, wherein each nucleic acid molecule is prepared in a well of a plate in an average amount of from about 50 femtomoles to about 15,000 femtomoles, wherein the well comprises at least one acid for the deprotection of the nucleic acid molecules and at least one proton carrier to reduce degradation of the nucleic acid molecules exposed to the at least one acid; b) combining the nucleic acid molecules generated in (a) to produce a pool; c) joining some or all of the nucleic acid molecules present in the pool formed in (b) to form a plurality of larger nucleic acid molecules; d) eliminating nucleic acid molecules which contain sequence errors from the plurality of larger nucleic acid molecules formed in (c) to produce an error corrected nucleic acid molecule pool; and e) assembling the nucleic acid molecules in the error corrected nucleic acid molecule pool to form the assembled nucleic acid molecule.

75. A system for the generation of an assembled nucleic acid molecule, the system comprising: a processor; and a memory encoded with processor-executable instructions for: a) synthesizing a plurality of nucleic acid molecules, wherein each nucleic acid molecule is prepared in a well of a plate in an average amount of from about 50 femtomoles to about 15,000 femtomoles, wherein the well comprises at least one acid for the deprotection of the nucleic acid molecules and at least one proton carrier to reduce degradation of the nucleic acid molecules exposed to the at least one acid; b) combining the nucleic acid molecules generated in (a) to produce a pool; c) joining some or all of the nucleic acid molecules present in the pool formed in (b) to form a plurality of larger nucleic acid molecules; d) eliminating nucleic acid molecules which contain sequence errors from the plurality of larger nucleic acid molecules formed in (c) to produce an error corrected nucleic acid molecule pool; and e) assembling the nucleic acid molecules in the error corrected nucleic acid molecule pool to form the assembled nucleic acid molecule.

76. A method for retrieving a nucleic acid linked to a solid support by a base-cleavable linker, the method comprising: a) generating an electrochemically generated base; b) cleaving the nucleic acid from the solid support with the electrochemically generated base; c) contacting the cleaved nucleic acid with a solid phase material such that nucleic acid remains on the solid phase material; and d) eluting the nucleic acid on the solid phase material with an agent for removing a protecting group from the nucleic acid, wherein the solid support is a bead having a diameter ranging from about 1.0 µm to about 100 µm, and wherein the bead is located in each of a plurality of wells of a multiwell plate.

77. The method of clause 76, wherein the agent for removing a protecting group from the nucleic acid is methylamine.

78. The method of clause 76 or 77, wherein the solid support is a bead having a diameter ranging from about 30 µm to about 40 µm.

79. The method of clause 78, wherein the bead is in a well of a multiwell plate, wherein the total volume of each well of the multiwell plate ranges from about 1×10-6 µl to about 1×10-4 µl.

80. The method of clause 79, wherein the well is operably connected to a least one electrode.

81. The method of any one of clauses 76-80, wherein the electrochemically generated base is generated from azomethane reduced by the at least one electrode.

82. The method of any one of clauses 76-80, further comprising at least one aqueous washing step after the cleaved nucleic acid is contacted with the solid phase material.

83. The method of clause 82, further comprising at least one drying step after the washing step.

84. The method of clause 83, wherein the at least one drying step is performed with at least one of nitrogen and air.

85. The method of any one of clauses 76-84, wherein the amount of the agent for removing a protecting group from the nucleic acid is between 0.1 and 10 µl.

86. The method of any one of clauses 76-85, wherein the solid phase material is loaded into a multiwell plate, wherein the total volume of each well of the multiwell plate ranges from 0.1 to 25 µl.

87. A non-transitory computer-readable storage medium encoded with instructions, executable by a processor, for retrieving a nucleic acid linked to a solid support by a base-cleavable linker, the instructions comprising instructions for: a) generating an electrochemically generated base; b) cleaving the nucleic acid from the solid support with the electrochemically generated base; c) contacting the cleaved nucleic acid with a solid phase material such that nucleic acid remains on the solid phase material; and d) eluting the nucleic acid on the solid phase material with an agent for removing a protecting group from the nucleic acid, wherein the solid support is a bead having a diameter ranging from about 1.0 µm to about 100 µm, and wherein the bead is located in each of a plurality of wells of a multiwell plate.

88. A system for retrieving a nucleic acid linked to a solid support by a base-cleavable linker, the system comprising: a processor; and a memory encoded with processor-executable instructions for: a) generating an electrochemically generated base;

b) cleaving the nucleic acid from the solid support with the electrochemically generated base; c) contacting the cleaved nucleic acid with a solid phase material such that nucleic acid remains on the solid phase material; and d) eluting the nucleic acid on the solid phase material with an agent for removing a protecting group from the nucleic acid, wherein the solid support is a bead having a diameter ranging from about 1.0 µm to about 100 µm, and wherein the bead is located in each of a plurality of wells of a multiwell plate.

89. A method for retrieving a nucleic acid molecule from a multiwell plate or microarray for non-directed synthesis of nucleic acid molecules, the method comprising: a) synthesizing a first plurality of nucleic acid molecules, wherein each nucleic acid molecule of said first plurality is designed to have a defined sequence and is prepared in a well of a first multiwell plate in an average amount of from about 10 attomoles to about 1 picomole; b) synthesizing a second plurality of nucleic acid molecules, wherein each nucleic acid molecule of said second plurality is designed to be complementary to the nucleic acid molecules of said first plurality and is prepared in a well of a second multiwell plate in an average amount of from about 10 attomoles to about 1 picomole; c) deprotecting and cleaving the first plurality of nucleic acid molecules from the first multiwell plate; d) deprotecting the second plurality of nucleic acid molecules from the second multiwell plate; e) contacting the first plurality of nucleic acid molecules with the second plurality of nucleic acid molecules under hybridizing conditions to generate hybridized nucleic acid molecules; f) denaturing the hybridized nucleic acid molecules by adding a denaturing solution to the second multiwell plate; and g) retrieving the denatured nucleic acid molecules from the second multiwell plate.

90. The method of clause 89, wherein the denaturing solution comprises NaOH.

91. The method of clause 89 or 90, further comprising a washing step before the denaturing step.

92. A non-transitory computer-readable storage medium encoded with instructions, executable by a processor, for retrieving a nucleic acid molecule from a multiwell plate for non-directed synthesis of nucleic acid molecules, the instructions comprising instructions for: a) synthesizing a first plurality of nucleic acid molecules, wherein each nucleic acid molecule of said first plurality is designed to have a defined sequence and is prepared in a well of a first multiwell plate in an average amount of from about 10 attomoles to about 1 picomole; b) synthesizing a second plurality of nucleic acid molecules, wherein each nucleic acid molecule of said second plurality is designed to be complementary to the nucleic acid molecules of said first plurality and is prepared in a well of a second multiwell plate in an average amount of from about 10 attomoles to about 1 picomole; c) deprotecting and cleaving the first plurality of nucleic acid molecules from the first multiwell plate; d) deprotecting the second plurality of nucleic acid molecules from the second multiwell plate; e) contacting the first plurality of nucleic acid molecules with the second plurality of nucleic acid molecules under hybridizing conditions to generate hybridized nucleic acid molecules; f) denaturing the hybridized nucleic acid molecules by adding a denaturing solution to the second multiwell plate; and g) retrieving the denatured nucleic acid molecules from the second multiwell plate.

93. A system for retrieving a nucleic acid molecule from a multiwell plate for non-directed synthesis of nucleic acid molecules, the system comprising: a processor; and a memory encoded with processor-executable instructions for: a) synthesizing a first plurality of nucleic acid molecules, wherein each nucleic acid molecule of said first plurality is designed to have a defined sequence and is prepared in a well of a first multiwell plate in an average amount of from about 10 attomoles to about 1 picomoles; b) synthesizing a second plurality of nucleic acid molecules, wherein each nucleic acid molecule of said second plurality is designed to be complementary to the nucleic acid molecules of said first plurality and is prepared in a well of a second multiwell plate in an average amount of from about 10 attomoles to about 1 picomole; c) deprotecting and cleaving the first plurality of nucleic acid molecules from the first multiwell plate; d) deprotecting the second plurality of nucleic acid molecules from the second multiwell plate; e) contacting the first plurality of nucleic acid molecules with the second plurality of nucleic acid molecules under hybridizing conditions to generate hybridized nucleic acid molecules; f) denaturing the hybridized nucleic acid molecules by adding a denaturing solution to the second multiwell plate; and g) retrieving the denatured nucleic acid molecules from the second multiwell plate.

94. A method of concentrating a nucleic acid molecule synthesized on a microchip, the method comprising: transferring in a first volume of fluid one or more solid supports from a plurality of well structures formed on the microchip to a second volume of fluid in a well of a first multiwell collection plate, wherein a nucleic acid that has been synthesized on the microchip is attached to the one or more solid supports, wherein the one or more solid supports are transferred using a bead collection device, wherein the bead collection device is in fluid connection with the microchip and the first multiwell collection plate, wherein the first multiwell collection plate comprises a plurality of wells and a fluid-permeable structure formed on a top surface of or within the plurality of wells, optionally wherein the bead collection device comprises a controller that is operable to move the microfluidic device in one or more degrees of freedom to deliver the one or more solid supports from the microchip into the well of the first multiwell collection plate, and wherein the second volume of fluid in the well of the first multiwell collection plate is less than the first volume of fluid, thereby concentrating the nucleic acid molecule synthesized on the microchip.

95. The method of clause 94, wherein the concentrating comprises reducing the first volume of fluid by a factor of about 10 to about 1,000.

96. The method of clause 94 or clause 95, wherein the one or more solid supports is a bead having a diameter ranging from about 1.0 µm to about 100 µm.

97. The method of clause 96, wherein the bead is monodisperse.

98. The method of any one of clauses 94-97, wherein each well of the plurality of well structures in the microchip has a total volume ranging from between $1 \times 10^{-6}$ µl and $1 \times 10^{-4}$ µl.

99. The method of any one of clauses 94-98, further comprising a second multiwell collection plate, wherein the second multiwell collection plate comprises a plurality of well structures and a fluid-permeable structure formed on a bottom surface of the plurality of well structures, wherein the second multiwell collection plate is placed on top of the first multiwell collection plate such that the plurality of well structures in the second multiwell collection plate are aligned with the plurality of well structures in the first multiwell collection plate.

100. The method of any one of clauses 94-99, further comprising a step of cleaving the nucleic acid from the one or more solid supports after the one or more solid supports are transferred to the fluid-permeable structure.

101. The method of clause 100, further comprising a step of eluting the cleaved nucleic acid into the well of the first multiwell collection plate.

102. The method of any one of clauses 94-101, further comprising a step of puncturing the fluid-permeable structure to deliver the one or more solid supports to the well of the first multiwell collection plate.

103. The method of clause 102, wherein a pressure is applied to puncture the fluid-permeable structure.

104. The method of any one of clauses 94 to 103, wherein the bead collection device used to transfer the one or more solid supports is a microfluidic chip.

105. The method according to any one of clauses 94 to 103, wherein the bead collection device comprises a needle structure that is operable to 1) place the one or more solid supports from the microchip into the well of the first multiwell collection plate by puncturing the fluid-permeable structure, and/or 2) remove fluid from the well in the first multiwell collection plate in which the one or more solid supports were placed.

106. The method of clause 105, wherein the needle structure comprises a first lumen that is operable to place the one or more solid supports from the microchip into a well of the first multiwell collection plate by puncturing the fluid-permeable structure and a second lumen that is operable to remove fluid from the well in the first multiwell collection plate in which the one or more solid supports were placed.

107. The method according to any of clauses 94-106, wherein the microchip is programmed to extract the solid support from a specific well of interest in the microchip and transfer the solid support via the bead collection device to an addressable well in the plurality of wells in the first multiwell collection plate.

108. The method according to any of clauses 94-107, wherein the total volume of each well of the first multiwell collection plate is between 1 and 25 µl.

109. The method according to any one of clauses 94-108, further comprising a step of synthesizing a nucleic acid on the solid support in a well of the plurality of well structures formed on the microchip before transferring the one or more solid supports to the well of the first multiwell collection plate.

110. The method according to any one of clauses 94-109, wherein each well has formed therein a first electrode at a bottom of the well that is individually controllable by a controller, wherein the microchip further comprises a lid member arranged on top of the microchip and comprising a fluidic channel formed therein to provide fluid path for the solid support, wherein the lid member comprises a second electrode, and wherein the controller is operable to provide a voltage between the first electrode and the second electrode that is sufficient to cause fluid in the well to undergo electrolysis producing one or more bubbles in the fluid to rise to a top of the well along with the solid support.

111. A non-transitory computer-readable storage medium encoded with instructions, executable by a processor, for concentrating a nucleic acid molecule synthesized on a microchip, the instructions comprising instructions for: transferring in a first volume of fluid one or more solid supports from a plurality of well structures formed on a microchip to a second volume of fluid in a well of a first multiwell collection plate, wherein a nucleic acid that has been synthesized on the microchip is attached to the one or more solid supports, wherein the one or more solid supports are transferred using a bead collection device, wherein the bead collection device is in fluid connection with the microchip and the first multiwell collection plate, wherein the first multiwell collection plate comprises a plurality of wells and a fluid-permeable structure formed on a top surface of or within the plurality of wells, wherein the bead collection device comprises a controller that is operable to move the bead collection device in one or more degrees of freedom to deliver the one or more solid supports from the microchip into the well of the first multiwell collection plate, and wherein the second volume of fluid in the well of the first multiwell collection plate is less than the first volume of fluid, thereby concentrating the nucleic acid molecule synthesized on the microchip.

112. A system for concentrating a nucleic acid molecule synthesized on a microchip, the system comprising: a processor; and a memory encoded with processor-executable instructions for: transferring in a first volume of fluid one or more beads from a plurality of well structures formed on a microchip to a second volume of fluid in a well of a first multiwell collection plate, wherein a nucleic acid that has been synthesized on the microchip is attached to the one or more beads, a bead collection device for transferring the one or more beads, wherein the bead collection device is in fluid connection with the microchip and a first multiwell collection plate, wherein the first multiwell collection plate comprises a plurality of wells, optionally, a controller that is operable to move the bead collection device in one or more degrees of freedom to deliver the one or more solid supports from the microchip into the well of the first multiwell collection plate.

113. The system according to clause 112, wherein the bead collection device is a microfluidic chip comprising a first channel to allow for the one or more beads to move a first direction and a second channel to allow for fluid to move in a second direction different than the first direction.

114. The system according to clause 113, wherein the microfluidic chip further comprises an acoustic module that is controllable by a controller to facilitate movement of the bead in the first channel, the fluid in the second channel, or both.

115. The system according to clause 112, wherein the bead collection device comprises a needle structure and associated tubing.

116. The system according to clause 115, wherein the first multiwell collection plate comprises a fluid-permeable structure formed on a top surface of or within the plurality of wells and wherein the needle structure comprises a first lumen that is operable to place the one or more beads from the microchip into a well of the first multiwell collection plate by puncturing the fluid-permeable structure and a second lumen that is operable to remove fluid from the well in the first multiwell collection plate in which the one or more beads were placed.

117. The system according to clause 116, further comprising a second multiwell collection plate, wherein the second multiwell collection plate comprises a plurality of well structures and a fluid-permeable structure formed on a bottom surface of the plurality of well structures, wherein the second multiwell collection plate is placed on top of the first multiwell collection plate such that the plurality of well structures in the second multiwell collection plate are aligned with the plurality of well structures in the first multiwell collection plate.

118. A monodisperse porous bead for solid-phase synthesis of oligonucleotides of a length of between 35 and 200 bases, wherein the bead is a polystyrene bead coated with reactive groups and wherein said bead comprises: a diameter of between 10 and 100 µm with a coefficient of variation of less than 10%, a surface area within a range of between 100 and 500 m2/g, a porosity within a range of about 60% to about 80%, optionally, an amine content of between about 2% and about 8%, a linker loading capacity of between 15 µmol/g to 100 µmol/g, optionally, wherein said bead carries a linker, and wherein the linker is a universal linker.

The invention claimed is:

1. A system for synthesis of a nucleic acid molecule, the system comprising:
   a microchip comprising a plurality of well structures formed thereon, each well of the plurality of well structures sized to accommodate a bead for synthesis of the nucleic acid molecule, wherein each well has formed therein a first electrode at a bottom of the well that is individually controllable by a controller; and
   a lid member arranged on top of the microchip and comprising a fluidic channel formed therein to provide a fluid path for the bead, wherein the fluid path leads to a multiwell collection plate, and wherein the lid member comprises a second electrode,
   wherein the multiwell collection plate comprises a plate comprising a plurality of well structures and a fluid-permeable structure formed on a top surface of or within the plurality of well structures, and
   wherein the controller is operable to provide a voltage between the first electrode and the second electrode that is sufficient to cause fluid in the well to undergo electrolysis producing one or more bubbles in the fluid to rise to a top of the well along with the bead or to lift the bead to the top of the fluid-filled well.

2. The system of claim 1, further comprising a bead-collection device operable to collect the bead that is removed from the well.

3. The system of claim 1, wherein the fluid comprises an aqueous or a non-aqueous buffer solution.

4. The system of claim 1, wherein the fluid comprises water, methanol, acetonitrile, and Net4pTsO.

5. The system of claim 1, wherein each well of the microchip has a depth between about 40 and about 60 μm.

6. The system of claim 1, wherein the microchip is a complementation metal-oxide-semiconductor ("CMOS") chip.

7. A system for synthesis of a nucleic acid molecule, the system comprising:
   a microchip comprising a plurality of well structures formed thereon, each well of the plurality of well structures sized to accommodate a monodisperse bead for synthesis of the nucleic acid molecule, wherein each well has formed therein a first electrode at a bottom of the well that is individually controllable by a controller, and wherein the diameter of the monodisperse bead is smaller than the diameter of each well by about 5% to about 20%; and
   a lid member arranged on top of the microchip and comprising a fluidic channel formed therein to provide fluid path for the bead, wherein the lid member comprises a second electrode,
   wherein the controller is operable to provide a voltage between the first electrode and the second electrode that is sufficient to cause fluid in the well to undergo electrolysis producing one or more bubbles in the fluid to rise to a top of the well along with the bead or to lift the bead to the top of the fluid-filled well, and
   wherein the monodisperse bead has a linker loading capacity of the oligonucleotide synthesis substrate within a range of 30 to 100 μmol/g.

8. The system of claim 7, wherein the diameter of the monodisperse bead varies less than 10%.

9. The system of claim 7, wherein the diameter of the monodisperse bead is between about 29 to 35 μm, the diameter of each well is between about 40 μm to about 45 μm, and the depth of each well is between about 45 μm to about 55 μm.

* * * * *